United States Patent
Migaud et al.

(10) Patent No.: US 10,000,520 B2
(45) Date of Patent: Jun. 19, 2018

(54) B-VITAMIN AND AMINO ACID CONJUGATES OF NICOTINOYL RIBOSIDES AND REDUCED NICOTINOYL RIBOSIDES, DERIVATIVES THEREOF, AND METHODS OF PREPARATION THEREOF

(71) Applicants: ChromaDex Inc., Irvine, CA (US); The Queen's University of Belfast, Belfast (GB)

(72) Inventors: Marie Eugenie Migaud, Lurgan (GB); Philip Redpath, Portadown (GB); Kerri Crossey, Magherafelt (GB); Richard Cunningham, Portadown (GB); Ryan Dellinger, Azusa, CA (US); Troy Rhonemus, Mission Viejo, CA (US); Sylesh Venkataraman, Irvine, CA (US); Brian Nettles, Irvine, CA (US)

(73) Assignees: ChromaDex Inc., Irvine, CA (US); The Queen's University of Belfast, Belfast, Northern Ireland (GB)

( * ) Notice: Subject to any disclaimer, the term of this patent is extended or adjusted under 35 U.S.C. 154(b) by 0 days. days.

(21) Appl. No.: 15/461,126

(22) Filed: Mar. 16, 2017

(65) Prior Publication Data
US 2017/0267709 A1 Sep. 21, 2017

Related U.S. Application Data

(60) Provisional application No. 62/309,273, filed on Mar. 16, 2016.

(51) Int. Cl.
| | | |
|---|---|---|
| C07H 19/00 | (2006.01) | |
| C07H 19/048 | (2006.01) | |
| C07H 1/00 | (2006.01) | |
| C07H 19/04 | (2006.01) | |

(52) U.S. Cl.
CPC ............ *C07H 19/048* (2013.01); *C07H 1/00* (2013.01); *C07H 19/04* (2013.01)

(58) Field of Classification Search
None
See application file for complete search history.

(56) References Cited

U.S. PATENT DOCUMENTS

| | | |
|---|---|---|
| 7,601,332 B2 | 10/2009 | Vlahov et al. |
| 8,105,568 B2 | 1/2012 | Vlahov et al. |
| 8,106,184 B2 | 1/2012 | Sauve et al. |
| 8,197,807 B2 | 6/2012 | Brenner |
| 8,383,086 B2 | 2/2013 | Brenner |
| 9,321,797 B2 | 4/2016 | Sauve et al. |
| 2006/0229265 A1 | 10/2006 | Milburn et al. |
| 2015/0175645 A1 | 6/2015 | Milburn et al. |

FOREIGN PATENT DOCUMENTS

| | | | |
|---|---|---|---|
| EP | 2805719 A1 | 11/2014 | |
| WO | 2015014722 A1 | 2/2015 | |
| WO | 2015066382 A1 | 5/2015 | |
| WO | 2015186114 A1 | 12/2015 | |
| WO | WO 2015/186114 A1 * | 12/2015 | ........... C07H 19/048 |
| WO | 2016014927 A2 | 1/2016 | |
| WO | 2016144660 A1 | 9/2016 | |

OTHER PUBLICATIONS

M. Jarman, "4-Substituted Nicotinic Acids and Nicotinamides. Part III. Preparation of 4-Methylnicotinic Acid Riboside," Journal of the Chemical Society 918-20 (1969).
Masaharu Yoshikawa et al., Studies of Phosphorylation. III. Selective Phosphorylation of Unprotected Nucleosides, 42 Bulletin of the Chemical Society of Japan, 3505 (Dec. 1969).
Stephen M. Berge et al., Pharmaceutical Salts, 66(1) Journal of Pharmaceutical Sciences 1 (Jan. 1977).
Francesco Ravalico et al., Rapid synthesis of nucleotide pyrophosphate linkages in a ball mill, 9 Org. Biol. Chem. 6496 (2011).
Philip Redpath et al., Nicotinamide Benzimidazolide Dinucleotides, Non-Cyclisable Analogues of NAD+, 25 Synlett 2331 (2014).

* cited by examiner

Primary Examiner — Patrick T Lewis
(74) Attorney, Agent, or Firm — Amin Talati Upadhye LLP; Adam D. Sussman; George M. Carrera, Jr.

(57) ABSTRACT

The present disclosure provides nicotinate/nicotinamide riboside compounds or derivatives of formula (I):

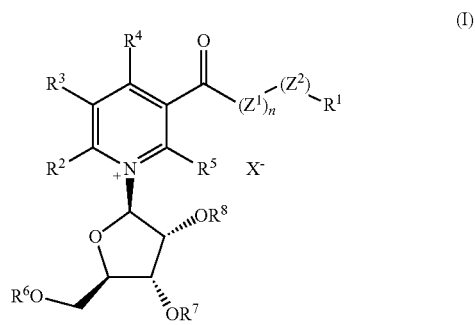

wherein $X^-$, $Z^1$, $Z^2$, n, $R^1$, $R^2$, $R^3$, $R^4$, $R^5$, $R^6$, $R^7$, and $R^8$ are described herein, reduced analogs thereof, and synthetic processes for the preparation thereof.

9 Claims, No Drawings

B-VITAMIN AND AMINO ACID CONJUGATES OF NICOTINOYL RIBOSIDES AND REDUCED NICOTINOYL RIBOSIDES, DERIVATIVES THEREOF, AND METHODS OF PREPARATION THEREOF

This application claims the benefit of U.S. Provisional Application No. 62/309,273, filed on Mar. 16, 2016. The disclosure of this prior application is incorporated herein by reference in its entirety for all purposes.

TECHNICAL FIELD

The present disclosure relates to compounds that are modified B-vitamin or amino acid conjugates or derivatives of nicotinamide riboside ("NR"), nicotinic acid riboside ("NAR"), the reduced forms thereof ("NRH" and "NARH," respectively), or salts, hydrates, or solvates thereof, and processes to prepare the compounds. The processes involve preparation of the said conjugates or derivatives, or salts, hydrates, or solvates thereof, using solvent based synthetic techniques and mechano-chemical and/or solvent-free synthetic techniques.

BACKGROUND

Vitamin B3, and other B-vitamins such as thiamine (vitamin B1), riboflavin (vitamin B2), and pyridoxine (vitamin B6) are extracted in their coenzyme forms from foodstuffs. During digestion, the coenzymes are catabolized to the free circulating vitamins, which are then passively or actively transported across membranes, and salvaged intracellularly to their respective cofactors, Mammals are entirely reliant on a dietary source of vitamin B1 and heavily dependent on the dietary supply of vitamins B2, B3, and B6. Of note, acute deficiencies in vitamin B1 and vitamin B3 affect identical organs, with identical outcomes if left untreated: dementia and death. Conditions such as diabetes and obesity, alcoholism, a high fat diet, and conditions where therapy impacts nutrition can compromise suitable absorption of these vitamins.

The dietary vitamin B3, which encompasses nicotinamide ("Nam" or "NM"), nicotinic acid ("NA"), and nicotinamide riboside ("NR"), is a precursor to the coenzyme nicotinamide adenine dinucleotide ("$NAD^+$"), its phosphorylated parent ("$NADP^+$" or "$NAD(P)^+$"), and their respective reduced forms ("NADH" and "NADPH," respectively).

Eukaryotes can synthesize $NAD^+$ de novo via the kynurenine pathway from tryptophan. See W. A. Krehl et al., *Growth-retarding Effect of Corn in Nicotinic Acid-Low Rations and its Counteraction by Tryptophane*, 101 SCIENCE 489 (1945); Gunther Schutz & Philip Feigelson, *Purification and Properties of Rat Liver Tryptophan Oxygenase*, 247 J. BIOL. CHEM. 5327 (1972); each of which is incorporated by reference herein in its entirety. The kynurenine pathway is a de novo pathway that originates from tryptophan. Through the sequential enzymatic action of tryptophan 2,3-dioxygenase ("TDO"), indoleamine 2,3-dioxygenase ("IDO"), kynurenine formamidase ("KFase"), kynurenine 3-hydroxylase ("K3H"), kynureninase, and 3-hydroxyanthranylate 3,4-dioxygenase ("3HAO"), tryptophan ("Trp") is converted to quinolinic acid ("QA"). See Javed A. Khan et al., *Nicotinamide adenine dinucleotide metabolism as an attractive target for drug discovery*, 11 EXPERT OPIN. THER. TARGETS 695 (2007), incorporated by reference herein in its entirety. Quinolinic acid (QA) is converted to nicotinic acid mononucleotide ("NaMN") through the action of quinolinic phosphoribosyltransferase ("QAPRTase"). See Khan et al., 2007.

The de novo kynureninase pathway, which produces nicotinic acid mononucleotide (NaMN) from quinolinic acid (QA), feeds into the well-established Preiss-Handler pathway, in which nicotinic acid mononucleotide (NaMN) is an intermediate. The Preiss-Handler pathway is a salvage pathway that starts with the conversion of nicotinic acid (NA) to nicotinic acid mononucleotide (NaMN), catalyzed by the enzyme nicotinate phosphoribosyltransferase ("NAPRT" or "NAPRTase"). Nicotinic acid mononucleotide (NaMN) is then adenylylated to form nicotinic acid adenine dinucleotide ("NaAD"), catalyzed by the enzyme nicotinic acid/nicotinamide mononucleotide adenylyltransferase ("NMNAT"). Nicotinic acid adenine dinucleotide (NaAD) is in turn amidated to form nicotinamide adenine dinucleotide ($NAD^+$), catalyzed by the enzyme nicotinamide adenine dinucleotide synthetase ("NADS"). Nicotinamide (Nam or NM), which is a breakdown product of $NAD^+$, can be converted to nicotinic acid (NA), catalyzed by the enzyme nicotinamide deamidase ("NM deamidase"). See Jack Preiss & Philip Handler, *Biosynthesis of Diphosphopyridine Nucleotide*, 233 J. BIOL. CHEM. 493 (1958), incorporated by reference herein in its entirety. See also Khan et al., 2007.

Another salvage pathway can convert nicotinamide (Nam or NM), the breakdown product of nicotinamide adenine dinucleotide ($NAD^+$), into nicotinamide mononucleotide ("NMN"), by the action of the enzyme nicotinamide phosphoribosyltransferase ("NMPRT" or "NMPRTase"). Nicotinamide mononucleotide (NMN) can then be directly converted into nicotinamide adenine dinucleotide ($NAD^+$) by nicotinic acid/nicotinamide mononucleotide adenylyltransferase (NMNAT). Alternatively, nicotinamide (Nam or NM) can be deamidated to form nicotinic acid (NA), which can then enter the Preiss-Handler pathway. Analysis of genome sequences suggests that the above two salvage pathways are often mutually exclusive; many organisms contain either NM deamidase or NMPRTase. See Khan et al., 2007.

Nicotinamide riboside (NR) can also be used as a precursor for nicotinamide adenine dinucleotide ($NAD^+$) biosynthesis, and nicotinamide riboside kinase ("NRK") catalyzes the phosphorylation of nicotinamide riboside (NR) to produce nicotinamide mononucleotide (NMN). See Khan et al., 2007.

Notably, nicotinamide riboside (NR) has not been considered a precursor to nicotinamide adenine dinucleotide ($NAD^+$) via the Preiss-Handler salvage pathway, or via conversion into nicotinic acid mononucleotide (NaMN) or nicotinic acid adenine dinucleotide (NaAD) as intermediates. Instead, the biosynthetic pathway for nicotinic acid riboside (NAR) is known to proceed directly to nicotinic acid mononucleotide (NaMN), then nicotinic acid adenine dinucleotide (NaAD), and ultimately to form $NAD^+$.

Nicotinamide adenine dinucleotide ($NAD^+$) is an enzyme co-factor and the central reduction-oxidation coenzyme that is essential for the function of several enzymes related to reduction-oxidation reactions and cellular energy metabolism, See Peter Belenky et al., *$NAD^+$ metabolism in health and disease*, 32 TRENDS IN BIOCHEMICAL SCIS. 12 (2007); Katrina L. Bogan & Charles Brenner, *Nicotinic Acid, Nicotinamide, and Nicotinamide Riboside: A Molecular Evaluation of $NAD^+$ Precursor Vitamins in Human Nutrition*, 28 ANNUAL REV. OF NUTRITION 115 (2008); each of which is incorporated by reference herein in its entirety. Nicotinamide adenine dinucleotide ($NAD^+$) functions as an electron carrier or hydride group acceptor in cell metabolism, forming reduced nicotinamide adenine dinucleotide (NADH), with concomitant oxidation of metabolites derived from carbohydrates, amino acids, and fats. See Bogan & Brenner, 2008. The $NAD^+/NADH$ ratio controls the degree to which such reactions proceed in oxidative versus reductive directions. Whereas fuel oxidation reactions require $NAD^+$ as a hydride acceptor, the processes of gluconeogenesis, oxidative phosphorylation, ketogenesis, detoxification of reactive oxygen species, and lipogenesis require reduced co-factors, NADH and NADPH, to act as hydride donors.

In addition to its role as a coenzyme, $NAD^+$ is the consumed substrate, and thus activator, of enzymes such as: poly-ADP-ribose polymerases ("PARPs"); sirtuins, a family of protein deacetylases that have been implicated in metabolic function and extended lifespan in lower organisms; and cyclic ADP-ribose synthetases. See Laurent Mouchiroud et al., *The $NAD^+$/Sirtuin Pathway Modulates Longevity through Activation of Mitochondrial UPR and FOXO Signaling*, 154 CELL 430 (2013), incorporated by reference herein in its entirety. See also Belenky et al., 2006. The co-enzymatic activity of $NAD^+$, together with the tight regulation of its biosynthesis and bioavailability, makes it an important metabolic monitoring system that is clearly involved in the aging process.

Once converted intracellularly to $NADP^+$, vitamin B3 is used as a co-substrate in two types of intracellular modifications, which control numerous essential signaling events (adenosine diphosphate ribosylation and deacetylation), and is a cofactor for over 400 reduction-oxidation enzymes, thus controlling metabolism. This is demonstrated by a range of metabolic endpoints including the deacetylation of key regulatory proteins, increased mitochondrial activity, and oxygen consumption. Critically, the NADPH-cofactor family can promote mitochondrial dysfunction and cellular impairment if present in sub-optimal intracellular concentrations. Vitamin B3 deficiency yields to evidenced compromised cellular activity through $NAD^+$ depletion.

In reduction-oxidation reactions, the nucleotide structures of $NAD^+$, NADH, $NADP^+$, and NADPH are preserved. In contrast, PARP, sirtuin, and cyclic ADP-ribose synthetase activities hydrolyze the glycosidic linkage between the nicotinamide (Nam or NM) and the ADP-ribosyl moieties of $NAD^+$ to signal DNA damage, alter gene expression, control post-translational modifications, and regulate calcium signaling.

In animals, $NAD^+$-consuming activities and cell division necessitate ongoing $NAD^+$ synthesis, either through the de novo pathway that originates with tryptophan, or via the salvage pathways from $NAD^+$-precursor vitamins nicotinamide (Nam or NM), nicotinic acid (NA), and nicotinamide riboside (NR). See Bogan & Brenner, 2008. Dietary $NAD^+$ precursors, which include tryptophan and the three $NAD^+$-precursor vitamins, prevent pellagra, a disease characterized by dermatitis, diarrhea, and dementia. The beneficial effect of additional $NAD^+$ bioavailability through nicotinamide (Nam or NM), nicotinic acid (NA), and nicotinamide riboside (NR) supplementation is primarily observed in cells and tissues where metabolism and mitochondrial function had been compromised.

Interestingly, supplementation with nicotinic acid (NA) and nicotinamide (Nam or NM), while critical in acute vitamin B3 deficiency, does not demonstrate the same physiological outcomes compared with that of nicotinamide riboside (NR) supplementation, even though, at the cellular level, all three metabolites are responsible for $NAD^+$ biosynthesis. This emphasizes the complexity of the pharmacokinetics and bio-distribution of B3-vitamin components. The bulk of intracellular $NAD^+$ is believed to be regenerated via the effective salvage of nicotinamide (Nam or NM), while de novo $NAD^+$ is obtained from tryptophan. See Anthony Rongvaux et al., *Reconstructing eukaryotic NAD metabolism*, 25 BIOESSAYS 683 (2003), incorporated by reference herein in its entirety. Crucially, these salvage and de novo pathways depend on the functional forms of vitamin B1, B2, and B6 to generate $NAD^+$ via a phosphoriboside pyrophosphate intermediate. Nicotinamide riboside (NR) is the only form of vitamin B3 from which $NAD^+$ can be generated in a manner independent of vitamin B1, B2, and B6, and the salvage pathway using NR for the production of $NAD^+$ is expressed in most eukaryotes.

Thiamine (vitamin B1), riboflavin (vitamin B2), niacin (vitamin B3), and pyridoxine (vitamin B6) are salvaged from food and converted back intracellularly to their respective, bioactive forms: Thiamine DiPhosphate ("ThDP"); Flavin Adenine Dinucleotide ("FAD"); Nicotinamide Adenine Dinucleotide ($NAD^+$); and PyridoxaL Phosphate ("PLP"). The conversion of vitamins B1, B2, and B6 to ThDP, FAD, and PLP, respectively, is ATP-dependent. Two of the three salvage pathways that convert vitamin B3 to $NAD^+$ are dependent on ThDP (B1), with the de novo production of $NAD^+$ from tryptophan depending on the bioactive forms of vitamins B1, B2, and B6. The vitamin B1 dependency comes from the fact that ThDP (B1) is cofactor for the transketolases involved in the biosynthesis of phosphoriboside pyrophosphate, an essential substrate in these aforementioned $NAD^+$ salvage and de novo pathways. The most recently identified, yet so far believed redundant, third $NAD^+$ salvage pathway, the Nicotinamide Riboside (NR) dependent $NAD^+$ biosynthetic pathway, does not require phosphoriboside pyrophosphate and is independent of vitamins B1, B2, and B6.

Though nicotinamide riboside (NR) is present in milk, the cellular concentrations of $NAD^+$, NADH, $NADP^+$, and NADPH are much higher than those of any other $NAD^+$ metabolites, such that dietary $NAD^+$ precursor vitamins are largely derived from enzymatic breakdown of $NAD^+$. See Pawel Bieganowski & Charles Brenner, *Discoveries of Nicotinamide Riboside as a Nutrient and Conserved NRK Genes Establish a Preiss-Handler Independent Route to $NAD^+$ in Fungi and Humans*, 117 CELL 495 (2002); Charles Evans et al., *$NAD^+$ metabolite levels as a function of vitamins and calorie restriction: evidence for different mechanisms of longevity*, 10 BMC CHEM. BIOL. 2 (2010); Samuel A. J. Trammell & Charles Branner, *Targeted, LCMS-Based Metabolomics for Quantitative Measurement of $NAD^+$ Metabolites*, 4 COMPUTATIONAL & STRUCTURAL BIOTECH. J. 1 (2013); each of which is incorporated by reference herein in its entirety. Put another way, though milk is a source of nicotinamide riboside (NR), the more abundant sources of nicotinamide riboside (NR), nicotinamide (Nam or NM), and nicotinic acid (NA) are any whole foodstuffs in which cellular $NAD^+$ is broken down to these compounds. Human digestion and the microbiome play roles in the provision of these vitamins in ways that are not fully characterized.

Different tissues maintain $NAD^+$ levels through reliance of different biosynthetic routes. See Federica Zamporlini et al., Novel assay for simultaneous measurement of pyridine mononucleotides synthesizing activities allows dissection of the $NAD^+$ biosynthetic machinery in mammalian cells, 281 FEBS J. 5104 (2014); Valerio Mori et al., Metabolic Profiling of Alternative NAD Biosynthetic Routes in Mouse Tissues, 9 PLOS ONE e113939 (2014); each of which is incorporated by reference herein in its entirety. Because $NAD^+$-consuming activities frequently occur as a function of cellular stresses and produce nicotinamide (Nam or NM), the ability of a cell to salvage nicotinamide (Nam or NM) into productive NAD$^+$ synthesis through nicotinamide phosphoribosyltransferase ("NAMPT") activity versus methylation of nicotinamide (Nam or NM) to N-methylnicotinamide ("MeNam") regulates the efficiency of NAD$^+$-dependent processes. See Charles Brenner, Metabolism: Targeting a fat-accumulation gene, 508 NATURE 194 (2014); Véronique J. Bouchard et al., PARP-1, a determinant of cell survival in response to DNA damage, 31 EXPERIMENTAL HEMATOLOGY 446 (2003); each of which is incorporated by reference herein in its entirety. NAD$^+$ biosynthetic genes are also under circadian control, and both NAMPT expression and NAD$^+$ levels are reported to decline in a number of tissues as a function of aging and overnutrition. See Kathryn Moynihan Ramsey et al., Circadian Clock Feedback Cycle Through NAMPT-Mediated NAD$^+$ Biosynthesis, 324 SCIENCE 651 (2009); Yasukazu Nakahata et al., Circadian Control of the NAD$^+$ Salvage Pathway by CLOCK-SIRT1, 324 SCIENCE 654 (2009); Jun Yoshino et al., Nicotinamide Mononucleotide, a Key NAD$^+$ Intermediate Treats the Pathophysiology of Diet- and Age-Induced Diabetes in Mice, 14 CELL METABOLISM 528 (2011); Ana P. Gomes et al., Declining NAD$^+$ Induces a Pseudohypoxic State Disrupting Nuclear-Mitochondrial Communication during Aging, 155 CELL 1624 (2013); Nady Braidy et al., Mapping NAD$^+$ metabolism in the brain of ageing Wistar rats: potential targets for influencing brain senescence, 15 BIOGERONTOLOGY 177 (2014); Eric Verdin, NAD$^+$ in aging, metabolism, and neurodegeneration, 350 SCIENCE 1208 (2015); each of which is incorporated by reference herein in its entirety.

High-dose nicotinic acid (NA), but not high-dose nicotinamide (Nam or NM), has been used by people for decades to treat and prevent dyslipidemias, though its use is limited by painful flushing. See Joseph R. DiPalma & William S. Thayer, *Use of Niacin as a Drug*, 11 ANNUAL REV. OF NUTRITION 169 (1991); Jeffrey T. Kuvin et al., *Effects of Extended-Release Niacin on Lipoprotein Particle Size, Distribution, and Inflammatory Markers in Patients With Coronary Artery Disease*, 98 AM. J. OF CARDIOLOGY 743 (2006); each of which is incorporated by reference herein in its entirety. Though only approximately 15 milligrams per day of either nicotinic acid (NA) or nicotinamide (Nam or NM) is required to prevent pellagra, pharmacological doses of nicotinic acid (NA) can be as high as 2-4 grams. Despite the >100-fold difference in effective dose between pellagra prevention and treatment of dyslipidemias, the beneficial effects of nicotinic acid (NA) on plasma lipids depend on function of nicotinic acid (NA) as an NAD$^+$-boosting compound. See Belenky et al., 2007. According to this view, sirtuin activation would likely be part of the mechanism because nicotinamide (Nam or NM) is an NAD$^+$ precursor in most cells but is a sirtuin inhibitor at high doses. See Kevin J. Bitternnan et al., *Inhibition of Silencing and Accelerated Aging by Nicotinamide, a Putative Negative Regulator of Yeast Sir2 and Human SIRT1*, 277 J. BIOL. CHEM. 45099 (2002), incorporated by reference herein in its entirety. See also Zamporlini et al., 2014; Mori et al., 2014.

As discussed above, the main NAD$^+$ precursors that feed the Preiss-Handler salvage pathway and other salvage pathways are nicotinamide (Nam or NM) and nicotinamide riboside (NR). See Bogan & Brenner, 2008. Further, studies have shown that nicotinamide riboside (NR) is used in a conserved salvage pathway that leads to NAD$^+$ synthesis through the formation of nicotinamide mononucleotide (NMN). Upon entry into the cell, nicotinamide riboside (NR) is phosphorylated by the NR kinases ("NRKs"), generating nicotinamide mononucleotide (NMN), which is then converted to NAD$^+$ by nicotinic acid/nicotinamide mononucleotide adenylyltransferase (NMNAT). See Bogan & Brenner, 2008. Because nicotinamide mononucleotide (NMN) is the only metabolite that can be converted to NAD$^+$ in mitochondria, nicotinamide (Nam or NM) and nicotinamide riboside (NR) are the two candidate NAD$^+$ precursors that can replenish NAD$^+$ and thus improve mitochondrial fuel oxidation. A key difference is that nicotinamide riboside (NR) has a direct two-step pathway to NAD$^+$ synthesis that bypasses the rate-limiting step of the salvage pathway, nicotinamide phosphoribosyltransferase (NAMPT). Nicotinamide (Nam or NM) requires NAMPT activity to produce NAD$^+$. This reinforces the fact that nicotinamide riboside (NR) is a very effective NAD$^+$ precursor. Conversely, deficiency in dietary NAD$^+$ precursors and/or tryptophan (Trp) causes pellagra. See Bogan & Brenner, 2008. In summary, NAD$^+$ is required for normal mitochondrial function, and because mitochondria are the powerhouses of the cell, NAD$^+$ is required for energy production within cells.

NAD$^+$ was initially characterized as a co-enzyme for oxidoreductases. Though conversions between NAD$^+$, NADH, NADP$^+$, and NADPH would not be accompanied by a loss of total co-enzyme, it was discovered that NAD$^+$ is also turned over in cells for unknown purposes. See Morelly L. Maayan, *NAD$^+$-Glycohydrolase of Thyroid Homogenates*, 2014 NATURE 1169 (1964), incorporated by reference herein in its entirety. Sirtuin enzymes such as Sir2 of *S. cerevisiae* and its homologs deacetylate lysine residues with consumption of an equivalent of NAD$^+$, and this activity is required for Sir2 function as a transcriptional silencer. See S. Imai et al., Sir2: *An NAD-dependent Histone Deacetylase That Connects Chromatin Silencing, Metabolism, and Aging*, 65 COLD SPRING HARBOR SYMPOSIA ON QUANTITATIVE BIOLOGY 297 (2000), incorporated by reference herein in its entirety. NAD$^+$-dependent deacetylation reactions are required, not only for alterations in gene expression, but also for repression of ribosomal DNA recombination and extension of lifespan in response to calorie restriction. See Lin et al., *Requirement of NAD and SIR2 for Life-Span Extension by Calorie Restriction in Saccharomyces cerevisiae*, 289 SCIENCE 2126 (2000); Lin et al., *Calorie restriction extends Saccharomyces cerevisiae lifespan by increasing respiration*, 418 NATURE 344 (2002); each of which is incorporated by reference herein in its entirety. NAD$^+$ is consumed by Sir2 to produce a mixture of 2'- and 3'-O-acetylated ADP-ribose plus nicotinamide (Nam or NM) and the deacetylated polypeptide. See Anthony A. Sauve et al., *Chemistry of Gene Silencing: the Mechanism of NAD$^+$-Dependent Deacetylation Reactions*, 40 BIOCHEMISTRY 15456 (2001), incorporated by reference herein in its entirety. Additional enzymes, including poly(ADP-ribose) polymerases and cADP-ribose synthases are also NAD$^+$-dependent and produce nicotinamide (Nam or NM) and ADP-ribosyl products. See Mathias Ziegler, *New functions of a long-known molecule*, 267 FEBS J. 1550 (2000); Alexander Birkle, *Physiology and pathophysiology of poly(ADP-ribosyl)ation*, 23 BIOESSAYS 795 (2001); each of which is incorporated by reference herein in its entirety.

The non-coenzymatic properties of NAD$^+$ have renewed interest in NAD$^+$ biosynthesis. Based on the ability of nicotinamide riboside (NR) to elevate NAD$^+$ synthesis, increase sirtuin activity, and extend lifespan in yeast, nicotinamide riboside (NR) has been employed in mice to elevate NAD$^+$ metabolism and improve health in models of metabolic stress. See Peter Belenky et al., *Nicotinamide Riboside Promotes Sir2 Silencing and Extends Lifespan via*

*Nrk and Urh1/Pnp1/Meu1 Pathways to NAD+*, 129 CELL 473 (2007), incorporated by reference herein in its entirety. See also Bieganoski & Brenner, 2004. Notably, nicotinamide riboside (NR) allowed mice to resist weight gain on a high-fat diet, and to prevent noise-induced hearing loss. See Carles Cantó et al., *The NAD+Precursor Nicotinamide Riboside Enhances Oxidative Metabolism and Protects against High-Fat Diet-Induced Obesity*, 15 CELL METABOLISM 838 (2012); Kevin D. Brown et al., *Activation of SIRT3 by the NAD+Precursor Nicotinamide Riboside Protects from Noise-Induced Hearing Loss*, 20 CELL METABOLISM 1059 (2014); each of which is incorporated by reference herein in its entirety. Data indicate that nicotinamide riboside (NR) is a mitochondrially favored $NAD^+$ precursor and, indeed, in vivo activities of nicotinamide riboside (NR) have been interpreted as depending upon mitochondrial sirtuin activities, though not to the exclusion of nucleocytosolic targets. Andrey Nikiforov et al., *Pathways and Subcellular Compartmentation of NAD Biosynthesis in Human Cells*, 286 J. BIOLOGICAL CHEM. 21767 (2011); Charles Brenner, *Boosting NAD to Spare Hearing*, 20 CELL METABOLISM 926 (2014); Carles Cantó et al., *NAD+Metabolism and the Control of Energy Homeostasis: A Balancing Act between Mitochondria and the Nucleus*, 22 CELL METABOLISM 31 (2015); each of which is incorporated by reference herein in its entirety. Similarly, nicotinamide mononucleotide (NMN), the phosphorylated form of nicotinamide riboside (NR), has been used to treat declining $NAD^+$ in mouse models of overnutrition and aging. See J. Yoshino et al., 2011; A. P. Gomes et al., 2013. Because of the abundance of $NAD^+$-dependent processes, it is not known to what degree $NAD^+$-boosting strategies are mechanistically dependent upon particular molecules such as SIRT1 or SIRT3. In addition, the quantitative effect of nicotinamide riboside (NR) on the $NAD^+$ metabolome has not been reported in any system.

In conclusion, vitamins B1, B2, B3, and B6 are closely intertwined in their biosynthetic pathways, with the maintenance and regeneration of the NADPH intracellular pool depending on the availability of ThDP (vitamin B1), FAD (vitamin B2), and PLP (vitamin B6), along with that of ATP. Critically, the latter is produced through $NAD^+$-dependent OXPHOS and glycolysis, and is necessary for the functionalization of the vitamins B1, B2, and B6 to ThDP, FAD, and PLP, respectively. A shortage of any of these vitamins would impact negatively on the biology of the others. Maximizing these vitamins' bioavailabilities is achieved by conjugating these vitamins to NR, NAR, —NRH, or NARH, or their related derivatives, and by using the NR/NAR uptake to achieve improved vitamin bioavailability.

The compounds and derivatives of the present invention, or salts, hydrates, or solvates thereof, aim at modulating the absorption of vitamins or bioactive compounds of known therapeutic and nutraceutical value by conjugating said vitamins or bioactive compounds to specific B3 vitamins, more specifically NAR, —NR, NARH, —NRH, NMN, NaMN, NMNH, and NaMNH, and partial derivatives thereof.

The compounds and derivatives of the present invention, or salts, hydrates, or solvates thereof, provide improvements on the individual nutrients and B-vitamins in terms of modulating their bioavailabilities.

The compounds and derivatives of the present invention, or salts, hydrates, or solvates thereof, can be used to reduce the risk of developing symptoms, diseases, disorders, or conditions associated with, or having etiologies involving, vitamin B3 deficiencies and/or that would benefit from increased mitochondrial activity, as the key component is nicotinic acid riboside (NAR).

Alcoholism, its link to deficiencies of B-vitamins, and psychological outcomes remain a primary area of research in the modern developed world. Studies have indicated that in patients with alcoholic pellagra, vitamin B3 deficiency may be an important factor influencing both the onset and severity of the condition, and patients with alcoholism are being recommended vitamin B1 as a supplement to minimize dementia and psychological episodes associated with alcohol abuse. Yet combination supplementations are not yet considered, as the pharmacological network between vitamins B1 and B3, in terms of $NAD^+$ bioavailability, has never been demonstrated. This invention aims at tackling vitamin B1/B3 synergistic deficiencies in this class of patients. See W. Todd Penberthy & James B. Kirkland, Niacin, in PRESENT KNOWLEDGE IN NUTRITION 293 (10th ed., 2012), incorporated by reference herein in its entirety.

Mitochondria are critical for the survival and proper function of almost all types of eukaryotic cells. Mitochondria in virtually any cell type can have congenital or acquired defects that affect their function. Thus, the clinically significant signs and symptoms of mitochondrial defects affecting respiratory chain function are heterogeneous and variable, depending on the distribution of defective mitochondria among cells and the severity of their deficits, and upon physiological demands upon the affected cells. Nondividing tissues with high energy requirements, e.g., nervous tissue, skeletal muscle, and cardiac muscle are particularly susceptible to mitochondrial respiratory chain dysfunction, but any organ system can be affected.

Symptoms, diseases, disorders, and conditions associated with mitochondrial dysfunction include symptoms, diseases, disorders, and conditions in which deficits in mitochondrial respiratory chain activity contribute to the development of pathophysiology of such symptoms, diseases, disorders, or conditions in a mammal. This includes congenital genetic deficiencies in activity of one or more components of the mitochondrial respiratory chain, wherein such deficiencies are caused by a) elevated intracellular calcium; b) exposure of affected cells to nitric oxide; c) hypoxia or ischemia; d) microtubule-associated deficits in axonal transport of mitochondria; or e) expression of mitochondrial uncoupling proteins.

Symptoms, diseases, disorders, or conditions that would benefit from increased mitochondrial activity generally include for example, diseases in which free radical mediated oxidative injury leads to tissue degeneration, diseases in which cells inappropriately undergo apoptosis, and diseases in which cells fail to undergo apoptosis. Exemplary symptoms, diseases, disorders, or conditions that would benefit from increased mitochondrial activity include, for example, AMDF (Ataxia, Myoclonus and Deafness), auto-immune disease, cancer, CIPO (Chronic Intestinal Pseudoobstruction with myopathy and Ophthalmoplegia), congenital muscular dystrophy, CPEO (Chronic Progressive External Ophthalmoplegia), DEAF (Maternally inherited DEAFness or aminoglycoside-induced DEAFness), DEMCHO (Dementia and Chorea), diabetes mellitus (Type I or Type II), DIDMOAD (Diabetes Insipidus, Diabetes Mellitus, Optic Atrophy, Deafness), DMDF (Diabetes Mellitus and Deafness), dystonia, Exercise Intolerance, ESOC (Epilepsy, Strokes, Optic atrophy, and Cognitive decline), FBSN (Familial Bilateral Striatal Necrosis), FICP (Fatal Infantile Cardiomyopathy Plus, a MELAS-associated cardiomyopathy), GER (Gastrointestinal Reflux), HD (Huntington's Disease), KSS (Kearns Sayre Syndrome), "later-onset" myopathy, LDYT (Leber's hereditary optic neuropathy and DYsTonia), Leigh's Syndrome, LHON (Leber Hereditary Optic Neuropathy), LIMM (Lethal Infantile Mitochondrial Myopathy), MDM (Myopathy and Diabetes Mellitus), MELAS (Mitochondrial Encephalomyopathy, Lactic Acidosis, and Stroke-like episodes), MEPR (Myoclonic Epilepsy and Psychomotor Regression), MERME (MERRF/MELAS overlap disease), MERRF (Myoclonic Epilepsy and Ragged Red Muscle Fibers), MHCM (Maternally Inherited Hypertrophic CardioMyopathy), MICM (Maternally Inherited CardioMyopathy), MILS (Maternally Inherited Leigh Syndrome), Mitochondrial Encephalocardiomyopathy, Mitochondrial Encephalomyopathy, MM (Mitochondrial Myopathy), MMC (Maternal Myopathy and Cardiomyopathy), MNGIE (Myopathy and external ophthalmoplegia, Neuropathy, Gastro-Intestinal, Encephalopathy), Multisystem Mitochondrial Disorder (myopathy, encephalopathy, blindness, hearing loss, peripheral neuropathy), NARP (Neurogenic muscle weakness, Ataxia, and Retinitis Pigmentosa; alternate phenotype at this locus is reported as Leigh Disease), Pearson's Syndrome, PEM (Progressive Encephalopathy), PEO (Progressive External Ophthalmoplegia), PME (Progressive Myoclonus Epilepsy), PMPS (Pearson Marrow-Pancreas Syndrome), psoriasis, RTT (Rett syndrome), schizophrenia, SIDS (Sudden Infant Death Syndrome), SNHL (Sensorineural Hearing Loss), Varied Familial Presentation (clinical manifestations range from spastic paraparesis to multisystem progressive disorder & fatal cardiomyopathy to truncal ataxia, dysarthria, severe hearing loss, mental regression, ptosis, ophthalmoparesis, distal cyclones, and diabetes mellitus), or Wolfram syndrome.

Other symptoms, diseases, disorders, and conditions that would benefit from increased mitochondrial activity include, for example, Friedreich's ataxia and other ataxias, amyotrophic lateral sclerosis ("ALS") and other motor neuron diseases, macular degeneration, epilepsy, Alpers syndrome, Multiple mitochondrial DNA deletion syndrome, MtDNA depletion syndrome, —Complex I deficiency, Complex II (SDH) deficiency, Complex III deficiency, Cytochrome c oxidase ("COX," Complex IV) deficiency, Complex V deficiency, Adenine Nucleotide Translocator ("ANT") deficiency, Pyruvate dehydrogenase ("PDH") deficiency, Ethylmalonic aciduria with lactic academia, Refractory epilepsy with declines during infection, Autism with declines during infection, Cerebral palsy with declines during infection, materially inherited thrombocytopenia and leukemia syndrome, MARIAHS syndrome (Mitochondrial ataxia, recurrent infections, aphasia, hypouricemia/hypomyelination, seizures, and dicarboxylic aciduria), ND6 dystonia, Cyclic vomiting syndrome with declines during infection, 3-Hydroxy isobutyric aciduria with lactic academia, Diabetes mellitus with lactic academia, Uridine responsive neurologic syndrome ("URNS"), Dilated cardiomyopathy, Splenic Lymphoma, or Renal Tubular Acidosis/Diabetes/Ataxis syndrome.

Other symptoms, diseases, disorders, and conditions associated with mitochondrial disorders include, but are not limited to, Post-traumatic head injury and cerebral edema, Stroke, Lewy body dementia, Hepatorenal syndrome, Acute liver failure, NASH (non-alcoholic steatohepatitis), Antimetastasis/prodifferentiation therapy of cancer, Idiopathic congestive heart failure, Atrial fibrillation (non-valvular), Wolff-Parkinson-White Syndrome, Idiopathic heart block, Prevention of reperfusion injury in acute myocardial infarctions, Familial migraines, Irritable bowel syndrome, Secondary prevention of non-Q wave myocardial infarctions, Premenstrual syndrome, Prevention of renal failure in hepatorenal syndrome, Anti-phospholipid antibody syndrome, Eclampsia/pre-eclampsia, Ischemic heart disease/Angina, and Shy-Drager and unclassified dysautonomia syndromes.

Common symptoms of mitochondrial diseases include cardiomyopathy, muscle weakness and atrophy, developmental delays (involving motor, language, cognitive, or executive function), ataxia, epilepsy, renal tubular acidosis, peripheral neuropathy, optic neuropathy, autonomic neuropathy, neurogenic bowel dysfunction, sensorineural deafness, neurogenic bladder dysfunction, dilating cardiomyopathy, hepatic failure, lactic acidemia, and diabetes mellitus.

Diseases or disorders that would benefit from increased mitochondrial activity include, but are not limited to, neuromuscular disorders (e.g., Friedreich's Ataxia, muscular dystrophy, multiple sclerosis, etc.), disorders of neuronal instability (e.g., seizure disorders, migraine, etc.), developmental delay, ischemia, renal tubular acidosis, chemotherapy fatigue, mitochondrial myopathies, mitochondrial damage (e.g., calcium accumulation, excitotoxicity, nitric oxide exposure, hypoxia, etc.), and mitochondrial deregulation.

A gene defect underlying Friedreich's Ataxia ("FA"), the most common hereditary ataxia, was recently identified and is designated "frataxin." In FA, after a period of normal development, deficits in coordination develop that progress to paralysis and death, typically between the ages of 30 and 40. The tissues affected most severely are the spinal cord, peripheral nerves, myocardium, and pancreas. Patients typically lose motor control and are confined to wheel chairs, and are commonly afflicted with heart failure and diabetes. The genetic basis for FA involves GAA trinucleotide repeats in an intron region of the gene encoding frataxin. The presence of these repeats results in reduced transcription and expression of the gene. Frataxin is involved in regulation of mitochondrial iron content. When cellular frataxin content is subnormal, excess iron accumulates in mitochondria, promoting oxidative damage and consequent mitochondrial degeneration and dysfunction. When intermediate numbers of GAA repeats are present in the frataxin gene intron, the severe clinical phenotype of ataxia may not develop. However, these intermediate-length trinucleotide extensions are found in 25% to 30% of patients with non-insulin dependent diabetes mellitus, compared to about 5% of the nondiabetic population.

Muscular dystrophy refers to a family of diseases involving deterioration of neuromuscular structure and function, often resulting in atrophy of skeletal muscle and myocardial dysfunction. In the case of Duchenne muscular dystrophy, mutations or deficits in a specific protein, dystrophin, are implicated in its etiology. Mice with their dystrophin genes inactivated display some characteristics of muscular dystrophy, and have an approximately 50% deficit in mitochondrial respiratory chain activity. A final common pathway for neuromuscular degeneration, in most cases, is calcium-mediated impairment of mitochondrial function.

Epilepsy is often present in patients with mitochondrial cytopathies, involving a range of seizure severity and frequency, e.g., absence, tonic, atonic, myoclonic, and status epilepticus, occurring in isolated episodes or many times daily.

Delays in neurological or neuropsychological development are often found in children with mitochondrial diseases. Development and remodeling of neural connections requires intensive biosynthetic activity, particularly involving synthesis of neuronal membranes and myelin, both of which require pyrimidine nucleotides as cofactors. Uridine nucleotides are involved in activation and transfer of sugars to glycolipids and glycoproteins. Cytidine nucleotides are derived from uridine nucleotides, and are crucial for synthesis of major membrane phospholipid constituents like phosphatidylcholine, which receives its choline moiety from cytidine diphosphocholine. In the case of mitochondrial dysfunction (due to either mitochondrial DNA defects or any of the acquired or conditional deficits like excitotoxic or nitric oxide-mediated mitochondrial dysfunction) or other conditions resulting in impaired pyrimidine synthesis, cell proliferation and axonal extension are impaired at crucial stages in development of neuronal interconnections and circuits, resulting in delayed or arrested development of neuropsychological functions like language, motor, social, executive function, and cognitive skills. In autism, for example, magnetic resonance spectroscopy measurements of cerebral phosphate compounds indicate that there is global undersynthesis of membranes and membrane precursors indicated by reduced levels of uridine diphosphosugars, and cytidine nucleotide derivatives involved in membrane synthesis. Disorders characterized by developmental delay include Rett's Syndrome, pervasive developmental delay (or PDD-NOS "pervasive developmental delay not otherwise specified" to distinguish it from specific subcategories like autism), autism, Asperger's Syndrome, and Attention Deficit/Hyperactivity Disorder ("ADHD"), which is becoming recognized as a delay or lag in development of neural circuitry underlying executive functions.

Oxygen deficiency results in both direct inhibition of mitochondrial respiratory chain activity by depriving cells of a terminal electron acceptor for Cytochrome c reoxidation at Complex IV, and indirectly, especially in the nervous system, via secondary post-anoxic excitotoxicity and nitric oxide formation. In conditions like cerebral anoxia, angina or sickle cell anemia crises, tissues are relatively hypoxic. In such cases, compounds that increase mitochondrial activity provide protection of affected tissues from deleterious effects of hypoxia, attenuate secondary delayed cell death, and accelerate recovery from hypoxic tissue stress and injury.

Acidosis due to renal dysfunction is often observed in patients with mitochondrial disease, whether the underlying respiratory chain dysfunction is congenital or induced by ischemia or cytotoxic agents like cisplatin. Renal tubular acidosis often requires administration of exogenous sodium bicarbonate to maintain blood and tissue pH.

Mitochondrial DNA damage is more extensive and persists longer than nuclear DNA damage in cells subjected to oxidative stress or cancer chemotherapy agents like cisplatin due to both greater vulnerability and less efficient repair of mitochondrial DNA. Although mitochondrial DNA may be more sensitive to damage than nuclear DNA, it is relatively resistant, in some situations, to mutagenesis by chemical carcinogens. This is because mitochondria respond to some types of mitochondrial DNA damage by destroying their defective genomes rather than attempting to repair them. This results in global mitochondrial dysfunction for a period after cytotoxic chemotherapy. Clinical use of chemotherapy agents like cisplatin, mitomycin, and cytoxan is often accompanied by debilitating "chemotherapy fatigue," prolonged periods of weakness and exercise intolerance that may persist even after recovery from hematologic and gastrointestinal toxicities of such agents.

Mitochondrial myopathies range from mild, slowly progressive weakness of the extraocular muscles to severe, fatal infantile myopathies and multisystem encephalomyopathies. Some syndromes have been defined, with some overlap between them. Established syndromes affecting muscle include progressive external ophthalmoplegia, the Kearns-Sayre syndrome (with ophthalmoplegia, pigmentary retinopathy, cardiac conduction defects, cerebellar ataxia, and sensorineural deafness), the MELAS syndrome (mitochondrial encephalomyopathy, lactic acidosis, and stroke-like episodes), the MERFF syndrome (myoclonic epilepsy and ragged red fibers), limb-girdle distribution weakness, and infantile myopathy (benign or severe and fatal). Muscle biopsy specimens stained with modified Gomori's trichrome stain show ragged red fibers due to excessive accumulation of mitochondria. Biochemical defects in substrate transport and utilization, the Krebs cycle, oxidative phosphorylation, or the respiratory chain are detectable. Numerous mitochondrial DNA point mutations and deletions have been described, transmitted in a maternal, nonmendlian inheritance pattern. Mutations in nuclear-encoded mitochondrial enzymes occur.

A fundamental mechanism of cell injury, especially in excitable tissues, involves excessive calcium entry into cells, as a result of either leakage through the plasma membrane or defects in intracellular calcium handling mechanisms. Mitochondria are major sites of calcium sequestration, and preferentially utilize energy from the respiratory chain for taking up calcium rather than for ATP synthesis, which results in a downward spiral of mitochondrial failure, because calcium uptake into mitochondria results in diminished capabilities for energy transduction.

Excessive stimulation of neurons with excitatory amino acids is a common mechanism of cell death or injury in the central nervous system. Activation of glutamate receptors, especially of the subtype designated NMDA receptors, results in mitochondrial dysfunction, in part through elevation of intracellular calcium during excitotoxic stimulation. Conversely, deficits in mitochondrial respiration and oxidative phosphorylation sensitizes cells to excitotoxic stimuli, resulting in cell death or injury during exposure to levels of excitotoxic neurotransmitters or toxins that would be innocuous to normal cells.

Nitric oxide (about 1 micromolar) inhibits cytochrome oxidase (Complex IV) and thereby inhibits mitochondrial respiration; moreover, prolonged exposure to nitric oxide (NO) irreversibly reduces Complex I activity. Physiological or pathophysiological concentrations of NO thereby inhibit pyrimidine biosynthesis. Nitric oxide is implicated in a variety of neurodegenerative disorders including inflammatory and autoimmune diseases of the central nervous system, and is involved in mediation of excitotoxic and post-hypoxic damage to neurons.

Oxygen is the terminal electron acceptor in the respiratory chain. Oxygen deficiency impairs electron transport chain activity, resulting in diminished pyrimidine synthesis as well as diminished ATP synthesis via oxidative phosphorylation. Human cells proliferate and retain viability under virtually anaerobic conditions if provided with uridine and pyruvate (or a similarly effective agent for oxidizing NADH to optimize glycolytic ATP production).

Transcription of mitochondrial DNA encoding respiratory chain components requires nuclear factors. In neuronal axons, mitochondria must shuttle back and forth to the nucleus in order to maintain respiratory chain activity. If axonal transport is impaired by hypoxia or by drugs like taxol that affect microtubule stability, mitochondria distant from the nucleus undergo loss of cytochrome oxidase activity.

Mitochondria are the primary source of free radicals and reactive oxygen species, due to spillover from the mitochondrial respiratory chain, especially when defects in one or more respiratory chain components impairs orderly transfer of electrons from metabolic intermediates to molecular oxygen. To reduce oxidative damage, cells can compensate by expressing mitochondrial uncoupling proteins ("UCP"), of which several have been identified. UCP-2 is transcribed in response to oxidative damage, inflammatory cytokines, or excess lipid loads, e.g., fatty liver and steatohepatitis. UCPs reduce spillover of reactive oxidative species from mitochondria by discharging proton gradients across the mitochondrial inner membrane, in effect wasting energy produced by metabolism and rendering cells vulnerable to energy stress as a trade-off for reduced oxidative injury.

A rationale for synergy between vitamins B1, B2, B3, and B6 is explained herein. Pairing vitamins B1, B2, or B6 with nicotinamide riboside (NR) is hypothesized to act synergistically on the $NAD^+$ biosynthetic pathway and have a positive effect. This is due to the fact that vitamins B1, B2, and B6 are required for $NAD^+$ biosynthesis through NAMPT-dependent pathways, allowing for the further recycling of nicotinamide (Nam or NM) generated from the NR-produced $NAD^+$. Of all the B3-vitamins, only NR functions independently of NAMPT for $NAD^+$ synthesis, in a mole to mole perspective. See Penberthy & Kirkland, 2012. See also Yuling Chi & Anthony A. Sauve, *Nicotinamide riboside, a trace nutrient in foods, is a vitamin B3 with effects on energy metabolism and neuroprotection*, 16 CURR. OPINION IN CLIN. NUTRITION & METABOLIC CARE 657 (2013), incorporated by reference herein in its entirety. Additionally, vitamin B2 (FAD precursor) is a key vitamin for mitochondrial fatty acid oxidation and OXPHOS processes. Mitochondrial dysfunction can arise from $FAD/FADH_2$ imbalance or deficiency, and it is hypothesized that pairing vitamin B2 to vitamin B3 NAD-precursors would address multiple pathways of mitochondrial dysfunction.

One embodiment of the compounds and derivatives of this invention, or salts, hydrates, or solvates thereof, is represented by the co-supplementation of NR (or NAR and other vitamin B3 derivatives) with choline. The normal process for eliminating nicotinamide (Nam or NM) from the body is by methylation. It has been known for a long time that mice given high-dose nicotinamide (Nam or NM) display growth inhibition due to a choline deficiency. Co-supplementation of nicotinamide (Nam or NM) and methionine (choline precursor) completely reversed the growth inhibition. See M. Knip et al., *Safety of high-dose nicotinamide: a review*, 43 DIABETOLOGIA 1337 (2000), incorporated by reference herein in its entirety. One possible underlying mechanism proposes that, in the brain, the methyl group being added to the nicotinamide (Nam or NM) to eliminate it comes from choline (a methyl donor). All of the $NAD^+$ precursors disclosed herein eventually become nicotinamide (Nam or NM), and are then eliminated through this pathway.

Resveratrol and other related sirtuin activators (like pterostilbene, for example) represent another embodiment of the compounds and derivatives of the present invention, or salts, hydrates, or solvates thereof. Sirtuins are $NAD^+$-dependent enzymes that play vital roles in protecting the genome through histone deacetylation. Several reports have shown that sirtuins play a role in lifespan/healthspan of an organism, and the activity of sirtuins requires available $NAD^+$. See Penberthy & Kirkland, 2012. Thus, resveratrol (and similar compounds), which can induce sirtuin expression, requires a concomitant increase in $NAD^+$ availability in order to realize the increased sirtuin activity. Preferably, resveratrol (and/or similar compounds) is co-supplemented with one of the $NAD^+$-precursors reported herein.

One embodiment of the compounds and derivatives of the present invention, or salts, hydrates, or solvates thereof, is represented by the products formed as a result of joining the nicotinic acid (NA) ester at the 5'-hydroxy of NR and NR, and the corresponding reduced forms thereof. Synergistic effects of nicotinate and NR (or derivatives thereof) are anticipated. Nicotinic acid (NA) and nicotinamide riboside (NR) use different pathways to both ultimately induce $NAD^+$ levels.

Another embodiment of the compounds and derivatives of the present invention, or salts, hydrates, or solvates thereof, is represented by the derivatives of all of these nicotinoyl riboside conjugates and reduced nicotinoyl riboside conjugates, or salts, hydrates, or solvates thereof.

It is expected that certain conjugate molecules will have better physiochemical properties than the parent molecules. This increased stability will be observed in formulations and during the digestive process or other breakdown processes for these molecules (in the blood/cells after oral or topical delivery). The improved properties are advantageous for certain formulation and delivery applications. For instance, it is considered that non-specific plasma protein binding of such derivatives will decrease and allow for increased concentration of free circulating $NAD^+$ precursors.

If new compounds and derivatives comprising nicotinoyl riboside conjugates and reduced nicotinoyl riboside conjugates could be found, this would represent a useful contribution to the art. Furthermore, if new methods of preparing compounds and derivatives comprising nicotinoyl riboside conjugates and reduced nicotinoyl riboside conjugates, or salts, hydrates, or solvates thereof, could be found, this would also represent a useful contribution to the art.

SUMMARY OF THE INVENTION

In accordance with one embodiment, the present disclosure provides modified conjugates or derivatives of nicotinamide riboside (NR), nicotinic acid riboside (NAR), the reduced forms of the same (NRH and NARH, respectively), salts, hydrates, or solvates thereof, and the use thereof. The derivatives may include B-vitamin conjugates, and the like.

In an embodiment, the preparation of analogs of nicotinamide riboside (NR) and reduced or modified derivatives thereof, or salts, hydrates, or solvates thereof, is provided.

In another embodiment, the present disclosure relates to the preparation of analogs of nicotinic acid riboside (NAR) and reduced or modified derivatives thereof, or salts, hydrates, or solvates thereof. Prototype product ribonucleoside compounds include compounds or derivatives of formula (I), or a salt, hydrate, or solvate thereof.

In another embodiment, the use of these derivatives, or salts, hydrates, or solvates thereof, is described, e.g., oral and topical use.

In accordance with an embodiment, prototype product nicotinate/nicotinamide ribonucleoside compounds (NR or NAR, respectively) include nicotinate/nicotinamide riboside compounds or derivatives of formula (I), or a salt, hydrate, or solvate thereof:

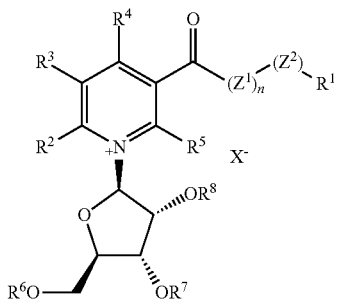

(I)

wherein X⁻ is selected from the group consisting of fluoride, chloride, bromide, iodide, formate, acetate, ascorbate, benzoate, carbonate, citrate, carbamate, formate, gluconate, lactate, methyl bromide, methyl sulfate, nitrate, phosphate, diphosphate, succinate, sulfate, trifluoromethanesulfonate, trichloromethanesulfonate, tribromomethanesulfonate, and trifluoroacetate;

$Z^1$ and $Z^2$ are independently NH or oxygen;

n is 0 or 1;

$R^1$ is selected from the group consisting of hydrogen, substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^A$)—$CO_2R^B$; wherein the substituted $(C_1$-$C_8)$alkyl, substituted $(C_1$-$C_8)$cycloalkyl, substituted aryl, substituted heteroaryl, and substituted heterocycle are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —C(O)$R^C$, —C(O)O$R^C$, —C(O)NR$^C_2$, —C(=NR$^C$)NR$^C_2$, —OR$^C$, —OC(O)($C_1$-$C_6$)alkyl, —OC(O)O($C_1$-$C_6$)alkyl, —OC(O)NR$^C_2$, —($C_1$-$C_6$)alkylene-NR$^C_2$, —NR$^C_2$, —NR$^C$C(O)R$^C$, —NR$^C$C(O)O($C_1$-$C_6$)alkyl, —NR$^C$C(O)NR$^C_2$, —NR$^C$SO$_2$NR$^C$, —SR$^C$, —S(O)R$^C$, —SO$_2$R$^C$, —OSO$_2$($C_1$-$C_6$)alkyl, —SO$_2$NR$^C_2$, —($C_1$-$C_6$)perfluoroalkyl, and —($C_1$-$C_6$)alkylene-OR$^C$;

$R^A$ is selected from the group consisting of —H, —($C_1$-$C_6$)alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$, and —CH$_2$—CH$_3$;

$R^B$ is hydrogen or —($C_1$-$C_8$)alkyl;

each $R^C$ is independently selected from the group consisting of hydrogen, —($C_1$-$C_8$)alkyl, substituted or unsubstituted pyridyl, substituted or unsubstituted 1,4-dihydropyridyl, a radical of the compound of formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —NO$_2$, —C(O)$R^B$, —C(O)OR$^B$, —C(O)NR$^B_2$, —C(=NR$^B$)NR$^B_2$, —OR$^B$, —OC(O)($C_1$-$C_6$)alkyl, —OC(O)O($C_1$-$C_6$)alkyl, —OC(O)NR$^B_2$, —($C_1$-$C_6$)alkylene-NR$^B_2$, —NR$^B_2$, —NR$^B$C(O)R$^B$, —NR$^B$C(O)O($C_1$-$C_6$)alkyl, —NR$^B$C(O)NR$^B_2$, —NR$^B$SO$_2$NR$^B$, —SR$^B$, —S(O)R$^B$, —SO$_2$R$^B$, —OSO$_2$($C_1$-$C_6$)alkyl, —SO$_2$NR$^B_2$, —($C_1$-$C_6$)perfluoroalkyl, and —($C_1$-$C_6$)alkylene-OR$^B$;

$R^2$, $R^3$, $R^4$, and $R^5$ are each independently selected from the group consisting of hydrogen, —($C_1$-$C_6$)alkyl, —($C_2$-$C_6$)alkenyl, —($C_2$-$C_6$)alkynyl, halogen, —CN, —NO$_2$, —C(O)$R^C$, —C(O)OR$^C$, —C(O)NR$^C_2$, —C(=NR$^C$)NR$^C_2$, —OR$^C$, —OC(O)($C_1$-$C_6$)alkyl, —OC(O)O($C_1$-$C_6$)alkyl, —OC(O)NR$^C_2$, —($C_1$-$C_6$)alkylene-NR$^C_2$, —NR$^C_2$, —NR$^C$C(O)R$^C$, —NR$^C$C(O)O($C_1$-$C_6$)alkyl, —NR$^C$C(O)NR$^C_2$, —NR$^C$SO$_2$NR$^C$, —SR$^C$, —S(O)R$^C$, —SO$_2$R$^C$, —OSO$_2$($C_1$-$C_6$)alkyl, —SO$_2$NR$^C_2$, —($C_1$-$C_6$)perfluoroalkyl, and —($C_1$-$C_6$)alkylene-OR$^C$;

$R^6$ is selected from the group consisting of hydrogen, —C(O)R', —C(O)OR', —C(O)NHR', —P(O)(OY$^1$)(OY$^2$), —P(O)(OY$^1$)(NHR"), substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —NO$_2$, —C(O)$R^C$, —C(O)OR$^C$, —C(O)NR$^C_2$, —C(=NR$^C$)NR$^C_2$, —OR$^C$, —OC(O)($C_1$-$C_6$)alkyl, —OC(O)O($C_1$-$C_6$)alkyl, —OC(O)NR$^C_2$, ($C_1$-$C_6$)alkylene-NR$^C_2$, —N$_2$, —NR$^C_2$, —NR$^C$C(O)R$^C$, —NR$^C$C(O)O($C_1$-$C_6$)alkyl, —NR$^C$C(O)NR$^C_2$, —NR$^C$SO$_2$NR$^C$, —SR$^C$, —S(O)R$^C$, —SO$_2$R$^C$, —OSO$_2$($C_1$-$C_6$)alkyl, —SO$_2$NR$^C_2$, —($C_1$-$C_6$)perfluoroalkyl, and —($C_1$-$C_6$)alkylene-OR$^C$;

R' is selected from the group consisting of hydrogen, substituted or unsubstituted —($C_1$-$C_8$)alkyl, substituted or unsubstituted —($C_1$-$C_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —NO$_2$, —C(O)$R^C$, —C(O)OR$^C$, —C(O)NR$^C_2$, —C(=NR$^C$)NR$^C_2$, —OR$^C$, —OC(O)($C_1$-$C_6$)alkyl, —OC(O)O($C_1$-$C_6$)alkyl, —OC(O)NR$^C_2$, —($C_1$-$C_6$)alkylene-NR$^C_2$, —NR$^C_2$, —NR$^C$C(O)R$^C$, —NR$^C$C(O)O($C_1$-$C_6$)alkyl, —NR$^C$C(O)NR$^C_2$, —NR$^C$SO$_2$NR$^C$, —SR$^C$, —S(O)R$^C$, —SO$_2$R$^C$, —OSO$_2$($C_1$-$C_6$)alkyl, —SO$_2$NR$^C_2$, —($C_1$-$C_6$)perfluoroalkyl, and —($C_1$-$C_6$)alkylene-OR$^C$;

R" is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —NO$_2$, —C(O)$R^C$, —C(O)OR$^C$, —C(O)NR$^C_2$, —C(=NR$^C$)NR$^C_2$, —OR$^C$, —OC(O)($C_1$-$C_6$)alkyl, —OC(O)O($C_1$-$C_6$)alkyl, —OC(O)NR$^C_2$, ($C_1$-$C_6$)alkylene-NR$^C_2$, —NR$^C_2$, —NR$^C$C(O)R$^C$, —NR$^C$C(O)O($C_1$-$C_6$)alkyl, —NR$^C$C(O)NR$^C_2$, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C_2$, —(C$_1$-C$_6$) perfluoroalkyl, and —(C$_1$-C$_6$)alkylene-OR$^C$;

R$^7$ and R$^8$ are independently selected from the group consisting of hydrogen, —C(O)R', —C(O)OR', —C(O) NHR', substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$) alkyl, substituted (C$_1$-C$_8$)cycloalkyl, substituted aryl, substituted heteroaryl, substituted heterocycle, substituted aryl (C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC (O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$) alkyl, —NR$^C$C(O)NR$^C_2$, —NR$^C$SO$_2$NR$^C$, —SR$^C$, —S(O) R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

Y$^1$ and Y$^2$ are independently selected from the group consisting of hydrogen, sodium, potassium, lithium, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle; wherein the substituted (C$_1$-C$_8$) alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$) alkenyl, —(C$_2$-C$_6$)alkynyl, halogen, —CN, —NO$_2$, —C(O) R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O) NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C$, —SR$^C$, —S(O)R$^C$, —SO$_2$R$^C$, —OSO$_2$ (C$_1$-C$_6$)alkyl, —SO$_2$NR$^C_2$, —(C$_1$-C$_6$)perfluoroalkyl, and —(C$_1$-C$_6$)alkylene-OR$^C$; or, alternatively, Y$^1$ and Y$^2$ taken together are selected from the group consisting of sodium, potassium, lithium, magnesium, calcium, strontium, and barium;

provided that when Z$^2$ is NH, the absolute configuration of C** is R or S, or a mixture of R and S;

further provided that when n is 0, Z$^2$ is NH, and R$^1$ is hydrogen, then R$^6$, R$^7$, and R$^8$ are not all simultaneously hydrogen;

further provided that when n is 0, Z$^2$ is oxygen, and R$^1$ is hydrogen, then R$^6$, R$^7$, and R$^8$ are not all simultaneously hydrogen, acetyl, or benzoyl; and further provided that when n is 0, Z$^2$ is oxygen, and R$^1$ is —(C$_1$-C$_8$)alkyl, then R$^6$, R$^7$, and R$^8$ are not all simultaneously acetyl or benzoyl.

In accordance with an alternative embodiment, prototype product nicotinate/nicotinamide ribonucleoside compounds (NR or NAR respectively) include nicotinate/nicotinamide riboside compounds or derivatives of formula (I), or a salt, hydrate, or solvate thereof:

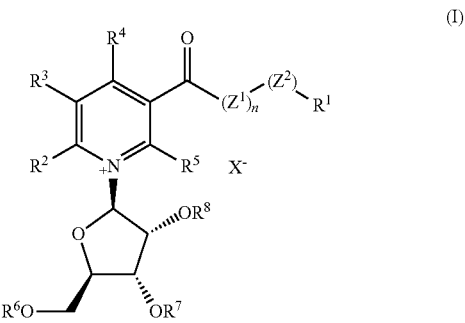

wherein X$^-$ is selected from the group consisting of fluoride, chloride, bromide, iodide, formate, acetate, ascorbate, benzoate, carbonate, citrate, carbamate, formate, gluconate, lactate, methyl bromide, methyl sulfate, nitrate, phosphate, diphosphate, succinate, sulfate, trifluoromethanesulfonate, trichloromethanesulfonate, tribromomethanesulfonate, and trifluoroacetate;

Z$^1$ and Z$^2$ are independently NH or oxygen;

n is 0 or 1;

R$^1$ is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—(R$^4$)— CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, (C$_2$-C$_6$)alkynyl, halogen, —CN, —NO$_2$, —C(O)R$^C$, —C(O)OR$^C$, —C(O) NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$) alkyl, —NR$^C$C(O)NR$^C_2$, —NR$^C$SO$_2$NR$^C$, —SR$^C$, —S(O) R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R$^A$ is selected from the group consisting of —H, —(C$_1$-C$_6$)alkyl, —(CH$_2$)$_3$—NH C(NH$_2$)(=NH), —CH$_2$C(=O) NH$_2$, —CH$_2$COOH, —CH$_2$SH, —(CH$_2$)$_2$C(=O) NH$_2$, —(CH$_2$)$_2$COOH, —CH$_2$-(2-imidazolyl), —CH(CH$_3$)— CH$_2$—CH$_3$, —CH$_2$CH(CH$_3$)$_2$, —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$, and —CH$_2$—CH$_3$;

R$^B$ is hydrogen or —(C$_1$-C$_8$)alkyl;

each R$^C$ is independently selected from the group consisting of hydrogen, —(C$_1$-C$_8$)alkyl, substituted or unsubstituted pyridyl, substituted or unsubstituted 1,4-dihydropyridyl, a radical of the compound of formula (I), and vitamin B7 ester (biotinyl); wherein the substituted pyridyl and substituted 1,4-dihydropyridyl are substituted with one to five substituents independently selected from the group consisting of —(C$_1$-C$_6$)alkyl, —(C$_2$-C$_6$)alkenyl, —(C$_2$-C$_6$) alkynyl, halogen, —CN, —NO$_2$, —C(O)R$^B$, —C(O)OR$^B$, —C(O)NR$^B_2$, —C(=NR)NR$^B_2$, —OR$^B$, —OC(O)(C$_1$-C$_6$) alkyl, —OC(O)O(C$_1$-C$_6$)alkyl, —OC(O)NR$^B_2$, —(C$_1$-C$_6$) alkylene-NR$^B_2$, —NR$^B_2$, —NR$^B$C(O)R$^B$, —NR$^B$C(O)O(C$_1$-C$_6$)alkyl, —NR$^B$C(O)NR$^B_2$, —NR$^B$SO$_2$NR$^B$, —SR$^B$, —S(O)R$^B$, —SO$_2$R$^B$, —OSO$_2$(C$_1$-C$_6$)alkyl, —SO$_2$NR$^B_2$, —(C$_1$-C$_6$)perfluoroalkyl, and —(C$_1$-C$_6$)alkylene-OR$^B$;

$R^2$, $R^3$, $R^4$, and $R^5$ are each independently selected from the group consisting of hydrogen, —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-$OR^C$;

$R^6$ is selected from the group consisting of hydrogen, —C(O)R', —C(O)OR', —C(O)NHR', —P(O)($OY^1$)($OY^2$), —P(O)($OY^1$)(NHR''), substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)$OR^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-$OR^C$;

R' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)$OR^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-$OR^C$;

R'' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)$OR^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-$OR^C$;

$R^7$ and $R^8$ are independently selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$)cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)$OR^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-$OR^C$;

$Y^1$ and $Y^2$ are independently selected from the group consisting of hydrogen, sodium, potassium, lithium, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)$OR^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-$OR^C$; or, alternatively, $Y^1$ and $Y^2$ taken together are selected from the group consisting of sodium, potassium, lithium, magnesium, calcium, strontium, and barium;

provided that when $Z^2$ is NH, the absolute configuration of C** is R or S, or a mixture of R or S;

further provided that when n is 0, $Z^2$ is NH, and $R^1$ is hydrogen, then $R^6$, $R^7$, and $R^8$ are not all simultaneously hydrogen;

further provided that when n is 0, $Z^2$ is NH, and $R^1$, $R^2$, $R^3$, $R^4$, and $R^5$ are each hydrogen, then $R^6$ is not —C(O)R' or —C(O)OR' where R' is alkyl, and each of $R^7$ and $R^8$ are not independently hydrogen, —C(O)R', or —C(O)OR', where R' is alkyl;

further provided that when n is 0, $Z^2$ is NH, $R^1$ is ($C_1$-$C_8$)alkyl or ($C_1$-$C_8$)cycloalkyl, and $R^2$, $R^3$, $R^4$, and $R^5$ are each hydrogen, then each of $R^6$, $R^7$, and $R^8$ are not independently hydrogen or —C(O)R';

further provided that when n is 0, $Z^2$ is oxygen, $R^1$ is ($C_1$-$C_8$)alkyl, ($C_1$-$C_8$)cycloalkyl, aryl, or substituted aryl, and $R^2$, $R^3$, $R^4$, and $R^5$ are each hydrogen, then $R^6$, $R^7$, and $R^8$ are not all simultaneously —C(O)R'.

In accordance with an embodiment, prototype product reduced nicotinate/nicotinamide ribonucleoside compounds (NRH or NARH, respectively) include reduced nicotinate/ nicotinamide riboside compounds or derivatives of formula (II), or a salt, hydrate, or solvate thereof:

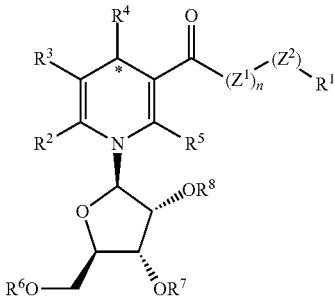
(II)

$Z^1$ and $Z^2$ are independently NH or oxygen;

n is 0 or 1;

$R^1$ is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B ester, vitamin B2 ester, vitamin B6 ester, and —C**H—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)NR$^C_2$, —C(=N$R^C$)NR$^C_2$, —O$R^C$, —OC(O)($C_1$-$C_6$)alkyl, —OC(O)O($C_1$-$C_6$)alkyl, —OC(O)NR$^C_2$, —($C_1$-$C_6$)alkylene-NR$^C_2$, —NR$^C_2$, —NR$^C$C(O)$R^C$, —NR$^C$C(O)O($C_1$-$C_6$)alkyl, —NR$^C$C(O)NR$^C_2$, —NR$^C$SO$_2$NR$^C$, —S$R^C$, —S(O)$R^C$, —SO$_2R^C$, —OSO$_2$($C_1$-$C_6$)alkyl, —SO$_2$NR$^C_2$, —($C_1$-$C_6$)perfluoroalkyl, and —($C_1$-$C_6$)alkylene-O$R^C$;

$R^A$ is selected from the group consisting of —H, —($C_1$-$C_6$)alkyl, —($CH_2$)$_3$—NH—C(NH$_2$)(=NH), —$CH_2$C(=O)NH$_2$, —$CH_2$COOH, —$CH_2$SH, —($CH_2$)$_2$C(=O)—NH$_2$, —($CH_2$)$_2$COOH, —$CH_2$-(2-imidazolyl), —CH(CH$_3$)—CH$_2$—CH$_3$, —$CH_2$CH(CH$_3$)$_2$, —($CH_2$)$_4$—N$_2$, —($CH_2$)$_2$—S—CH$_3$, phenyl, —$CH_2$-phenyl, —$CH_2$—OH, —CH(OH)—CH$_3$, —$CH_2$-(3-indolyl), —$CH_2$-(4-hydroxyphenyl), —CH(CH$_3$)$_2$, and —$CH_2$—CH$_3$;

$R^B$ is hydrogen or —($C_1$-$C_8$)alkyl;

each $R^C$ is independently selected from the group consisting of hydrogen, —($C_1$-$C_8$)alkyl, substituted or unsubstituted pyridyl, substituted or unsubstituted 1,4-dihydropyridyl, a radical of the compound of formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^B$, —C(O)O$R^B$, —C(O)NR$^B_2$, —C(=N$R^B$)NR$^B_2$, —O$R^B$, —OC(O)($C_1$-$C_6$)alkyl, —OC(O)O($C_1$-$C_6$)alkyl, —OC(O)NR$^B_2$, —($C_1$-$C_6$)alkylene-NR$^B_2$,—NR$^B_2$,—NR$^B$C(O)$R^B$, —NR$^B$C(O)O($C_1$-$C_6$)alkyl, —NR$^B$C(O)NR$^B_2$, —NR$^B$SO$_2$NR$^B$, —S$R^B$, —S(O)$R^B$, —SO$_2R^B$, —OSO$_2$($C_1$-$C_6$)alkyl, —SO$_2$NR$^B_2$, —($C_1$-$C_6$)perfluoroalkyl, and —($C_1$-$C_6$)alkylene-O$R^B$;

$R^2$ and $R^3$ are each independently selected from the group consisting of hydrogen, —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)NR$^C_2$, —C(=N$R^C$)NR$^C_2$, —O$R^C$, —OC(O)($C_1$-$C_6$)alkyl, —OC(O)O($C_1$-$C_6$)alkyl, —OC(O) NR$^C_2$, —($C_1$-$C_6$)alkylene-NR$^C_2$, —NR$^C_2$, —NR$^C$C(O)$R^C$, —NR$^C$C(O)O($C_1$-$C_6$)alkyl, —NR$^C$C(O)NR$^C_2$, —NR$^C$SO$_2$NR$^C$, —S$R^C$, —S(O)$R^C$, —SO$_2R^C$, —OSO$_2$($C_1$-$C_6$)alkyl, —SO$_2$NR$^C_2$, —($C_1$-$C_6$)perfluoroalkyl, and —($C_1$-$C_6$)alkylene-O$R^C$;

$R^4$ is selected from the group consisting of hydrogen, —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)NR$^C_2$, —C(=N$R^C$)NR$^C_2$, —O$R^C$, —OC(O)($C_1$-$C_6$)alkyl, —OC(O)O($C_1$-$C_6$)alkyl, —OC(O)NR$^C_2$, —($C_1$-$C_6$)alkylene-NR$^C_2$, —NR$^C_2$, —NR$^C$C(O)$R^C$, —NR$^C$C(O)O($C_1$-$C_6$) alkyl, —NR$^C$C(O)NR$^C_2$, —NR$^C$SO$_2$NR$^C$, —S$R^C$, —S(O) $R^C$, —SO$_2R^C$, —OSO$_2$($C_1$-$C_6$)alkyl, —SO$_2$NR$^C_2$, —($C_1$-$C_6$)perfluoroalkyl, and —($C_1$-$C_6$)alkylene-O$R^C$;

provided that C* has an absolute configuration of R or S, or a mixture of R and S;

$R^5$ is selected from the group consisting of hydrogen, —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)NR$^C_2$, —C(=N$R^C$)NR$^C_2$, —O$R^C$, —OC(O)($C_1$-$C_6$)alkyl, —OC(O)O($C_1$-$C_6$)alkyl, —OC(O)NR$^C_2$, —($C_1$-$C_6$)alkylene-NR$^C_2$, —NR$^C_2$, —NR$^C$C(O)$R^C$, —NR$^C$C(O)O($C_1$-$C_6$) alkyl, —NR$^C$C(O)NR$^C_2$, —NR$^C$SO$_2$NR$^C$, —S$R^C$, —S(O) $R^C$, —SO$_2R^C$, —OSO$_2$($C_1$-$C_6$)alkyl, —SO$_2$NR$^C_2$, —($C_1$-$C_6$)perfluoroalkyl, and —($C_1$-$C_6$)alkylene-O$R^C$;

$R^6$ is selected from the group consisting of hydrogen, —C(O)R', —C(O)OR', —C(O)NHR', —P(O)(OY$^1$)(OY$^2$), —P(O)(OY$^1$)(NHR"), substituted or unsubstituted ($C_1$-$C_8$) alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^A$)—$CO_2R^B$; wherein the substituted ($C_1$-$C_8$) alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$) alkenyl, —($C_2$-$C_6$)alkynyl, halogen, —CN, —$NO_2$, —C(O) $R^C$, —C(O)O$R^C$, —C(O)NR$^C_2$, —C(=N$R^C$)NR$^C_2$, —O$R^C$, —OC(O)($C_1$-$C_6$)alkyl, —OC(O)O($C_1$-$C_6$)alkyl, —OC(O) NR$^C_2$, —($C_1$-$C_6$)alkylene-NR$^C_2$, —NR$^C_2$, —NR$^C$C(O)$R^C$, —NR$^C$C(O)O($C_1$-$C_6$)alkyl, —NR$^C$C(O)NR$^C_2$, —NR$^C$SO$_2$NR$^C$, —S$R^C$, —S(O)$R^C$, —SO$_2R^C$, —OSO$_2$ ($C_1$-$C_6$)alkyl, —SO$_2$NR$^C_2$, —($C_1$-$C_6$)perfluoroalkyl, and —($C_1$-$C_6$)alkylene-O$R^C$;

R' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)NR$^C_2$, —C(=N$R^C$)NR$^C_2$, —O$R^C$, —OC(O)($C_1$-$C_6$)alkyl, —OC(O)O($C_1$-$C_6$)alkyl, —OC(O)NR$^C_2$, —($C_1$-$C_6$)alkylene-NR$^C_2$, —NR$^C_2$, —NR$^C$C(O)$R^C$, —NR$^C$C(O)O($C_1$-$C_6$) alkyl, —NR$^C$C(O)NR$^C_2$, —NR$^C$SO$_2$NR$^C$, —S$R^C$, —S(O) $R^C$, —SO$_2R^C$, —OSO$_2$($C_1$-$C_6$)alkyl, —SO$_2$NR$^C_2$, —($C_1$-$C_6$)perfluoroalkyl, and —($C_1$-$C_6$)alkylene-O$R^C$;

R" is selected from the group consisting of hydrogen, substituted or unsubstituted ($C_1$-$C_8$)alkyl, substituted or unsubstituted (C₁-C₈)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, aryl(C₁-C₄)alkyl, heterocycle(C₁-C₄)alkyl, and —C**H—(R^A)—CO₂R^B; wherein the substituted (C₁-C₈)alkyl, substituted (C₁-C₈)cycloalkyl, substituted aryl, substituted heteroaryl, and substituted heterocycle are substituted with one to five substituents independently selected from the group consisting of —(C₁-C₆)alkyl, —(C₂-C₆)alkenyl, —(C₂-C₆)alkynyl, halogen, —CN, —NO₂, —C(O)R^C, —C(O)OR^C, —C(O)NR^C₂, —C(=NR^C)NR^C₂, —OR^C, —OC(O)(C₁-C₆)alkyl, —OC(O)O(C₁-C₆)alkyl, —OC(O)NR^C₂, —(C₁-C₆)alkylene-NR^C₂, —NR^C₂, —NR^CC(O)R^C, —NR^CC(O)O(C₁-C₆)alkyl, —NR^CC(O)NR^C₂, —NR^CSO₂NR^C, —SR^C, —S(O)R^C, —SO₂R^C, —OSO₂(C₁-C₆)alkyl, —SO₂NR^C₂, —(C₁-C₆)perfluoroalkyl, and —(C₁-C₆)alkylene-OR^C;

R⁷ and R⁸ are independently selected from the group consisting of hydrogen, —C(O)R', —C(O)OR', —C(O)NHR', substituted or unsubstituted (C₁-C₈)alkyl, substituted or unsubstituted (C₁-C₈)cycloalkyl, substituted or unsubstituted aryl, substituted or unsubstituted heteroaryl, substituted or unsubstituted heterocycle, substituted or unsubstituted aryl(C₁-C₄)alkyl, and substituted or unsubstituted heterocycle(C₁-C₄)alkyl; wherein the substituted (C₁-C₈)alkyl, substituted (C₁-C₈)cycloalkyl, substituted aryl, substituted heteroaryl, substituted heterocycle, substituted aryl(C₁-C₄)alkyl, and substituted heterocycle(C₁-C₄)alkyl are substituted with one to five substituents independently selected from the group consisting of —(C₁-C₆)alkyl, —(C₂-C₆)alkenyl, —(C₂-C₆)alkynyl, halogen, —CN, —NO₂, —C(O)R^C, —C(O)OR^C, —C(O)NR^C₂, —C(=NR^C)NR^C₂, —OR^C, —OC(O)(C₁-C₆)alkyl, —OC(O)O(C₁-C₆)alkyl, —OC(O)NR^C₂, —(C₁-C₆)alkylene-NR^C₂, —NR^C₂, —NR^CC(O)R^C, —NR^CC(O)O(C₁-C₆)alkyl, —NR^CC(O)NR^C₂, —NR^CSO₂NR^C, —SR^C, —S(O)R^C, —SO₂R^C, —OSO₂(C₁-C₆)alkyl, —SO₂NR^C₂, —(C₁-C₆)perfluoroalkyl, and —(C₁-C₆)alkylene-OR^C;

Y¹ and Y² are independently selected from the group consisting of hydrogen, sodium, potassium, lithium, substituted or unsubstituted (C₁-C₈)alkyl, substituted or unsubstituted (C₁-C₈)cycloalkyl, substituted or unsubstituted aryl, substituted or unsubstituted heteroaryl, and substituted or unsubstituted heterocycle; wherein the substituted (C₁-C₈)alkyl, substituted (C₁-C₈)cycloalkyl, substituted aryl, substituted heteroaryl, and substituted heterocycle are substituted with one to five substituents independently selected from the group consisting of —(C₁-C₆)alkyl, —(C₂-C₆)alkenyl, —(C₂-C₆)alkynyl, halogen, —CN, —NO₂, —C(O)R^C, —C(O)OR^C, —C(O)NR^C₂, —C(=NR^C)NR^C₂, —OR^C, —OC(O)(C₁-C₆)alkyl, —OC(O)O(C₁-C₆)alkyl, —OC(O)NR^C₂, —(C₁-C₆)alkylene-NR^C₂, —NR^C₂, —NR^CC(O)R^C, —NR^CC(O)O(C₁-C₆)alkyl, —NR^CC(O)NR^C₂, —NR^CSO₂NR^C, —SR^C, —S(O)R^C, —SO₂R^C, —OSO₂(C₁-C₆)alkyl, —SO₂NR^C₂, —(C₁-C₆)perfluoroalkyl, and —(C₁-C₆)alkylene-OR^C; or, alternatively, Y¹ and Y² taken together are selected from the group consisting of sodium, potassium, lithium, magnesium, calcium, strontium, and barium;

provided that when Z² is NH, the absolute configuration of C** is R or S, or a mixture of R and S.

In accordance with an alternative embodiment, prototype product reduced nicotinate/nicotinamide ribonucleoside compounds (NRH or NARH, respectively) include reduced nicotinate/nicotinamide riboside compounds or derivatives of formula (II), or a salt, hydrate, or solvate thereof:

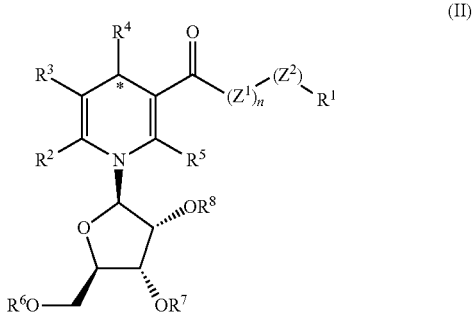

(II)

Z¹ and Z² are independently NH or oxygen;
n is 0 or 1;
R¹ is selected from the group consisting of hydrogen, substituted or unsubstituted (C₁-C₈)alkyl, substituted or unsubstituted (C₁-C₈)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—(R^A)—CO₂R^B; wherein the substituted (C₁-C₈)alkyl, substituted (C₁-C₈)cycloalkyl, substituted aryl, substituted heteroaryl, and substituted heterocycle are substituted with one to five substituents independently selected from the group consisting of —(C₁-C₆)alkyl, —(C₂-C₆)alkenyl, —(C₂-C₆)alkynyl, halogen, —CN, —NO₂, —C(O)R^C, —C(O)OR^C, —C(O)NR^C₂, —C(=NR^C)NR^C₂, —OR^C, —OC(O)(C₁-C₆)alkyl, —OC(O)O(C₁-C₆)alkyl, —OC(O)NR^C₂, —(C₁-C₆)alkylene-NR^C₂, —NR^C₂, —NR^CC(O)R^C, —NR^CC(O)O(C₁-C₆)alkyl, —NR^CC(O)NR^C₂, —NR^CSO₂NR^C, —SR^C, —S(O)R^C, —SO₂R^C, —OSO₂(C₁-C₆)alkyl, —SO₂NR^C₂, —(C₁-C₆)perfluoroalkyl, and —(C₁-C₆)alkylene-OR^C;

R^A is selected from the group consisting of —H, —(C₁-C₆)alkyl, —(CH₂)₃—NH—C(NH₂)(=NH), —CH₂C(=O)NH₂, —CH₂COOH, —CH₂SH, —(CH₂)₂C(=O)—NH₂, —(CH₂)₂COOH, —CH₂-(2-imidazolyl), —CH(CH₃)—CH₂—CH₃, —CH₂CH(CH₃)₂, —(CH₂)₄—NH₂, —(CH₂)₂—S—CH₃, phenyl, —CH₂-phenyl, —CH₂—OH, —CH(OH)—CH₃, —CH₂-(3-indolyl), —CH₂-(4-hydroxyphenyl), —CH(CH₃)₂, and —CH₂—CH₃;

R^B is hydrogen or —(C₁-C₈)alkyl;

each R^C is independently selected from the group consisting of hydrogen, —(C₁-C₈)alkyl, substituted or unsubstituted pyridyl, substituted or unsubstituted 1,4-dihydropyridyl, a radical of the compound of formula (I), and vitamin B7 ester (biotinyl); wherein the substituted pyridyl and substituted 1,4-dihydropyridyl are substituted with one to five substituents independently selected from the group consisting of —(C₁-C₆)alkyl, —(C₂-C₆)alkenyl, —(C₂-C₆)alkynyl, halogen, —CN, —NO₂, —C(O)R^B, —C(O)OR^B, —C(O)NR^B2, —C(=NR)NR^B₂, —OR^B, —OC(O)(C₁-C₆)alkyl, —OC(O)O(C₁-C₆)alkyl, —OC(O)NR^B₂, —(C₁-C₆)alkylene-NR^B₂, —NR^B₂, —NR^BC(O)R^B, —NR^BC(O)O(C₁-C₆)alkyl, —NR^BC(O)NR^B₂, —NR^BSO₂NR^B, —SR, —S(O)R^B, —SO₂R^B, —OSO₂(C₁-C₆)alkyl, —SO₂NR^B₂, —(C₁-C₆)perfluoroalkyl, and —(C₁-C₆)alkylene-OR^B;

R² and R³ are each independently selected from the group consisting of hydrogen, —(C₁-C₆)alkyl, —(C₂-C₆)alkenyl, —(C₂-C₆)alkynyl, halogen, —CN, —NO₂, —C(O)R^C, —C(O)OR^C, —C(O)NR^C₂, —C(=NR^C)NR^C₂, —OR^C, —OC(O)(C₁-C₆)alkyl, —OC(O)O(C₁-C₆)alkyl, —OC(O)NR^C₂, —(C₁-C₆)alkylene-NR^C₂, —NR^C₂, —NR^CC(O)R^C, —NR^CC(O)O(C₁-C₆)alkyl, —NR^CC(O)NR^C₂, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R$^4$ is selected from the group consisting of hydrogen, —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

provided that C* has an absolute configuration of R or S, or a mixture of R and S;

R$^5$ is selected from the group consisting of hydrogen, —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C_2$, (C$_1$-C$_6$)perfluoroalkyl, and —(C$_1$-C$_6$)alkylene-OR$^C$;

R$^6$ is selected from the group consisting of hydrogen, —C(O)R', —C(O)OR', —C(O)NHR', —P(O)(OY$^1$)(OY$^2$), —P(O)(OY$^1$)(NHR''), substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle, vitamin B ester, vitamin B2 ester, vitamin B6 ester, and —C**H—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R' is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl(C$_1$-C$_4$)alkyl, heterocyle(C$_1$-C$_4$)alkyl, and —C**H (R$^A$)—CO$_2$R; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R'' is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, aryl(C$_1$-C$_4$)alkyl, heterocycle(C$_1$-C$_4$)alkyl, and —C**H—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, (C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R$^7$ and R$^8$ are independently selected from the group consisting of hydrogen, —C(O)R', —C(O)OR', —C(O)NHR', substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$)alkyl, substituted (C$_1$-C$_8$)cycloalkyl, substituted aryl, substituted heteroaryl, substituted heterocycle, substituted aryl(C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

Y$^1$ and Y$^2$ are independently selected from the group consisting of hydrogen, sodium, potassium, lithium, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, (C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$; or, alternatively, Y$^1$ and Y$^2$ taken together are selected from the group consisting of sodium, potassium, lithium, magnesium, calcium, strontium, and barium;

provided that when Z$^2$ is NH, the absolute configuration of C** is R or S, or a mixture of R and S;

further provided that when n is 0, Z$^2$ is NH, and R$^1$, R$^2$, R$^3$, R$^4$, and R$^5$ are each hydrogen, then R$^6$ is not —C(O)R' or —C(O)OR' where R' is alkyl, and each of R$^7$ and R$^8$ are not independently hydrogen, —C(O)R', or —C(O)OR', where R' is alkyl;

further provided that when n is 0 and $Z^2$ is oxygen, then $R^1$, $R^2$, $R^3$, $R^4$, $R^5$, $R^6$, $R^7$, and $R^8$ are not all simultaneously hydrogen;

further provided that when n is 0, $Z^2$ is oxygen, $R^1$ is hydrogen or $(C_1-C_4)$alkyl, and $R^2$, $R^3$, $R^4$, and $R^5$ are each hydrogen, then each of $R^6$, $R^7$, and $R^8$ is not —C(O)R', —C(O)OR', or —C(O)NHR', where R' is hydrogen, unsubstituted $(C_1-C_8)$alkyl, unsubstituted $(C_1-C_8)$cycloalkyl, unsubstituted aryl, unsubstituted heteroaryl, unsubstituted aryl$(C_1-C_4)$alkyl, or unsubstituted heterocycle$(C_1-C_4)$alkyl.

In accordance with an embodiment, optionally for the compounds or derivatives of formulae (I) or (II), or salts, hydrates, or solvates thereof, wherein $X^-$ as counterion is absent, or when $X^-$ is present is selected from the group consisting of fluoride, chloride, bromide, iodide, formate, acetate, ascorbate, benzoate, carbonate, citrate, carbamate, formate, gluconate, lactate, methyl bromide, methyl sulfate, nitrate, phosphate, diphosphate, succinate, sulfate, trifluoromethanesulfonate, trichloromethanesulfonate, tribromomethanesulfonate, and trifluoroacetate;

optionally wherein when $X^-$ is absent optionally the counterion is an internal salt.

In certain embodiments, generally solvent-based chemical laboratory techniques may be employed in the processes to prepare the compounds or derivatives of formulae (I) or (II), or salts, hydrates, or solvates thereof.

In other embodiments, generally solvent-free conditions may be employed in the processes to prepare the compounds or derivatives of formulae (I) or (II), or salts, hydrates, or solvates thereof, using appropriate mechano-chemical techniques as described.

In an embodiment, a method of making a nicotinate/nicotinamide riboside compound or derivative of formula (I), or a salt, hydrate, or solvate thereof, can include the steps of:

(a) providing a nicotinate/nicotinamide compound or derivative having formula (1), or a salt thereof, optionally, in one or more solvent(s); (b) treating the compound or derivative having formula (1), or salt thereof, with at least about one molar equivalent amount of a riboside compound or derivative having formula (2), or a salt thereof, optionally, in one or more solvent(s); (b)(1) optionally adding a catalyst; (c) reacting the nicotinate/nicotinamide compound or derivative having formula (1), or salt thereof, optionally, in one or more solvent(s), with the riboside compound or derivative having formula (2), or salt thereof, optionally, in one or more solvent(s), and, optionally, the catalyst, according to solvent-based chemical laboratory techniques so as to produce the compound or derivative of formula (I), or salt, hydrate, or solvate thereof; (d) adding water to the nicotinate/nicotinamide compound or derivative having formula (1), or salt thereof, optionally, in one or more solvent(s), the riboside compound or derivative having formula (2), or salt thereof, optionally, in one or more solvent(s), optionally, the catalyst, and the compound or derivative of formula (I), or salt, hydrate, or solvate thereof; (e) extracting the nicotinate/nicotinamide compound or derivative having formula (1), or salt thereof, optionally, in one or more solvent(s), the riboside compound or derivative having formula (2), or salt thereof, optionally, in one or more solvent(s), the compound or derivative of formula (I), or salt, hydrate, or solvate thereof, optionally, the catalyst, and the water with organic solvent; (e)(1) optionally adjusting the pH of the combined organic extracts with an aqueous solution of acid or base, if necessary; (f) precipitating or isolating the compound or derivative of formula (I), or salt, hydrate, or solvate thereof, or removing the organic solvent used for extraction; and, optionally, (g) purifying the compound or derivative of formula (I), or salt, hydrate, or solvate thereof. This process effects a chemical, solvent-based synthesis of modified conjugates or derivatives of nicotinate/nicotinamide ribonucleoside compounds (NR or NAR, respectively) of formula (I), or salt, hydrate, or solvate thereof.

In another embodiment, an alternative method of making a nicotinate/nicotinamide riboside compound or derivative of formula (I), or a salt, hydrate, or solvate thereof, can include the steps of:

(a) providing a riboside compound or derivative having formula (2), or a salt thereof, optionally, in one or more solvent(s); (b) treating the compound or derivative having formula (2), or salt thereof, with at least about one molar equivalent amount of a Lewis acid, optionally, in one or more solvent(s); (c) treating the mixture of the compound or derivative having formula (2), or salt thereof, and Lewis acid, optionally, in one or more solvent(s), with at least about one molar equivalent amount of a nicotinate/nicotinamide compound or derivative having formula (1), or a salt thereof, optionally, in one or more solvent(s); (d) reacting the riboside compound or derivative having formula (2), or salt thereof, and Lewis acid, optionally, in one or more solvent(s), with the nicotinate/nicotinamide compound or derivative having formula (1), or salt thereof, optionally, in one or more solvent(s), according to solvent-based chemical laboratory techniques so as to produce the compound or derivative of formula (I), or salt, hydrate, or solvate thereof; (e) adding water to the riboside compound or derivative having formula (2), or salt thereof, optionally, in one or more solvent(s), the Lewis acid, optionally, in one or more solvent(s), the nicotinate/nicotinamide compound or derivative having formula (1), or salt thereof, optionally, in one or more solvent(s), and the compound or derivative of formula (I), or salt, hydrate, or solvate thereof; (f) extracting the riboside compound or derivative having formula (2), or salt thereof, optionally, in one or more solvent(s), the Lewis acid, optionally, in one or more solvent(s), the nicotinate/nicotinamide compound or derivative having formula (1), or salt thereof, optionally, in one or more solvent(s), the compound or derivative of formula (I), or salt, hydrate, or solvate thereof, and the water, with organic solvent; (f)(1) optionally adjusting the pH of the combined organic extracts with an aqueous solution of acid or base, if necessary; (g) precipitating or isolating the compound or derivative of formula (I), or salt, hydrate, or solvate thereof, or removing the organic solvent used for extraction; and, optionally, (h) purifying the compound or derivative of formula (I), or salt, hydrate, or solvate thereof. This process effects a chemical, solvent-based synthesis of modified conjugates or derivatives of nicotinate/nicotinamide ribonucleoside compounds (NR or NAR, respectively) of formula (I), or salt, hydrate, or solvate thereof.

In yet another embodiment, a method of making a nicotinate/nicotinamide riboside compound or derivative of formula (I), or a salt, hydrate, or solvate thereof, can include the steps of:

(a) providing a nicotinate/nicotinamide compound or derivative having formula (1), or a salt thereof; (b) treating the compound or derivative having formula (1), or salt thereof, with at least about one molar equivalent amount of a riboside compound or derivative having formula (2), or a salt thereof; (b)(1) optionally adding a catalyst; (c) mechanically grinding and/or milling the nicotinate/nicotinamide compound or derivative having formula (1), or salt thereof, the riboside compound or derivative having formula (2), or salt thereof, and, optionally, the catalyst so as to produce the compound or derivative of formula (I), or salt, hydrate, or solvate thereof; (d) adding water to the nicotinate/nicotinamide compound or derivative having formula (1), or salt thereof, the riboside compound or derivative having formula (2), or salt thereof, the compound or derivative of formula (I), or salt, hydrate, or solvate thereof, and, optionally, the catalyst; (e) extracting the nicotinate/nicotinamide compound or derivative having formula (1), or salt thereof, the riboside compound or derivative having formula (2), or salt thereof, the compound or derivative of formula (I), or salt, hydrate, or solvate thereof, optionally, the catalyst, and the water with organic solvent; (e)(1) optionally adjusting the pH of the combined organic extracts with an aqueous solution of acid or base, if necessary; (f) precipitating or isolating the compound or derivative of formula (I), or salt, hydrate, or solvate thereof, or removing the organic solvent used for extraction; and, optionally, (g) purifying the compound or derivative of formula (I), or salt, hydrate, or solvate thereof. This process effects a chemical, mechano-chemical, and/or solvent-free synthesis of modified conjugates or derivatives of nicotinate/nicotinamide ribonucleoside compounds (NR or NAR, respectively) of formula (I), or salt, hydrate, or solvate thereof.

In yet another embodiment, an alternative method of making a nicotinate/nicotinamide riboside compound or derivative of formula (I), or a salt, hydrate, or solvate thereof, can include the steps of:
(a) providing a riboside compound or derivative having formula (2), or a salt thereof; (b) treating the compound or derivative having formula (2), or salt thereof, with at least about one molar equivalent amount of a Lewis acid; (c) mechanically grinding and/or milling the riboside compound or derivative having formula (2), or salt thereof, and the Lewis acid; (d) treating the mixture of the riboside compound or derivative having formula (2), or salt thereof, and the Lewis acid with at least about one molar equivalent amount of a nicotinate/nicotinamide compound or derivative having formula (1), or a salt thereof; (e) mechanically grinding and/or milling the mixture of the riboside compound or derivative having formula (2), or salt thereof, and the Lewis acid and the nicotinate/nicotinamide compound or derivative having formula (1), or salt thereof, so as to produce the compound or derivative of formula (I), or salt, hydrate, or solvate thereof; (f) adding water to the riboside compound or derivative having formula (2), or salt thereof, the Lewis acid, the nicotinate/nicotinamide compound or derivative having formula (1), or salt thereof, and the compound or derivative of formula (I), or salt, hydrate, or solvate thereof; (g) extracting the riboside compound or derivative having formula (2), or salt thereof, the Lewis acid, the nicotinate/nicotinamide compound or derivative having formula (1), or salt thereof, the compound or derivative of formula (I), or salt, hydrate, or solvate thereof, and the water with an organic solvent; (g)(1) optionally adjusting the pH of the combined organic extracts with an aqueous solution of acid or base, if necessary; (h) precipitating or isolating the compound or derivative of formula (I), or salt, hydrate, or solvate thereof, or removing the organic solvent used for extraction; and, optionally, (i) purifying the compound of formula (I), or salt, hydrate, or solvate thereof. This process effects a chemical, mechano-chemical, and/or solvent-free synthesis of modified conjugates or derivatives of nicotinate/nicotinamide ribonucleoside compounds (NR or NAR, respectively) of formula (I), or salt, hydrate, or solvate thereof.

In yet another embodiment, a method of making a nicotinate/nicotinamide riboside compound or derivative of formula (I), or a salt, hydrate, or solvate thereof, can include the steps of:
(a) providing a riboside compound or derivative having formula (2), or a salt thereof; (b) treating the compound or derivative having formula (2), or salt thereof, with molar equivalents ($3<x<100$) of an alcohol (e.g., methanol, or ethanol) and molar equivalents ($3 \leq x<20$) of a Brønsted inorganic acid; (c) treating the mixture of the riboside compound or derivative having formula (2), or salt thereof, the alcohol, and the Brønsted inorganic acid with at least about one molar equivalent amount of a nicotinate/nicotinamide compound or derivative having formula (1), or salt thereof; (d) reacting the riboside compound or derivative having formula (2), or salt thereof, the alcohol, the Brønsted inorganic acid, and the nicotinate/nicotinamide compound or derivative having formula (1), or salt thereof, so as to produce the compound or derivative of formula (I), or salt, hydrate, or solvate thereof; (e) filtering the precipitated compound or derivative having formula (I), or salt, hydrate, or solvate thereof; optionally, (e1) washing the compound or derivative having formula (I), or salt, hydrate, or solvate thereof with cold alcohol (e.g., methanol, or ethanol); (f) precipitating or isolating the compound or derivative of formula (I), or salt, hydrate, or solvate thereof; and, optionally, (g) purifying the compound or derivative of formula (I), or salt, hydrate, or solvate thereof. This process effects a chemical, solvent-based synthesis of modified conjugates or derivatives of nicotinate/nicotinamide ribonucleoside compounds (NR or NAR, respectively) of formula (I), or salt, hydrate, or solvate thereof.

In yet another embodiment, an alternative method of making a nicotinate/nicotinamide riboside compound or derivative of formula (I), or a salt, hydrate, or solvate thereof, can include the steps of:
(a) providing a riboside compound or derivative having formula (2), or a salt thereof; (b) treating the compound or derivative having formula (2), or salt thereof, with molar equivalents ($3<x<100$) of an alcohol (e.g., methanol, or ethanol) and molar equivalents ($3 \leq x<20$) of acetyl chloride; (c) treating the mixture of the riboside compound or derivative having formula (2), or salt thereof, the alcohol, and the acetyl chloride with at least about one molar equivalent amount of a nicotinate/nicotinamide compound or derivative having formula (1), or salt thereof; (d) reacting the riboside compound or derivative having formula (2), or salt thereof, the alcohol, the acetyl chloride, and the nicotinate/nicotinamide compound or derivative having formula (1), or salt thereof, so as to produce the compound or derivative of formula (I), or salt, hydrate, or solvate thereof; (e) filtering the precipitated compound or derivative having formula (I), or salt, hydrate, or solvate thereof; optionally, (e1) washing the compound or derivative having formula (I), or salt, hydrate, or solvate thereof with cold alcohol (e.g., methanol, or ethanol); (f) precipitating or isolating the compound or derivative of formula (I), or salt, hydrate, or solvate thereof; and, optionally, (g) purifying the compound or derivative of formula (I), or salt, hydrate, or solvate thereof. This process effects a chemical, solvent-based synthesis of modified conjugates or derivatives of nicotinate/nicotinamide ribonucleoside compounds (NR or NAR, respectively) of formula (I), or salt, hydrate, or solvate thereof.

In accordance with an embodiment of a method of making a nicotinate/nicotinamide riboside compound or derivative of formula (I), or a salt, hydrate, or solvate thereof, there is described a compound or derivative having formula (1), or salt thereof:

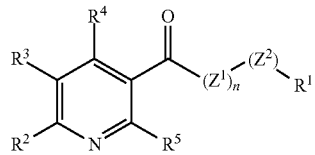

(1)

wherein $Z^1$ and $Z^2$ are independently NH or oxygen;
n is 0 or 1;
$R^1$ is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^A$)—$CO_2R$; wherein the substituted ($C_1$-$C_8$)alkyl, substituted ($C_1$-$C_8$) cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$$SO_2$N$R^C$, —S$R^C$, —S(O)$R^C$, —$SO_2R^C$, —$OSO_2$($C_1$-$C_6$)alkyl, —$SO_2$N$R^C_2$, —($C_1$-$C_6$)perfluoroalkyl, and —($C_1$-$C_6$)alkylene-O$R^C$;
$R^A$ is selected from the group consisting of —H, —($C_1$-$C_6$)alkyl, —$(CH_2)_3$—NH—C(NH_2)(=NH), —$CH_2$C(=O)$NH_2$, —$CH_2$COOH, —$CH_2$SH, —$(CH_2)_2$C(=O)—$NH_2$, —$(CH_2)_2$COOH, —$CH_2$-(2-imidazolyl), —CH(CH_3)—$CH_2$—$CH_3$, —$CH_2$CH(CH_3)_2, —$(CH_2)_4$—$NH_2$, —$(CH_2)_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —CH(CH_3)_2, and —$CH_2$—$CH_3$;
$R^B$ is hydrogen or —($C_1$-$C_8$)alkyl;
each $R^C$ is independently selected from the group consisting of hydrogen, —($C_1$-$C_8$)alkyl, substituted or unsubstituted pyridyl, substituted or unsubstituted 1,4-dihydropyridyl, a radical of the compound of formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$) alkynyl, halogen, —CN, —$NO_2$, —C(O)$R^B$, —C(O)O$R^B$, —C(O)N$R^B_2$, —C(=N$R^B$)N$R^B_2$, —O$R^B$, —OC(O)($C_1$-$C_6$) alkyl, —OC(O)O($C_1$-$C_6$)alkyl, —OC(O)N$R^B_2$, —($C_1$-$C_6$) alkylene-N$R^B_2$, —N$R^B_2$, —N$R^B$C(O)$R^B$, —N$R^B$C(O)O($C_1$-$C_6$)alkyl, —N$R^B$C(O)N$R^B_2$, —N$R^B$$SO_2$N$R^B$, —S$R^B$, —S(O)$R^B$, —$SO_2R^B$, —$OSO_2$($C_1$-$C_6$)alkyl, —$SO_2$N$R^B_2$, —($C_1$-$C_6$)perfluoroalkyl, and —($C_1$-$C_6$)alkylene-O$R^B$;
$R^2$, $R^3$, $R^4$, and $R^5$ are each independently selected from the group consisting of hydrogen, —($C_1$-$C_6$)alkyl, —($C_2$-$C_6$)alkenyl, —($C_2$-$C_6$)alkynyl, halogen, —CN, —$NO_2$, —C(O)$R^B$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$$SO_2$N$R^C$, —S$R^C$, —S(O)$R^C$, —$SO_2R^C$, —$OSO_2$($C_1$-$C_6$)alkyl, —$SO_2$N$R^C_2$, —($C_1$-$C_6$)perfluoroalkyl, and —($C_1$-$C_6$)alkylene-O$R^C$;

provided that when $Z^2$ is NH, the absolute configuration of C** is R or S, or a mixture of R and S.

In accordance with an embodiment of a method of making a nicotinate/nicotinamide riboside compound or derivative of formula (I), or a salt, hydrate, or solvate thereof, there is described a compound or derivative having formula (2), or salt thereof:

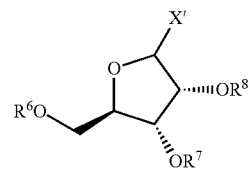

(2)

wherein X' is selected from fluoro, chloro, bromo, iodo, $HCO_2$, acetoxy, propionoxy, butyroxy, glutamyloxy, aspartyloxy, ascorbyloxy, benzoxy, $HOCO_2$, citryloxy, carbamyloxy, gluconyloxy, lactyloxy, succinyloxy, sulfoxy, trifluoromethanesulfoxy, trichloromethanesulfoxy, tribromomethanesulfoxy, and trifluoroacetoxy;
$R^6$ is selected from the group consisting of hydrogen, —C(O)R', —C(O)OR', —C(O)NHR', —P(O)(O$Y^1$)(O$Y^2$), —P(O)(O$Y^1$)(NHR''), substituted or unsubstituted ($C_1$-$C_8$) alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^A$)—$CO_2R^B$; wherein the substituted ($C_1$-$C_8$) alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$) alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$$SO_2$N$R^C$, —S$R^C$, —S(O)$R^C$, —$SO_2R^C$, —$OSO_2$ ($C_1$-$C_6$)alkyl, —$SO_2$N$R^C_2$, —($C_1$-$C_6$)perfluoroalkyl, and —($C_1$-$C_6$)alkylene-O$R^C$;
$R^A$ is selected from the group consisting of —H, —($C_1$-$C_6$)alkyl, —$(CH_2)_3$—NH—C(NH_2)(=NH), —$CH_2$C(=O)$NH_2$, —$CH_2$COOH, —$CH_2$SH, —$(CH_2)_2$C(=O)—$NH_2$, —$(CH_2)_2$COOH, —$CH_2$-(2-imidazolyl), —CH(CH_3)—$CH_2$—$CH_3$, —$CH_2$CH(CH_3)_2, —$(CH_2)_4$—$NH_2$, —$(CH_2)_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —CH(CH_3)_2, and —$CH_2$—$CH_3$;
$R^B$ is hydrogen or —($C_1$-$C_8$)alkyl;
each $R^C$ is independently selected from the group consisting of hydrogen, —($C_1$-$C_8$)alkyl, substituted or unsubstituted pyridyl, substituted or unsubstituted 1,4-dihydropyridyl, a radical of the compound of formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$) alkynyl, halogen, —CN, —$NO_2$, —C(O)$R^B$, —C(O)O$R^B$, —C(O)N$R^B_2$, —C(N$R^B$)N$R^B_2$, —O$R^B$, —OC(O)($C_1$-$C_6$) alkyl, —OC(O)O($C_1$-$C_6$)alkyl, —OC(O)N$R^B_2$, —($C_1$-$C_6$) alkylene-N$R^B_2$, —N$R^B_2$, —N$R^B$C(O)$R^B$, —N$R^B$C(O)O($C_1$-$C_6$)alkyl, —N$R^B$C(O)N$R^B_2$, —N$R^B$$SO_2$N$R^B$, —S$R^B$, —S(O)R$^B$, —SO$_2$R$^B$, —OSO$_2$(C$_1$-C$_6$)alkyl, —SO$_2$NR$^B{}_2$, —(C$_1$-C$_6$)perfluoroalkyl, and —(C$_1$-C$_6$)alkylene-OR$^B$;

R' is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl(C$_1$-C$_4$)alkyl, heterocycle(C$_1$-C$_4$)alkyl, and —C**H—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C{}_2$, —C(=NR$^C$)NR$^C{}_2$, —OR$^C$, —OC(O)(C$_1$-C$_6$)alkyl, —OC(O)O(C$_1$-C$_6$)alkyl, —OC(O)NR$^C{}_2$, —(C$_1$-C$_6$)alkylene-NR$^C{}_2$, —NR$^C{}_2$, —NR$^C$C(O)R$^C$, —NR$^C$C(O)O(C$_1$-C$_6$)alkyl, —NR$^C$C(O)NR$^C{}_2$, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C{}_2$, —(C$_1$-C$_6$)perfluoroalkyl, and —(C$_1$-C$_6$)alkylene-OR$^C$;

R" is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, aryl(C$_1$-C$_4$)alkyl, heterocycle(C$_1$-C$_4$)alkyl, and —C**H—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$) alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C{}_2$, —C(=NR$^C$)NR$^C{}_2$, —OR$^C$, —OC(O)(C$_1$-C$_6$)alkyl, —OC(O)O(C$_1$-C$_6$)alkyl, —OC(O)NR$^C{}_2$, —(C$_1$-C$_6$)alkylene-NR$^C{}_2$, —NR$^C{}_2$, —NR$^C$C(O)R$^C$, —NR$^C$C(O)O(C$_1$-C$_6$) alkyl, —NR$^C$C(O)NR$^C{}_2$, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C{}_2$, —(C$_1$-C$_6$)perfluoroalkyl, and —(C$_1$-C$_6$)alkylene-OR$^C$;

R$^7$ and R$^8$ are independently selected from the group consisting of hydrogen, —C(O)R', —C(O)OR', —C(O)NHR', substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$) alkyl, substituted (C$_1$-C$_8$)cycloalkyl, substituted aryl, substituted heteroaryl, substituted heterocycle, substituted aryl (C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C{}_2$, —C(=NR$^C$)NR$^C{}_2$, —OR$^C$, —OC(O)(C$_1$-C$_6$)alkyl, —OC(O)O(C$_1$-C$_6$)alkyl, —OC(O)NR$^C{}_2$, —(C$_1$-C$_6$)alkylene-NR$^C{}_2$, —NR$^C{}_2$, —NR$^C$C(O)R$^C$, —NR$^C$C(O)O(C$_1$-C$_6$) alkyl, —NR$^C$C(O)NR$^C{}_2$, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C{}_2$, —(C$_1$-C$_6$)perfluoroalkyl, and —(C$_1$-C$_6$)alkylene-OR$^C$;

Y$^1$ and Y$^2$ are independently selected from the group consisting of hydrogen, sodium, potassium, lithium, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle; wherein the substituted (C$_1$-C$_8$) alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$) alkenyl, —(C$_2$-C$_6$)alkynyl, halogen, —CN, —NO$_2$, —C(O)R$^C$, —C(O)OR$^C$, —C(O)NR$^C{}_2$, —C(=NR$^C$)NR$^C{}_2$, —OR$^C$, —OC(O)(C$_1$-C$_6$)alkyl, —OC(O)O(C$_1$-C$_6$)alkyl, —OC(O)NR$^C{}_2$, —(C$_1$-C$_6$)alkylene-NR$^C{}_2$, —NR$^C{}_2$, —NR$^C$C(O)R$^C$, —NR$^C$C(O)O(C$_1$-C$_6$)alkyl, —NR$^C$C(O)NR$^C{}_2$, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C{}_2$, —(C$_1$-C$_6$)perfluoroalkyl, and —(C$_1$-C$_6$)alkylene-OR$^C$; or, alternatively, Y$^1$ and Y$^2$ taken together are selected from the group consisting of sodium, potassium, lithium, magnesium, calcium, strontium, and barium;

provided that when Z$^2$ is NH, the absolute configuration of C** is R or S, or a mixture of R and S.

In yet another embodiment, a method of making a nicotinate/nicotinamide riboside compound or derivative of formula (I), or a salt, hydrate, or solvate thereof, can include the steps of:

(a) providing a nicotinate/nicotinamide riboside compound or derivative having formula (3), or a salt thereof, optionally, in one or more solvent(s); (b) treating the compound or derivative having formula (3), or salt thereof, with at least about one equivalent amount of one or more reagent(s), optionally, in one or more solvent(s); (b)(1) optionally adding a catalyst; (c) reacting the nicotinate/nicotinamide compound or derivative having formula (3), or salt thereof, optionally, in one or more solvent(s), with the one or more reagent(s), optionally, in one or more solvent(s), and, optionally, the catalyst, according to solvent-based chemical laboratory techniques so as to produce the compound or derivative of formula (I), or salt, hydrate, or solvate thereof; (d) adding water to the nicotinate/nicotinamide riboside compound or derivative having formula (3), or salt thereof, optionally, in one or more solvent(s), the one or more reagent(s), optionally, in one or more solvent(s), optionally, the catalyst, and the compound or derivative of formula (I), or salt, hydrate, or solvate thereof; (e) extracting the nicotinate/nicotinamide riboside compound or derivative having formula (3), or salt thereof, optionally, in one or more solvent(s), the one or more reagent(s), optionally, in one or more solvent(s), the compound or derivative having formula (I), or salt, hydrate, or solvate thereof, optionally, the catalyst, and the water, with organic solvent; (e)(1) optionally adjusting the pH of the combined organic extracts with an aqueous solution of acid or base, if necessary; (f) precipitating or isolating the compound or derivative of formula (I), or salt, hydrate, or solvate thereof, or removing the organic solvent used for extraction; and, optionally, (g) purifying the compound or derivative of formula (I), or salt, hydrate, or solvate thereof. This process effects a chemical, solvent-based synthesis of modified conjugates or derivatives of nicotinate/nicotinamide ribonucleoside compounds (NR or NAR, respectively) of formula (I), or salt, hydrate, or solvate thereof.

In yet another embodiment, an alternative method of making a nicotinate/nicotinamide riboside compound or derivative of formula (I), or a salt, hydrate, or solvate thereof, can include the steps of:

(a) providing a nicotinate/nicotinamide riboside compound or derivative having formula (3), or a salt thereof; (b) treating the compound or derivative having formula (3), or salt thereof, with at least about one molar equivalent amount of one or more activated reagent(s); (b)(1) optionally adding a catalyst; (c) mechanically grinding and/or milling the nicotinate/nicotinamide riboside compound or derivative having formula (3), or salt thereof, the one or more activated reagent(s), and, optionally, the catalyst so as to produce the compound or derivative of formula (I), or salt, hydrate, or solvate thereof; (d) adding water to the nicotinate/nicotinamide riboside compound or derivative having formula (3), or salt thereof, the one or more activated reagent(s), the compound or derivative of formula (I), or salt, hydrate, or solvate thereof, and, optionally, the catalyst; (e) extracting the nicotinate/nicotinamide compound or derivative having formula (3), or salt, hydrate, or solvate thereof, the one or more activated reagent(s), optionally, the catalyst, the compound or derivative of formula (I), or salt, hydrate, or solvate thereof, and the water with organic solvent; (e)(1) optionally adjusting the pH of the combined organic extracts with an aqueous solution of acid or base, if necessary; (f) precipitating or isolating the compound or derivative of formula (I), or salt, hydrate, or solvate thereof, or removing the organic solvent used for extraction; and, optionally, (g) purifying the compound or derivative of formula (I), or salt, hydrate, or solvate thereof. This process effects a chemical, mechano-chemical, and/or solvent-free synthesis of modified conjugates or derivatives of nicotinate/nicotinamide ribonucleoside compounds (NR or NAR, respectively) of formula (I), or salt, or solvate thereof.

In accordance with an embodiment of a method of making a nicotinate/nicotinamide riboside compound or derivative of formula (I), or a salt, hydrate, or solvate thereof, there is described a compound or derivative having formula (3), or a salt thereof:

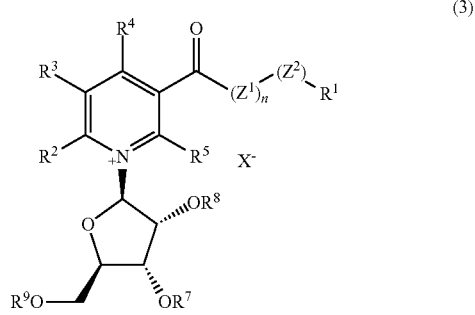

wherein X⁻ is selected from the group consisting of fluoride, chloride, bromide, iodide, formate, acetate, ascorbate, benzoate, carbonate, citrate, carbamate, gluconate, lactate, methyl bromide, methyl sulfate, nitrate, phosphate, diphosphate, succinate, sulfate, trifluoromethanesulfonate, trichloromethanesulfonate, tribromomethanesulfonate, and trifluoroacetate;

$Z^1$ and $Z^2$ are independently NH or oxygen;

n is 0 or 1;

$R^1$ is selected from the group consisting of hydrogen, substituted or unsubstituted $(C_1-C_8)$alkyl, substituted or unsubstituted $(C_1-C_8)$cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^A$)—$CO_2R^B$; wherein the substituted $(C_1-C_8)$alkyl, substituted $(C_1-C_8)$cycloalkyl, substituted aryl, substituted heteroaryl, and substituted heterocycle are substituted with one to five substituents independently selected from the group consisting of —$(C_1-C_6)$alkyl, —$(C_2-C_6)$alkenyl, —$(C_2-C_6)$alkynyl, halogen, —CN, —$NO_2$, —C(O)$R^C$, —C(O)O$R^C$, —C(O)NR$^C_2$, —C(=NR$^C$)NR$^C_2$, —OR$^C$, —OC(O)($C_1-C_6$)alkyl, —OC(O)O($C_1-C_6$)alkyl, —OC(O)NR$^C_2$, —$(C_1-C_6)$alkylene-NR$^C_2$, —NR$^C_2$, —NR$^C$C(O)R$^C$, —NR$^C$C(O)O($C_1-C_6$)alkyl, NR$^C$C(O)NR$^C_2$, —NR$^C$SO$_2$NR$^C$, —SR$^C$, —S(O)R$^C$, —SO$_2$R$^C$, —OSO$_2$($C_1-C_6$)alkyl, —SO$_2$NR$^C_2$, —$(C_1-C_6)$perfluoroalkyl, and —$(C_1-C_6)$alkylene-OR$^C$;

$R_A$ is selected from the group consisting of —H, —($C_1$-$C_6$)alkyl, —$(CH_2)_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$, and —CH$_2$—CH$_3$;

$R^B$ is hydrogen or —($C_1$-$C_8$)alkyl;

each $R^C$ is independently selected from the group consisting of hydrogen, —($C_1$-$C_8$)alkyl, substituted or unsubstituted pyridyl, substituted or unsubstituted 1,4-dihydropyridyl, a radical of the compound of formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —NO$_2$, —C(O)R$^B$, —C(O)OR$^B$, —C(O)NR$^B_2$, —C(=NR$^B$)NR$^B_2$, —OR$^B$, —OC(O)($C_1$-$C_6$)alkyl, —OC(O)O($C_1$-$C_6$)alkyl, —OC(O)NR$^B_2$, —($C_1$-$C_6$)alkylene-NR$^B_2$, —NR$^B_2$, —NR$^B$C(O)R$^B$, —NR$^B$C(O)O($C_1$-$C_6$)alkyl, —NR$^B$C(O)NR$^B_2$, —NR$^B$SO$_2$NR$^B$, —SR$^B$, —S(O)R$^B$, —SO$_2$R$^B$, —OSO$_2$($C_1$-$C_6$)alkyl, —SO$_2$NR$^B_2$, —($C_1$-$C_6$)perfluoroalkyl, and —($C_1$-$C_6$)alkylene-OR$^B$;

$R^2$, $R^3$, $R^4$, and $R^5$ are each independently selected from the group consisting of hydrogen, —($C_1$-$C_6$)alkyl, —($C_2$-$C_6$)alkenyl, —($C_2$-$C_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)($C_1$-$C_6$)alkyl, —OC(O)O($C_1$-$C_6$)alkyl, —OC(O)NR$^C_2$, —($C_1$-$C_6$)alkylene-NR$^C_2$, —NR$^C_2$, —NR$^C$C(O)R$^C$, —NR$^C$C(O)O($C_1$-$C_6$)alkyl, —NR$^C$C(O)NR$^C_2$, —NR$^C$SO$_2$NR$^C$, —SR$^C$, —S(O)R$^C$, —SO$_2$R$^C$, —OSO$_2$($C_1$-$C_6$)alkyl, —SO$_2$NR$^C_2$, —($C_1$-$C_6$)perfluoroalkyl, and —($C_1$-$C_6$)alkylene-OR$^C$;

$R^7$ and $R^8$ are independently selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$)cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)($C_1$-$C_6$)alkyl, —OC(O)O($C_1$-$C_6$)alkyl, —OC(O)NR$^C_2$, —($C_1$-$C_6$)alkylene-NR$^C_2$, —NR$^C_2$, —NR$^C$C(O)R$^C$, —NR$^C$C(O)O($C_1$-$C_6$)alkyl, —NR$^C$C(O)NR$^C_2$, —NR$^C$SO$_2$NR$^C$, —SR$^C$, —S(O)R$^C$, —SO$_2$R$^C$, —OSO$_2$($C_1$-$C_6$)alkyl, —SO$_2$NR$^C_2$, —($C_1$-$C_6$)perfluoroalkyl, and —($C_1$-$C_6$)alkylene-OR$^C$;

R' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_8$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C$, —S$R^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-O$R^C$;

$R^9$ is selected from the group consisting of hydrogen, —C(O)R', —C(O)OR', —C(O)NHR', —P(O)(O$Y^1$)(O$Y^2$), —P(O)(O$Y^1$)(NHR''), substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^A$)—$CO_2R^B$; wherein the substituted ($C_1$-$C_8$)alkyl, substituted ($C_1$-$C_8$)cycloalkyl, substituted aryl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C$, —S$R^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-O$R^C$;

R'' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, ($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2NR^C$, —S$R^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-O$R^C$;

$Y^1$ and $Y^2$ are independently selected from the group consisting of hydrogen, sodium, potassium, lithium, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2NR^C$, —S$R^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-O$R^C$; or, alternatively, $Y^1$ and $Y^2$ taken together are selected from the group consisting of sodium, potassium, lithium, magnesium, calcium, strontium, and barium;

provided that when $Z^2$ is NH, the absolute configuration of C** is R or S, or a mixture of R and S.

In yet another embodiment, a method of making a nicotinate/nicotinamide riboside compound or derivative of formula (I), or a salt, hydrate, or solvate thereof, can include the steps of:

(a) providing a reduced nicotinate/nicotinamide riboside compound or derivative (II), or a salt, hydrate, or solvate thereof; (b) oxidizing the reduced nicotinate/nicotinamide riboside compound or derivative of formula (II), or salt, hydrate, or solvate thereof, with at least about one molar equivalent amount of an oxidizing agent, optionally, in one or more solvent(s), so as to produce the compound or derivative of formula (I), or salt, hydrate, or solvate thereof; (c) precipitating or isolating the compound or derivative of formula (I), or salt, hydrate, or solvate thereof, or removing the one or more solvent(s); and, optionally, (d) purifying the compound or derivative of formula (I), or salt, hydrate, or solvate thereof. This process effects a chemical, solvent-based synthesis of modified conjugates or derivatives of nicotinate/nicotinamide riboside compounds (NR or NAR, respectively) of formula (I), or salt, hydrate, or solvate thereof.

In yet another embodiment, an alternative method of making a nicotinate/nicotinamide riboside compound or derivative (I), or a salt, hydrate, or solvate thereof, can include the steps of:

(a) providing a reduced nicotinate/nicotinamide riboside compound or derivative of formula (II), or a salt, hydrate, or solvate thereof; (b) oxidizing the reduced nicotinate/nicotinamide riboside compound or derivative of formula (II), or salt, hydrate, or solvate thereof, with at least about one molar equivalent amount of an oxidizing agent, so as to produce the compound or derivative of formula (I), or salt, hydrate, or solvate thereof; and, optionally, (c) purifying and/or isolating the compound or derivative of formula (I), or salt, hydrate, or solvate thereof. This process effects a chemical, mechano-chemical, and/or solvent-free synthesis of modified conjugates or derivatives of nicotinate/nicotinamide riboside compounds (NR or NAR, respectively) of formula (I), or salt, hydrate, or solvate thereof.

In an embodiment, a method of making a reduced nicotinate/nicotinamide riboside compound or derivative of formula (II), or a salt, hydrate, or solvate thereof, can include the steps of:

(a) providing a reduced nicotinate/nicotinamide riboside compound or derivative having formula (4), or a salt thereof, optionally, in one or more solvent(s); (b) treating the compound or derivative having formula (4), or salt thereof, optionally, in one or more solvent(s) with at least about 0.5 molar equivalent amount of one or more activated reagent(s), optionally, in one or more solvent(s); (b)(1) optionally adding a catalyst; (c) reacting the reduced nicotinate/nicotinamide riboside compound or derivative having formula (4), or salt thereof, optionally, in one or more solvent(s), with the one or more activated reagent(s), optionally, in one or more solvent(s), and, optionally, the catalyst, according to solvent-based chemical laboratory techniques so as to produce the compound or derivative of formula (II), or salt, hydrate, or solvate thereof; (d) adding water to the reduced nicotinate/nicotinamide riboside compound or derivative having formula (4), or salt thereof, optionally, in one or more solvent(s), the one or more activated reagent(s), optionally, in one or more solvent(s), optionally, the catalyst, and the compound or derivative of formula (II), or salt, hydrate, or solvate thereof; (e) extracting the reduced nicotinate/nicotinamide riboside compound or derivative having formula (4), or salt thereof, optionally, in one or more solvent(s), the one or more activated reagent(s), optionally, in one or more solvent(s), the compound or derivative of formula (II), or salt, hydrate, or solvate thereof, optionally, the catalyst, and the water with organic solvent; (e)(1) optionally adjusting the pH of the combined organic extracts with an aqueous solution of acid or base, if necessary; (f) precipitating or isolating the compound or derivative of formula (II), or salt, hydrate, or solvate thereof, or removing the organic solvent used for extraction; and, optionally, (g) purifying the compound or derivative of formula (II), or salt, hydrate, or solvate thereof. This process effects a chemical, solvent-based synthesis of modified conjugates or derivatives of reduced nicotinate/nicotinamide ribonucleoside compounds (NRH or NARH, respectively) of formula (II), or salt, hydrate, or solvate thereof.

In another embodiment, an alternative method of making a reduced nicotinate/nicotinamide riboside compound or derivative of formula (II), or a salt, hydrate, or solvate thereof, can include the steps of:

(a) providing a reduced nicotinate/nicotinamide riboside compound or derivative having formula (4), or a salt thereof; (b) treating the compound or derivative having formula (4), or salt thereof, with at least about 0.5 molar equivalent amount of one or more activated reagent(s); (b)(1) optionally adding a catalyst; (c) mechanically grinding and/or milling the compound or derivative having formula (4), or salt thereof, the one or more activated reagent(s), and, optionally, the catalyst, so as to produce the compound or derivative of formula (II), or salt, hydrate, or solvate thereof; (d) adding water to the compound or derivative having formula (4), or salt thereof, the one or more activated reagent(s), optionally, the catalyst, and the compound or derivative of formula (II), or salt, hydrate, or solvate thereof; (e) extracting the compound or derivative having formula (4), or salt thereof, the one or more activated reagent(s), optionally, the catalyst, and the compound or derivative of formula (II), or salt, hydrate, or solvate thereof with organic solvent; (e)(1) optionally adjusting the pH of the combined organic extracts with an aqueous solution of acid or base, if necessary; (f) precipitating or isolating the compound or derivative of formula (II), or salt, hydrate, or solvate thereof, or removing the organic solvent used for extraction; and, optionally, (g) purifying the compound of formula (II), or salt, hydrate, or solvate thereof. This process effects a chemical, mechano-chemical, and/or solvent-free synthesis of modified conjugates or derivatives of reduced nicotinate/nicotinamide ribonucleoside compounds (NRH or NARH, respectively) of formula (II), or salt, hydrate, or solvate thereof.

In accordance with an embodiment, there is described a reduced nicotinate/nicotinamide riboside compound or derivative having formula (4), or a salt thereof:

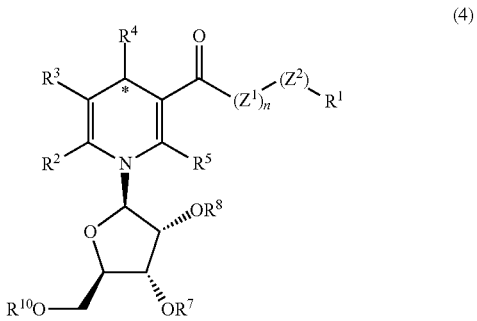

(4)

wherein $Z^1$ and $Z^2$ are independently NH or oxygen;
n is 0 or 1;
$R^1$ is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —$NR^C$C(O)$R^C$, —$NR^C$C(O)O($C_1$-$C_6$)alkyl, —$NR^C$C(O)N$R^C_2$, —$NR^C$$SO_2$N$R^C$, —$SR^C$, —S(O)$R^C$, —$SO_2R^C$, —$OSO_2$($C_1$-$C_6$)alkyl, —$SO_2$N$R^C_2$, —($C_1$-$C_6$)perfluoroalkyl, and —($C_1$-$C_6$)alkylene-O$R^C$;

$R^A$ is selected from the group consisting of —H, —($C_1$-$C_6$)alkyl, —($CH_2$)$_3$—NH—C($NH_2$)(=NH), —$CH_2$C(=O)$NH_2$, —$CH_2$COOH, —$CH_2$SH, —($CH_2$)$_2$C(=O)—$NH_2$, —($CH_2$)$_2$COOH, —$CH_2$-(2-imidazolyl), —CH($CH_3$)—$CH_2$—$CH_3$, —$CH_2$CH($CH_3$)$_2$, —($CH_2$)$_4$—$NH_2$, —($CH_2$)$_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —CH($CH_3$)$_2$, and —$CH_2$—$CH_3$;

$R^B$ is hydrogen or —($C_1$-$C_8$)alkyl;

each $R^C$ is independently selected from the group consisting of hydrogen, —($C_1$-$C_8$)alkyl, substituted or unsubstituted pyridyl, substituted or unsubstituted 1,4-dihydropyridyl, a radical of the compound of formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^B$, —C(O)O$R^B$, —C(O)N$R^B_2$, —C(=N$R^B$)N$R^B_2$, —O$R^B$, —OC(O)($C_1$-$C_6$)alkyl, —OC(O)O($C_1$-$C_6$)alkyl, —OC(O)N$R^B_2$, —($C_1$-$C_6$)alkylene-N$R^B_2$, —N$R^B_2$, —$NR^B$C(O)$R^B$, —$NR^B$C(O)O($C_1$-$C_6$)alkyl, —$NR^B$C(O)N$R^B_2$, —$NR^B$$SO_2$N$R^B$, —$SR^B$, —S(O)$R^B$, —$SO_2R^B$, —$OSO_2$($C_1$-$C_6$)alkyl, —$SO_2$N$R^B_2$, —($C_1$-$C_6$)perfluoroalkyl, and —($C_1$-$C_6$)alkylene-O$R^B$;

$R^2$ and $R^3$ are each independently selected from the group consisting of hydrogen, —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —$NR^C$C(O)$R^C$, —$NR^C$C(O)O($C_1$-$C_6$)alkyl, —$NR^C$C(O)N$R^C_2$, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R$^4$ is selected from the group consisting of hydrogen, —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and (C$_1$-C$_6$)alkylene-OR$^C$;

provided that C* has an absolute configuration of R or S, or a mixture of R and S;

R$^5$ is selected from the group consisting of hydrogen, —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene OR$^C$;

R$^7$ and R$^8$ are independently selected from the group consisting of hydrogen, —C(O)R', —C(O)OR', —C(O)NHR', substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$)alkyl, substituted (C$_1$-C$_8$)cycloalkyl, substituted aryl, substituted heteroaryl, substituted heterocycle, substituted aryl(C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R' is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl(C$_1$-C$_4$)alkyl, heterocycle(C$_1$-C$_4$)alkyl, and —C**H—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R$^{10}$ is selected from the group consisting of hydrogen, —C(O)R', —C(O)OR', —C(O)NHR', —P(O)(OY$^1$)(OY$^2$), —P(O)(OY$^1$)(NHR"), substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —C$_1$-C$_6$)alkylene—NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R" is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, aryl(C$_1$-C$_4$)alkyl, heterocycle(C$_1$-C$_4$)alkyl, and —C**H—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

Y$^1$ and Y$^2$ are independently selected from the group consisting of hydrogen, sodium, potassium, lithium, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_8$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$; or, alternatively, Y$^1$ and Y$^2$ taken together are selected from the group consisting of sodium, potassium, lithium, magnesium, calcium, strontium, and barium;

provided that when Z$^2$ is NH, the absolute configuration of C** is R or S, or a mixture of R and S.

In yet another embodiment, a method of making a reduced nicotinate/nicotinamide riboside compound or derivative of formula (II), or a salt, hydrate, or solvate thereof, can include the steps of:

(a) providing a reduced nicotinate/nicotinamide riboside compound or derivative of formula (II), or a salt, hydrate, or solvate thereof; (b) reducing the compound or derivative of formula (I), or salt, hydrate, or solvate thereof, with at least about one molar equivalent amount of a reducing agent, optionally, in one or more solvent(s), so as to produce the compound or derivative of formula (II), or salt, hydrate, or solvate thereof; (c) precipitating or isolating the compound or derivative of formula (II), or salt, hydrate, or solvate thereof, or removing the one or more solvent(s); and, optionally, (d) precipitating the compound or derivative of formula (II), or salt, hydrate, or solvate thereof. This process effects a chemical, solvent-based synthesis of modified conjugates or derivatives of reduced nicotinate/nicotinamide riboside compounds (NRH or NARH, respectively) of formula (II), or salt, hydrate, or solvate thereof.

In yet another embodiment, an alternative method of making a reduced nicotinate/nicotinamide riboside compound or derivative of formula (II), or a salt, hydrate, or solvate thereof, can include the steps of:

(a) providing a reduced nicotinate/nicotinamide riboside compound or derivative of formula (II), or a salt, hydrate, or solvate thereof; (b) reducing a compound or derivative of formula (I), or salt, hydrate, or solvate thereof, with at least one molar equivalent amount of a reducing agent so as to produce the compound or derivative of formula (II), or salt, hydrate, or solvate thereof; and, optionally, (c) purifying and/or isolating the compound or derivative of formula (II), or salt, hydrate, or solvate thereof. This process effects a chemical, mechano-chemical, and/or solvent-free synthesis of modified conjugates or derivatives of reduced nicotinate/nicotinamide ribonucleoside compounds (NRH or NARH, respectively) of formula (II), or salt, hydrate, or solvate thereof.

In yet another embodiment, a method of making a reduced nicotinate/nicotinamide riboside compound or derivative of formula (II), or a salt, hydrate, or solvate thereof, can include the steps of:

(a) providing a nicotinate/nicotinamide riboside compound or derivative having formula (3), or a salt thereof, optionally, in one or more solvent(s); (b) treating the compound or derivative having formula (3), or salt thereof, optionally, in one or more solvent(s), with at least one molar equivalent amount of one or more activated reducing reagent(s), optionally, in one or more solvent(s); (b)(1) optionally adding a catalyst; (c) reacting the nicotinate/nicotinamide compound or derivative having formula (3), or salt thereof, optionally, in one or more solvent(s), with the one or more activated reducing reagent(s), optionally, in one or more solvent(s), and, optionally, the catalyst, so as to produce the compound or derivative of formula (II), or salt, hydrate, or solvate thereof; (d) adding water to the nicotinate/nicotinamide compound or derivative having formula (3), or salt thereof, optionally, in one or more solvent(s), the one or more activated reducing reagent(s), optionally, in one or more solvent(s), optionally, the catalyst, and the compound or derivative of formula (II), or salt, hydrate, or solvate thereof; (e) extracting the nicotinate/nicotinamide compound or derivative having formula (3), or salt thereof, optionally, in one or more solvent(s), the one or more activated reducing reagent(s), optionally, in one or more solvent(s), the compound or derivative of formula (II), or salt, hydrate, or solvate thereof, optionally, the catalyst, and the water with organic solvent; (e)(1) optionally adjusting the pH of the combined organic extracts with an aqueous solution of acid or base, if necessary; (f) precipitating or isolating the compound or derivative of formula (II), or salt, hydrate, or solvate thereof, or removing the organic solvent used for extraction; and, optionally, (g) purifying the compound or derivative of formula (II), or salt, hydrate, or solvate thereof. This process effects a chemical, solvent-based synthesis of modified conjugates or derivatives of reduced nicotinate/nicotinamide riboside compounds (NRH or NARH, respectively) of formula (II), or salt, hydrate, or solvate thereof. Without limitation, and for illustrative purposes, one of ordinary skill in the art may refer to WO2015014722 A1, filed on Jul. 24, 2014, and incorporated by reference herein in its entirety, for further details on performing the above method(s).

In yet another embodiment, an alternative method of making a reduced nicotinate/nicotinamide riboside compound or derivative of formula (II), or a salt, hydrate, or solvate thereof, can include the steps of:

(a) providing a nicotinate/nicotinamide riboside compound or derivative having formula (3), or a salt thereof; (b) treating the compound or derivative having formula (3), or salt thereof, with at least about one molar equivalent amount of one or more activated reducing reagent(s); (b)(1) optionally adding a catalyst; (c) mechanically grinding and/or milling the nicotinate/nicotinamide riboside compound or derivative having formula (3), or salt thereof, the one or more activated reducing reagent(s), and, optionally, the catalyst, so as to produce the compound or derivative of formula (II), or salt, hydrate, or solvate thereof; (d) adding water to the nicotinate/nicotinamide riboside compound or derivative having formula (3), or salt thereof, the one or more activated reducing reagent(s), optionally, the catalyst, and the compound or derivative of formula (II), or salt, hydrate, or solvate thereof; (e) extracting the nicotinate/nicotinamide riboside compound or derivative having formula (3), or salt thereof, the one or more activated reducing reagent(s), the compound or derivative of formula (II), or salt, hydrate, or solvate thereof, optionally, the catalyst, and the water with organic solvent; (e)(1) optionally adjusting the pH of the combined organic extracts with an aqueous solution of acid or base, if necessary; (f) precipitating or isolating the compound or derivative of formula (II), or salt, hydrate, or solvate thereof, or removing the organic solvent used for extraction; and, optionally, (g) purifying the compound or derivative of formula (II), or salt, hydrate, or solvate thereof. This process effects a chemical, mechano-chemical, and/or solvent-free synthesis of modified conjugates or derivatives of reduced nicotinate/nicotinamide riboside compounds (NRH or NARH, respectively) of formula (II), or salt, hydrate, or solvate thereof.

DETAILED DESCRIPTION

In one aspect, the present invention surprisingly demonstrates novel modified conjugates or derivatives of nicotinamide riboside ("NR"), nicotinic acid riboside ("NAR"), reduced or modified forms thereof ("NRH" and "NARH," respectively), and processes to prepare said novel conjugates or derivatives and reduced forms thereof. In an embodiment, novel modified conjugates or derivatives of nicotinamide riboside (NR) and/or reduced or modified forms thereof (NRH) are described. In another embodiment, novel modified conjugates or derivatives of nicotinic acid riboside (NAR) and/or reduced or modified forms thereof (NARH) are described. In yet another embodiment, the preparation of nicotinamide riboside (NR) and/or reduced or modified forms thereof (NRH) are described, employing solvent-based chemical laboratory techniques. In yet another embodiment, the preparation of nicotinamide riboside (NR) and/or reduced or modified forms thereof (NRH) are described. Solvent-free conditions are employed in combination with appropriate mechano-chemical techniques. This combination yields a process that is atom-efficient in terms of reagent equivalency, that bypasses the need for polar solvents, and that is versatile in terms of limitations associated with reagents' solubility and reagents' mixing. In yet another embodiment, the preparation of nicotinic acid riboside (NAR) and/or reduced or modified forms thereof (NARH) are described, employing solvent-based chemical laboratory techniques. In yet another embodiment, the preparation of nicotinic acid riboside (NAR) and/or reduced or modified forms thereof (NARH) are described. Solvent-free conditions are employed in combination with appropriate mechano-chemical techniques. This combination yields a process that is atom-efficient in terms of reagent equivalency, that bypasses the need for polar solvents, and that is versatile in terms of limitations associated with reagents' solubility and reagents' mixing.

In certain embodiments, the processes for preparation of the novel modified conjugates or derivatives of nicotinamide riboside (NR), nicotinic acid riboside (NAR), and/or reduced or modified forms thereof (NRH and NARH, respectively), of the present disclosure, include solvent-based chemical laboratory techniques, and enable efficient production of many different compounds to produce conjugates or derivatives.

In certain embodiments, the processes for preparation of the novel modified conjugates or derivatives of nicotinamide riboside (NR), nicotinic acid riboside (NAR), and/or reduced or modified forms thereof (NRH and NARH, respectively), of the present disclosure, include milling, grinding, and all related continuous processes including extrusion, and enable efficient production of many different compounds to produce conjugates or derivatives under a solvent-free production protocol.

In certain embodiments, the processes for preparation of the novel modified conjugates or derivatives of nicotinamide riboside (NR), nicotinic acid riboside (NAR), and/or reduced or modified forms thereof (NRH and NARH, respectively), of the present disclosure, include solvent-based chemical laboratory techniques.

In certain embodiments, the processes for preparation of the novel modified conjugates or derivatives of nicotinamide riboside (NR), nicotinic acid riboside (NAR), and/or reduced or modified forms thereof (NRH and NARH, respectively), of the present disclosure, include grinding the respective components together in a mechano-chemical fashion utilizing mills such as ball mills, planetary mills, extruders, etc.

The embodiments of the processes for preparation of the novel modified conjugates or derivatives of nicotinamide riboside (NR), nicotinic acid riboside (NAR), and/or reduced or modified forms thereof (NRH and NARH, respectively), of the present disclosure, using solvent-based chemical laboratory techniques, have not been demonstrated before, particularly for producing biologically relevant nucleosides, such as nicotinamide mononucleotide ("NMN"), nicotinic acid mononucleotide ("NaMN"), the reduced analogs thereof ("NMNH" and "NaMNH," respectively), and the like. The preparation technology has the ability to produce several other modified conjugates or derivatives efficiently including isotopically labeled derivatives.

The embodiments of the processes for preparation of the novel modified conjugates or derivatives of nicotinamide riboside (NR), nicotinic acid riboside (NAR), and/or reduced or modified forms thereof (NRH and NARH, respectively), of the present-disclosure, using mechano-chemical principles have not been demonstrated before, particularly for producing biologically relevant nucleosides, such as NMN, NaMN, NMNH, and NaMNII, and the like. The preparation technology has the ability to produce several other modified conjugates or derivatives efficiently including isotopically labeled derivatives.

Additionally, the embodiments of the processes for preparation of the novel modified conjugates or derivatives of nicotinamide riboside (NR), nicotinic acid riboside (NAR), and/or reduced or modified forms thereof (NRH and NARH, respectively), address limitations of existing technologies.

In accordance with an embodiment, prototype product nicotinate/nicotinamide ribonucleoside compounds (NR or NAR, respectively) include nicotinate/nicotinamide riboside compounds or derivatives of formula (I), or a salt, hydrate, or solvate thereof:

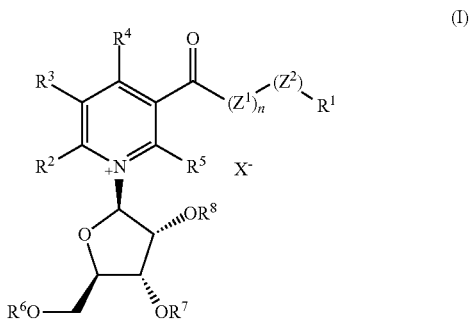

wherein $X^-$ is selected from the group consisting of fluoride, chloride, bromide, iodide, formate, acetate, ascorbate, benzoate, carbonate, citrate, carbamate, formate, gluconate, lactate, methyl bromide, methyl sulfate, nitrate, phosphate, diphosphate, succinate, sulfate, trifluoromethanesulfonate, trichloromethanesulfonate, tribromomethanesulfonate, and trifluoroacetate;

optionally wherein when $X^-$ as counterion is absent optionally the counterion is an internal salt;

optionally $X^-$ is an anion of a substituted or unsubstituted carboxylic acid selected from a monocarboxylic acid, a dicarboxylic acid, or a polycarboxylic acid; and, optionally $X^-$ is an anion of a substituted monocarboxylic acid, further optionally an anion of a substituted propanoic acid (propanoate or propionate), or an anion of a substituted acetic acid (acetate), or an anion of a hydroxyl-propanoic acid, or an anion of 2-hydroxypropanoic acid (being lactic acid; the anion of lactic acid being lactate), or a trihaloacetate selected from trichloroacetate, tribromoacetate, and trifluoroacetate; and, optionally $X^-$ is an anion of an unsubstituted monocarboxylic acid selected from formic acid, acetic acid, propionic acid, or butyric acid, being formate, acetate, propionate, and butyrate, respectively; and, optionally $X^-$ is an anion of a substituted or unsubstituted amino acid, i.e., amino-monocarboxylic acid or an amino-dicarboxylic acid, optionally selected from glutamic acid and aspartic acid, being glutamate and aspartate, respectively; and, optionally $X^-$ is an anion of ascorbic acid, being ascorbate; and, optionally $X^-$ is a halide selected from fluoride, chloride, bromide, or iodide; and, optionally $X^-$ is an anion of a substituted or unsubstituted sulfonate, further optionally a trihalomethanesulfonate selected from trifluoromethanesulfonate, tribromomethanesulfonate, or trichloromethanesulfonate; and, optionally X⁻ is an anion of a substituted or unsubstituted carboxylic acid, further optionally hydrogen carbonate;

wherein the substituted carboxylic acid, substituted monocarboxylic acid, substituted propanoic acid, the substituted acetic acid, substituted amino acid, substituted sulfonate, and substituted carbonate are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-$OR^C$;

$Z^1$ and $Z^2$ are independently NH or oxygen;

n is 0 or 1;

$R^1$ is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-$OR^C$;

$R^A$ is selected from the group consisting of —H, —($C_1$-$C_6$)alkyl, —($CH_2$)$_3$—NH—C($NH_2$)(=NH), —$CH_2$C(=O)$NH_2$, —$CH_2$COOH, —$CH_2$SH, —($CH_2$)$_2$C(=O)—$NH_2$, —($CH_2$)$_2$COOH, —$CH_2$-(2-imidazolyl), —CH($CH_3$)—$CH_2$—$CH_3$, —$CH_2$CH($CH_3$)$_2$, —($CH_2$)$_4$—$NH_2$, —($CH_2$)$_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —CH($CH_3$)$_2$, and —$CH_2$—$CH_3$;

$R^B$ is hydrogen or —($C_1$-$C_8$)alkyl;

each $R^C$ is independently selected from the group consisting of hydrogen, —($C_1$-$C_8$)alkyl, substituted or unsubstituted pyridyl, substituted or unsubstituted 1,4-dihydropyridyl, a radical of the compound of formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^B$, —C(O)O$R^B$, —C(O)$NR^B_2$, —C(=$NR^B$)$NR^B_2$, —$OR^B$, —OC(O)($C_1$-$C_6$)alkyl, —OC(O)O($C_1$-$C_6$)alkyl, —OC(O)$NR^B_2$, —($C_1$-$C_6$)alkylene-$NR^B_2$, —$NR^B_2$, —$NR^B$C(O)$R^B$, —$NR^B$C(O)O($C_1$-$C_6$)alkyl, —$NR^B$C(O)$NR^B_2$, —$NR^B$$SO_2$$NR^B$, —$SR^B$, —S(O)$R^B$, —$SO_2R^B$, —$OSO_2$($C_1$-$C_6$)alkyl, —$SO_2NR^B_2$, —($C_1$-$C_6$)perfluoroalkyl, and —($C_1$-$C_6$)alkylene-$OR^B$;

$R^2$, $R^3$, $R^4$, and $R^5$ are each independently selected from the group consisting of hydrogen, —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-$OR^C$;

$R^6$ is selected from the group consisting of hydrogen, —C(O)R', —C(O)OR', —C(O)NHR', —P(O)($OY^1$)($OY^2$), —P(O)($OY^1$)(NHR''), substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$)alkylene $NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-$OR^C$;

R' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-$OR^C$;

R'' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—($R^A$)—$CO_2R^B$; wherein the substituted ($C_1$-$C_7$)alkyl, substituted ($C_1$-$C_7$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C$, —$SR^C$, —S(O)$R^C$, —$SO_2R^C$, —$OSO_2$($C_1$-$C_6$)alkyl, —$SO_2NR^C_2$, —($C_1$-$C_8$)perfluoroalkyl, and —($C_1$-$C_8$)alkylene-$OR^C$;

$R^7$ and $R^8$ are independently selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$) alkyl, substituted ($C_1$-$C_8$)cycloalkyl, substituted aryl, substituted heteroaryl, substituted heterocycle, substituted aryl ($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C{}_2$, —C(=N$R^C$)N$R^C{}_2$, —O$R^C$, —OC(O)($C_1$-$C_6$)alkyl, —OC(O)O($C_1$-$C_6$)alkyl, —OC(O)N$R^C{}_2$, —($C_1$-$C_6$)alkylene-N$R^C{}_2$, —N$R^C{}_2$, —N$R^C$C(O)$R^C$, —N$R^C$C(O)O($C_1$-$C_6$)alkyl, —N$R^C$C(O)N$R^C{}_2$, —N$R^C$SO$_2$N$R^C$, —S$R^C$, —S(O)$R^C$, —SO$_2R^C$, —OSO$_2$($C_1$-$C_6$)allyl, —SO$_2$N$R^C{}_2$, —($C_1$-$C_6$)perfluoroalkyl, and —($C_1$-$C_6$)alkylene-O$R^C$;

$Y^1$ and $Y^2$ are independently selected from the group consisting of hydrogen, sodium, potassium, lithium, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle; wherein the substituted ($C_1$-$C_8$) alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C{}_2$, —C(=N$R^C$)N$R^C{}_2$, —O$R^C$, —OC(O)($C_1$-$C_6$)alkyl, —OC(O)O($C_1$-$C_6$)alkyl, —OC(O)N$R^C{}_2$, —($C_1$-$C_6$)alkylene N$R^C{}_2$, —N$R^C{}_2$, —N$R^C$C(O)$R^C$, —N$R^C$C(O)O($C_1$-$C_6$)alkyl, —N$R^C$C(O)N$R^C{}_2$, —N$R^C$SO$_2$N$R^C$, —S$R^C$, —S(O)$R^C$, —SO$_2R^C$, —OSO$_2$($C_1$-$C_6$)alkyl, —SO$_2$N$R^C{}_2$, —($C_1$-$C_6$)perfluoroalkyl, and —($C_1$-$C_6$)alkylene-O$R^C$; or, alternatively, $Y^1$ and $Y^2$ taken together are selected from the group consisting of sodium, potassium, lithium, magnesium, calcium, strontium, and barium;

provided that when $Z^2$ is NH, the absolute configuration of C** is R or S, or a mixture of R and S;

further provided that when n is 0, $Z^2$ is NH, and $R^1$ is hydrogen, then $R^6$, $R^7$, and $R^8$ are not all simultaneously hydrogen;

further provided that when n is 0, $Z^2$ is oxygen, and $R^1$ is hydrogen, then $R^6$, $R^7$, and $R^8$ are not all simultaneously hydrogen, acetyl, or benzoyl; and further provided that when n is 0, $Z^2$ is oxygen, and $R^1$ is —($C_1$-$C_8$)alkyl, then $R^6$, $R^7$, and $R^8$ are not all simultaneously acetyl or benzoyl.

In accordance with an alternative embodiment, prototype product nicotinate/nicotinamide ribonucleoside compounds (NR or NAR, respectively) include nicotinate/nicotinamide riboside compounds or derivatives of formula (I), or a salt, hydrate, or solvate thereof:

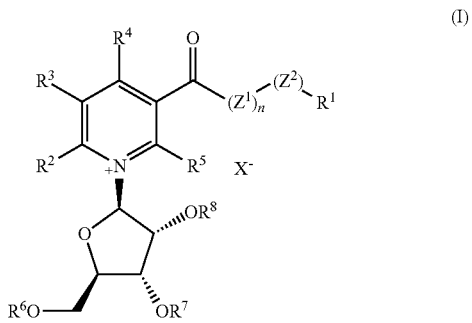

(I)

wherein $X^-$ is selected from the group consisting of fluoride, chloride, bromide, iodide, formate, acetate, ascorbate, benzoate, carbonate, citrate, carbamate, formate, gluconate, lactate, methyl bromide, methyl sulfate, nitrate, phosphate, diphosphate, succinate, sulfate, trifluoromethanesulfonate, trichloromethanesulfonate, tribromomethanesulfonate, and trifluoroacetate;

optionally wherein when $X^-$ is absent optionally the counterion is an internal salt;

optionally $X^-$ is an anion of a substituted or unsubstituted carboxylic acid selected from a monocarboxylic acid, a dicarboxylic acid, or a polycarboxylic acid; and, optionally $X^-$ is an anion of a substituted monocarboxylic acid, further optionally an anion of a substituted propanoic acid (propanoate or propionate), or an anion of a substituted acetic acid (acetate), or an anion of a hydroxyl-propanoic acid, or an anion of 2-hydroxypropanoic acid (being lactic acid; the anion of lactic acid being lactate), or a trihaloacetate selected from trichloroacetate, tribromoacetate, and trifluoroacetate; and, optionally $X^-$ is an anion of an unsubstituted monocarboxylic acid selected from formic acid, acetic acid, propionic acid, or butyric acid, being formate, acetate, propionate, and butyrate, respectively; and, optionally $X^-$ is an anion of a substituted or unsubstituted amino acid, i.e., amino-monocarboxylic acid or an amino-dicarboxylic acid, optionally selected from glutamic acid and aspartic acid, being glutamate and aspartate, respectively; and, optionally $X^-$ is an anion of ascorbic acid, being ascorbate; and, optionally $X^-$ is a halide selected from fluoride, chloride, bromide, or iodide; and, optionally $X^-$ is an anion of a substituted or unsubstituted sulfonate, further optionally a trihalomethanesulfonate selected from trifluoromethanesulfonate, tribromomethanesulfonate, or trichloromethanesulfonate; and, optionally $X^-$ is an anion of a substituted or unsubstituted carbonate, further optionally hydrogen carbonate;

wherein the substituted carboxylic acid, substituted monocarboxylic acid, substituted propanoic acid, substituted acetic acid, substituted amino acid, substituted sulfonate, and substituted carbonate are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C{}_2$, —C(=N$R^C$)N$R^C{}_2$, —O$R^C$, —OC(O)($C_1$-$C_6$)alkyl, —OC(O)O($C_1$-$C_6$)alkyl, —OC(O)N$R^C{}_2$, —($C_1$-$C_6$)alkylene-N$R^C{}_2$, —N$R^C{}_2$, —N$R^C$C(O)$R^C$, —N$R^C$C(O)O($C_1$-$C_6$)alkyl, —N$R^C$C(O)N$R^C{}_2$, —N$R^C$SO$_2$N$R^C$, —S$R^C$, —S(O)$R^C$, —SO$_2R^C$, —OSO$_2$($C_1$-$C_6$)alkyl, —SO$_2$N$R^C{}_2$, —($C_1$-$C_6$)perfluoroalkyl, and —($C_1$-$C_6$)alkylene-O$R^C$;

$Z^1$ and $Z^2$ are independently NH or oxygen;

n is 0 or 1;

$R^1$ is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^4$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —OR, —OC(O)($C_1$-$C_6$)alkyl, —OC(O)O($C_1$-$C_6$)alkyl, —OC(O)N$R^C_2$, —($C_1$-$C_6$)alkylene N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$$SO_2$N$R^C$, —S$R^C$, —S(O)$R^C$, —$SO_2R^C$, —$OSO_2$($C_1$-$C_6$)alkyl, —$SO_2$N$R^C_2$, —($C_1$-$C_6$)perfluoroalkyl, and —($C_1$-$C_6$)alkylene-O$R^C$;

$R^4$ is selected from the group consisting of —H, —($C_1$-$C_6$)alkyl, —($CH_2$)$_3$—NH—C($NH_2$)(=NH), —$CH_2$C(=O)$NH_2$, —$CH_2$COOH, —$CH_2$SH, —($CH_2$)$_2$C(=O)—$NH_2$, —($CH_2$)$_2$COOH, —$CH_2$-(2-imidazolyl), —CH($CH_3$)—$CH_2$—$CH_3$, —$CH_2$CH($CH_3$)$_2$, —($CH_2$)$_4$—$NH_2$, —($CH_2$)$_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —CH($CH_3$)$_2$, and —$CH_2$—$CH_3$;

$R^B$ is hydrogen or —($C_1$-$C_8$)alkyl;

each $R^C$ is independently selected from the group consisting of hydrogen, —($C_1$-$C_8$)alkyl, substituted or unsubstituted pyridyl, substituted or unsubstituted 1,4-dihydropyridyl, a radical of the compound of formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^B$, —C(O)O$R^B$, —C(O)N$R^B_2$, —C(=N$R^B$)N$R^B_2$, —O$R^B$, —OC(O)($C_1$-$C_6$)alkyl, —OC(O)O($C_1$-$C_6$)alkyl, —OC(O)N$R^B_2$, —($C_1$-$C_6$)alkylene-N$R^B_2$, —N$R^B_2$, —N$R^B$C(O)$R^B$, —N$R^B$C(O)O($C_1$-$C_6$)alkyl, —N$R^B$C(O)N$R^B_2$, —N$R^B$$SO_2$N$R^B$, —S$R^B$, —S(O)$R^B$, —$SO_2R^B$, —$OSO_2$($C_1$-$C_6$)alkyl, —$SO_2$N$R^B_2$, —($C_1$-$C_6$)perfluoroalkyl, and —($C_1$-$C_6$)alkylene-O$R^B$;

$R^2$, $R^3$, $R^4$, and $R^5$ are each independently selected from the group consisting of hydrogen, —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$$SO_2$N$R^C$, —S$R^C$, —S(O)$R^C$, —$SO_2R^C$, —$OSO_2$($C_1$-$C_6$)alkyl, —$SO_2$N$R^C_2$, —($C_1$-$C_6$)perfluoroalkyl, and —($C_1$-$C_6$)alkylene-O$R^C$;

$R^6$ is selected from the group consisting of hydrogen, —C(O)R', —C(O)OR', —C(O)NHR', —P(O)(O$Y^1$)(O$Y^2$), —P(O)(O$Y^1$)(NHR''), substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^4$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$$SO_2$N$R^C$, —S$R^C$, —S(O)($C_1$-$C_6$)alkyl, —$SO_2$N$R^C_2$, —($C_1$-$C_6$)perfluoroalkyl, and —($C_1$-$C_6$)alkylene-O$R^C$;

R' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—($R^4$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$$SO_2$N$R^C$, —S$R^C$, —S(O)$R^C$, —$SO_2R^C$, —$OSO_2$($C_1$-$C_6$)alkyl, —$SO_2$N$R^C_2$, —($C_1$-$C_6$)perfluoroalkyl, and —($C_1$-$C_6$)alkylene-O$R^C$;

R'' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—($R^4$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$$SO_2$N$R^C$, —S$R^C$, —S(O)$R^C$, —$SO_2R^C$, —$OSO_2$($C_1$-$C_6$)alkyl, —$SO_2$N$R^C_2$, —($C_1$-$C_6$)perfluoroalkyl, and —($C_1$-$C_6$)alkylene-O$R^C$;

$R^7$ and $R^8$ are independently selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_6$)alkyl, substituted ($C_1$-$C_8$)cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$$SO_2$N$R^C$, —S$R^C$, —S(O)

$R^C$, —$SO_2R^C$, —$OSO_2(C_1$-$C_6)$alkyl, —$SO_2NR^C_2$, —$(C_1$-$C_6)$perfluoroalkyl, and —$(C_1$-$C_6)$alkylene-$OR^C$;

$Y^1$ and $Y^2$ are independently selected from the group consisting of hydrogen, sodium, potassium, lithium, substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, and substituted or unsubstituted heterocycle; wherein the substituted $(C_1$-$C_8)$alkyl, substituted $(C_1$-$C_8)$cycloalkyl, substituted aryl, substituted heteroaryl, and substituted heterocycle are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —C(O)$R^C$, —C(O)O$R^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —$(C_1$-$C_6$)alkylene-$NR^C_2$, —$NR^C_2$, —$NR^CC(O)R^C$, —$NR^CC(O)O(C_1$-$C_6$)alkyl, —$NR^CC(O)NR^C_2$, —$NR^CSO_2NR^C$, —$SR^C$, —S(O)$R^C$, —$SO_2R^C$, —$OSO_2(C_1$-$C_6$)alkyl, —$SO_2NR^C_2$, —$(C_1$-$C_6$)perfluoroalkyl, and —$(C_1$-$C_6$)alkylene-$OR^C$; or, alternatively, $Y^1$ and $Y^2$ taken together are selected from the group consisting of sodium, potassium, lithium, magnesium, calcium, strontium, and barium;

provided that when $Z^2$ is NH, the absolute configuration of C** is R or S, or a mixture of R and S;

further provided that when n is 0, $Z^2$ is NH, and $R^1$ is hydrogen, then $R^6$, $R^7$, and $R^8$ are not all simultaneously hydrogen;

further provided that when n is 0, $Z^2$ is NH, and $R^1$, $R^2$, $R^3$, $R^4$, and $R^5$ are each hydrogen, then $R^6$ is not —C(O)R' or —C(O)OR' where R' is alkyl, and each of $R^7$ and $R^8$ are not independently hydrogen, —C(O)R', or —C(O)OR', where R' is alkyl;

further provided that when n is 0, $Z^2$ is NH, $R^1$ is $(C_1$-$C_8)$alkyl or $(C_1$-$C_8)$cycloalkyl, and $R^2$, $R^3$, $R^4$, and $R^5$ are each hydrogen, then each of $R^6$, $R^7$, and $R^8$ are not independently hydrogen or —C(O)R';

further provided that when n is 0, $Z^2$ is oxygen, $R^1$ is $(C_1$-$C_8)$alkyl, $(C_1$-$C_8)$cycloalkyl, aryl, or substituted aryl, and $R^2$, $R^3$, $R^4$, and $R^5$ are each hydrogen, then $R^6$, $R^7$, and $R^8$ are not all simultaneously —C(O)R'.

In accordance with an embodiment, prototype product reduced nicotinate/nicotinamide ribonucleoside compounds (NRH or NARH, respectively) include reduced nicotinate/nicotinamide riboside compounds or derivatives of formula (II), or a salt, hydrate, or solvate thereof:

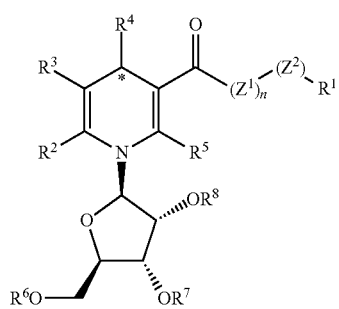

(II)

$Z^1$ and $Z^2$ are independently NH or oxygen;

n is 0 or 1;

$R^1$ is selected from the group consisting of hydrogen, substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^4$)—$CO_2R^B$; wherein the substituted $(C_1$-$C_8)$alkyl, substituted $(C_1$-$C_8)$cycloalkyl, substituted aryl, substituted heteroaryl, and substituted heterocycle are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —C(O)$R^C$, —C(O)O$R^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —$(C_1$-$C_6$)alkylene-$NR^C_2$, —$NR^C_2$, —$NR^CC(O)R^C$, —$NR^CC(O)O(C_1$-$C_6$)alkyl, —$NR^CC(O)NR^C_2$, —$NR^CSO_2NR^C$, —$SR^C$, —S(O)$R^C$, —$SO_2R^C$, —$OSO_2(C_1$-$C_6$)alkyl, —$SO_2NR^C_2$, —$(C_1$-$C_6$)perfluoroalkyl, and —$(C_1$-$C_6$)alkylene-$OR^C$;

$R^A$ is selected from the group consisting of —H, —$(C_1$-$C_6)$alkyl, —$(CH_2)_3$—NH—C($NH_2$)(=NH), —$CH_2$C(=O)$NH_2$, —$CH_2COOH$, —$CH_2SH$, —$(CH_2)_2$C(=O)—$NH_2$, —$(CH_2)_2COOH$, —$CH_2$-(2-imidazolyl), —CH($CH_3$)—$CH_2$—$CH_3$, —$CH_2CH(CH_3)_2$, —$(CH_2)_4$—$NH_2$, —$(CH_2)_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —CH($CH_3)_2$, and —$CH_2$—$CH_3$;

$R^B$ is hydrogen or —$(C_1$-$C_8$)alkyl;

each $R^C$ is independently selected from the group consisting of hydrogen, —$(C_1$-$C_8$)alkyl, substituted or unsubstituted pyridyl, substituted or unsubstituted 1,4-dihydropyridyl, a radical of the compound of formula (I), and vitamin B7 ester (biotinyl); wherein the substituted pyridyl and substituted 1,4-dihydropyridyl are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —C(O)$R^B$, —C(O)O$R^B$, —C(O)$NR^B_2$, —C(=$NR^B$)$NR^B_2$, —$OR^B$, —OC(O)($C_1$-$C_6$)alkyl, —OC(O)O($C_1$-$C_6$)alkyl, —OC(O)$NR^B_2$, —$(C_1$-$C_6$)alkylene-$NR^B_2$, —$NR^B_2$, —$NR^BC(O)R^B$, —$NR^BC(O)O(C_1$-$C_6$)alkyl, —$NR^BC(O)NR^B_2$, —$NR^BSO_2NR^B$, —$SR^B$, —S(O)$R^B$, —$SO_2R^B$, —$OSO_2(C_1$-$C_6$)alkyl, —$SO_2NR^B_2$, —$(C_1$-$C_6$)perfluoroalkyl, and —$(C_1$-$C_6$)alkylene-$OR^B$;

$R^2$ and $R^3$ are each independently selected from the group consisting of hydrogen, —$(C_1$-$C_6)$alkyl, —$(C_2$-$C_6)$alkenyl, —$(C_2$-$C_6)$alkynyl, halogen, —CN, —$NO_2$, —C(O)$R^C$, —C(O)O$R^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —$(C_1$-$C_6$)alkylene $NR^C_2$, —$NR^C_2$, —$NR^CC(O)R^C$, —$NR^CC(O)O(C_1$-$C_6$)alkyl, —$NR^CC(O)NR^C_2$, —$NR^CSO_2NR^C$, —$SR^C$, —S(O)$R^C$, —$SO_2R^C$, —$OSO_2(C_1$-$C_6$)alkyl, —$SO_2NR^C_2$, —$(C_1$-$C_6$)perfluoroalkyl, and —$(C_1$-$C_6$)alkylene-$OR^C$;

$R^4$ is selected from the group consisting of hydrogen, —$(C_1$-$C_6)$alkyl, —$(C_2$-$C_6)$alkenyl, —$(C_2$-$C_6)$alkynyl, halogen, —CN, —$NO_2$, —C(O)$R^C$, —C(O)O$R^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —$(C_1$-$C_6$)alkylene-$NR^C_2$, —$NR^C_2$, —$NR^CC(O)R^C$, —$NR^CC(O)O(C_1$-$C_6$)alkyl, —$NR^CC(O)NR^C_2$, —$NR^CSO_2NR^C$, —$SR^C$, —S(O)$R^C$, —$SO_2R^C$, —$OSO_2(C_1$-$C_6$)alkyl, —$SO_2NR_2$, —$(C_1$-$C_6$)perfluoroalkyl, and —$(C_1$-$C_6$)alkylene $OR^C$;

provided that C* has an absolute configuration of R or S, or a mixture of R and S;

$R^5$ is selected from the group consisting of hydrogen, —$(C_1$-$C_6)$alkyl, —$(C_2$-$C_6)$alkenyl, —$(C_2$-$C_6)$alkynyl, halogen, —CN, —$NO_2$, —C(O)$R^C$, —C(O)O$R^C$, —C(O)$NR^C_2$, —C($NR^C$)$NR^C_2$, —$OR^C$, —OC(O)($C_1$-$C_6$)alkyl, —OC(O)O($C_1$-$C_6$)alkyl, —OC(O)$NR^C_2$, —$(C_1$-$C_6$)alkylene-$NR^C_2$, —$NR^C_2$, —$NR^CC(O)R^C$, —$NR^CC(O)O(C_1$-$C_6$)alkyl, —$NR^CC(O)NR^C_2$, —$NR^CSO_2NR^C$, —$SR^C$, —S(O)$R^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R$^6$ is selected from the group consisting of hydrogen, —C(O)R', —C(O)OR', —C(O)NHR', —P(O)(OY$^1$)(OY$^2$), —P(O)(OY$^1$)(NHR"), substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R' is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl(C$_1$-C$_4$)alkyl, heterocycle(C$_1$-C$_4$)alkyl, and —C**H—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R" is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, aryl(C$_1$-C$_4$)alkyl, heterocycle(C$_1$-C$_4$)alkyl, and —C**H—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R$^7$ and R$^8$ are independently selected from the group consisting of hydrogen, —C(O)R', —C(O)OR', —C(O)NHR', substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$)alkyl, substituted (C$_1$-C$_8$)cycloalkyl, substituted aryl, substituted heteroaryl, substituted heterocycle, substituted aryl(C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

Y$^1$ and Y$^2$ are independently selected from the group consisting of hydrogen, sodium, potassium, lithium, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$; or, alternatively, Y$^1$ and Y$^2$ taken together are selected from the group consisting of sodium, potassium, lithium, magnesium, calcium, strontium, and barium;

provided that when Z$^2$ is NH, the absolute configuration of C** is R or S, or a mixture of R and S.

In accordance with an alternative embodiment, prototype product reduced nicotinate/nicotinamide ribonucleoside compounds (NRH or NARH, respectively) include reduced nicotinate/nicotinamide riboside compounds or derivatives of formula (II), or a salt, hydrate, or solvate thereof:

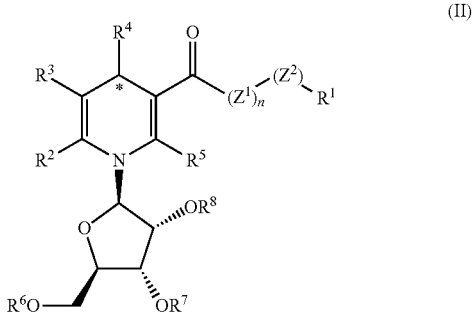

(II)

Z$^1$ and Z$^2$ are independently NH or oxygen;

n is 0 or 1;

R$^1$ is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C{}_2$, —C(=$NR^C$)$NR^C{}_2$, —$OR^C$, —OC(O)($C_1$-$C_6$)alkyl, —OC(O)O($C_1$-$C_6$)alkyl, —OC(O)$NR^C{}_2$, —($C_1$-$C_6$)alkylene-$NR^C{}_2$, —$NR^C{}_2$, —$NR^C$C(O)$R^C$, —$NR^C$C(O)O($C_1$-$C_6$)alkyl, —$NR^C$C(O)$NR^C{}_2$, —$NR^C$$SO_2NR^C$, —$SR^C$, —S(O)$R^C$, —$SO_2R^C$, —$OSO_2$($C_1$-$C_6$)alkyl, —$SO_2NR^C{}_2$, —($C_1$-$C_6$)perfluoroalkyl, and —($C_1$-$C_6$)alkylene-$OR^C$;

$R^A$ is selected from the group consisting of —H, —($C_1$-$C_6$)alkyl, —($CH_2$)$_3$—NH—C($NH_2$)(NH), —$CH_2$C(=O)$NH_2$, —$CH_2$COOH, —$CH_2$SH, —($CH_2$)$_2$C(=O)—$NH_2$, —($CH_2$)$_2$COOH, —$CH_2$-(2-imidazolyl), —CH($CH_3$)—$CH_2$—$CH_3$, —$CH_2$CH($CH_3$)$_2$, —($CH_2$)$_4$—$NH_2$, —($CH_2$)$_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —CH($CH_3$)$_2$, and —$CH_2$—$CH_3$;

$R^B$ is hydrogen or —($C_1$-$C_8$)alkyl;

each $R^C$ is independently selected from the group consisting of hydrogen, —($C_1$-$C_8$)alkyl, substituted or unsubstituted pyridyl, substituted or unsubstituted 1,4-dihydropyridyl, a radical of the compound of formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^B$, —C(O)O$R^B$, —C(O)$NR^B{}_2$, —C(=$NR^B$)$NR^B{}_2$, —$OR^B$, —OC(O)($C_1$-$C_6$)alkyl, —OC(O)O($C_1$-$C_6$)alkyl, —OC(O)$NR^B{}_2$, —($C_1$-$C_6$)alkylene-$NR^B{}_2$, —$NR^B{}_2$, —$NR^B$C(O)$R^B$, —$NR^B$C(O)O($C_1$-$C_6$)alkyl, —$NR^B$C(O)$NR^B{}_2$, —$NR^B$$SO_2NR^B$, —$SR^B$, —S(O)$R^B$, —$SO_2R^B$, —$OSO_2$($C_1$-$C_6$)alkyl, —$SO_2NR^B{}_2$, —($C_1$-$C_6$)perfluoroalkyl, and —($C_1$-$C_6$)alkylene-$OR^B$;

$R^2$ and $R^3$ are each independently selected from the group consisting of hydrogen, —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C{}_2$, —C(=NR)$NR^C{}_2$, —$OR^C$, —OC(O)($C_1$-$C_6$)alkyl, —OC(O)O($C_1$-$C_6$)alkyl, —OC(O)$NR^C{}_2$, —($C_1$-$C_6$)alkylene-$NR^C{}_2$, —$NR_2$, —$NR^C$C(O)$R^C$, —$NR^C$C(O)O($C_1$-$C_6$)alkyl, —$NR^C$C(O)$NR^C{}_2$, —$NR^C$$SO_2NR^C$, —$SR^C$, —S(O)$R^C$, —$SO_2R^C$, —$OSO_2$($C_1$-$C_6$)alkyl, —$SO_2NR^C{}_2$, —($C_1$-$C_6$)perfluoroalkyl, and —($C_1$-$C_6$)alkylene-$OR^C$;

$R^4$ is selected from the group consisting of hydrogen, —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C{}_2$, —C(=$NR^C$)$NR^C{}_2$, —$OR^C$, —OC(O)($C_1$-$C_6$)alkyl, —OC(O)O($C_1$-$C_6$)alkyl, —OC(O)$NR^C{}_2$, —($C_1$-$C_6$)alkylene-$NR^C{}_2$, —$NR^C{}_2$, —$NR^C$C(O)$R^C$, —$NR^C$C(O)O($C_1$-$C_6$)alkyl, —$NR^C$C(O)$NR^C{}_2$, —$NR^C$$SO_2NR^C$, —$SR^C$, —S(O)$R^C$, —$SO_2R^C$, —$OSO_2$($C_1$-$C_6$)alkyl, —$SO_2NR^C{}_2$, —($C_1$-$C_6$)perfluoroalkyl, and —($C_1$-$C_6$)alkylene-$OR^C$;

provided that C* has an absolute configuration of R or S, or a mixture of R and S;

$R^5$ is selected from the group consisting of hydrogen, —($C_1$-$C_6$)alkyl, —($C_1$-$C_6$)alkenyl, —($C_2$-$C_6$)alkynyl, halogen, —CN, —$NO_2$, —C(O)$R^C$, —C(O)O$R^C$, —C(O)$NR^C{}_2$, —C(=$NR^C$)$NR^C{}_2$, —$OR^C$, —OC(O)($C_1$-$C_6$)alkyl, —OC(O)O($C_1$-$C_6$)alkyl, —OC(O)$NR^C{}_2$, —($C_1$-$C_6$)alkylene-$NR^C{}_2$, —$NR^B{}_2$, —$NR^C$C(O)$R^C$, —$NR^C$C(O)O($C_1$-$C_6$)alkyl, —$NR^C$C(O)$NR^C{}_2$, —$NR^C$$SO_2NR^C$, —$SR^C$, —S(O)$R^C$, —$SO_2R^C$, —$OSO_2$($C_1$-$C_6$)alkyl, —$SO_2NR^C{}_2$, —($C_1$-$C_6$)perfluoroalkyl, and —($C_1$-$C_6$)alkylene-$OR^C$;

$R^6$ is selected from the group consisting of hydrogen, —C(O)R', —C(O)OR', —C(O)NHR', —P(O)(O$Y^1$)(O$Y^2$), —P(O)(O$Y^1$)(NHR''), substituted or unsubstituted ($C_1$-$C_8$) alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^A$)—$CO_2R^B$; wherein the substituted ($C_1$-$C_6$) alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$) alkenyl, —($C_2$-$C_6$)alkynyl, halogen, —CN, —$NO_2$, —C(O)$R^C$, —C(O)O$R^C$, —C(O)$NR^C{}_2$, —C(=$NR^C$)$NR^C{}_2$, —$OR^C$, —OC(O)($C_1$-$C_6$)alkyl, —OC(O)O($C_1$-$C_6$)alkyl, —OC(O)$NR^C{}_2$, —($C_1$-$C_6$)alkylene-$NR^C{}_2$, —$NR^C{}_2$, —$NR^C$C(O)$R^C$, —$NR^C$C(O)O($C_1$-$C_6$)alkyl, —$NR^C$C(O)$NR^C{}_2$, —$NR^C$$SO_2NR^C$, —$SR^C$, —S(O)$R^C$, —$SO_2R^C$, —$OSO_2$($C_1$-$C_6$)alkyl, —$SO_2NR^C{}_2$, —($C_1$-$C_6$)perfluoroalkyl, and —($C_1$-$C_6$)alkylene-$OR^C$;

R' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, vitamin B ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C{}_2$, —C(=$NR^C$)$NR^C{}_2$, —$OR^C$, —OC(O)($C_1$-$C_6$)alkyl, —OC(O)O($C_1$-$C_6$)alkyl, —OC(O)$NR^C{}_2$, —($C_1$-$C_6$)alkylene-$NR^C{}_2$, —$NR^C{}_2$, —$NR^C$C(O)$R^C$, —$NR^C$C(O)O($C_1$-$C_6$)alkyl, —$NR^C$C(O)$NR^C{}_2$, —$NR^C$$SO_2NR^C$, —$SR^C$, —S(O)$R^C$, —$SO_2R^C$, —$OSO_2$($C_1$-$C_6$)alkyl, —$SO_2NR^C{}_2$, —($C_1$-$C_6$)perfluoroalkyl, and —($C_1$-$C_6$)alkylene-$OR^C$;

R'' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C{}_2$, —C(=$NR^C$)$NR^C{}_2$, —$OR^C$, —OC(O)($C_1$-$C_6$)alkyl, —OC(O)O($C_1$-$C_6$)alkyl, —OC(O)$NR^C{}_2$, —($C_1$-$C_6$)alkylene—$NR^C{}_2$, —$NR^C{}_2$, —$NR^C$C(O)$R^C$, —$NR^C$C(O)O($C_1$-$C_6$)alkyl, —$NR^C$C(O)$NR^C{}_2$, —$NR^C$$SO_2NR^C$, —$SR^C$, —S(O)$R^C$, —$SO_2R^C$, —$OSO_2$($C_1$-$C_6$)alkyl, —$SO_2NR^C{}_2$, —($C_1$-$C_6$)perfluoroalkyl, and —($C_1$-$C_6$)alkylene-$OR^C$;

$R^7$ and $R^8$ are independently selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_6$)alkyl; wherein the substituted ($C_1$-$C_8$) alkyl, substituted ($C_1$-$C_8$)cycloalkyl, substituted aryl, substituted heteroaryl, substituted heterocycle, substituted aryl ($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —OR, —OC(O)($C_1$-$C_6$)alkyl, —OC(O)O($C_1$-$C_6$)alkyl, —OC(O)N$R^C_2$, —($C_1$-$C_6$)alkylene-N$R_2$, —N$R^C_2$, —N$R^C$C(O)$R^C$, —N$R^C$C(O)O($C_1$-$C_6$)alkyl, —N$R^C$C(O)N$R^C_2$, —N$R^C$$SO_2$N$R^C$, —S$R^C$, —S(O)$R^C$, —$SO_2R^C$, —$OSO_2$($C_1$-$C_6$)alkyl, —$SO_2$N$R^C_2$, —($C_1$-$C_6$)perfluoroalkyl, and —($C_1$-$C_6$)alkylene-O$R^C$;

$Y^1$ and $Y^2$ are independently selected from the group consisting of hydrogen, sodium, potassium, lithium, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle; wherein the substituted ($C_1$-$C_8$) alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$) alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —OR$^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$$SO_2$N$R^C$, —S$R^C$, —S(O)$R^C$, —$SO_2R^C$, —$OSO_2$($C_1$-$C_6$)alkyl, —$SO_2$N$R^C_2$, —($C_1$-$C_6$)perfluoroalkyl, and —($C_1$-$C_6$)alkylene-O$R^C$; or, alternatively, $Y^1$ and $Y^2$ taken together are selected from the group consisting of sodium, potassium, lithium, magnesium, calcium, strontium, and barium;

provided that when $Z^2$ is NH, the absolute configuration of C** is R or S, or a mixture of R and S;

further provided that when n is 0, $Z^2$ is NH, and $R^1$, $R^2$, $R^3$, $R^4$, and $R^5$ are each hydrogen, then $R^6$ is not —C(O)R' or —C(O)OR' where R' is alkyl, and each of $R^7$ and $R^8$ are not independently hydrogen, —C(O)R', or —C(O)OR', where R' is alkyl;

further provided that when n is 0 and $Z^2$ is oxygen, then $R^1$, $R^2$, $R^3$, $R^4$, $R^5$, $R^6$, $R^7$, and $R^8$ are not all simultaneously hydrogen;

further provided that when n is 0, $Z^2$ is oxygen, $R^1$ is hydrogen or ($C_1$-$C_4$)alkyl, and $R^2$, $R^3$, $R^4$, and $R^5$ are each hydrogen, then each of $R^6$, $R^7$, and $R^8$ is not —C(O)R', —C(O)OR', or —C(O)NHR', where R' is hydrogen, unsubstituted ($C_1$-$C_8$)alkyl, unsubstituted ($C_1$-$C_8$)cycloalkyl, unsubstituted aryl, unsubstituted heteroaryl, unsubstituted aryl($C_1$-$C_4$)alkyl, or unsubstituted heterocycle($C_1$-$C_6$)alkyl.

In accordance with an embodiment of a method of making a nicotinate/nicotinamide compound or derivative of formula (I), or a salt, hydrate, or solvate thereof, there is described a nicotinate/nicotinamide compound or derivative having formula (1), or salt thereof:

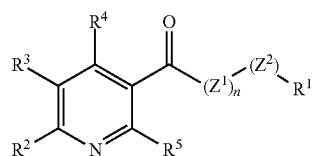

(1)

wherein $Z^1$ and $Z^2$ are independently NH or oxygen;
n is 0 or 1;
$R^1$ is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —OR$^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$) alkyl, —N$R^C$C(O)N$R^C_2$, —N$R^C$$SO_2$N$R^C$, —S$R^C$, —S(O) $R^C$, —$SO_2R^C$, —$OSO_2$($C_1$-$C_6$)alkyl, —$SO_2$N$R^C_2$, —($C_1$-$C_6$)perfluoroalkyl, and —($C_1$-$C_6$)alkylene-O$R^C$;

$R^A$ is selected from the group consisting of —H, —($C_1$-$C_6$)alkyl, —($CH_2$)$_3$—NH—C($NH_2$)(=NH), —$CH_2$C(=O) $NH_2$, —$CH_2$COOH, —$CH_2$SH, —($CH_2$)$_2$C(=O)—$NH_2$, —($CH_2$)$_2$COOH, —$CH_2$-(2-imidazolyl), —CH($CH_3$)—$CH_2$—$CH_3$, —$CH_2$CH($CH_3$)$_2$, —($CH_2$)$_4$—$NH_2$, —($CH_2$)$_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —CH($CH_3$)$_2$, and —$CH_2$—$CH_3$;

$R^B$ is hydrogen or —($C_1$-$C_8$)alkyl;

each $R^C$ is independently selected from the group consisting of hydrogen, —($C_1$-$C_8$)alkyl, substituted or unsubstituted pyridyl, substituted or unsubstituted 1,4-dihydropyridyl, a radical of the compound of formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$) alkynyl, halogen, —CN, —$NO_2$, —C(O)$R^B$, —C(O)O$R^B$, —C(O)N$R^B_2$, —C(=N$R^B$)N$R^B_2$, —OR, —OC(O)($C_1$-$C_6$) alkyl, —OC(O)O($C_1$-$C_6$)alkyl, —OC(O)N$R^B_2$, —($C_1$-$C_6$) alkylene-N$R^B_2$, —N$R^B_2$, —N$R^B$C(O)$R^B$, —N$R^B$C(O)O($C_1$-$C_6$)alkyl, —N$R^B$C(O)N$R^B_2$, —N$R^B$$SO_2$N$R^B$, —S$R^B$, —S(O), —$SO_2R^B$, —$OSO_2$($C_1$-$C_6$)alkyl, —$SO_2$N$R^B_2$, —($C_1$-$C_6$)perfluoroalkyl, and —($C_1$-$C_6$)alkylene-O$R^B$;

$R^2$, $R^3$, $R^4$, and $R^5$ are each independently selected from the group consisting of hydrogen, —($C_2$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —OR$^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O) N$R^C_2$, —N$R^C$$SO_2$N$R^C$, —S$R^C$, —S(O)$R^C$, —$SO_2R^C$, —$OSO_2$($C_1$-$C_6$)alkyl, —$SO_2$N$R^C_2$, —($C_1$-$C_6$)perfluoroalkyl, and —($C_1$-$C_6$)alkylene-O$R^C$;

provided that when $Z^2$ is NH, the absolute configuration of C** is R or S, or a mixture of R and S.

In accordance with an embodiment of a method of making a riboside compound or derivative of formula (I), or a salt, hydrate, or solvate thereof, there is described a riboside compound or derivative having formula (2), or salt thereof:

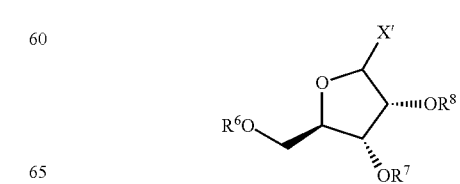

(2)

wherein X' is selected from the group consisting of fluoro, chloro, bromo, iodo, $HCO_2$, acetoxy, propionoxy, butyroxy, glutamyloxy, aspartyloxy, ascorbyloxy, benzoxy, $HOCO_2$, citryloxy, carbamyloxy, gluconyloxy, lactyloxy, succinyloxy, sulfoxy, trifluoromethanesulfoxy, trichloromethanesulfoxy, tribromomethanesulfoxy, and trifluoroacetoxy;

optionally wherein $X^-$ as counterion is absent, or when $X^-$ is present is selected from the group consisting of fluoride, chloride, bromide, iodide, formate, acetate, ascorbate, benzoate, carbonate, citrate, carbamate, formate, gluconate, lactate, methyl bromide, methyl sulfate, nitrate, phosphate, diphosphate, succinate, sulfate, trifluoromethanesulfonate, trichloromethanesulfonate, tribromomethanesulfonate, and trifluoroacetate;

optionally wherein when $X^-$ is absent optionally the counterion is an internal salt;

optionally $X^-$ is an anion of a substituted or unsubstituted carboxylic acid selected from a monocarboxylic acid, a dicarboxylic acid, or a polycarboxylic acid; and, optionally $X^-$ is an anion of a substituted monocarboxylic acid, further optionally an anion of a substituted propanoic acid (propanoate or propionate), or an anion of a substituted acetic acid (acetate), or an anion of a hydroxy-propanoic acid, or an anion of 2-hydroxypropanoic acid (being lactic acid; the anion of lactic acid being lactate), or a trihaloacetate selected from trichloroacetate, tribromoacetate, and trifluoroacetate; and, optionally $X^-$ is an anion of an unsubstituted monocarboxylic acid selected from formic acid, acetic acid, propionic acid, or butyric acid, being formate, acetate, propionate, and butyrate, respectively; and, optionally $X^-$ is an anion of a substituted or unsubstituted amino acid, i.e., amino-monocarboxylic acid or an amino-dicarboxylic acid, optionally selected from glutamic acid and aspartic acid, being glutamate and aspartate, respectively; and, optionally $X^-$ is an anion of ascorbic acid, being ascorbate; and, optionally $X^-$ is a halide selected from fluoride, chloride, bromide, or iodide; and, optionally $X^-$ is an anion of a substituted or unsubstituted sulfonate, further optionally a trihalomethanesulfonate selected from trifluoromethanesulfonate, tribromomethanesulfonate, or trichloromethanesulfonate; and, optionally $X^-$ is an anion of a substituted or unsubstituted carbonate, further optionally hydrogen carbonate;

wherein the substituted carboxylic acid, substituted monocarboxylic acid, substituted propanoic acid, the substituted acetic acid, substituted amino acid, substituted sulfonate, and substituted carbonate are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$S$O_2$N$R^C$, —S$R^C$, —S(O)$R^C$, —S$O_2$$R^C$, —OS$O_2$($C_1$-$C_6$)alkyl, —S$O_2$N$R^C_2$, —($C_1$-$C_6$)perfluoroalkyl, and —($C_1$-$C_6$)alkylene-O$R^C$;

$Z^1$ and $Z^2$ are independently NH or oxygen;

n is 0 or 1;

$R^6$ is selected from the group consisting of hydrogen, —C(O)R', —C(O)OR', —C(O)NHR', —P(O)(O$Y^1$)(O$Y^2$), —P(O)(O$Y^1$)(NHR''), substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^A$)—C$O_2$$R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$S$O_2$N$R^C$, —S$R^C$, —S(O)$R^C$, —S$O_2$$R^C$, —OS$O_2$($C_1$-$C_6$)alkyl, —S$O_2$N$R^C_2$, —($C_1$-$C_6$)perfluoroalkyl, and —($C_1$-$C_6$)alkylene-O$R^C$;

$R^A$ is selected from the group consisting of —H, —($C_1$-$C_6$)alkyl, —($CH_2$)$_3$—NH—C(N$H_2$)(=NH), —$CH_2$C(=O)N$H_2$, —C—$H_2$COOH, —$CH_2$SH, —($CH_2$)$_2$C(=O)—N$H_2$, —($CH_2$)$_2$COOH, —$CH_2$-(2-imidazolyl), —CH($CH_3$)—$CH_2$—$CH_3$, —$CH_2$CH($CH_3$)$_2$, —($CH_2$)$_4$—N$H_2$, —($CH_2$)$_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —CH($CH_3$)$_2$, and —$CH_2$—$CH_3$;

$R^B$ is hydrogen or —($C_1$-$C_8$)alkyl;

each $R^C$ is independently selected from the group consisting of hydrogen, —($C_1$-$C_8$)alkyl, substituted or unsubstituted pyridyl, substituted or unsubstituted 1,4-dihydropyridyl, a radical of the compound of formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^B$, —C(O)O$R^B$, —C(O)N$R^B_2$, —C(=N$R^B$)N$R_2$, —O$R^B$, —OC(O)($C_1$-$C_6$)alkyl, —OC(O)O($C_1$-$C_6$)alkyl, —OC(O)N$R^B_2$, —($C_1$-$C_6$)alkylene-N$R^B_2$, —N$R^B_2$, —N$R^B$C(O)$R^B$, —N$R^B$C(O)O($C_1$-$C_6$)alkyl, —N$R^B$C(O)N$R^B_2$, —N$R^B$S$O_2$N$R^B$, —S$R^B$, —S(O)$R^B$, —S$O_2$$R^B$, —OS$O_2$($C_1$-$C_6$)alkyl, —S$O_2$N$R^B_2$, —($C_1$-$C_6$)perfluoroalkyl, and —($C_1$-$C_6$)alkylene-O$R^B$;

R' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—($R^A$)—C$O_2$$R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$S$O_2$N$R^C$, —S$R^C$, —S(O)$R^C$, —S$O_2$$R^C$, —OS$O_2$($C_1$-$C_6$)alkyl, —S$O_2$N$R^C_2$, —($C_1$-$C_6$)perfluoroalkyl, and —($C_1$-$C_6$)alkylene-O$R^C$;

R'' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—($R^A$) C$O_2$$R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C$, —$SR^C$, —S(O)$R^C$, —$SO_2$$R^C$, —$OSO_2$($C_1$-$C_6$)alkyl, —$SO_2$$NR^C_2$, —($C_1$-$C_6$)perfluoroalkyl, and —($C_1$-$C_6$)alkylene-O$R^C$;

$R^7$ and $R^8$ are independently selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$) alkyl, substituted ($C_1$-$C_8$)cycloalkyl, substituted aryl, substituted heteroaryl, substituted heterocycle, substituted aryl ($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —OR, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C$, —$SR^C$, —S(O)$R^C$, —$SO_2$$R^C$, —$OSO_2$($C_1$-$C_6$)alkyl, —$SO_2$$NR^C_2$, —($C_1$-$C_6$)perfluoroalkyl, and —($C_1$-$C_6$)alkylene-O$R^C$;

$Y^1$ and $Y^2$ are independently selected from the group consisting of hydrogen, sodium, potassium, lithium, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle; wherein the substituted ($C_1$-$C_8$) alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$) alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene $NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C$, —$SR^C$, —S(O)$R^C$, —$SO_2$$R^C$, —$OSO_2$($C_1$-$C_6$)alkyl, —$SO_2$$NR^C_2$, —($C_1$-$C_6$)perfluoroalkyl, and —($C_1$-$C_6$)alkylene-O$R^C$; or, alternatively, $Y^1$ and $Y^2$ taken together are selected from the group consisting of sodium, potassium, lithium, magnesium, calcium, strontium, and barium;

provided that when $Z^2$ is NH, the absolute configuration of C** is R or S, or a mixture of R and S.

In accordance with an embodiment of a method of making a nicotinate/nicotinamide riboside compound or derivative of formula (I), or a salt, hydrate, or solvate thereof, there is described a nicotinate/nicotinamide riboside compound or derivative having formula (3), or a salt

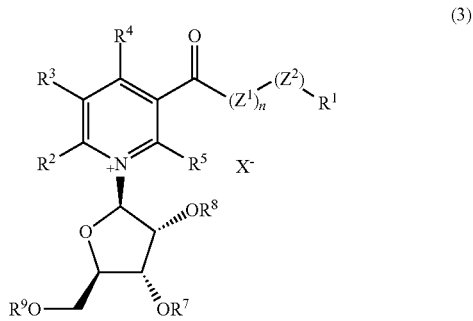

(3)

wherein $X^-$ is selected from the group consisting of fluoride, chloride, bromide, iodide, formate, acetate, ascorbate, benzoate, carbonate, citrate, carbamate, formate, gluconate, lactate, methyl bromide, methyl sulfate, nitrate, phosphate, diphosphate, succinate, sulfate, trifluoromethanesulfonate, trichloromethanesulfonate, tribromomethanesulfonate, and trifluoroacetate;

optionally wherein when $X^-$ is absent optionally the counterion is an internal salt;

optionally $X^-$ is an anion of a substituted or unsubstituted carboxylic acid selected from a monocarboxylic acid, a dicarboxylic acid, or a polycarboxylic acid; and, optionally $X^-$ is an anion of a substituted monocarboxylic acid, further optionally an anion of a substituted propanoic acid (propanoate or propionate), or an anion of a substituted acetic acid (acetate), or an anion of a hydroxyl-propanoic acid, or an anion of 2-hydroxypropanoic acid (being lactic acid; the anion of lactic acid being lactate), or a trihaloacetate selected from trichloroacetate, tribromoacetate, and trifluoroacetate; and, optionally $X^-$ is an anion of an unsubstituted monocarboxylic acid selected from formic acid, acetic acid, propionic acid, or butyric acid, being formate, acetate, propionate, and butyrate, respectively; and, optionally $X^-$ is an anion of a substituted or unsubstituted amino acid, i.e., amino-monocarboxylic acid or an amino-dicarboxylic acid, optionally selected from glutamic acid and aspartic acid, being glutamate and aspartate, respectively; and, optionally $X^-$ is an anion of ascorbic acid, being ascorbate; and, optionally $X^-$ is a halide selected from fluoride, chloride, bromide, or iodide; and, optionally $X^-$ is an anion of a substituted or unsubstituted sulfonate, further optionally a trihalomethanesulfonate selected from trifluoromethanesulfonate, tribromomethanesulfonate, or trichloromethanesulfonate; and, optionally $X^-$ is an anion of a substituted or unsubstituted carbonate, further optionally hydrogen carbonate;

wherein the substituted carboxylic acid, substituted monocarboxylic acid, substituted propanoic acid, substituted acetic acid, substituted amino acid, substituted sulfonate, and substituted carbonate are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$) alkyl, —$NR^C$C(O)$NR^C_2$, —$NR^C$$SO_2$$NR^C$, —$SR^C$, —S(O)$R^C$, —$SO_2$$R^C$, —$OSO_2$($C_1$-$C_6$)alkyl, —$SO_2$$NR^C_2$, —($C_1$-$C_6$)perfluoroalkyl, and —($C_1$-$C_6$)alkylene-O$R^C$;

$Z^1$ and $Z^2$ are independently NH or oxygen;

n is 0 or 1;

$R^1$ is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^4$)—CO$_2$$R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —NO$_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$) alkyl, —N$R^C$C(O)N$R^C_2$, —N$R^C$SO$_2$N$R^C$, —S$R^C$, —S(O)$R^C$, —SO$_2$$R^C$, —OSO$_2$($C_1$-$C_6$)alkyl, —SO$_2$N$R^C_2$, —($C_1$-$C_6$)perfluoroalkyl, and —($C_1$-$C_6$)alkylene-O$R^C$;

$R^4$ is selected from the group consisting of —H, —($C_1$-$C_6$)alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O) NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, —CH$_2$-phenyl, —CH$_2$—OH, —CH(O)—CH$_3$, —CH$_2$-(3-indolyl), —CH$_2$-(4-hydroxyphenyl), —CH(CH$_3$)$_2$, and —CH$_2$—CH$_3$;

$R^B$ is hydrogen or —($C_1$-$C_8$)alkyl;

each $R^C$ is independently selected from the group consisting of hydrogen, —($C_1$-$C_8$)alkyl, substituted or unsubstituted pyridyl, substituted or unsubstituted 1,4-dihydropyridyl, a radical of the compound of formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —NO$_2$, —C(O)$R^B$, —C(O)O$R^B$, —C(O)N$R^B_2$, —C(=N$R^B$)N$R^B_2$, —O$R^B$, —OC(O)($C_1$-$C_6$)alkyl, —OC(O)O($C_1$-$C_6$)alkyl, —OC(O)N$R^B_2$, —($C_1$-$C_6$)alkylene-N$R^B_2$, —N$R^B_2$, —N$R^B$C(O)$R^B$, —N$R^B$C(O)O($C_1$-$C_6$)alkyl, —N$R^B$C(O)N$R_2$, —N$R^B$SO$_2$N$R^B$, —S$R^B$, —S(O)$R^B$, —SO$_2$$R^B$, —OSO$_2$($C_1$-$C_6$)alkyl, —SO$_2$N$R^B_2$, —($C_1$-$C_6$)perfluoroalkyl, and —($C_1$-$C_6$)alkylene-O$R^B$;

$R^2$, $R^3$, $R^4$, and $R^5$ are each independently selected from the group consisting of hydrogen, —($C_1$-$C_6$)alkyl, —($C_2$-$C_6$)alkenyl, —($C_2$-$C_6$)alkynyl, halogen, —CN, —NO$_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)NR$_2$, —N$R^C$SO$_2$N$R^C$, —S$R^C$, —S(O)$R^C$, —SO$_2$$R^C$, —OSO$_2$($C_1$-$C_6$)alkyl, —SO$_2$N$R^C_2$, —($C_1$-$C_6$)perfluoroalkyl, and —($C_1$-$C_6$)alkylene-O$R^C$;

$R^7$ and $R^8$ are independently selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$)cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —NO$_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$) alkyl, —N$R^C$C(O)N$R^C_2$, —N$R^C$SO$_2$N$R^C$, —S$R^C$, —S(O)$R^C$, —SO$_2$$R^C$, —OSO$_2$($C_1$-$C_6$)alkyl, —SO$_2$N$R^C_2$, —($C_1$-$C_6$)perfluoroalkyl, and —($C_1$-$C_6$)alkylene-O$R^C$;

R' is selected form the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—($R^4$)—CO$_2$$R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —NO$_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$) alkyl, —N$R^C$C(O)N$R^C_2$, —N$R^C$SO$_2$N$R^C$, —S$R^C$, —S(O)$R^C$, —SO$_2$$R^C$, —OSO$_2$($C_1$-$C_6$)alkyl, —SO$_2$N$R^C_2$, —($C_1$-$C_6$)perfluoroalkyl, and —($C_1$-$C_6$)alkylene-O$R^C$;

$R^9$ is selected from the group consisting of hydrogen, —C(O)R', —C(O)OR', —C(O)NHR', —P(O)(O$Y^1$)(O$Y^2$), —P(O)(O$Y^1$)(NHR"), substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^4$)—CO$_2$$R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$) alkenyl, —($C_2$-$C_6$)alkynyl, halogen, —CN, —NO$_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$SO$_2$N$R^C$, —S$R^C$, —S(O)$R^C$, —SO$_2$$R^C$, —OSO$_2$($C_1$-$C_6$)alkyl, —SO$_2$N$R^C_2$, —($C_1$-$C_6$)perfluoroalkyl, and —($C_1$-$C_6$)alkylene-O$R^C$;

R" is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—($R^4$)—CO$_2$$R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$) alkyl, —($C_2$-$C_6$)alkenyl, —($C_2$-$C_6$)alkynyl, halogen, —CN, —NO$_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$) alkyl, —N$R^C$C(O)N$R^C_2$, —N$R^C$SO$_2$N$R^C$, —S$R^C$, —S(O)

$R^C$, —$SO_2R^C$, —$OSO_2(C_1$-$C_6)$alkyl, —$SO_2NR^C_2$, —$(C_1$-$C_6)$perfluoroalkyl, and —$(C_1$-$C_6)$alkylene-$OR^C$;

$Y^1$ and $Y^2$ are independently selected from the group consisting of hydrogen, sodium, potassium, lithium, substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, and substituted or unsubstituted heterocycle; wherein the substituted $(C_1$-$C_8)$alkyl, substituted $(C_1$-$C_8)$cycloalkyl, substituted aryl, substituted heteroaryl, and substituted heterocycle are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —$C(O)R^C$, —$C(O)OR^C$, —$C(O)NR^C_2$, —$C(=NR^C)NR^C_2$, —$OR^C$, —$OC(O)(C_1$-$C_6)$alkyl, —$OC(O)O(C_1$-$C_6)$alkyl, —$OC(O)NR^C_2$, —$(C_1$-$C_6)$alkylene-$NR^C_2$, —$NR^C_2$, —$NR^CC(O)R^C$, —$NR^CC(O)O(C_1$-$C_6)$alkyl, —$NR^CC(O)NR^C_2$, —$NR^CSO_2NR^C$, —$SR^C$, —$S(O)R^C$, —$SO_2R^C$, —$OSO_2(C_1$-$C_6)$alkyl, —$SO_2NR^C_2$, —$(C_1$-$C_6)$perfluoroalkyl, and —$(C_1$-$C_6)$alkylene-$OR^C$; or, alternatively, $Y^1$ and $Y^2$ taken together are selected from the group consisting of sodium, potassium, lithium, magnesium, calcium, strontium, and barium;

provided that when $Z^2$ is NH, the absolute configuration of C** is R or S, or a mixture of R and S.

In accordance with an embodiment of a method of making a reduced nicotinate/nicotinamide riboside compound or derivative of formula (II), or a salt, hydrate, or solvate thereof, there is described a reduced nicotinate/nicotinamide riboside compound or derivative having formula (4), or salt thereof:

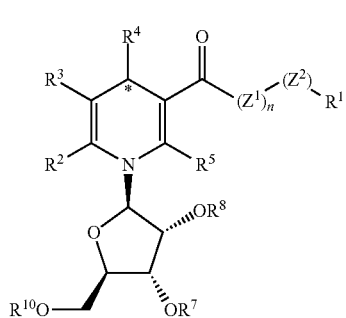

(4)

wherein $Z^1$ and $Z^2$ are independently NH or oxygen;
n is 0 or 1;
$R^1$ is selected from the group consisting of hydrogen, substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—$(R^A)$—$CO_2R^B$; wherein the substituted $(C_1$-$C_8)$alkyl, substituted $(C_1$-$C_8)$cycloalkyl, substituted aryl, substituted heteroaryl, and substituted heterocycle are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —$C(O)R^C$, —$C(O)OR^C$, —$C(O)NR^C_2$, —$C(=NR^C)NR^C_2$, —$OR^C$, —$OC(O)(C_1$-$C_6)$alkyl, —$OC(O)O(C_1$-$C_6)$alkyl, —$OC(O)NR^C_2$, —$(C_1$-$C_6)$alkylene-$NR^C_2$, —$NR^C_2$, —$NR^CC(O)R^C$, —$NR^CC(O)O(C_1$-$C_6)$alkyl, —$NR^CC(O)NR^C_2$, —$NR^CSO_2NR^C$, —$SR^C$, —$S(O)R^C$, —$SO_2R^C$, —$OSO_2(C_1$-$C_6)$alkyl, —$SO_2NR^C_2$, —$(C_1$-$C_6)$perfluoroalkyl, and —$(C_1$-$C_6)$alkylene-$OR^C$;

$R^A$ is selected from the group consisting of —H, —$(C_1$-$C_6)$alkyl, —$(CH_2)_3$—NH—$C(NH_2)(=NH)$, —$CH_2C(=O)NH_2$, —$CH_2COOH$, —$CH_2SH$, —$(CH_2)_2C(=O)$—$NH_2$, —$(CH_2)_2COOH$, —$CH_2$-(2-imidazolyl), —$CH(CH_3)$—$CH_2$—$CH_3$, —$CH_2CH(CH_3)_2$, —$(CH_2)_4$—$NH_2$, —$(CH_2)_2S$—$CH_3$, phenyl, —$CH_2$-phenyl, —$CH_2$—OH, —$CH(OH)$—$CH_3$, —$CH_2$-(3-indolyl), —$CH_2$-(4-hydroxyphenyl), —$CH(CH_3)_2$, and —$CH_2$—$CH_3$;

$R^B$ is hydrogen or —$(C_1$-$C_8)$alkyl;

each $R^C$ is independently selected from the group consisting of hydrogen, —$(C_1$-$C_8)$alkyl, substituted or unsubstituted pyridyl, substituted or unsubstituted 1,4-dihydropyridyl, a radical of the compound of formula (I), and vitamin B7 ester (biotinyl); wherein the substituted pyridyl and substituted 1,4-dihydropyridyl are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —$C(O)R^B$, —$C(O)OR^B$, —$C(O)NR^B_2$, —$C(NR^B)NR^B_2$, —$OR^B$, —$OC(O)(C_1$-$C_6)$alkyl, —$OC(O)O(C_1$-$C_6)$alkyl, —$OC(O)NR^B_2$, —$(C_1$-$C_6)$alkylene-$NR^B_2$, —$NR^B_2$, —$NR^BC(O)R^B$, —$NR^BC(O)O(C_1$-$C_6)$alkyl, —$NR^BC(O)NR^B_2$, —$NR^BSO_2NR^B$, —$SR^B$, —$S(O)R^B$, —$SO_2R^B$, —$OSO_2(C_1$-$C_6)$alkyl, —$SO_2NR^B_2$, —$(C_1$-$C_6)$perfluoroalkyl, and —$(C_1$-$C_6)$alkylene-$OR^B$;

$R^2$ and $R^3$ are each independently selected from the group consisting of hydrogen, —$(C_1$-$C_6)$alkyl, —$(C_2$-$C_6)$alkenyl, —$(C_2$-$C_6)$alkynyl, halogen, —CN, —$NO_2$, —$C(O)R^C$, —$C(O)OR^C$, —$C(O)NR^C_2$, —$C(=NR^C)NR^C_2$, —$OR^C$, —$OC(O)(C_1$-$C_6)$alkyl, —$OC(O)O(C_1$-$C_6)$alkyl, —$OC(O)NR^C_2$, —$(C_1$-$C_6)$alkylene-$NR^C_2$, —$NR^C_2$, —$NR^CC(O)R^C$, —$NR^CC(O)O(C_1$-$C_6)$alkyl, —$NR^CC(O)NR^C_2$, —$NR^CSO_2NR^C$, —$SR^C$, —$S(O)R^C$, —$SO_2R^C$, —$OSO_2(C_1$-$C_6)$alkyl, —$SO_2NR^C_2$, —$(C_1$-$C_6)$perfluoroalkyl, and —$(C_1$-$C_6)$alkylene-$OR^C$;

$R^4$ is selected from the group consisting of hydrogen, —$(C_1$-$C_6)$alkyl, —$(C_2$-$C_6)$alkenyl, —$(C_2$-$C_6)$alkynyl, halogen, —CN, —$NO_2$, —$C(O)R^C$, —$C(O)OR^C$, —$C(O)NR^C_2$, —$C(=NR^C)NR^C_2$, —$OR^C$, —$OC(O)(C_1$-$C_6)$alkyl, —$OC(O)O(C_1$-$C_6)$alkyl, —$OC(O)NR^C_2$, —$(C_1$-$C_6)$alkylene-$NR^C_2$, —$NR^C_2$, —$NR^CC(O)R^C$, —$NR^CC(O)O(C_1$-$C_6)$alkyl, —$NR^CC(O)NR^C_2$, —$NR^CSO_2NR^C$, —$SR^C$, —$S(O)R^C$, —$SO_2R^C$, —$OSO_2(C_1$-$C_6)$alkyl, —$SO_2NR^C_2$, —$(C_1$-$C_6)$perfluoroalkyl, and $(C_1$-$C_6)$alkylene-$OR^C$;

provided that C* has an absolute configuration of R or S, or a mixture of R and S;

$R^5$ is selected from the group consisting of hydrogen, —$(C_1$-$C_6)$alkyl, —$(C_2$-$C_6)$alkenyl, —$(C_2$-$C_6)$alkynyl, halogen, —CN, —$NO_2$, —$C(O)R^C$, —$C(O)OR^C$, —$C(O)NR^C_2$, —$C(=NR^C)NR^C_2$, —$OR^C$, —$OC(O)(C_1$-$C_6)$alkyl, —$OC(O)O(C_1$-$C_6)$alkyl, —$OC(O)NR^C_2$, —$(C_1$-$C_6)$alkylene-$NR^C_2$, —$NR^C_2$, —$NR^CC(O)R^C$, —$NR^CC(O)O(C_1$-$C_6)$alkyl, —$NR^CC(O)NR^C_2$, —$NR^CSO_2NR^C$, —$SR^C$, —$S(O)R^C$, —$SO_2R^C$, —$OSO_2(C_1$-$C_6)$alkyl, —$SO_2NR^C_2$, —$(C_1$-$C_6)$perfluoroalkyl, and —$(C_1$-$C_6)$alkylene-$OR^C$;

$R^7$ and $R^8$ are independently selected from the group consisting of hydrogen, —$C(O)R'$, —$C(O)OR'$, —$C(O)NHR'$, substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, substituted or unsubstituted heterocycle, substituted or unsubstituted aryl$(C_1$-$C_4)$alkyl, and substituted or unsubstituted heterocycle$(C_1$-$C_4)$alkyl; wherein the substituted $(C_1$-$C_8)$alkyl, substituted $(C_1$-$C_8)$cycloalkyl, substituted aryl, substituted heteroaryl, substituted heterocycle, substituted aryl $(C_1$-$C_4)$alkyl, and substituted heterocycle$(C_1$-$C_4)$alkyl are substituted with one to five substituents independently selected from the group consisting of —$(C_1$-$C_6)$alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R' is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl(C$_1$-C$_4$)alkyl, heterocycle(C$_1$-C$_4$)alkyl, and —C**H—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R$^{10}$ is selected from the group consisting of hydrogen, —C(O)R', —C(O)OR', —C(O)NHR', —P(O)(OY$^1$)(OY$^2$), —P(O)(OY$^1$)(NHR''), substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R'' is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, aryl(C$_1$-C$_4$)alkyl, heterocycle(C$_1$-C$_4$)alkyl, and —C**H—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$) alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, NR$^C$C(O)O(C$_1$-C$_6$)alkyl, —NR$^C$C(O)NR$^C_2$, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C_2$, —(C$_1$-C$_6$) perfluoroalkyl, and —(C$_1$-C$_6$)alkylene-OR$^C$;

Y$^1$ and Y$^2$ are independently selected from the group consisting of hydrogen, sodium, potassium, lithium, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle; wherein the substituted (C$_1$-C$_8$) alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$) alkenyl, —(C$_2$-C$_6$)alkynyl, halogen, —CN, —NO$_2$, —C(O) R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O) NR$^C_2$, —(C$_1$-C$_6$)alkylene-NR$^C_2$, —NR$^C_2$, —NR$^C$C(O)R$^C$, —NR$^C$C(O)O(C$_1$-C$_8$)alkyl, —NR$^C$C(O)NR$^C_2$, —NR$^C$SO$_2$NR$^C$, —SR$^C$, —S(O)R$^C$, —SO$_2$R$^C$, —OSO$_2$ (C$_1$-C$_6$)alkyl, —SO$_2$NR$^C_2$, —(C$_1$-C$_6$)perfluoroalkyl, and —(C$_1$-C$_6$)alkylene-OR$^C$; or, alternatively, Y$^1$ and Y$^2$ taken together are selected from the group consisting of sodium, potassium, lithium, magnesium, calcium, strontium, and barium;

provided that when Z$^2$ is NH, the absolute configuration of C** is R or S, or a mixture of R and S.

Definitions

Vitamin B1, which is also known as thiamine, is a compound having the formula (III):

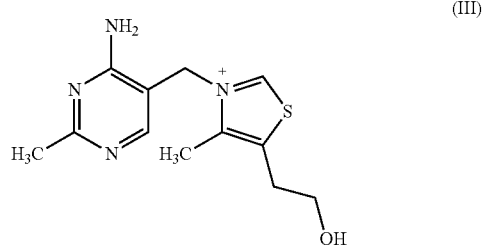

(III)

Vitamin B2, which is also known as riboflavin, is a compound having the formula (IV):

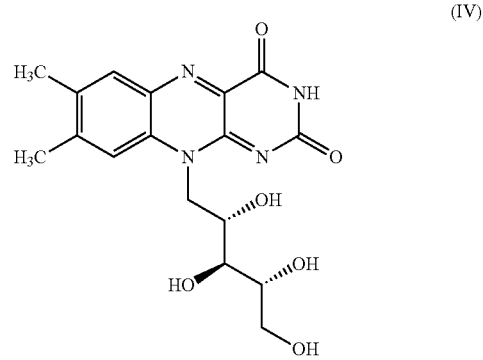 [SMILES: Cc1cc2nc3c(=O)[nH]c(=O)nc-3n(C[C@H](O)[C@H](O)[C@H](O)CO)c2cc1C]

(IV)

Vitamin B3, which is also known as nicotinic acid, or niacin, is a pyridine compound having the formula (V):

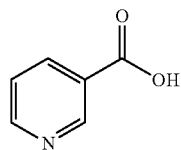

(V)

Vitamin B6, which is also known as pyridoxine in the form most commonly given as a supplement, is a compound having the formula (VI):

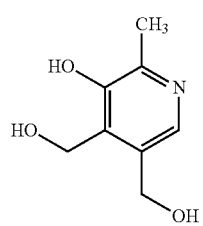

(VI)

Pterostilbene is a compound having the formula (VII):

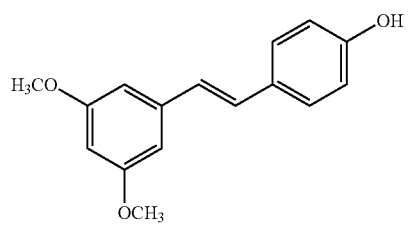

(VII)

Resveratrol is a compound having the formula (VIII):

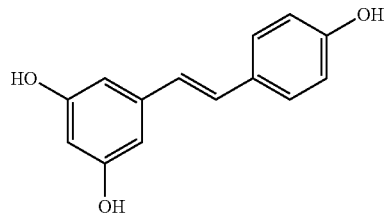

(VIII)

Tryptophan is an amino acid having the formula (IX):

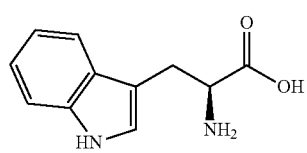

(IX)

Isoleucine is an amino acid having the formula (X):

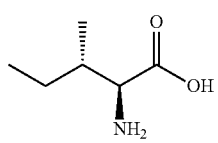

(X)

Alanine is an amino acid having the formula (XI):

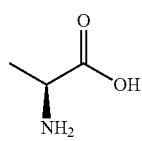

(XI)

Phenylalanine is an amino acid having the formula (XII):

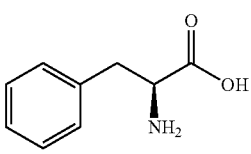

(XII)

Valine is an amino acid having the formula (XIII):

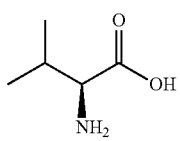

(XIII)

Methionine is an amino acid having the formula (XIV):

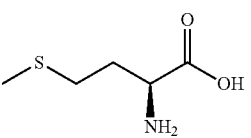

(XIV)

Valine is an amino acid having the formula (XV):

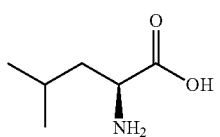

(XV)

As used in the specification and the appended claims, the singular forms of "a," "an," and "the" include plural referents and vice versa, unless the context clearly dictates otherwise.

As used herein, the term "Lewis acid" refers to any chemical species that can accept a pair of nonbonding valence electrons, i.e., an electron-pair acceptor. Without limitation, non-limiting examples of Lewis acids include $BF_3$, TMSOTf, and $SnCl_4$.

As used herein, the term "solvent-based chemical laboratory techniques" refer to reactions that change the empirical, molecular, and/or structural formula of a compound, which are performed in laboratory apparatuses subsequent to the mixture of chemical starting materials and/or reagents with aqueous and/or organic solvent phases, and after which treatment and removal of solvent provides molecularly transformed products.

As used herein, the term "solvent" refers to a compound or mixture of compounds including, but not limited to, water, water in which an ionic compound has been dissolved, acetic acid, acetone, acetonitrile, benzene, 1-butanol, 2-butanol, t-butyl alcohol ("TBA"), 2-butanone, carbon tetrachloride, chlorobenzene, chloroform, cyclohexane, 1,2-dichloroethane ("DCE"), diethylene glycol, diethyl eter ("$Et_2O$"), diglyme (diethylene glycol dimethyl ether), 1,2-dimethoxyethane ("DME"), N,N-dimethylformamide ("DMF"), dimethylsulfoxide ("DMSO"), 1,4-dioxane, ethanol, ethyl acetate ("EtOAc"), ethylene glycol, glycerin, heptanes, hexamethylphosphoramide ("HMPA"), hexamethylphosphorus triamide ("HMPT"), hexane, methanol ("MeOH"), methyl t-butyl ether ("MTBE"), methylene chloride ("DCM," "$CH_2C_{12}$"), N-methyl-2-pyrrolidinone ("NMP"), nitromethane, pentane, petroleum ether, 1-propanol ("n-propanol," "n-PrOH"), 2-propanol ("isopropanol," "iPrOH"), pyridine, tetrahydrofuran ("THF"), toluene, triethylamine ("TEA," "$Et_3N$"), o-xylene, m-xylene, and/or p-xylene, and the like. Solvent classes may include hydrocarbon, aromatic, aprotic, polar, alcoholic, and mixtures thereof.

As used herein, the terms "mechano-chemical mixing," "mechanochemistry," and "mechanical processing" refer to standard techniques known to those of ordinary skill in the art, in which chemical starting materials and/or reagents with disparate solubility properties are reacted, for example, by direct milling, liquid-assisted milling, triturating, mixing, or grinding, generally in the absence of solvents. Interchangeable terms may include "mechano-chemcial," or the like. See F. Ravalico et al., *Rapid synthesis of nucleotide pyrophosphate linkages in a ball mill*, 9 ORG. BIOMOL. CHEM. 6496 (2011); Dritan Hasa et al., *Cocrystal Formation through Mechanochemistry: From Neat and Liquid-Assisted Grinding to Polymer-Assisted Grinding*, 127 ANGEWANDTE CHEMIE 7371 (2015); and references cited therein, all of which are incorporated by reference herein in their entireties.

Without limitation, non-limiting examples of Brønsted acids include HI, HCl, HBr, $H_2SO_4$, $H_3O^+$, $HNO_3$, $H_3PO_4$, —$CH_3CO_2H$.

The term "alkyl," by itself or as part of another substituent, means, unless otherwise stated, a straight, branched, or cyclic chain hydrocarbon ("cycloalkyl") having the number of carbon atoms designated (i.e., $C_1$-$C_6$ means one to six carbons). Examples include methyl, ethyl, propyl, isopropyl, butyl, isobutyl, tert-butyl, pentyl, neopentyl, hexyl, cyclohexyl, and cyclopropyl. Most preferred are —($C_1$-$C_3$)alkyl, particularly ethyl, methyl, and isopropyl.

The term "alkenyl," by itself or as part of another substituent, means, unless otherwise stated, a stable mono-unsaturated or di-unsaturated straight chain, the unsaturation meaning a carbon-carbon double bond (—CH=CH—), branched chain or cyclic hydrocarbon group having the stated number of carbon atoms. Examples include vinyl, propenyl, allyl, crotyl, isopentenyl, butadienyl, 1,3-pentadienyl, 1,4-pentadienyl, cyclopentenyl, cyclopentadienyl, and the higher homologs and isomers. Functional groups representing an alkene are exemplified by —CH=CH—$CH_2$— and $CH_2$=CH—$CH_2$—.

"Substituted alkyl" or "substituted alkenyl" means alkyl or alkenyl, respectively, as defined above, substituted by one, two, or three substituents. The substituents may, for example, be selected from the group consisting of halogen, —OH, —$NH_2$, —$N(CH_3)_2$, —C(=O)OH, —C(=O)O($C_1$-$C_4$)alkyl, methoxy, ethoxy, trifluoromethyl, —C(=O)$NH_2$, —$SO_2NH_2$, —C(=NH)$NH_2$, —C≡N, and —$NO_2$, preferably selected from halogen and —OH. Examples of substituted alkyls, include, but are not limited to, 2,2-difluoromethyl, 2-carboxycyclopentyl, and 3-chloropropyl.

The term "alkynyl," by itself or as part of another substituent, means, unless otherwise stated, a stable carbon-carbon triple bond-containing radical (—C≡C—), branched chain, or cyclic hydrocarbon group having the stated number of carbon atoms. Examples include ethynyl and propargyl.

The term "alkoxy," by itself or as part of another substituent, means, unless otherwise stated, an alkyl group having the designated number of carbon atoms, as defined above, connected to the rest of the molecule via an oxygen atom, such as, for example, methoxy, ethoxy, 1-propoxy, 2-propoxy ("isopropoxy"), and the higher homologs and isomers. Preferred are —($C_1$-$C_3$)alkoxy, particularly ethoxy and methoxy.

The terms "carbamyl" or "carbamoyl" mean the group —C(=O)NRR', wherein R and R' are independently selected from hydrogen or a hydrocarbyl functional group, or wherein R and R' combined form a heterocycle. Examples of carbamyl groups include: —C(=O)$NH_2$ and —C(=O)$N(CH_3)_2$.

The term "cyano" refers to a —C≡N group.

The term "heteroalkyl," by itself or as part of another substituent, means, unless otherwise stated, a stable straight or branched chain alkyl group consisting of the stated number of carbon atoms and one or two heteroatoms selected from the group consisting of O, N, and S, and wherein the nitrogen and sulfur heteroatoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2$—$CH_2$—S(=O)—$CH_3$. Up to two heteroatoms may be consecutive, such as, for example, —$CH_2$—NH—$OCH_3$, or —$CH_2$—$CH_2$—S—S—$CH_3$.

The terms "halo" or "halogen," by themselves or as part of other substituents, mean, unless otherwise stated, a monovalent fluorine, chlorine, bromine, or iodine atom.

The term "nitro" refers to a —$NO_2$ group.

The term "($C_x$-$C_y$)perfluoroalkyl," wherein x<y, means an alkyl group with a minimum of x carbons and a maximum of y carbons, wherein all hydrogen atoms are replaced by fluorine atoms. Preferred is —($C_1$-$C_6$)perfluoroalkyl, more preferred is —($C_1$-$C_3$)perfluoroalkyl, most preferred is —$CF_3$.

The term "aromatic" generally refers to a carbocycle or heterocycle having one or more polyunsaturated rings having aromatic character (i.e., having (4n+2) delocalized π (pi) electrons where n is an integer).

The term "aryl," by itself or in combination with another substituent, means, unless otherwise stated, a carbocyclic aromatic system containing one or more rings (typically one, two, or three rings) wherein such rings may be attached together in a pendant manner, such as a biphenyl, or may be fused, such as naphthalene. Examples include phenyl; anthracyl; and naphthyl. Preferred are phenyl and naphthyl, most preferred is phenyl.

The terms "heterocycle" or "heterocyclyl" or "heterocyclic," by themselves or as part of other substituents, mean, unless otherwise stated, an unsubstituted or substituted, stable, mono- or multi-cyclic heterocyclic ring system that consists of carbon atoms and at least one heteroatom independently selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure.

The terms "heteroaryl" or "heteroaromatic," by themselves or as part of other substituents, refer, unless otherwise stated, to a heterocyclic having aromatic character. Similarly, the term "heteroaryl($C_1$-$C_3$)alkyl" means a functional group wherein a one to three carbon alkylene chain is attached to a heteroaryl group, e.g., —$CH_2$—$CH_2$-pyridyl. The term "substituted heteroaryl($C_1$-$C_3$)alkyl" means a heteroaryl($C_1$-$C_3$)alkyl functional group in which the heteroaryl group is substituted. A polycyclic heteroaryl may include fused rings. Examples include indole, 1H-indazole, 1H-pyrrolo[2,3-b]pyridine, and the like. A polycyclic heteroaryl may include one or more rings that are partially saturated. Examples include indoline, tetrahydroquinoline, and 2,3-dihydrobenzofuryl.

Non-limiting examples of non-aromatic heterocycles include monocyclic groups such as: aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, piperazine, N-methylpiperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxidine.

Non-limiting examples of heteroaryl groups include: pyridyl; pyrazinyl; pyrimidinyl, particularly 2- and 4-pyrimidinyl; pyridazinyl; thienyl; furyl; pyrrolyl, particularly 2-pyrrolyl; imidazolyl; thiazolyl; oxazolyl; pyrazolyl, particularly 3- and 5-pyrazolyl; isothiazolyl; 1,2,3-triazolyl; 1,2,4-triazolyl; 1,3,4-triazolyl; tetrazolyl; 1,2,3-thiadiazolyl; 1,2,3-oxadiazolyl; 1,3,4-thiadiazolyl; and 1,3,4-oxadiazolyl.

Polycyclic heterocycles include both aromatic and non-aromatic polycyclic heterocycles. Non-limiting examples of polycyclic heterocycles include: indolyl, particularly 3-, 4-, 5-, 6-, and 7-indolyl; indolinyl; indazolyl, particularly 1H-indazol-5-yl; quinolyl; tetrahydroquinolyl; isoquinolyl, particularly 1- and 5-isoquinolyl; 1,2,3,4-tetrahydroisoquinolyl; cinnolyl; quinoxalinyl, particularly 2- and 5-quinoxalinyl; quinazolinyl; phthalazinyl; naphthyridinyl, particularly 1,5- and 1,8-naphthyridinyl; 1,4-benzodioxanyl; coumaryl; dihydrocoumaryl; benzofuryl, particularly 3-, 4-, 5-, 6-, and 7-benzofuryl; 2,3-dihydrobenzofuryl; 1,2-benzisoxazoyl; benzothienyl, particularly 3-, 4-, 5-, 6-, and 7-benzothienyl; benzoxazolyl; benzothiazolyl, particularly 2- and 5-benzothiazolyl; purinyl; benzimidazolyl, particularly 2-benzimidazolyl; benztriazolyl; thioxanthinyl; carbazolyl; carbolinyl; acridinyl; pyrrolizidinyl; pyrrolo[2,3-b]pyridinyl, particularly 1H-pyrrolo[2,3-b]pyridine-5-yl; and quinolizidinyl. Particularly preferred are 4-indolyl, 5-indolyl, 6-indolyl, 1H-indazol-5-yl, and 1H-pyrrolo[2,3-b]pyridin-5-yl.

The aforementioned listing of heterocyclic and heteroaryl moieties is intended to be representative and not limiting.

The term "substituted" means that an atom or group of atoms has replaced hydrogen as the substituent attached to another group. For aryl and heteroaryl groups, the term "substituted" refers to any level of substitution, namely mono-, di-, tri-, tetra-, or penta-substitution, where such substitution is permitted. The substituents are independently selected, and substitution may be at any chemically accessible position.

The term "unsubstituted" means that no atom or group of atoms has replaced hydrogen as the substituent attached to another group. For aryl and heteroaryl groups, the term "unsubstituted" refers to no level of substitution where such substitution is permitted.

D-Ribose stereochemistry has been indicated in compounds or derivatives having formulae (I), (Ia), (II), (IIa), (3), and (4) or salts, hydrates, or solvates thereof. It is understood that the configuration at the anomeric carbon can be reversed (i.e., L-), or can be a mixture of D- and L-.

Synthetic Preparation of Compounds and Derivatives Having Formulae (I) or (II), or Salts, Hydrates, or Solvates Thereof.

In certain embodiments, generally solvent-based chemical laboratory techniques may be employed in the processes to prepare the compounds or derivatives of formulae (I) or (II), or salts, hydrates, or solvates thereof.

In other embodiments, generally solvent-free conditions may be employed in the processes to prepare the compounds or derivatives of formulae (I) or (II), or salts, hydrates, or solvates thereof, using appropriate mechano-chemical techniques as described.

In an embodiment, a method of making a nicotinate/nicotinamide riboside compound or derivative of formula (I), or a salt, hydrate, or solvate thereof is provided. The nicotinate/nicotinamide riboside compounds or derivatives of formula (I) may be prepared by a method comprising the steps of:

(a) providing a nicotinate/nicotinamide compound or derivative having formula (1), or a salt thereof, optionally, in one or more solvent(s);

(b) treating the compound or derivative having formula (1), or salt thereof, with at least about one molar equivalent amount of a riboside compound or derivative having formula (2), or salt thereof, optionally, in one or more solvent(s);

optionally, (b)(1) adding a catalyst;

(c) reacting the nicotinate/nicotinamide compound or derivative having formula (1), or salt thereof, optionally, in one or more solvent(s), with the riboside compound or derivative having formula (2), or salt thereof, optionally, in one or more solvent(s), and, optionally, the catalyst, according to solvent-based chemical laboratory techniques so as to produce the compound or derivative of formula (I), or salt, hydrate, or solvate thereof;

(d) adding water to the nicotinate/nicotinamide compound or derivative having formula (1), or salt thereof, optionally, in one or more solvent(s), the riboside compound or derivative having formula (2), or salt thereof, optionally, in one or more solvent(s), the compound or derivative of formula (I), or salt, hydrate, or solvate thereof, and optionally, the catalyst;

(e) extracting the nicotinate/nicotinamide compound or derivative having formula (1), or salt thereof, optionally, in one or more solvent(s), the riboside compound or derivative having formula (2), or salt thereof, optionally, in one or more solvent(s), optionally, the catalyst, the compound or derivative of formula (I), or salt, hydrate, or solvate thereof, and the water with organic solvent;

optionally, (e)(1) adjusting the pH of the combined organic extracts with an aqueous solution of acid or base, if necessary;

(f) precipitating or isolating the compound or derivative of formula (I), or salt, hydrate, or solvate thereof, or removing the organic solvent used for extraction; and optionally, (g) purifying the compound or derivative of formula (I), or salt, solvate, or solvate thereof.

The process described herein effects a chemical, solvent-based synthesis of modified conjugates or derivatives of nicotinate/nicotinamide ribonucleoside compounds (NR or NAR, respectively) of formula (I), or salt, hydrate, or solvate thereof.

In another embodiment, an alternative method of making a nicotinate/nicotinamide riboside compound or derivative of formula (I), or a salt, hydrate, or solvate thereof is provided. The nicotinate/nicotinamide riboside compounds or derivatives of formula (I) may be prepared by a method comprising the steps of:

(a) providing a riboside compound or derivative having formula (2), or a salt thereof, optionally, in one or more solvent(s);

(b) treating the compound or derivative having formula (2), or salt thereof, with at least about one molar equivalent amount of a Lewis acid, optionally, in one or more solvent(s);

(c) treating the mixture of the compound or derivative having formula (2), or salt thereof, and Lewis acid, optionally, in one or more solvent(s), with at least about one molar equivalent amount of a nicotinate/nicotinamide compound or derivative having formula (1), or a salt thereof, optionally, in one or more solvent(s);

(d) reacting the riboside compound or derivative having formula (2), or salt thereof, and Lewis acid, optionally, in one or more solvent(s), with the nicotinate/nicotinamide compound or derivative having formula (1), or salt thereof, optionally, in one or more solvent(s), according to solvent-based chemical laboratory techniques so as to produce the compound or derivative of formula (I), or salt, hydrate, or solvate thereof;

(e) adding water to the riboside compound or derivative having formula (2), or salt thereof, optionally, in one or more solvent(s), the Lewis acid, optionally, in one or more solvent(s), the nicotinate/nicotinamide compound or derivative having formula (1), or salt thereof, optionally, in one or more solvent(s), and the compound or derivative of formula (I), or salt, hydrate, or solvate thereof;

(f) extracting the riboside compound or derivative having formula (2), or salt thereof, optionally, in one or more solvent(s), the Lewic acid, optionally, in one or more solvent(s), the nicotinate/nicotinamide compound or derivative having formula (1), or salt thereof, optionally, in one or more solvent(s), the compound or derivative of formula (I), or salt, hydrate, or solvate thereof, and the water, with organic solvent;

optionally, (f)(1) adjusting the pH of the combined organic extracts with an aqueous solution of acid or base, if necessary;

(g) precipitating or isolating the compound or derivative of formula (I), or salt, hydrate, or solvate thereof, or removing the organic solvent used for extraction; and optionally, (h) purifying the compound or derivative of formula (I), or salt, hydrate, or solvate thereof.

The process described herein effects a chemical, solvent-based synthesis of modified conjugates or derivatives of nicotinate/nicotinamide ribonucleoside compounds (NR or NAR, respectively) of formula (I), or salt, hydrate, or solvate thereof.

In yet another embodiment, a method of making a nicotinate/nicotinamide riboside compound or derivative of formula (I), or a salt, hydrate, or solvate thereof is provided. The nicotinate/nicotinamide riboside compounds or derivatives of formula (I) may be prepared by a method comprising the steps of:

(a) providing a nicotinate/nicotinamide compound or derivative having formula (1), or a salt thereof;

(b) treating the compound or derivative having formula (1), or salt thereof, with at least about one molar equivalent amount of a riboside compound or derivative having formula (2), or a salt thereof;

optionally, (b)(1) adding a catalyst;

(c) mechanically grinding and/or milling the nicotinate/nicotinamide compound or derivative having formula (1), or salt thereof, the riboside compound or derivative having formula (2), or salt thereof, and, optionally, the catalyst, so as to produce the compound or derivative of formula (I), or salt, hydrate, or solvate thereof;

(d) adding water to the nicotinate/nicotinamide compound or derivative having formula (1), or salt thereof, the riboside compound or derivative having formula (2), or salt thereof, the compound or derivative of formula (I), or salt, hydrate, or solvate thereof, and, optionally, the catalyst;

(e) extracting the nicotinate/nicotinamide compound or derivative having formula (1), or salt thereof, the riboside compound or derivative having formula (2), or salt thereof, the compound or derivative of formula (I), or salt, hydrate, or solvate thereof, optionally, the catalyst, and the water with organic solvent;

optionally, (e)(1) adjusting the pH of the combined organic extracts with an aqueous solution of acid or base, if necessary;

(f) precipitating or isolating the compound or derivative of formula (I), or salt, hydrate, or solvate thereof, or removing the organic solvent used for extraction; and optionally, (g) purifying the compound or derivative of formula (I), or salt, hydrate, or solvate thereof.

Grinding may be performed between about 50 RPM and about 200 RPM, preferably between about 75 RPM and about 150 RPM, and most preferably between about 100 RPM and about 130 RPM.

The process described herein effects a chemical, mechano-chemical, and/or solvent-free synthesis of modified conjugates or derivatives of nicotinate/nicotinamide ribonucleoside compounds (NR or NAR, respectively) of formula (I), or salt, hydrate, or solvate thereof.

In yet another embodiment, an alternative method of making a nicotinate/nicotinamide riboside compound or derivative of formula (I), or a salt, hydrate, or solvate thereof is provided. The nicotinate/nicotinamide riboside compounds or derivatives of formula (I) may be prepared by a method comprising the steps of:

(a) providing a riboside compound or derivative having formula (2), or a salt thereof;

(b) treating the compound or derivative having formula (2), or salt thereof, with at least about one molar equivalent amount of a Lewis acid;

(c) mechanically grinding and/or milling the riboside compound or derivative having formula (2), or salt thereof, and the Lewis acid;

(d) treating the mixture of the riboside compound or derivative having formula (2), or salt thereof, and the Lewis acid with at least about one molar equivalent amount of a nicotinate/nicotinamide compound or derivative having formula (1), or a salt thereof;

(e) mechanically grinding and/or milling the mixture of the riboside compound or derivative having formula (2), or salt thereof, the Lewis acid, and the nicotinate/nicotinamide compound or derivative having formula (1), or salt thereof, so as to produce the compound or derivative of formula (I), or salt, hydrate, or solvate thereof;

(f) adding water to the riboside compound or derivative having formula (2), or salt thereof, the Lewis acid, the nicotinate/nicotinamide compound or derivative having formula (1), or salt thereof, and the compound or derivative of formula (I), or salt, hydrate, or solvate thereof;

(g) extracting the riboside compound or derivative having formula (2), or salt thereof, the Lewis acid, the nicotinate/nicotinamide compound or derivative having formula (1), or salt thereof, the compound or derivative of formula (I), or salt, hydrate, or solvate thereof, and the water with organic solvent;

optionally, (g)(1) adjusting the pH of the combined organic extracts with an aqueous solution of acid or base, if necessary;

(h) precipitating or isolating the compound or derivative of formula (I), or salt, hydrate, or solvate thereof, or removing the organic solvent used for extraction; and optionally, (i) purifying the compound of formula (I), or salt, hydrate, or solvate thereof.

Grinding may be performed between about 50 RPM and about 200 RPM, preferably between about 75 RPM and about 150 RPM, and most preferably between about 100 RPM and about 130 RPM.

The process described herein effects a chemical, mechano-chemical, and/or solvent-free synthesis of modified conjugates or derivatives of nicotinate/nicotinamide ribonucleoside compounds (NR or NAR, respectively) of formula (I), or salt, hydrate, or solvate thereof.

In yet another embodiment, a method of making a nicotinate/nicotinamide riboside compound or derivative of formula (I), or a salt, hydrate, or solvate thereof, is provided. The nicotinate/nicotinamide riboside compounds or derivatives of formula (I) may be prepared by a method comprising the steps of:

(a) providing a riboside compound or derivative having formula (2), or a salt thereof;

(b) treating the compound or derivative having formula (2), or salt thereof, with molar equivalents ($3<x<100$) of an alcohol (e.g., methanol, or ethanol) and molar equivalents ($3 \leq x<20$) of a Brønsted inorganic acid;

(c) treating the mixture of the riboside compound or derivative having formula (2), or salt thereof, the alcohol, and the Brønsted inorganic acid with at least about one molar equivalent amount of a nicotinate/nicotinamide compound or derivative having formula (1), or salt thereof;

(d) reacting the riboside compound or derivative having formula (2), or salt thereof, the alcohol, the Brønsted inorganic acid, and the nicotinate/nicotinamide compound or derivative having formula (1), or salt thereof, so as to produce the compound or derivative of formula (I), or salt, hydrate, or solvate thereof;

(e) filtering the precipitated compound or derivative having formula (I), or salt, hydrate, or solvate thereof;

optionally, (e1) washing the compound or derivative having formula (I), or salt, hydrate, or solvate thereof with cold alcohol (e.g., methanol, or ethanol);

(f) precipitating or isolating the compound or derivative of formula (I), or salt, hydrate, or solvate thereof; and optionally, (g) purifying the compound or derivative of formula (I), or salt, hydrate, or solvate thereof.

This process effects a chemical, solvent-based synthesis of modified conjugates or derivatives of nicotinate/nicotinamide ribonucleoside compounds (NR or NAR, respectively) of formula (I), or salt, hydrate, or solvate thereof.

In yet another embodiment, a method of making a nicotinate/nicotinamide riboside compound or derivative of formula (I), or a salt, hydrate, or solvate thereof, is provided. The nicotinate/nicotinamide riboside compounds or derivatives of formula (I) may be prepared by a method comprising the steps of:

(a) providing a riboside compound or derivative having formula (2), or a salt thereof;

(b) treating the compound or derivative having formula (2), or salt thereof, with molar equivalents ($3<x<100$) of an alcohol (e.g., methanol, or ethanol) and molar equivalents ($3 \leq x<20$) of acetyl chloride;

(c) treating the mixture of the riboside compound or derivative having formula (2), or salt thereof, the alcohol, and the acetyl chloride with at least about one molar equivalent amount of a nicotinate/nicotinamide compound or derivative having formula (1), or salt thereof;

(d) reacting the riboside compound or derivative having formula (2), or salt thereof, the alcohol, the acetyl chloride, and the nicotinate/nicotinamide compound or derivative having formula (1), or salt thereof, so as to produce the compound or derivative of formula (I), or salt, hydrate, or solvate thereof;

(e) filtering the precipitated compound or derivative having formula (I), or salt, hydrate, or solvate thereof;

optionally, (e1) washing the compound or derivative having formula (I), or salt, hydrate, or solvate thereof with cold alcohol (e.g., methanol, or ethanol);

(f) precipitating or isolating the compound or derivative of formula (I), or salt, hydrate, or solvate thereof; and optionally, (g) purifying the compound or derivative of formula (I), or salt, hydrate, or solvate thereof.

This process effects a chemical, solvent-based synthesis of modified conjugates or derivatives of nicotinate/nicotinamide ribonucleoside compounds (NR or NAR, respectively) of formula (I), or salt, hydrate, or solvate thereof.

In yet another embodiment, a method of making a nicotinate/nicotinamide riboside compound or derivative of formula (I), or a salt, hydrate, or solvate thereof is provided. The nicotinate/nicotinamide riboside compounds or derivatives of formula (I) may be prepared by a method comprising the steps of:

(a) providing a nicotinate/nicotinamide riboside compound or derivative having formula (3), or a salt thereof, optionally, in one or more solvent(s);

(b) treating the compound or derivative having formula (3), or salt thereof, with at least about one molar equivalent amount of one or more reagent(s), optionally, in one or more solvent(s);

optionally, (b)(1) adding a catalyst;

(c) reacting the nicotinate/nicotinamide compound or derivative having formula (3), or salt thereof, optionally, in one or more solvent(s), with the one or more reagent(s), optionally, in one or more solvent(s), and, optionally, the catalyst, according to solvent-based chemical laboratory techniques so as to produce the compound or derivative of formula (I), or salt, hydrate, or solvate thereof;

(d) adding water to the nicotinate/nicotinamide riboside compound or derivative having formula (3), or salt thereof, optionally, in one or more solvent(s), the one or more reagent(s), optionally, in one or more solvent(s), optionally, the catalyst, and the compound or derivative of formula (I), or salt, hydrate, or solvate thereof;

(e) extracting the nicotinate/nicotinamide riboside compound or derivative having formula (3), or salt thereof, optionally, in one or more solvent(s), the one or more reagent(s), optionally, in one or more solvent(s), the compound or derivative of formula (I), or salt, hydrate, or solvate thereof, optionally, the catalyst, and the water, with organic solvent;

optionally, (e)(1) adjusting the pH of the combined organic extracts with an aqueous solution of acid or base, if necessary;

(f) precipitating or isolating the compound or derivative of formula (I), or salt, hydrate, or solvate-thereof, or removing the organic solvent used for extraction; and optionally, (g) purifying the compound or derivative of formula (I), or salt, hydrate, or solvate thereof.

The process described herein effects a chemical, solvent-based synthesis of modified conjugates or derivatives of nicotinate/nicotinamide ribonucleoside compounds (NR or NAR, respectively) of formula (I), or salt, hydrate, or solvate thereof.

In yet another embodiment, an alternative method of making a nicotinate/nicotinamide riboside compound or derivative of formula (I), or a salt, hydrate, or solvate thereof is provided. The nicotinate/nicotinamide riboside compounds or derivatives of formula (I) may be prepared by a method comprising the steps of:

(a) providing a nicotinate/nicotinamide riboside compound or derivative having formula (3), or a salt thereof;

(b) treating the compound or derivative having formula (3), or salt thereof, with at least about one molar equivalent amount of one or more activated reagent(s);

optionally, (b)(1) adding a catalyst;

(c) mechanically grinding and/or milling the nicotinate/nicotinamide riboside compound or derivative having formula (3), or salt thereof, the one or more activated reagent(s), and, optionally, the catalyst, so as to produce the compound or derivative of formula (I), or salt, hydrate, or solvate thereof;

(d) adding water to the nicotinate/nicotinamide riboside compound or derivative having formula (3), or salt thereof, the one or more activated reagent(s), the compound or derivative of formula (I), or salt, hydrate, or solvate thereof, and, optionally, the catalyst;

(e) extracting the nicotinate/nicotinamide compound or derivative having formula (3), or salt, hydrate, or solvate thereof, the one or more activated reagent(s), optionally, the catalyst, the compound or derivative of formula (I), or salt, hydrate, or solvate thereof, and the water with organic solvent;

optionally, (e)(1) adjusting the pH of the combined organic extracts with an aqueous solution of acid or base, if necessary;

(f) precipitating or isolating the compound or derivative of formula (I), or salt, hydrate, or solvate thereof, or removing the organic solvent used for extraction; and optionally, (g) purifying the compound or derivative of formula (I), or salt, hydrate, or solvate thereof.

Grinding may be performed between about 50 RPM and about 200 RPM, preferably between about 75 RPM and about 150 RPM, and most preferably between about 100 RPM and about 130 RPM.

The process described herein effects a chemical, mechano-chemical, and/or solvent-free synthesis of modified conjugates or derivatives of nicotinate/nicotinamide ribonucleoside compounds (NR or NAR, respectively) of formula (I), or salt, hydrate, or solvate thereof.

In yet another embodiment, a method of making a nicotinate/nicotinamide riboside compound or derivative of formula (I), or a salt, hydrate, or solvate thereof is provided. The nicotinate/nicotinamide riboside compounds or derivatives of formula (I) may be prepared by a method comprising the steps of:

(a) providing a reduced nicotinate/nicotinamide riboside compound or derivative of formula (II), or a salt, hydrate, or solvate thereof;

(b) oxidizing the reduced nicotinate/nicotinamide riboside compound or derivative of formula (II), or salt, hydrate, or solvate thereof, with at least about one molar equivalent amount of an oxidizing agent, optionally, in one or more solvent(s), so as to produce the compound or derivative of formula (I), or salt, hydrate, or solvate thereof;

(c) precipitating or isolating the compound or derivative of formula (I), or salt, hydrate, or solvate thereof, or removing the one or more solvent(s); and optionally, (d) purifying the compound or derivative of formula (I), or salt, hydrate, or solvate thereof.

The process described herein effects a chemical, solvent-based synthesis of modified conjugates or derivatives of nicotinate/nicotinamide riboside compounds (NR or NAR, respectively) of formula (I), or salt, hydrate, or solvate thereof.

In yet another embodiment, an alternative method of making a nicotinate/nicotinamide riboside compound or derivative of formula (I), or a salt, hydrate, or solvate thereof is provided.

The nicotinate/nicotinamide riboside compounds or derivatives of formula (I) may be prepared by a method comprising the steps of:

(a) providing a reduced nicotinate/nicotinamide riboside compound or derivative of formula (II), or a salt, hydrate, or solvate thereof;

(b) oxidizing the reduced nicotinate/nicotinamide riboside compound or derivative of formula (II), or salt, hydrate, or solvate thereof, with at least about one molar equivalent amount of an oxidizing agent, so as to produce the compound or derivative of formula (I), or salt, hydrate, or solvate thereof; and optionally, (c) purifying and/or isolating the compound or derivative of formula (I), or salt, hydrate, or solvate thereof.

Grinding may be performed between about 50 RPM and about 200 RPM, preferably between about 75 RPM and about 150 RPM, and most preferably between about 100 RPM and about 130 RPM.

The process described herein effects a chemical, mechano-chemical, and/or solvent-free synthesis of modified conjugates or derivatives of nicotinate/nicotinamide riboside compounds (NR or NAR, respectively) of formula (I), or salt, hydrate, or solvate thereof.

In an embodiment, a method of making a reduced nicotinate/nicotinamide riboside compound or derivative of formula (II), or a salt, hydrate, or solvate thereof is provided. The reduced nicotinate/nicotinamide riboside compounds or derivatives of formula (II) may be prepared by a method comprising the steps of:

(a) providing a reduced nicotinate/nicotinamide riboside compound or derivative having formula (4), or a salt thereof, optionally, in one or more solvent(s);

(b) treating the compound or derivative having formula (4), or salt thereof, optionally, in one or more solvent(s) with at least about 0.5 molar equivalent amount of one or more activated reagent(s), optionally, in one or more solvent(s);

optionally, (b)(1) adding a catalyst;

(c) reacting the reduced nicotinate/nicotinamide riboside compound or derivative having formula (4), or salt thereof, optionally, in one or more solvent(s), with the one or more activated reagent(s), optionally, in one or more solvent(s), and, optionally, the catalyst, according to solvent-based chemical laboratory techniques so as to produce the compound or derivative of formula (II), or salt, hydrate, or solvate thereof;

(d) adding water to the reduced nicotinate/nicotinamide riboside compound or derivative having formula (4), or salt thereof, optionally, in one or more solvent(s), the one or more activated reagent(s), optionally, in one or more solvent(s), optionally, the catalyst, and the compound or derivative of formula (II), or salt, hydrate, or solvate thereof;

(e) extracting the reduced nicotinate/nicotinamide riboside compound or derivative having formula (4), or salt thereof, optionally, in one or more solvent(s), the one or more activated reagent(s), optionally, in one or more solvent(s), the compound or derivative of formula (II), or salt, hydrate, or solvate thereof, optionally, the catalyst, and the water with organic solvent;

optionally, (e)(1) adjusting the pH of the combined organic extracts with an aqueous solution of acid or base, if necessary;

(f) precipitating or isolating the compound or derivative of formula (II), or salt, hydrate, or solvate thereof, or removing the organic solvent used for extraction; and optionally, (g) purifying the compound of formula (II), or salt, hydrate, or solvate thereof.

The process described herein effects a chemical, solvent-based synthesis of modified conjugates or derivatives of reduced nicotinate/nicotinamide ribonucleoside compounds (NRH or NARH, respectively) of formula (II), or salt, hydrate, or solvate thereof.

In another embodiment, an alternative method of making a reduced nicotinate/nicotinamide riboside compound or derivative of formula (II), or a salt, hydrate, or solvate thereof is provided. The reduced nicotinate/nicotinamide riboside compounds or derivatives of formula (II) may be prepared by a method comprising the steps of:

(a) providing a reduced nicotinate/nicotinamide riboside compound or derivative having formula (4), or a salt thereof;

(b) treating the compound or derivative having formula (4), or salt thereof, with at least about 0.5 molar equivalent amount of one or more activated reagent(s);

optionally, (b)(1) adding a catalyst;

(c) mechanically grinding and/or milling the compound or derivative having formula (4), or salt thereof, the one or more activated reagent(s), and, optionally, the catalyst, so as to produce the compound or derivative of formula (II), or salt, hydrate, or solvate thereof;

(d) adding water to the compound or derivative having formula (4), or salt thereof, the one or more activated reagent(s), optionally, the catalyst, and the compound or derivative of formula (II), or salt, hydrate, or solvate thereof;

(e) extracting the compound or derivative having formula (4), or salt thereof, the one or more activated reagent(s), optionally, the catalyst, and the compound or derivative of formula (II), or salt, hydrate, or solvate thereof, with organic solvent;

optionally, (e)(1) adjusting the pH of the combined organic extracts with an aqueous solution of acid or base, if necessary;

(f) precipitating or isolating the compound or derivative of formula (II), or salt, hydrate, or solvate thereof, or removing the organic solvent used for extraction; and optionally, (g) purifying the compound of formula (II), or salt, hydrate, or solvate thereof.

Grinding may be performed between about 50 RPM and about 200 RPM, preferably between about 75 RPM and about 150 RPM, and most preferably between about 100 RPM and about 130 RPM.

The process described herein effects a chemical, mechano-chemical, and/or solvent-free synthesis of modified conjugates or derivatives of reduced nicotinate/nicotinamide ribonucleoside compounds (NRH or NARH, respectively) of formula (II), or salt, hydrate, or solvate thereof.

In yet another embodiment, a method of making a reduced nicotinate/nicotinamide riboside compound or derivative of formula (II), or a salt, hydrate, or solvate thereof is provided.

The reduced nicotinate/nicotinamide riboside compounds or derivatives of formula (II) may be prepared by a method comprising the steps of:

(a) providing a nicotinate/nicotinamide riboside compound or derivative of formula (I), or a salt, hydrate, or solvate thereof;

(b) reducing the nicotinate/nicotinamide riboside compound or derivative of formula (I), or salt, hydrate, or solvate thereof, with at least about one molar equivalent amount of a reducing agent, optionally, in one or more solvent(s), so as to produce the compound or derivative of formula (II), or salt, hydrate, or solvate thereof;

(c) precipitating or isolating the compound or derivative of formula (II), or salt, hydrate, or solvate thereof, or removing the one or more solvent(s); and optionally, (d) precipitating an the compound or derivative of formula (II), or salt, hydrate, or solvate thereof.

The process described herein effects a chemical, solvent-based synthesis of modified conjugates or derivatives of reduced nicotinate/nicotinamide riboside compounds (NRH or NARH, respectively) of formula (II), or salt, hydrate, or solvate thereof.

In yet another embodiment, an alternative method of making a reduced nicotinate/nicotinamide riboside compound or derivative of formula (II), or a salt, hydrate, or solvate thereof is provided. The reduced nicotinate/nicotinamide riboside compounds or derivatives of formula (II) may be prepared by a method comprising the steps of:

(a) providing a nicotinate/nicotinamide riboside compound or derivative of formula (I), or a salt, hydrate, or solvate thereof;

(b) reducing the compound or derivative of formula (I), or salt, hydrate, or solvate thereof, with at least about one molar equivalent amount of a reducing agent so as to produce the compound or derivative of formula (II), or salt, hydrate, or solvate thereof; and optionally, (c) purifying and/or isolating the compound or derivative of formula (II), or salt, hydrate, or solvate thereof.

The process described herein effects a chemical, mechano-chemical, and/or solvent-free synthesis of modified conjugates or derivatives of reduced nicotinate/nicotinamide ribonucleoside compounds (NRH or NARH, respectively) of formula (II), or salt, hydrate, or solvate thereof.

In yet another embodiment, a method of making a reduced nicotinate/nicotinamide riboside compound or derivative of formula (II), or a salt, hydrate, or solvate thereof is provided. The reduced nicotinate/nicotinamide riboside compounds or derivatives of formula (II) may be prepared by a method comprising the steps of:

(a) providing a nicotinate/nicotinamide riboside compound or derivative having formula (3), or a salt thereof, optionally, in one or more solvent(s);

(b) treating the compound or derivative having formula (3), or salt thereof, optionally, in one or more solvent(s), with at least about one molar equivalent amount of one or more activated reducing reagent(s), optionally, in one or more solvent(s);

optionally, (b)(1) adding a catalyst;

(c) reacting the nicotinate/nicotinamide compound or derivative having formula (3), or salt thereof, optionally, in one or more solvent(s), with the one or more activated reducing reagent(s), optionally, in one or more solvent(s), and, optionally, the catalyst, so as to produce the compound or derivative of formula (II), or salt, hydrate, or solvate thereof;

(d) adding water to the nicotinate/nicotinamide compound or derivative having formula (3), or salt thereof, optionally, in one or more solvent(s), the one or more activated reducing reagent(s), optionally, in one or more solvent(s), optionally, the catalyst, and the compound or derivative of formula (II), or salt, hydrate, or solvate thereof;

(e) extracting the nicotinate/nicotinamide compound or derivative having formula (3), or salt thereof, optionally, in one or more solvent(s), the one or more activated reducing reagent(s), optionally, in one or more solvent(s), the compound or derivative of formula (II), or salt, hydrate, or solvate thereof, optionally, the catalyst, and the water with organic solvent;

optionally, (e)(1) adjusting the pH of the combined organic extracts with an aqueous solution of acid or base, if necessary;

(f) precipitating or isolating the compound or derivative of formula (II), or salt, hydrate, or solvate thereof, or removing the organic solvent used for extraction; and optionally, (g) purifying the compound or derivative of formula (II), or salt, hydrate, or solvate thereof.

The process described herein effects a chemical, solvent-based synthesis of modified conjugates or derivatives of reduced nicotinate/nicotinamide riboside compounds (NRH or NARH, respectively) of formula (II), or salt, hydrate, or solvate thereof.

Without limitation, and for illustrative purposes, one of ordinary skill in the art may refer to WO2015014722 A1, filed on Jul. 24, 2014, and incorporated by reference herein in its entirety, for further details on performing the above method(s).

In yet another embodiment, an alternative method of making a reduced nicotinate/nicotinamide riboside compound or derivative or derivative of formula (II), or a salt, hydrate, or solvate thereof is provided. The reduced nicotinate/nicotinamide riboside compounds or derivatives of formula (II) may be prepared by a method comprising the steps of:

(a) providing a nicotinate/nicotinamide riboside compound or derivative having formula (3), or a salt thereof;

(b) treating the compound or derivative having formula (3), or salt thereof, with at least about one molar equivalent amount of one or more activated reducing reagent(s);

optionally, (b)(1) adding a catalyst;

(c) mechanically grinding and/or milling the nicotinate/nicotinamide riboside compound or derivative having formula (3), or salt thereof, the one or more activated reducing reagent(s), and, optionally, the catalyst, so as to produce the compound or derivative of formula (II), or salt, hydrate, or solvate thereof;

(d) adding water to the nicotinate/nicotinamide riboside compound or derivative having formula (3), or salt thereof, the one or more activated reducing reagent(s), optionally, the catalyst, and the compound or derivative of formula (II), or salt, hydrate, or solvate thereof;

(e) extracting the nicotinate/nicotinamide riboside compound or derivative having formula (3), or salt thereof, the one or more activated reducing reagent(s), the compound or derivative of formula (II), or salt, hydrate, or solvate thereof, optionally, the catalyst, and the water with organic solvent;

optionally, (e)(1) adjusting the pH of the combined organic extracts with an aqueous solution of acid or base, if necessary;

(f) precipitating or isolating the compound or derivative of formula (II), or salt, hydrate, or solvate thereof, or removing the organic solvent used for extraction; and optionally, (g) purifying the compound or derivative of formula (II), or salt, hydrate, or solvate thereof.

Grinding may be performed between about 50 RPM and about 200 RPM, preferably between about 75 RPM and about 150 RPM, and most preferably between about 100 RPM and about 130 RPM.

The process described herein effects a chemical, mechano-chemical, and/or solvent-free synthesis of modified conjugates or derivatives of reduced nicotinate/nicotinamide riboside compounds (NRH or NARH, respectively) of formula (II), or salt, hydrate, or solvate thereof.

It is understood that the pH can be adjusted to the isoelectric point of the product compound(s), or near neutral pH. Precipitation of the product compound(s) can be carried out using an appropriate water-miscible or other generally non-toxic solvent.

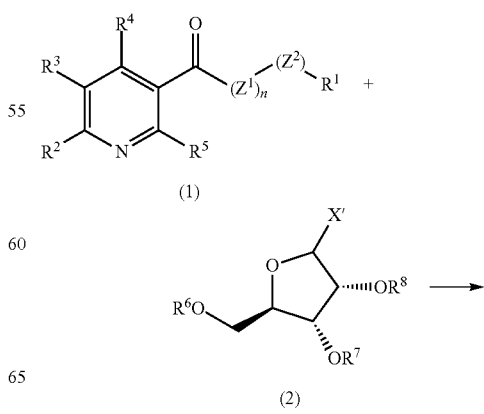

Scheme A

-continued

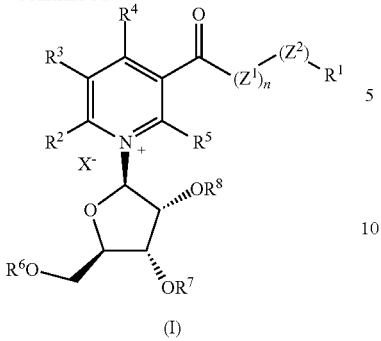

(I)

In one embodiment, the chemoselective synthesis of the compounds or derivatives of formula (I), or salts, hydrates, or solvates thereof, is shown above in Scheme A.

-continued

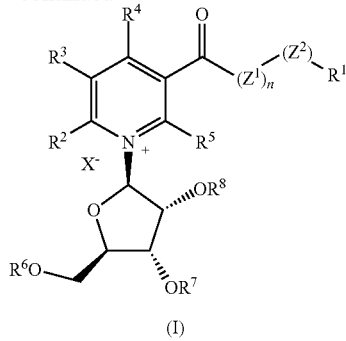

(I)

In yet another embodiment, the synthesis of the compounds or derivatives of formula (I), or salts, hydrates, or solvates thereof, is shown above in Scheme C.

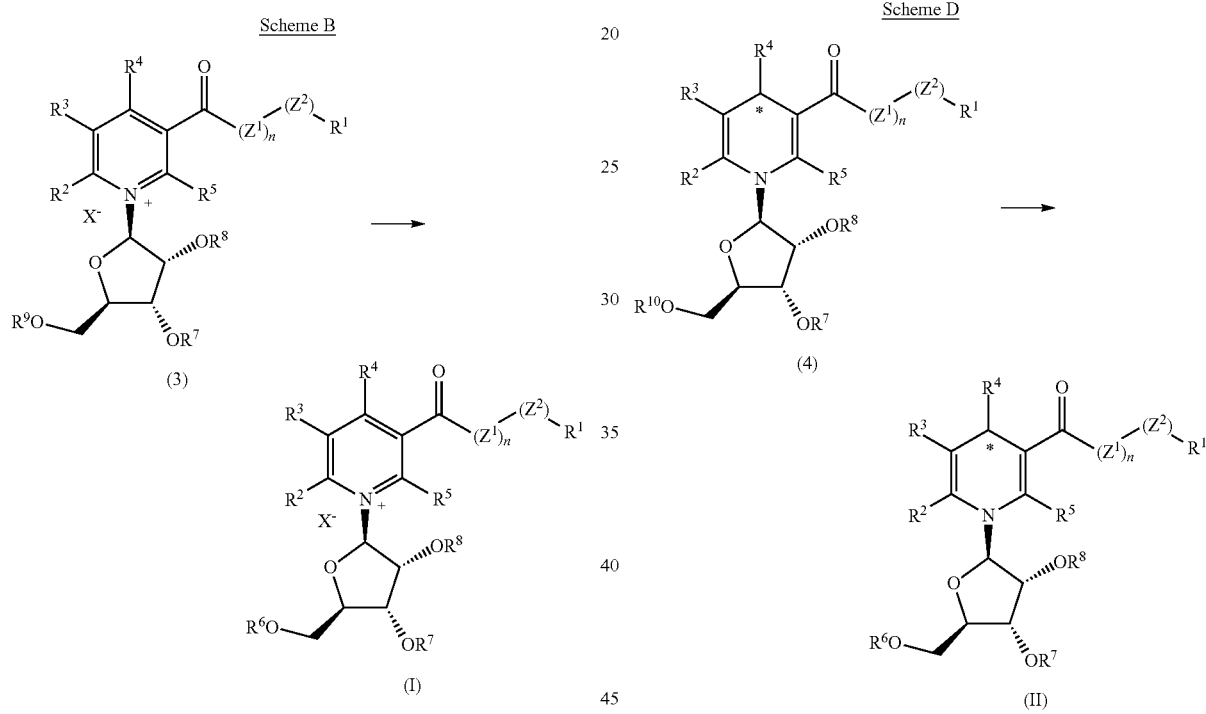

In another embodiment, the alternative chemoselective synthesis of the compounds or derivatives of formula (I), or salts, hydrates, or solvates thereof, is shown above in Scheme B.

In yet another embodiment, the alternative chemoselective synthesis of the compounds or derivatives of formula (II), or salts, hydrates, or solvates thereof, is shown above in Scheme D.

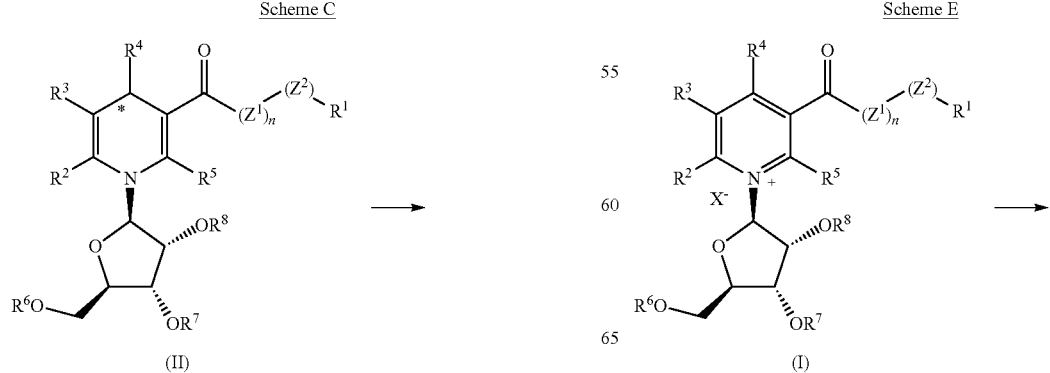

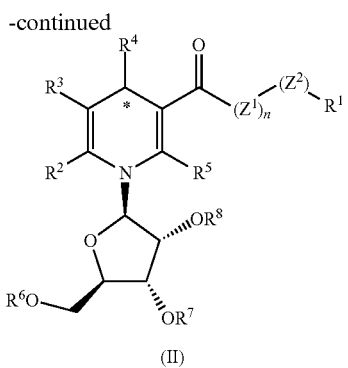

(II)

In yet another embodiment, the alternative chemoselective synthesis of the compounds or derivatives of formula (II), or salts, hydrates, or solvates thereof, is shown above in Scheme E.

In the embodiments shown above in Schemes A-E:

$X^-$ is selected from the group consisting of fluoride, chloride, bromide, iodide, formate, acetate, ascorbate, benzoate, carbonate, citrate, carbamate, formate, gluconate, lactate, methyl bromide, methyl sulfate, nitrate, phosphate, diphosphate, succinate, sulfate, trifluoromethanesulfonate, trichloromethanesulfonate, tribromomethanesulfonate, and trifluoroacetate;

optionally $X^-$ as counterion is absent optionally the counterion is an internal salt;

optionally $X^-$ is an anion of a substituted or unsubstituted carboxylic acid selected from a monocarboxylic acid, a dicarboxylic acid, or a polycarboxylic acid; and, optionally $X^-$ is an anion of a substituted monocarboxylic acid, further optionally an anion of a substituted propanoic acid (propanoate or propionate), or an anion of a substituted acetic acid (acetate), or an anion of a hydroxyl-propanoic acid, or an anion of 2-hydroxypropanoic acid (being lactic acid; the anion of lactic acid being lactate), or a trihaloacetate selected from trichloroacetate, tribromoacetate, and trifluoroacetate; and, optionally $X^-$ is an anion of an unsubstituted monocarboxylic acid selected from formic acid, acetic acid, propionic acid, or butyric acid, being formate, acetate, propionate, and butyrate, respectively; and, optionally $X^-$ is an anion of a substituted or unsubstituted amino acid, i.e., amino-monocarboxylic acid or an amino-dicarboxylic acid, optionally selected from glutamic acid and aspartic acid, being glutamate and aspartate, respectively; and, optionally $X^-$ is an anion of ascorbic acid, being ascorbate; and, optionally $X^-$ is a halide selected from fluoride, chloride, bromide, or iodide; and, optionally $X^-$ is an anion of a substituted or unsubstituted sulfonate, further optionally a trihalomethanesulfonate selected from trifluoromethanesulfonate, tribromomethanesulfonate, or trichloromethanesulfonate; and, optionally $X^-$ is an anion of a substituted or unsubstituted carbonate, further optionally hydrogen carbonate;

wherein the substituted carboxylic acid, substituted monocarboxylic acid, substituted propanoic acid, substituted acetic acid, substituted amino acid, substituted sulfonate, and substituted carbonate are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)$(C_1$-$C_6)$alkyl, —OC(O)O$(C_1$-$C_6)$alkyl, —OC(O)$NR^C_2$, —$(C_1$-$C_6)$alkylene-$NR^C_2$, —$NR^C_2$, —$NR^C$C(O)$R^C$, —$NR^C$C(O)O$(C_1$-$C_6)$alkyl, —$NR^C$C(O)$NR^C_2$, —$NR^C$$SO_2$$NR^C$, —$SR^C$, —S(O)$R^C$, —$SO_2R^C$, —$OSO_2(C_1$-$C_6)$alkyl, —$SO_2NR^C_2$, —$(C_1$-$C_6)$perfluoroalkyl, and —$(C_1$-$C_6)$alkylene-O$R^C$;

X' is selected from the group consisting of fluoro, chloro, bromo, iodo, $HCO_2$, acetoxy, propionoxy, butyroxy, glutamyloxy, aspartyloxy, ascorbyloxy, benzoxy, $HOCO_2$, citryloxy, carbamyloxy, gluconyloxy, lactyloxy, succinyloxy, sulfoxy, trifluoromethanesulfoxy, trichloromethanesulfoxy, tribromomethanesulfoxy, and trifluoroacetoxy;

$Z^1$ and $Z^2$ are independently NH or oxygen;

n is 0 or 1;

$R^1$ is selected from the group consisting of hydrogen, substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—$(R^A)$—$CO_2R^B$; wherein the substituted $(C_1$-$C_8)$alkyl, substituted $(C_1$-$C_8)$cycloalkyl, substituted aryl, substituted heteroaryl, and substituted heterocycle are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)$(C_1$-$C_6)$alkyl, —OC(O)O$(C_1$-$C_6)$alkyl, —OC(O)$NR^C_2$, —$(C_1$-$C_6)$alkylene-$NR^C_2$, —$NR^C_2$, —$NR^C$C(O)$R^C$, —$NR^C$C(O)O$(C_1$-$C_6)$alkyl, —$NR^C$C(O)$NR^C_2$, —$NR^C$$SO_2$$NR^C$, —$SR^C$, —S(O)$R^C$, —$SO_2R^C$, —$OSO_2(C_1$-$C_6)$alkyl, —$SO_2NR^C_2$, $(C_1$-$C_6)$perfluoroalkyl, and —$(C_1$-$C_6)$alkylene-O$R^C$;

$R^A$ is selected from the group consisting of —H, —$(C_1$-$C_6)$alkyl, —$(CH_2)_3$—NH C($NH_2$)(=NH), —$CH_2$C(=O)$NH_2$, —$CH_2COOH$, —$CH_2SH$, —$(CH_2)_2$C(=O)—$NH_2$, —$(CH_2)_2$COOH, —$CH_2$-(2-imidazolyl), —CH($CH_3$)—$CH_2$—$CH_3$, —$CH_2CH(CH_3)_2$, —$(CH_2)_4$—$NH_2$, —$(CH_2)_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —CH($CH_3)_2$, and —$CH_2$—$CH_3$;

$R^B$ is hydrogen or —$(C_1$-$C_8)$alkyl;

each $R^C$ is independently selected from the group consisting of hydrogen, —$(C_1$-$C_8)$alkyl, substituted or unsubstituted pyridyl, substituted or unsubstituted 1,4-dihydropyridyl, a radical of the compound of formula (I), and vitamin B7 ester (biotinyl); wherein the substituted pyridyl and substituted 1,4-dihydropyridyl are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —C(O)$R^B$, —C(O)O$R^B$, —C(O)$NR^B_2$, —C(=$NR^B$)$NR^B_2$, —O$R^B$, —OC(O)$(C_1$-$C_6)$alkyl, —OC(O)O$(C_1$-$C_6)$alkyl, —OC(O)$NR^B_2$, —$(C_1$-$C_6)$alkylene-$NR_2$, —$NR^B_2$, —$NR^B$C(O)$R^B$, —$NR^B$C(O)O$(C_1$-$C_6)$alkyl, —$NR^B$C(O)$NR^B_2$, —$NR^B$$SO_2NR^B$, —$SR^B$, —S(O)$R^B$, —$SO_2R^B$, —$OSO_2(C_1$-$C_6)$alkyl, —$SO_2NR^B_2$, —$(C_1$-$C_6)$perfluoroalkyl, and —$(C_1$-$C_6)$alkylene-O$R^B$;

$R^2$ and $R^3$ are each independently selected form the group consisting of hydrogen, $(C_1$-$C_6)$alkyl, —$(C_2$-$C_6)$alkenyl, —$(C_2$-$C_6)$alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)$(C_1$-$C_6)$alkyl, —OC(O)O$(C_1$-$C_6)$alkyl, —OC(O)$NR^C_2$, —$(C_1$-$C_6)$alkylene-$NR^C_2$, —$NR^C_2$, —$NR^C$C(O)$R^C$, —$NR^C$C(O)O$(C_1$-$C_6)$alkyl, —$NR^C$C(O)$NR^C_2$, —$NR^C$$SO_2NR^C$, —$SR^C$, —S(O)$R^C$, —$SO_2R^C$, —$OSO_2$$(C_1$-$C_6)$alkyl, —$SO_2NR^C_2$, —$(C_1$-$C_6)$perfluoroalkyl, and —$(C_1$-$C_6)$alkylene-O$R^C$;

$R^4$ is selected from the group consisting of hydrogen, —$(C_1-C_6)$alkyl, —$(C_2-C_6)$alkenyl, —$(C_2-C_6)$alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$SO$_2NR^C$, —S$R^C$, —S(O)$R^C$, —SO$_2R^C$, —OSO$_2$($C_1$-$C_6$)alkyl, —SO$_2NR^C_2$, —($C_1$-$C_6$)perfluoroalkyl, and —($C_1$-$C_6$)alkylene-O$R^C$;

provided that C* has an absolute configuration of R or S, or a mixture of R and S;

$R^5$ is selected from the group consisting of hydrogen, —$(C_1-C_6)$alkyl, —$(C_2-C_6)$alkenyl, —$(C_2-C_6)$alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$SO$_2NR^C$, —S$R^C$, —S(O)$R^C$, —SO$_2R^C$, —OSO$_2$($C_1$-$C_6$)alkyl, —SO$_2NR^C_2$, —($C_1$-$C_6$)perfluoroalkyl, and —($C_1$-$C_8$)alkylene-O$R^C$;

$R^6$ is selected from the group consisting of hydrogen, —C(O)R', —C(O)OR', —C(O)NHR', —P(O)(O$Y^1$)(O$Y^2$), —P(O)(O$Y^1$)(NHR''), substituted or unsubstituted ($C_1$-$C_8$) alkyl, substituted or unsubstituted ($C_1$-$C_8$)cycloalkyl, substituted or unsubstituted aryl, substituted or unsubstituted heteroaryl, and substituted or unsubstituted heterocycle, vitamin B11 ester, vitamin B2 ester, vitamin B6 ester, and —C**H—($R^A$)—CO$_2R^B$; wherein the substituted ($C_1$-$C_8$) alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$) alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$SO$_2NR^C$, —S$R^C$, —S(O)$R^C$, —SO$_2R^C$, —OSO$_2$($C_1$-$C_6$)alkyl, —SO$_2NR^C_2$, —($C_1$-$C_6$)perfluoroalkyl, and —($C_1$-$C_6$)alkylene-O$R^C$;

R' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—($R^A$)—CO$_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_8$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$SO$_2NR^C$, —S$R^C$, —S(O)$R^C$, —SO$_2R^C$, —OSO$_2$($C_1$-$C_6$)alkyl, —SO$_2NR^C_2$, —($C_1$-$C_6$)perfluoroalkyl, and —($C_1$-$C_6$)alkylene-O$R^C$;

R'' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—($R^A$)—CO$_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$) alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$) alkyl, —$NR^C$C(O)$NR^C_2$, —$NR^C$SO$_2NR^C$, —S$R^C$, —S(O)$R^C$, —SO$_2R^C$, —OSO$_2$($C_1$-$C_6$)alkyl, —SO$_2NR^C_2$, —($C_1$-$C_6$)perfluoroalkyl, and —($C_1$-$C_6$)alkylene-O$R^C$;

$R^7$ and $R^8$ are independently selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$) alkyl, substituted ($C_1$-$C_8$)cycloalkyl, substituted aryl, substituted heteroaryl, substituted heterocycle, substituted aryl ($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$SO$_2NR^C$, —S$R^C$, —S(O)$R^C$, —SO$_2R^C$, —OSO$_2$($C_1$-$C_6$)alkyl, —SO$_2NR^C_2$, —($C_1$-$C_6$)perfluoroalkyl, and —($C_1$-$C_6$)alkylene-O$R^C$;

$R^9$ is selected from the group consisting of hydrogen, —C(O)R', —C(O)OR', —C(O)NHR', —P(O)(O$Y^1$)(O$Y^2$), —P(O)(O$Y^1$)(NHR''), substituted or unsubstituted ($C_1$-$C_8$) alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^A$)—CO$_2R^B$; wherein the substituted ($C_1$-$C_8$) alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$) alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$SO$_2NR^C$, —S$R^C$, —S(O)$R^C$, —SO$_2R^C$, —OSO$_2$($C_1$-$C_8$)alkyl, —SO$_2NR^C_2$, —($C_1$-$C_6$)perfluoroalkyl, and —($C_1$-$C_6$)alkylene-O$R^C$;

$R^{10}$ is selected from the group consisting of hydrogen, —C(O)R', —C(O)OR', —C(O)NHR', —P(O)(O$Y^1$)(O$Y^2$), —P(O)(O$Y^1$)(NHR''), substituted or unsubstituted ($C_1$-$C_8$) alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^A$)—CO$_2R^B$; wherein the substituted ($C_1$-$C_8$) alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$) alkenyl, —($C_2$-$C_6$)alkynyl, halogen, —CN, —$NO_2$, —C(O)

R$^C$, —C(O)OR$^C$, —C(O)NR$^C{}_2$, —C(=NR$^C$)NR$^C{}_2$, —OR$^C$, —OC(O)(C$_1$-C$_6$)alkyl, —OC(O)O(C$_1$-C$_6$)alkyl, —OC(O)NR$^C{}_2$, —(C$_1$-C$_6$)alkylene-NR$^C{}_2$, —NR$^C{}_2$, —NR$^C$C(O)R$^C$, —NR$^C$C(O)O(C$_1$-C$_6$)alkyl, —NR$^C$C(O)NR$^C{}_2$, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C{}_2$, —(C$_1$-C$_6$)perfluoroalkyl, and —(C$_1$-C$_6$)alkylene-OR$^C$;

Y$^1$ and Y$^2$ are independently selected from the group consisting of hydrogen, sodium, potassium, lithium, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle; wherein the substituted (C$_1$-C$_8$) alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$) alkenyl, —(C$_2$-C$_6$)alkynyl, halogen, —CN, —NO$_2$, —C(O) R$^C$, —C(O)OR$^C$, —C(O)NR$^C{}_2$, —C(=NR$^C$)NR$^C{}_2$, —OR$^C$, —OC(O)(C$_1$-C$_6$)alkyl, —OC(O)O(C$_1$-C$_6$)alkyl, —OC(O) NR$^C{}_2$, —(C$_1$-C$_6$)alkylene-NR$^C{}_2$, —NR$^C{}_2$, —NR$^C$C(O)R$^C$, —NR$^C$C(O)O(C$_1$-C$_6$)alkyl, —NR$^C$C(O)NR$^C{}_2$, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C{}_2$, —(C$_1$-C$_6$)perfluoroalkyl, and —(C$_1$-C$_6$)alkylene-OR$^C$; or, alternatively, Y$^1$ and Y$^2$ taken together are selected from the group consisting of sodium, potassium, lithium, magnesium, calcium, strontium, and barium;

provided that when Z$^2$ is NH, the absolute configuration of C** is R or S, or a mixture of R and S.

As discussed above, the existing prior art approaches, for the most part, utilize enzymatic and solvent-mediated approaches to prepare the compounds or derivatives of formulae (I) and (II), or salts, hydrates, or solvates thereof. Such processes may be cumbersome, inefficient, and not scalable. One reference describes synthesizing nucleotide linkages in a ball mill. See Ravalico et al. (2011), as cited above, incorporated by reference herein in its entirety.

One suitable phosphorylating agent is phosphorus oxychloride (POCl$_3$). One suitable phosphorylating agents (or phosphorus reagent systems) include, but are not to, compounds having formula P(O)Cl(OR$^X$)(OR$^Y$) that include CAS Numbers 2524-64-3, 6609-64-9, 814-49-3, 14254-41-2, 2574-25-6, 813-77-4, 1499-17-8, 2510-89-6, 819-43-2, 5381-98-6, 538-37-4, 57188-46-2, 81639-99-8, 17672-53-6, 4090-55-5, 17776-78-2, 6630-13-3, 56119-60-9, 77075-54-8, 89104-48-3, 6546-97-0, 6630-15-5, 16383-57-6, 381-44-2, 124648-60-8, 17788-08-8, 58377-73-4, 6630-14-4, 17158-87-1, 17677-92-8, 51103-92-5, 52258-06-7, 56623-07-5, 58377-74-5, 85363-77-5, 112966-13-9, 167907-25-7, 179695-78-4, 877458-32-7, 1424937-89-2, 1424939-04-7, 2035-83-8, 127164-51-6, 6719-79-5, 59819-52-2, 69919-18-2, 77181-80-7, 4040-23-7, 6533-33-1, 6719-82-0, 6719-84-2, 22939-24-8, 27315-40-8, 28888-24-6, 61550-37-6, 73992-66-2, 86531-53-5, 96357-53-8, 108249-87-2, 343863-91-2, 875893-99-5, 714-87-4, 6087-94-1, 13674-83-4, 56883-17-1, 88805-00-9, 92401-83-7, 93115-98-1, 120628-26-4, 130312-59-3, 315179-27-2, 1388636-60-9, 1388636-61-0; and compounds having formula P(O)Cl$_2$ (OR$^Z$) that include CAS Numbers 770-12-7, 1498-51-7, 15074-54-1, 777-52-6, 677-24-7, 772-79-2, 4167-02-6, 1455-05-6, 31651-76-0, 53676-22-5, 18868-46-7, 53676-18-9, 940-18-1, 84681-46-9, 878-17-1, 105053-57-4, 149864-64-2, 6964-36-9, 18350-99-8, 53676-17-8, 60223-35-0, 25359-51-7, 2035-84-9, 2196-02-3, 382608-79-9, 775-08-6, 30333-08-5, 1479-10-3, 2213-71-0, 5305-82-8, 5995-77-7, 13674-82-3, 13825-97-3, 17788-07-7, 19430-76-3, 19430-77-4, 20056-41-1, 20464-68-0, 31735-82-7, 36196-79-9, 41998-90-7, 52198-45-5, 53121-39-4, 53121-41-8, 99884-77-2, 105053-58-5, 125440-36-0, 140468-02-6, 140468-03-7, 184528-42-5, 870673-87-3, 916893-01-1, 1498-52-8, 20464-67-9, 38135-34-1, 41240-73-7, 62485-00-1, 78840-91-2, 313946-12-2, 1242826-79-9. R$^X$, R$^Y$, and R$^Z$ may be the same or different, and include, but are not limited to, simple alkyl.

The present invention further embraces isolated compounds or derivatives according to formulae (I) and (II), or salts, hydrates, or solvates thereof. The expression "isolated compound(s) or derivative(s)" refers to a preparation of a compound or derivative of formulae (I) or (II), or salts, hydrates, or solvates thereof, or a mixture of compounds or derivatives according to formulae (I) and/or (II), or salts, hydrates, or solvates thereof, wherein the isolated compound or derivative has been separated from the reagents used, and/or byproducts formed, in the synthesis of the compound(s) or derivative(s). "Isolated" does not mean that the preparation is technically pure (homogeneous), but has sufficient purity to be used therapeutically.

The compounds or derivatives of the invention and intermediates may be isolated from their reaction mixtures and purified by standard techniques such as filtration, liquid-liquid extraction, solid phase extraction, distillation, recrystallization or chromatography, including flash column chromatography, preparative TLC, HPTLC, HPLC, or rp-HPLC. One preferred method for purification of the compounds according to formulae (I) or (II), or salts, hydrates, or solvates thereof, comprises crystallizing the compound or salt from a solvent to form, preferably, a crystalline form of the compounds or salts thereof. Following crystallization, the crystallization solvent is removed by a process other than evaporation, for example, filtration or decanting, and the crystals are then preferably washed using pure solvent (or a mixture of pure solvents). Preferred solvents for crystallization include, but are not limited to: water; alcohols, particularly alcohols containing up to four carbon atoms such as methanol, ethanol, isopropanol, and butan-1-ol, butan-2-ol, and 2-methyl-2-propanol; ethers, for example diethyl ether, diisopropyl ether, t-butyl methyl ether, 1,2-dimethoxyethane, tetrahydrofuran, and 1,4-dioxane; carboxylic acids, for example formic acid and acetic acid; and hydrocarbon solvents, for example pentane, hexane, toluene; and mixtures thereof, particularly aqueous mixtures, such as aqueous ethanol. Pure solvents, preferably at least analytical grade, and more preferably pharmaceutical grade, are preferably used. In the compounds or derivatives of the invention according to formulae (I) or (II), or salts, hydrates, or solvates thereof, and pharmaceutical compositions thereof, the compounds or derivatives according to formulae (I) or (II), or salts, hydrates, solvates thereof, are preferably in or prepared from a crystalline form, preferably prepared according to such a process. Alternatively, the compounds according to formulae (I) or (II), or salts, hydrates, or solvates thereof, can be isolated using lyophilization or freeze-drying techniques, thus avoiding use of non-aqueous solvents.

The synthetic methods described above reflect a convergent synthesis strategy. Thus two components may be synthesized and elaborated separately prior to condensing or coupling the two compounds or derivatives to form the target compounds or derivatives. These convergent synthetic schemes allow for arrangement of the assembly steps of the backbone of the target compounds or derivatives and derivatization of derivatizable functionalities to accommodate functional group sensitivity and/or to allow for functional groups or elements to be introduced either before or after the assembly of the backbone of the target compounds or derivatives via the condensation or coupling reactions described.

It will be appreciated by one skilled in the art that certain aromatic substituents in compounds or derivatives of the invention, intermediates used in the processes described above or precursors thereto, may be introduced by employing aromatic substitution reactions to introduce or replace a substituent, or by using functional group transformations to modify an existing substituent, or a combination thereof. Such reactions may be affected either prior to or immediately following the processes mentioned above, and are included as part of the process aspect of the invention. The reagents and reaction conditions for such procedures are known in the art. Specific examples of procedures which may be employed include, but are not limited to, electrophilic functionalization of an aromatic ring, for example via nitration, halogenation, or acylation; transformation of a nitro group to an amino group, for example via reduction, such as by catalytic hydrogenation; acylation, alkylation, or sulfonylation of an amino or hydroxyl group; replacement of an amino group by another functional group via conversion to an intermediate diazonium salt followed by nucleophilic or free radical substitution of the diazonium salt; or replacement of a halogen by another group, for example via nucleophilic or organometallically-catalyzed substitution reactions.

Additionally, in the aforementioned processes, certain functional groups which would be sensitive to the reaction conditions may be protected by protecting groups. A protecting group is a derivative of a chemical functional group which would otherwise be incompatible with the conditions required to perform a particular reaction which, after the reaction has been carried out, can be removed to re-generate the original functional group, which is thereby considered to have been "protected." Any chemical functionality that is a structural component of any of the reagents used to synthesize compounds or derivatives of this invention may be optionally protected with a chemical protecting group if such a protecting group is useful in the synthesis of compounds or derivatives of this invention. The person skilled in the art knows whne protecting groups are indicated, how to select such groups, and processes that can be used for selectively introducing and selectively removing them, because methods of selecting and using protecting groups have been extensively documented in the chemical literature. Techniques for selecting, incorporating, and removing chemical protecting groups may be found, for example, in THEODORA W. GREENE & PETER G. M. WUTS, PROTECTIVE GROUPS IN ORGANIC SYNTHESIS (John Wiley & Sons, Inc. 1999), the entire disclosure of which is incorporated herein by reference.

In addition to use of a protecting group, sensitive functional groups may be introduced as synthetic precursors to the functional group desired in the intermediate or final product. An example of this is an aromatic nitro (—NO₂) group. The aromatic nitro group does not undergo any of the nucleophilic reactions of an aromatic amino group. However, the nitro group can serve as the equivalent of a protected amino group because it is easily reduced to the amino group under mild conditions that are selected for the nitro group over most other functional groups.

It will be appreciated by one skilled in the art that the processes described are not the exclusive means by which compounds of the invention may be synthesized and that an extremely broad repertoire of synthetic organic reactions is available to be potentially employed in synthesizing compounds or derivatives of the invention. The person skilled in the art knows how to select and implement appropriate synthetic routes. Suitable synthetic methods may be identified by reference to the literature, including reference sources such as: COMPREHENSIVE ORGANIC SYNTHESIS (B. M. Trost & I. Fleming eds., Pergamon Press 1991); COMPREHENSIVE ORGANIC FUNCTIONAL GROUP TRANSFORMATIONS (A. R. Katritzky, O. Meth-Cohn, & C. W. Reese eds., Pergamon Press 1996); COMPREHENSIVE ORGANIC FUNCTIONAL GROUP TRANSFORMATIONS II (A. R. Katritzky & R. J. K. Taylor eds., 2d ed., Elsevier 2004); COMPREHENSIVE HETEROCYCLIC CHEMISTRY (A. R. Katritzky & C. W. Rees eds., Pergamon Press 1984); COMPREHENSIVE HETEROCYCLIC CHEMISTRY II (A. R. Katritzky, C. W. Rees, & E. F. V. Scriven eds., Pergamon Press 1996); and J. MARCH, ADVANCED ORGANIC CHEMISTRY (4th ed., John Wiley & Sons 1992).

Salts of Compounds or Derivatives According to the Invention

The compounds or derivatives of the present invention may take the form of salts. The term "salts" embraces addition salts of free acids or free bases which are compounds or derivatives of the invention. The term "pharmaceutically-accetable salt" refers to salts which possess toxicity profiles within a range that affords utility in pharmaceutical applications.

Suitable pharmaceutically-acceptable acid addition salts may be prepared from an inorganic acid or from an organic acid. Examples of inorganic acids include hydrochloric, hydrobromic, hydroiodic, nitro, carbonic, sulfuric, and phosphoric acids. Appropriate organic acids may be selected from aliphatic, cycloaliphatic, aromatic, aralphatic, heterocyclic, carboxylic, and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoroacetic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric, and galacturonic acid. In the present examples of compounds or derivatives of formulae (I) or (II), or salts, hydrates, or solvates thereof, i.e., compounds or derivatives containing amino groups, pyridine, or reduced pyridine, said compounds or derivatives can be isolated as salts of inorganic acids or strong organic acids, e.g., hydrochloric acid or trifluoroacetic acid.

Suitable pharmaceutically acceptable base addition salts of compounds of the invention include, for example, metallic salts including alkali metal, alkaline earth metal, and transition metal salts such as, for example, calcium, magnesium, potassium, sodium, and zinc salts. Pharmaceutically acceptable base addition salts also include organic salts made from basic amines such as, for example, N,N-dibenzylethylenediamine, chloroprocaine, choline, diethanolamine, ethylenediamine, meglumine (N-methylglucamine), tromethamine (tris(hydroxymethyl) aminomethane), and procaine.

All of these salts may be prepared by conventional means from the corresponding compounds or derivatives of formulae (I) or (II) by reacting, for example, the appropriate acid or base with the compounds or derivatives of formulae (I) or (II). Preferably, the salts are in crystalline form, or alternatively in dried or freeze-dried form. The person skilled in the art will know how to prepare and selected suitable salt forms, for example, as described in P. H. STAHL & C. G. WERMUTH, HANDBOOK OF PHARMACEUTICAL SALTS: PROPERTIES, SELECTION, AND USE (Wiley-VCH 2002).

The nutraceutical or pharmaceutical compositions of the present invention may be administered in combination with a nutraceutically or pharmaceutically acceptable carrier. The active ingredients in such formulations may comprise from 1% by weight to 99% by weight, or alternatively, 0.1% by weight to 99.9% by weight. "Nutraceutically acceptable carrier" and "pharmaceutically acceptable carrier" mean any carrier, diluent, or excipient that is compatible with the other ingredients of the formulation and not deleterious to the user. In accordance with one embodiment, suitable nutraceutically acceptable carriers can include ethanol, aqueous ethanol mixtures, water, fruit, and/or vegetable juices, and combinations thereof.

Delivery System

Suitable dosage forms include tablets, capsules, solutions, suspensions, powders, gums, and confectionaries. Sublingual delivery systems include, but are not limited to, dissolvable tabs under and on the tongue, liquid drops, and beverages. Edible films, hydrophilic polymers, oral dissolvable films, or oral dissolvable strips can be used. Other useful delivery systems comprise oral or nasal sprays or inhalers, and the like.

For oral administration, a compound or derivative of formulae (I) or (II), or a salt, hydrate, or solvate thereof, may be further combined with one or more solid inactive ingredients for the preparation of tablets, capsules, pills, powders, granules, or other suitable dosage forms. For example, the active agent may be combined with at least one excipient selected from the group consisting of fillers, binders, humectants, disintegrating agents, solution retarders, absorption accelerators, wetting agents, absorbents, or lubricating agents. Other useful excipients include magnesium stearate, calcium stearate, mannitol, xylitol, sweeteners, starch, carboxymethylcellulose, microcrystalline cellulose, silica, gelatin, silicon dioxide, and the like.

The components of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The components of the present invention can be administered in a wide variety of oral and parenteral dosage forms. It will be obvious to those skilled in the art that the following dosage forms may comprise, as the active component, either a chemical compound or derivative of the invention or a pharmaceutically acceptable salt of a chemical compound or derivative of the invention.

For preparing pharmaceutical compositions from a chemical compound or derivative of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid, which is in a mixture with the finely divided active component. In tablets, the active component is mixed with the carrier having the necessary binding capacity in suitable proportions and compacted in the shape and size desired.

The powders and tablets preferably contain from five or ten to about seventy percent of the active compound(s) or derivative(s), or salts, hydrates, or solvates thereof. Suitable carriers are microcrystalline cellulose, sugar, lactose, pectin, dextrin, starch, gelatin, tragacanth, methylcellulose, sodium carboxymethylcellulose, a low melting wax, cocoa butter, and the like, and other excipients may include magnesium stearate, stearic acid, talc, silicon dioxide, etc. The term "preparation" is intended to include the formulation of the active compound or derivative with encapsulating material as carrier providing a capsule in which the active component, with or without carriers, is surrounded by a carrier, which is thus in association with it. Tablets, powders, capsules, pills, sachets, and lozenges are included. Tablets, powders, capsules, pills, sachets, and lozenges can be used as solid forms suitable for oral administration.

Liquid preparations include solutions, suspensions, and emulsions, for example, water or water-propylene glycol solutions. For example, parenteral injection liquid preparations can be formulated as solutions in aqueous polyethylene glycol solution. The chemical compound or derivative according to the present invention may thus be formulated for parenteral administration (e.g., by injection, for example bolus injection or continuous infusion) and may be presented in unit dose or in ampoules, pre-filled syringes, small-volume infusion, or in multi-dose containers with an added preservative. The compositions may take such forms as suspensions, solutions, or emulsions in oily or aqueous vehicles, and may contain formulation agents such as suspending, stabilizing, and/or by dispersing agents. Alternatively, the active ingredient may be in powder form, obtained by aseptic isolation of sterile solid or by lyophilization from solution, for reconstitution with a suitable vehicle, e.g., sterile, pyrogen-free water, before use.

Aqueous solutions suitable for oral use can be prepared by dissolving the active component in water and adding suitable colorants, flavors, stabilizing and thickening agents, as desired. Aqueous suspensions suitable for oral use can be made by dispersing the finely divided active component in water with viscous material, such as natural or synthetic gums, resins, methylcellulose, sodium carboxymethylcellulose, or other well known suspending agents.

Compositions suitable for topical administration in the mouth include lozenges comprising the active agent in a flavored base, usually sucrose and acacia or tragacanth; pastilles comprising the active ingredient in an inert base such as gelatin and glycerine or sucrose and acacia; and mouthwashes comprising the active ingredient in suitable liquid carrier.

Solutions or suspensions are applied directly to the nasal cavity by conventional means, for example with a dropper, pipette, or spray. The compositions may be provided in single or multi-dose form. In compositions intended for administration to the respiratory tract, including intranasal compositions, the compound or derivative will generally have a small particle size, for example on the order of 5 microns or less. Such a particle size may be obtained by means known in the art, for example by micronization.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets, capsules, and lozenges for oral administration and liquids for oral use are preferred compositions. Solutions or suspensions for application to the nasal cavity or to the respiratory tract are preferred compositions. Transdermal patches for topical administration to the epidermis are preferred compositions.

Further details on techniques for formulation and administration may be found in the latest edition of REMINGTON'S PHARMACEUTICAL SCIENCES (Mack Publishing Co., Easton, Pa.).

Solid nutritional compositions for oral administration may optionally contain, in addition to the above-enumerated nutritional composition ingredients or compounds: carrier materials such as corn starch, gelatin, acacia, microcrystalline cellulose, kaolin, dicalcium phosphate, calcium carbonate, sodium chloride, alginic acid, and the like; disintegrators including microcrystalline cellulose, alginic acid, and the like; binders including acacia, methylcellulose, sodium carboxymethylcellulose, polyvinylpyrrolidone, hydroxypropylmethylcellulose, ethylcellulose, and the like; and lubricants such as magnesium stearate, stearic acid, silicon fluid, talc, waxes, oils, colloidal silica, and the like. The usefulness of such excipients is well known in the art.

Liquid nutritional compositions for oral administration in connection with a method for preventing and/or treating inflammation, colds, and/or flu can be prepared in water or other aqueous vehicles. In addition to the above enumerated ingredients or compounds, liquid nutritional compositions can include suspending agents such as, for example methylcellulose, alginates, tragacanth, pectin, kelgin, carrageenan, acacia, polyvinylpyrrolidone, polyvinyl alcohol, and the like. The liquid nutritional compositions can be in the form of a solution, emulsion, syrup, gel, or elixir including or containing, together with the above enumerated ingredients or compounds, wetting agents, sweeteners, and coloring and flavoring agents. Various liquid and powder nutritional compositions can be prepared by conventional methods. Various ready-to-drink formulations ("RTDs") are contemplated.

Routes of Administration

The compositions may be administered by any suitable route, including but not limited to oral, sublingual, buccal, ocular, pulmonary, rectal, and parenteral administration, or as an oral or nasal spray (e.g., inhalation of nebulized vapors, droplets, or solid particles). Parenteral administration includes, for example, intravenous, intramuscular, intraarterial, intraperitoneal, intranasal, intravaginal, intravesical (e.g., to the bladder), intradermal, transdermal, topical, or subcutaneous administration. Also contemplated within the scope of the invention is the installation of a pharmaceutical composition in the body of the patient in a controlled formulation, with systemic or local release of the drug to occur at a later time. For example, the drug may be localized in a depot for controlled release to the circulation, or for release to a local site.

Pharmaceutical compositions of the invention may be those suitable for oral, rectal, bronchial, nasal, pulmonal, topical (including buccal and sub-lingual), transdermal, vaginal, or parenteral (including cutaneous, subcutaneous, intramuscular, intraperitoneal, intravenous, intraarterial, intracerebral, intraocular injection, or infusion) administration, or those in a form suitable for administration by inhalation or insufflations, including powders and liquid aerosol administration, or by sustained release systems. Suitable examples of sustained release systems include semipermeable matrices of solid hydrophobic polymers containing the compound or derivative of the invention, which matrices may be in the form of shaped articles, e.g., films or microcapsules.

The methods described above may be further understood in connection with the following Examples. In addition, the following non-limiting examples are provided to illustrate the invention. The illustrated synthetic pathways are applicable to other embodiments of the invention. The synthetic procedures described as general methods describe what is believed will be typically effective to preform the synthesis indicated. However, the person skilled in the art will appreciate that it may be necessary to vary the procedures for any given embodiment of the invention, e.g., vary the order or steps and/or the chemical reagents used. Products may be purified by conventional techniques that will vary, for example, according to the amount of side products produced and the physical properties of the compounds.

EXAMPLE 1

A. Synthetic Preparation of Thiamine Nicotinate (Compound 1): Compound Having Formula (1): $R^1$=Vitamin B1, n=0, $Z^2$=Oxygen, $R^2$=$R^3$=$R^4$=$R^5$=Hydrogen Compound 1

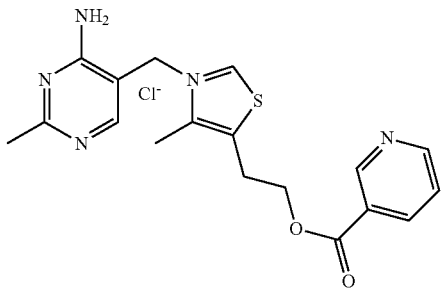

Thiamine (0.5 g, 1.66 mmol, 1.0 eq) was suspended in dry pyridine (14 mL), followed by the addition of nicotinic acid chloride (0.3 g, 1.67 mmol, 1.0 eq) and DMAP (0.2 g, 1.66 mmol, 1.0 eq). The suspension was heated to 80° C. and left stirring overnight under an atmosphere of $N_2$. The mixture was allowed to cool to room temperature, filtered, and then washed with chloroform to yield 0.45 g (73%) of the desired product as an off-white powder.

$^1$H NMR (400 MHz, $D_2O$): δ ppm 8.68 (1H, dd, J=5.1, 1.6 Hz), 8.38 (1H, dt, J=8.2, 1.8 Hz), 7.98 (1H, dd, J=2.0, 0.8 Hz), 7.57 (1H, s), 5.46 (2H, s), 4.59 (2H, t, J=5.8 Hz), 3.45 (2H, t, J=5.9 Hz), 2.51 (3H, s), 2.50 (3H, s). $^{13}$C NMR (125 MHz, $D_2O$): δ ppm 166.0, 163.9, 163.0, 152.3, 148.9, 145.8, 143.6, 139.1, 135.3, 126.1, 124.7, 105.9, 64.9, 50.2, 24.9, 11.3, 11.1. HRMS (ES, M+H$^+$) calculated 370.1338 for $C_{18}H_{20}N_5O_2S$, found 370.1572.

B. Synthetic Preparation of α/β Bromo Triacetate Riboside (Compound 2): Compound Having Formula (2): X=Bromide, $R^6=R^7=R^8$=Acetyl

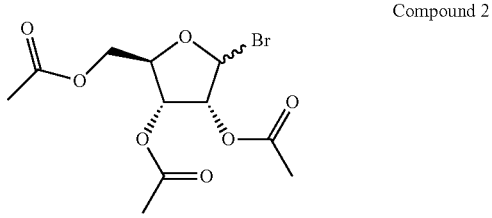 [SMILES: CC(=O)OC[C@H]1OC(Br)[C@H](OC(C)=O)[C@@H]1OC(C)=O]

Compound 2

To a solution of tetra-O-acetyl-β-D-ribofuranose (1.13 g, 3.54 mmol) in anhydrous dichloromethane (20 mL) at 0° C. was added dropwise hydrogen bromide 33 wt % in acetic acid (1.12 mL, 5.31 mmol). After 20 minutes, the solvent was evaporated, and the residual acetic acid was co-evaporated with toluene (3×5 mL). The orange oily residue was dried under vacuum for an additional hour protected from light (aluminum foil), to yield the bromo sugar as a 1:1 α/β mix in near quantitative yield.

Alternatively, to a dry round-bottom flask was added tetra-O-acetyl-β-D-ribofuranose (1.18 g, 3.71 mmol, 1.0 eq) and bromotrimethylsilane (3.94 mL, 29.66 mmol, 8.0 eq), and left stirring overnight at room temperature under an atmosphere of $N_2$. The solution was then concentrated under vacuum to give the desired bromosugar in near quantitative yield. 8:2 β/α isotopic mixture.

$^1$H NMR (CDCl$_3$, 400 MHz): δ ppm 6.25 (1H, s), 5.72-5.68 (1H, m), 5.65-5.59 (1H, m), 4.47-4.41 (2H, m), 4.20-4.13 (1H, m), 2.04-1.98 (9H, m).

EXAMPLE 2

A. Synthetic Preparation of Pterostilbene Nicotinate (Compound 3): Compound Having Formula (1): $R^1$=Pterostilbenyl (4-[(E)-2-(3,5-Dimethoxyphenyl) Etheny]Phenyl), n=0, $Z^2$=Oxygen, $R^2=R^3=R^4=R^5$=Hydrogen

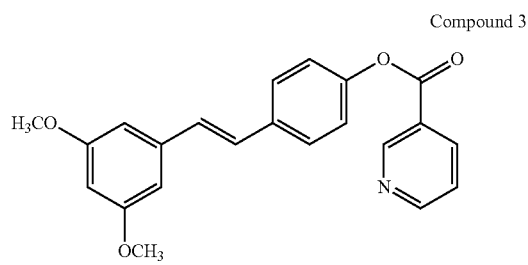 [SMILES: COc1cc(/C=C/c2ccc(OC(=O)c3cccnc3)cc2)cc(OC)c1]

Compound 3

Pterostilbene (2.00 g, 7.8 mmol, 1.0 eq) was solubilized in acetone (10 mL), followed by the addition of nicotinoyl chloride hydrogen chloride (1.67 g, 9.36 mmol, 1.2 eq) and TEA (3.26 mL, 23.41 mmol, 3.0 eq) and then heated to reflux, under an atmosphere of $N_2$ for 12 h. The mixture was then filtered, and concentrated under reduced pressure. The solid was concentrated and purified using biotage silica column chromatography using an eluent of 50% EtOAc in pet ether, to yield the desired product as a white fluffy solid in 85% yield.

$^1$H NMR (CDCl$_3$, 400 MHz): δ ppm 9.41 (1H, s), 8.87 (1H, dd, J=4.8, 3.2 Hz), 8.46 (1H, d, J=8.0 Hz), 7.58 (2H, d, J=8.3 Hz), 7.48 (1H, dd, J=7.8, 5.0 Hz), 7.24 (2H, m), 7.02 (2H, m), 6.68 (2H, m), 6.42 (1H, s), 3.84 (6H, s). $^{13}$C NMR (CDCl$_3$, 125 MHz): δ ppm 163.9, 161.0, 154.0, 151.4, 149.9, 139.1, 137.6, 135.4, 129.2, 127.6, 125.6, 125.3, 121.8, 104.7, 100.1, 55.4. HRMS (ES, M+H$^+$) calculated 362.1398 for $C_{22}H_{20}NO_4$, found 362.1392.

B. Synthetic Preparation of Pterostilbene Nicotinate Riboside Triflate (Compound 4): Compound of Formula (I): $R^1$=Pterostilbenyl (4-[(E)-2-(3,5-Dimethoxyphenyl)Ethenyl]Phenyl), n=0, $Z^2$=Oxygen, $R^2=R^3=R^4=R^5$=Hydrogen, X$^-$=Triflate (Trifluoromethanesulfonate), $R^6=R^7=R^8$=Acetyl

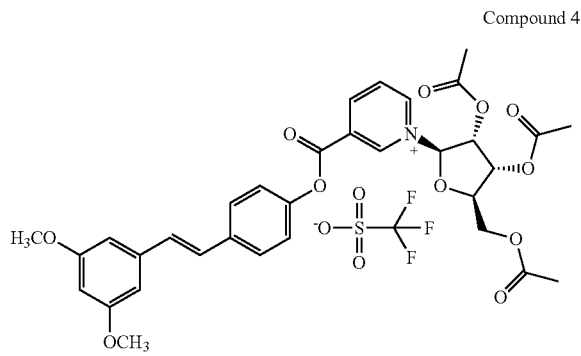

Compound 4

To a dry round-bottomed flask was added Compound 3 (300 mg, 0.83 mmol, 1.0 eq) and tetra-O-acetyl-β-D-ribofuranose (270 mg, 0.83 mmol, 1.0 eq). The solids were then kept under high vacuum for 30 minutes, then solubilized in anhydrous DCE (15 mL) and kept under nitrogen. With an air condenser attached, TMSOTf (151.23 µL, 0.83 mmol, 1.0 eq) was added dropwise, the yellow solution was then heated to 45° C. and left stirring for 3 hours, after which the reaction appeared to progress no further by TLC. The mixture was poured into water and washed with brine (3×30 mL). The organic layer was then separated, dried over magnesium sulfate, and concentrated. The crude was then purified using biotage column chromatography using an eluent of 10% methanol in EtOAc to give 90 mg, 18% yield of the desired product as a yellow hygroscopic solid. This preparation demonstrates one example of the method described above at paragraphs [0138]-[0139] and [0444]-[0454].

$^1$H NMR (MeOD, 400 MHz): δ ppm 9.84 (1H, s), 9.46 (2H, d, J=6.3 Hz), 9.39 (2H, dt, J=11.3, 8.2 Hz), 8.48 (1H, dd, J=7.9, 6.4 Hz), 7.72 (2H, d, J=8.8 Hz), 7.37 (2H, d, J=8.5 Hz), 7.20 (2H, m), 6.67 (2H, m), 6.69 (1H, d, J=3.8 Hz), 6.44 (11H, t, J=2.1 Hz), 5.65 (1H, dd, J=5.5, 3.8 Hz), 5.48 (1H, t, J=5.8 Hz), 4.86 (2H, dt, J=5.8 Hz), 4.59 (2H, m), 2.22 (3H, s), 2.17 (3H, s), 2.15 (3H, s). $^{13}$C NMR (125 MHz): δ ppm 170.5, 169.7, 161.0, 159.8, 149.6, 148.2, 145.8, 141.5, 139.1, 136.3, 131.0, 129.9, 129.5, 127.8, 121.6, 104.7, 100.3, 98.0, 82.9, 69.0, 61.9, 60.4, 55.4, 20.6, 20.4, 20.3, 14.2. HRMS (ES, M+H$^+$) calculated 620.2132 for $C_{33}H_{34}NO_{11}$, found 620.2132.

C. Synthetic Preparation of Pterostilbene Nicotinate Riboside Bromide (Compound 5): Compound of Formula (I): R$^1$=Pterostilbenyl (4-[(E)-2-(3,5-Dimethoxyphenyl)Ethenyl]Phenyl), n=0, Z$^2$=Oxygen, R$^2$=R$^3$=R$^4$=R$^5$=Hydrogen, X$^-$=Bromide, R$^6$=R$^7$=R$^8$=Acetyl Compound 5

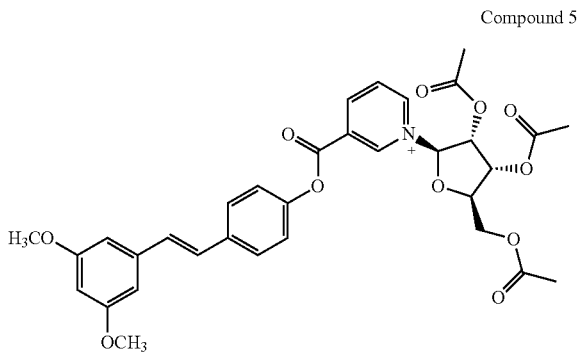

To a dry round-bottom flask was added Compound 2 (400 mg, 1.18 mmol, 2.0 eq), solubilized in freshly distilled acetonitrile. To this solution was added Compound 3 (213.13 mg, 0.59 mmol, 1.0 eq), and the mixture was left stirring at room temperature under an atmosphere of N$_2$ for 3 hr. TLC analysis showed complete consumption of Compound 3. Biotage chromatography using an eluent of 10% methanol in EtOAc was used to afford the desired β isomer in 6% yield. This preparation demonstrates one example of the method described above at paragraphs [0138]-[0139] and [0444]-[0454].

$^1$H NMR (MeOD, 400 MHz): δ ppm 9.81 (1H, s), 9.47-9.43 (2H, m), 9.38-9.32 (2H, m), 8.47-8.39 (1H, m), 7.72-7.65 (2H, m), 7.42-7.33 (2H, m), 7.26-7.23 (2H, m), 6.59 (1H, d, J=3.8 Hz), 6.66 (2H, m), 6.44-6.40 (1H, m), 5.63 (1H, s), 5.42 (1H, m), 4.82-4.80 (2H, m), 4.58 (2H, m), 2.22 (3H, s), 2.17 (3H, s), 2.15 (3H, s).

Example 3

A. Synthetic Preparation of Resveratrol Trinicotinate (Compound 6): Compound Having Formula (1): R$^1$=Resveratrol (Trans-3,5,4'-Trihydroxystilbenyl)), n=0, Z$^2$=Oxygen, R$^2$=R$^3$=R$^4$=R$^5$=Hydrogen Compound 6

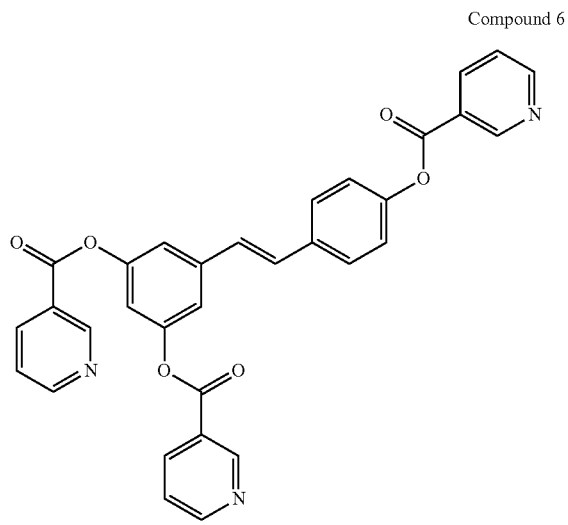 [SMILES: O=C(Oc1ccc(/C=C/c2cc(OC(=O)c3cccnc3)cc(OC(=O)c3cccnc3)c2)cc1)c1cccnc1]

To a stirred suspension of nicotinoyl chloride hydrochloride (4.17 g, 23.31 mmol, 5.8 eq) in 20 mL of acetone (fresh bottle) at 0° C., 14 mL dry trimethylamine was added, and then a solution of resveratrol (0.92 g, 4.10 mmol, 1.0 eq) in 15 mL of acetone was added dropwise. The reaction mixture was heated to reflux for 24 h. Then the reaction mixture was filtered, extracted, washed, and concentrated to obtain a yellow solid. The crude products were purified by biotage column chromatography from 100% DCM up to 10% MeOH in DCM over 1 L. Recrystallization of the residue (~1:1 CHCl$_3$:EtOH) provided 1.10 g, 50% yield of light yellow crystals.

$^1$H NMR (CDCl$_3$, 400 MHz): δ ppm 9.44-9.40 (3H, m), 8.90-8.86 (3H, m), 8.50-8.45 (3H, m), 7.59 (2H, d, J=8.8 Hz, Ar), 7.53-7.48 (31, m), 7.36 (1H, m), 7.37-7.36 (1H, m), 7.25 (2H, d, J=8.6 Hz), 7.21-7.08 (3H, m). $^{13}$C NMR (CDCl$_3$, 125 MHz): δ ppm 163.7, 163.5, 154.2, 154.0, 151.3, 151.2, 150.3, 150.2, 139.9, 137.7, 137.6, 134.7, 130.0, 127.9, 127.1, 125.5, 125.3, 123.6, 123.5, 117.4, 114.5.

B. Synthetic Preparation of Resveratrol Trinicotinate Riboside Triflate (Compound 7): Compound of Formula (I): $R^1$=Resveratryl (Trans-3,5,4'-Trihydroxystilbenyl), n=0, $Z^2$=Oxygen, $R^2$=$R^3$=$R^4$=$R^5$=Hydrogen, $X^-$=Trifluoromethanesulfonate, $R^6$=$R^7$=$R^8$=Acetyl mmol, 4.0 eq) solubilized in dry acetonitrile (10 mL). To this solution was added tresveratrol trinicotinate (Compound 7, 100 mg, 0.18 mmol, 1.0 eq) and the mixture was left stirring overnight under $N_2$. $^1H$ NMR analysis showed partial conversion to the desired product (~5%). Sample was not isolated; NMR of only crude was obtained. This preparation Compound 7

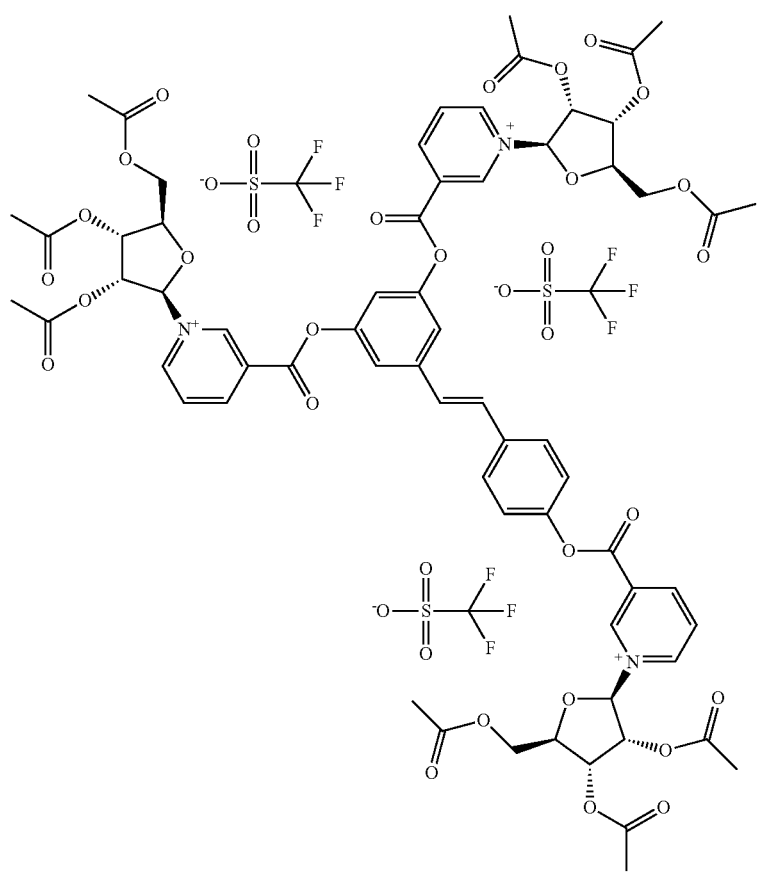

To a dry round-bottom flask was added resveratrol nicotinate (Compound 6, 0.16 g, 0.29 mmol, 1.0 eq) and tetraacetate riboside (0.33 g, 1.03 mmol, 3.5 eq), and the mixture was solubilized in fresh acetonitrile (10 mL). TMSOTf (0.19 mL, 1.03 mmol, 3.5 eq) was added dropwise, and the mixture was left stirring overnight at 40° C. under an atmosphere of $N_2$. The mixture was then allowed to cool to room temperature, excess TMSOTf was quenched by the addition of 1 M $NaHCO_3$ (1 mL), and the mixture was left stirring for an additional 30 minutes. The acetonitrile was then removed under reduced pressure, and the sample was suspended in water and extracted with ethyl acetate, dried over magnesium sulfate, and concentrated under reduced pressure. This residual solid was then washed with cold EtOAc and then dried under high vacuum, and NMR analysis indicated it was the desired tri-resveratrol NAR conjugate, obtained in 18% yield, as a yellow-green solid. This preparation demonstrates one example of the method described above at paragraphs [0138]-[0139] and [0444]-[0454].

Alternatively, to a dry round-bottom flask was added α/β bromo triacetate riboside (Compound 2, 249.58 mg, 0.74 demonstrates one example of the method described above at paragraphs [0138]-[0139] and [0444]-[0454].

$^1H$ NMR (400 MHz, MeOD): δ ppm 9.39-9.33 (3H, m), 8.81-8.72 (3H, m), 8.56-8.46 (3H, m), 8.46-8.33 (3H, m), 7.53 (1H), 7.51-7.45 (2H, m), 7.41 (1H, s), 7.16-7.13 (1H, m), 6.60-6.54 (3H, m), 5.59-5.48 (3H, m), 5.41-5.31 (3H, m), 4.78-4.70 (3H, m), 4.54-4.50 (3H, m), 4.43-4.40 (3H, m), (2.07-1.99) (27H, m).

EXAMPLE 4

A. Synthetic Preparation of Choline Nicotinate Bromide (Compound 8): Compound Having Formula (1): $R^1$=Cholinyl (2-N,N,N-Trimethylammonium)Ethyl), n=0, $Z^2$=Oxygen, $R^2$=$R^3$=$R^4$=$R^5$=Hydrogen Compound 8

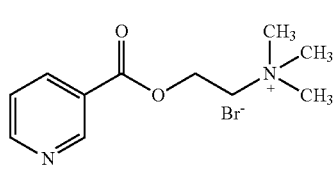

Nicotinic acid (5.00 g, 40.61 mmol, 1.0 eq), 2-bromoethanol (3.03 mL, 40.61 mmol, 1.0 eq), and DMAP (1.24 g, 10.15 mmol, 0.25 eq) were placed in a 250 mL round-bottom flask, and suspended in DCM (100 mL) under $N_2$. The reaction mixture was stirred at 0° C. followed by the portionwise addition of DCC (8.38 g, 40.61 mmol, 1.0 eq). The reaction mixture was allowed to warm to room temperature and was stirred for 24 h. After completion of the reaction, based on TLC, the mixture was filtered to remove dicyclohexylurea (and traces of nicotinic acid). The crude residue was purified using Biotage column chromatography using an eluent of 1:1 EtOAc:pet ether. 8.5 g, 90% yield of a clear oil was obtained. 2-bromoethyl pyridine-3-carboxylate (2 g, 8.93 mmol, 1.0 eq) was dissolved in toluene (15 mL) and trimethylamine (45% in $H_2O$, 5.71 g, 43.47 mmol, 5.0 eq) was added and refluxed for 24 h in a sealed tube. The biphasic mixture was concentrated via rotary evaporation to provide the desired product as a yellow solid in quantitative yield.

$^1$H NMR ($D_2O$, 400 MHz): δ ppm 9.84 (1H, s), 8.66-8.61 (2H, m), 7.83 (1H, t, J=6.7 Hz), 3.95-3.89 (2H, m), 3.42-3.37 (2H, m), 3.07 (9H, s). $^{13}$C NMR ($D_2O$, 400 MHz): δ ppm 168.3, 145.7, 143.2, 142.6, 135.4, 126.9, 67.4 (t, J=3.7 Hz), 55.6, 53.7 (t, J=4.6 Hz, N($\underline{C}H_3$)$_3$).

EXAMPLE 5

A. Synthetic preparation of 3-tert-butildimethylsilyloxy-5-(tert-butyldimethylsilyloxymethyl)-2-methylpyridine-4-carbaldehyde (Compound 9)

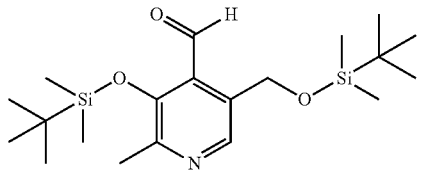

Compound 9

To a stirred solution of pyridoxal hydrochloride (3-hydroxy-5-(hydroxymethyl)-2-methylpyridine-4-carbaldehyde hydrochloride) (1.00 g, 4.91 mmol, 1.0 eq) in anhydrous DMF was added imidazole (1.67 g, 24.56 mmol), DMAP (0.30 g, 24.56 mmol, 5.0 eq), and TBDMSCl (3.70 g, 24.56 mmol, 5.0 eq). The reaction was stirred at room temperature overnight until disappearance of the starting material was observed by TLC (100% EtOAc). DMF was removed under high vacuum, water was added (20 mL), and the aqueous phase extracted with EtOAC (3×15 mL). The combined organic extracts were washed with aqueous saturated $NaHCO_3$, aqueous saturated $NH_4Cl$, and brine, dried over $MgSO_4$, and concentrated. The crude material was purified using Biotage chromatography on silica, beginning with an eluent of 3:7 hexane:EtOAc, increasing to 100% EtOAc, to afford 1.30 g (76% yield) of Compound 9 as a colorless oil.

$^1$H NMR (400 MHz, $CDCl_3$): δ ppm 7.95 (1H, s), 6.50 (1H, d, J=2.0 Hz), 5.0 (2H, $AB_q$, $\Delta\delta_{AB}$=0.07, $J_{AB}$=13.0 Hz), 2.43 (3H, s), 0.82 (9H, s), 0.81 (9H, s), 0.12 (3H, s), 0.03 (3H, s), -0.01 (3H, s), -0.10 (3H, s). $^{13}$C NMR (125 MHz, $CDCl_3$): δ ppm 145.7, 145.4, 134.3, 133.9, 133.4, 100.4, 70.8, 25.7, 18.0, 0.00, -3.56, -4.02, -4.72.

B. Synthetic Preparation of 3-Tert-Butldimethylsilyloxy-5-(Hydroxymethyl)-2-Methylpyridine-4-Carbaldehyde (Compound 10)

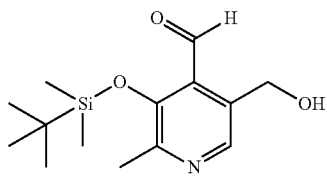

Compound 10

Compound 9 (0.21 g, 0.54 mmol, 1.0 eq) was dissolved in anhydrous MeOH (5 mL) at 0° C. and pyridinium p-toluenesulfonate (0.14 g, 0.57 mmol, 1.05 eq) was added. The reaction mixture was allowed to warm slowly to room temperature. The reaction was left to stir overnight. MeOH was removed under reduced pressure and the residue re-suspended in DCM (10 mL), and the drganic layer was washed with water, dried over $MgSO_4$, and then concentrated. The crude mixture was purified using Biotage silica column chromatography using an eluent of 1:1 hexane:EtOAc, increasing to 100% EtOAc, to afford 110 mg (73% yield) of Compound 10 as a white powder.

$^1$H NMR (400 MHz, $CDCl_3$): δ ppm 7.91 (1H, s), 6.46 (1H, d, J=2.0 Hz), 5.26 (2H, $AB_q$, $\Delta\delta_{AB}$=0.07, $J_{AB}$=12.9 Hz), 2.38 (3H, s), 0.79 (9H, s), 0.08 (3H, s), -0.14 (3H, s). $^{13}$C NMR (125 MHz, $CDCl_3$): δ ppm 145.6, 145.4, 134.3, 134.1, 133.3, 100.4, 70.8, 25.7, 17.9, 0.00, -4.01. HRMS (ES, M+H$^+$) calculated 282.1525 for $C_{14}H_{24}NO_3Si$, found 282.1512.

C. Synthetic Preparation of 5-Tert-Butyldimethylsilyloxy-6-Carbaldehyde-4-Methyl-3-Pyridinylmethyl Nicotinate (Compound 11)

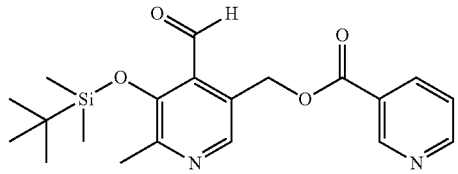

Compound 11

To a stirred solution of Compound 10 (0.20 g, 0.71 mmol, 1.0 eq) in dry pyridine (10 mL) was added trimethylamine (184 μL, 1.32 mmol, 1.9 eq) and nicotinoyl chloride (0.13 g, 0.71 mmol, 1.0 eq), and the reaction was stirred at room temperature overnight. TLC (100% EtOAc) indicated completion of reaction, and pyridine was removed under high vacuum. Purification was achieved using Biotage silica column chromatography using an eluent of 100% EtOAc to afford 0.25 g (91% yield) of Compound 11 as a white solid.

$^1$H NMR (400 MHz, $CDCl_3$): δ ppm 9.35 (1H, s), 8.84 (1H, d, J=3.48 Hz), 8.40 (1H, m), 8.35 (1H, s), 7.59 (1H, m), 6.44 (1H, d, J=1.5 Hz), 5.20 (2H, $AB_q$, $\Delta\beta_{AB}$=0.07, $J_{AB}$=12.8 Hz), 2.45 (3H, s), 0.67 (9H, s), -0.04 (3H, s), -0.11 (3H, s). 13C NMR (125 MHz, $CDCl_3$): δ ppm 161.3, 153.5, 150.5, 149.5, 140.4, 139.2, 136.7, 134.5, 122.6, 99.7, 69.1, 24.4, 17.9, 0.00, -5.32.

D. Synthetic Preparation of Pyridoxal (3-Hydroxy-5-(Hydroxymethyl)-2-Methylpyridine-4-Carbaldehyde) Nicotinate (Compound 12)

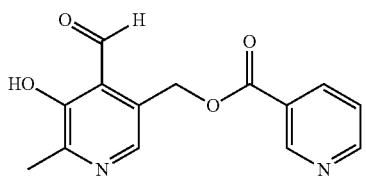

Compound 12

Pyridoxal (3-hydroxy-5-(hydroxymethyl)-2-methylpyridine-4-carbaldehyde) hydrochloride (500 mg, 2.46 mmol, 1.0 eq) was solubilized in 1:1 pyridine:DMF (10 mL) under an atmosphtere of $N_2$. To this was added nicotinoyl chloride (437.13 mg, 2.46 mmol, 1.0 eq) followed by TEA (1.37 mL, 9.82 mmol, 4.0 eq). The reaction was left stirring for 1 hr, after which TLC analysis (9:1 EtOAc:MeOH) showed completion of the reaction. The solvents were removed under high vacuum and the residual solid was loaded onto a Biotage silica column and purified using a gradient of 100% EtOAc, increasing slowly to 9:1 EtOAc:MeOH over 300 mL to isolate the desired compound as an off-white solid in 86% yield.

$^1$H NMR (400 MHz, CDCl$_3$): δ ppm 10.54 (1H, s, aldehyde), 9.38 (1H, d, J=1.6 Hz, Nicotinate), 8.88 (1H, m, Nicotinate), 8.44 (1H, m, Nicotinate), 8.43 (1H, s, Nicotinate), 7.53 (1H, m, pyridoxal), 6.51 (1H, s, pyridoxal), 5.32 (2H, AB$_q$, Δβ$_{AB}$=0.07, J$_{AB}$=13.0 Hz, —CH$_2$O), 2.53 (3H, s, —CH$_3$Ar). $^{13}$C NMR (125 MHz, CDCl$_3$): δ ppm 162.9 ((C=O)O), 154.5 (Ar), 151.4 (Nicotinate), 150.9 (HC=O), 140.9 (Ar), 140.1 (Ar), 137.9 (Ar), 135.5 (Ar), 123.7 (Nicotinate), 100.0 (Pyridoxal), 70.3 (CH$_2$O), 18.9 (CH$_3$Ar).

EXAMPLE 6

A. Synthetic Preparation of 3-Hydroxy-5-(Tert-Butyldimethylsilyloxylmethyl-2-Methylpyridine-4-Carbaldehyde (Compound 13)

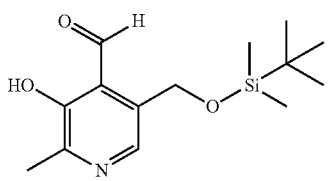

Compound 13

To a stirred solution of pyridoxal (3-hydroxy-5-(hydroxymethyl)-2-methylpyridine-4-carbaldehyde) hydrochloride (1.00 g, 4.91 mmol) in anhydrous DMF was added imidazole (0.50 g, 7.43 mmol), DMAP (0.30 g, 2.46 mmol), and TBDMSCl (0.89 g, 5.90 mmol). The reaction was stirred at room temperature overnight until disappearance of the starting material was observed by TLC (100% EtOAc). The DMF was removed under high vacuum, water was added (20 mL), and the aqueous phase was extracted with EtOAc (3×15 mL). The combined organics were washed with saturated aqueous NaHCO$_3$, saturated aqueous NH$_4$Cl, and brine, dried over MgSO$_4$, and concentrated. The crude material was purified by Biotage using a gradient of 3:7 hexane:EtOAc and increasing to 100% EtOAc to afford Compound 13 (1.01 g, 72% yield) as a fluffy white solid.

$^1$H NMR (400 MHz, CDCl$_3$): δ ppm 8.12 (1H, s), 6.52 (1H, d, J=1.76 Hz), 5.14 (2H, AB$_q$, Δδ$_{AB}$=0.07, J$_{AB}$=12.8 Hz), 2.50 (3H, s), 1.05 (9H, s), 0.20 (3H, s), 0.06 (3H, s). $^{13}$C NMR (125 MHz, CDCl$_3$): δ ppm 150.5, 145.3, 134.9, 134.8, 99.7, 70.2, 25.7, 18.6, 0.00, −3.67; HRMS (ES, M+H$^+$) calculated 282.1525 for C$_{14}$H$_{24}$NO$_3$Si, found 282.1512.

B. Synthetic Preparation of 3-(4-Nitrophenoxycarbonyl)-5-(Hydroxymethyl)-2-Methylpyridine-4-Carbaldehyde (Compound 14)

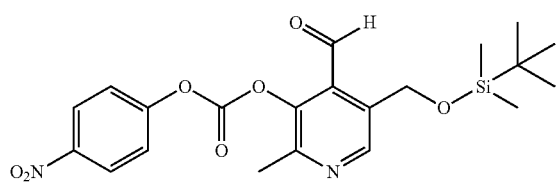

Compound 14

To a solution of Compound 13 (200 mg, 0.71 mmol) in dry DCM (10 mL) was added 4-nitrophenyl chloroformate (214.87 mg, 1.07 mmol) and TEA (184 µL, 1.07 mmol). The reaction stirred at room temperature and was followed by TLC (8:2 EtOAc:hexane). After completion of the reaction, the reaction was concentrated and purified directly on the Biotage using an eluent of 20% EtOAc in hexane, increasing to 80% EtOAc in hexane, affording 0.26 g (81% yield) of Compound 14 as an off-white solid.

$^1$H NMR (400 MHz, CDCl$_3$): δ ppm 8.24 (2H, d, J=9.3 Hz), 8.21 (1H, s), 7.19 (2H, d, J=9.3 Hz), 6.87 (1H, d, J=1.8 Hz), 5.29 (2H, AB$_q$, Δδ$_{AB}$=0.07, J$_{AB}$=12.8 Hz), 2.56 (3H, s), 0.93 (91, s), 0.17 (3H, s), 0.12 (3H, s).

EXAMPLE 7

A. Synthetic Preparation of Reduced Nicotinamide N-Fluorenylmethloxycarbonyl-Tryptophan Riboside (Compound 15): Compound of Formula (II): R$^1$=H, n=0, Z$^2$=NH, R$^2$=R$^3$=R$^4$=R$^5$=R$^7$=R$^8$=Hydrogen, R$^6$=N-Fluorenylmethyloxycarbonyltryptophan

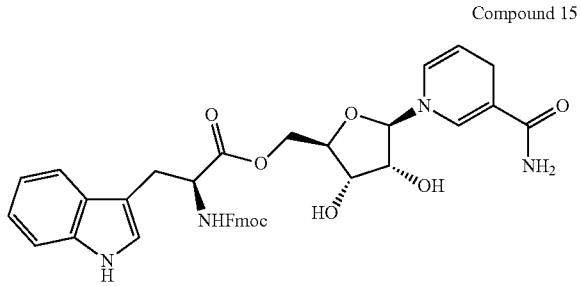

Compound 15

General NRL-Amino Acid Coupling Method 1:

To a dry round-bottom flask containing N-fluorenylmethyloxycarbonyltryptophan (0.5 g, 1.17 mmol, 1.0 eq) solubilized in anhydrous THF (5 mL) was added CDI (0.19 g, 1.17 mmol, 1.0 eq), and the mixture was left stirring overnight under N₂ with vigorous stirring. To the mixture was added dry NRH (0.6 g, 2.34 mmol, 2.0 eq) dissolved in anhydrous DMF (10 mL), and the mixture was left stirring at 40° C. for 3 hr and then DMF was removed under high vacuum. The solid was then resolubilized in EtOAc and washed with brine (3×10 mL), and the organic layers were combined and concentrated to give a pale yellow crystalline solid. The crude solid was solubilized in minimal EtOAc, then purified via biotage column purification using a gradient of 10% MeOH in EtOAc to give Compound 15 as a hygrosopic, yellow crystalline solid in 32% yield. This preparation demonstrates one example of the method described above at paragraphs [0193]-[0194] and [0546]-[0556].

¹H NMR (400 MHz, MeOD): δ ppm 7.68-7.56 (3H, m), 7.44-7.23 (5H, m), 7.17-7.10 (2H, m), 7.08-7.03 (1H, br), 6.06 (1H, d, J=9.0 Hz), 5.05-4.99 (1H, m), 4.84-4.79 (1H, m), 4.67 (1H, t, J=7.5 Hz), 4.38-4.34 (2H, m), 4.32-4.28 (1H, m), 4.24-4.19 (1H, m), 4.16-4.11 (1H, m), 3.56-3.42 (2H, m). HRMS (ES, M+H⁺) calculated 665.2611 for $C_{37}H_{37}N_4O_8$, found 665.2587.

Subsequent basic deprotection of Fmoc is expected to yield the reduced conjugate derivative.

EXAMPLE 8

A. Synthetic Preparation of Reduced Nicotinamide N-Tert-Butyloxycarbonyl-Tryptophan Riboside (Compound 16): Compound of Formula (II): $R^1$=H, n=0, $Z^2$=NH, $R^2$=$R^3$=$R^4$=$R^5$=$R^7$=$R^8$=Hydrogen, $R^6$=N-Tert-Butyloxycarbonyltryptophan

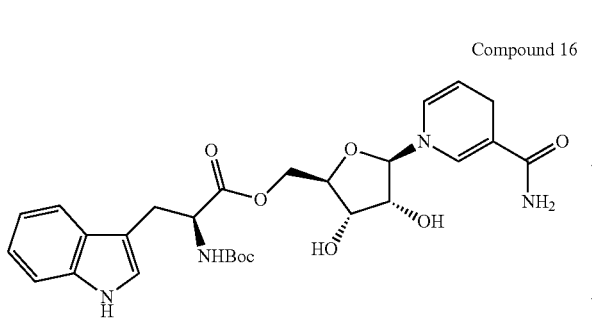

Compound 16

To a dry round-bottom flask containing N-tert-butyloxycarbonyltrypopan (0.5 g, 1.64 mmol, 1.0 eq) solubilized in anhydrous THF (5 mL) was added CDI (0.27 g, 1.64 mmol, 1.0 eq), and the mixture was left stirring overnight under N₂ with vigorous stirring. To the mixture was added NRH (0.84 g, 3.29 mmol, 2.0 eq), dissolved in anhydrous DMF (10 mL), and the mixture was left stirring at 40° C. for 5 h. DMF was then removed under high vacuum. The solid was then solubilized in EtOAc and washed with brine (3×10 mL), and the organic layer was concentrated to give a pale yellow crystalline solid. The solid was then resolubilized in the minimal amount of EtOAc and purified using biotage column chromatography using an eluent of 6% MeOH in EtOAc to give Compound 16 in 44% yield. Monitored at 320 nm. This preparation demonstrates one example of the method described above at paragraphs [0193]-[0194] and [0546]-[0556].

¹H NMR (400 MHz, CDCl₃): δ ppm 7.06 (1H, d, J=8.0 Hz), 7.37 (1H, d, J=8.0 Hz), 7.18-7.02 (3H, m), 7.09-7.04 (1H, m), 6.08 (1H, d, J=8.0 Hz), 5.02-4.99 (1H, m), 4.85- 4.81 (1H, m), 4.58 (1H, t, J=7.4 Hz), 4.37 (1H, d, J=7.8 Hz), 4.17-4.13 (1H, m), 3.56-3.42 (2H, m), 3.37 (1H, m), 3.24 (1H, d, J=7.8 Hz), 1.47-1.39 (9H, m). HRMS (ES, M+Na⁺) calculated 565.2274 for $C_{27}H_{34}N_4O_8Na$, found 565.2283.

General NRH-Amino Acid Coupling Method 2:

Alternatively, to a dry round-bottom flask was added N-tert-butyloxycarbonyltryptophan (500 mg, 1.67 mmol, 1.0 eq), HATU (760.46 mg, 2 mmol, 1.2 eq), and the mixture was left stirring in dry DMF (5 mL) and DIEA (1451.52 μL, 8.33 mmol, 5.0 eq) for 30 minutes. To the mixture was then added NRH (875 ing, 3.12 mmol, 1.9 eq) and the mixture was left stirring at room temperature overnight with monitoring by TLC (10% MeOH in EtOAc). The reaction mixture was concentrated and resolubilized in EtOAc and washed with brine (3×10 mL). The organic layer was then concentrated under reduced pressure to give a yellow crystalline solid. Biotage silica column purification using an eluent of 7.5% MeOH in EtOAc to give Compound 16 in 5% yield. This preparation demonstrates one example of the method described above at paragraphs [0193]-[0194] and [0546]-[0556].

B. Synthetic Preparation of Nicotinamide N-Tert-Butyloxycarbonyl-Tryptophan Riboside Chloride (Compound 17): Compound of Formula (I): X⁻=Chloride, $R^1$=H, n=0, $Z^2$=NH, $R^2$=$R^3$=$R^4$=$R^5$=$R^7$=$R^5$=Hydrogen, $R^6$=N-Tert-butyloxycarbonyltryptophan

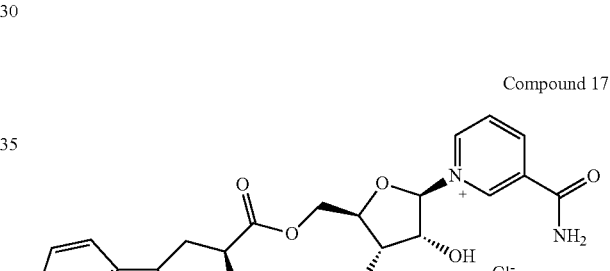

Compound 17

General Oxidation Method 1:

To a round-bottom flask was added Compound 16 (300 mg, 0.55 mmol, 1.0 eq) and it was solubilized in 5 mL of distilled water and 5 mL MeOH, with 1 mass equivalent of activated charcoal and ammonium chloride (59.15 mg, 1.15 mmol, 2.0 eq). After 2 h, the re-oxidation appeared complete by the complete disappearance of the spot corresponding to Compound 16 both by the UV spot under 320 nm and staining with permanganate. The sample was then filtered under suction and the residue washed with distilled water followed by methanol. The sample was then concentrated to give a crude solid. This preparation demonstrates one example of the methods described above at paragraphs [0189]-[0190] and [0534]-[0539].

General Oxidation Method 2:

To Compound 16 (400 mg, 0.74 mmol, 1.0 eq) was added hexchloroacetone (1.63 mL, 8.85 mmol, 12.0 eq) and EtOAc (2 mL) then left stirring overnight at room temperature. This solution was then concentrated under high vacuum and the sample was purified using Biotage silica column chromatography with 30% methanol in EtOAc over 800 mL to give 284 mg (67% yield) of the desired conjugate as a yellow crystalline solid.

$^1$H NMR (400 MHz, MeOD): δ ppm 9.47 (1H, s), 9.19-9.15 (1H, m), 8.96-8.91 (1H, m), 8.19-8.13 (1H, m), 7.51 (1H, d, J=7.7 Hz), 7.25-7.22 (1H, d, J=8.0 Hz), 7.10 (1H, s), 7.03-6.92 (2H, m), 5.63 (1H; d, J=6.5 Hz), 5.08 (1H, d, J=5.1 Hz), 4.51-4.46 (1H, m), 4.44-4.38 (1H, m), 4.34-4.28 (1H, m), 3.65-3.61 (2H, m), 3.16-3.13 (2H, m), 1.33 (9H, s).

C. Synthetic Preparation of Nicotinamide Tryptophan Riboside Chloride (Compound 18): Compound of Formula (I): X$^-$=Chloride, R$^1$=H, n=0, Z$^2$=NH, R$^2$=R$^3$=R$^4$=R$^5$=R$^7$=R$^8$=Hydrogen, R$^6$=Tryptophan

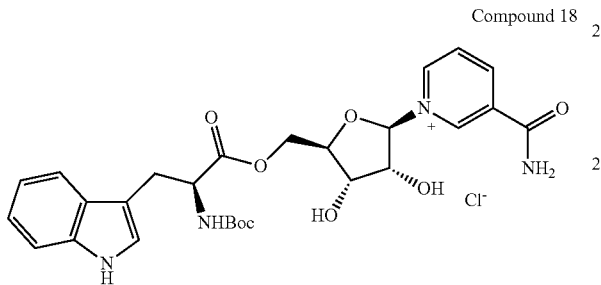

Compound 18

General Boc Deprotection Method 1:

Addition of TFA to a solution of Compound 17, followed by stirring of the mixture, results in complete deprotection of the N-tert-butyloxycarbonyl protecting group. Progress of the deprotection can be monitored by either $^1$H NMR or TLC analysis.

General Boc Deprotection Method 2:

To Compound 17 (200 mg, 0.35, 1.0 eq) was added 10 mL of a freshly made HCl/EtOAc solution and the flask was sealed, the desired product began to crash out of solution as a cloudy white precipitate and stirring was continued for 4 h. The mixture was concentrated to dryness then resuspended into EtOAc (10 mL), filtered, then washed with additional EtOAc. The solid was then solubilized in water and freeze-dried to isolate 43 mg (24% yield) of the desired NR conjugate as a yellow crystalline solid.

$^1$H NMR (400 MHz, MeOD): δ ppm 9.49 (1H, s), 9.21 (1H, d, J=6.2 Hz), 8.96 (1H, m), 8.23-8.16 (1H, m), 7.51 (1H, d, J=7.7 Hz), 7.30 (1H, d, J=8.0 Hz), 7.19 (1H, s), 7.09-7.00 (2H, m), 5.80 (11H, d, J=6.5 Hz), 5.24 (1H, d, J=5.1 Hz), 4.51 (1H, t, J=11.6 Hz), 4.43-4.38 (1H, m), 3.83-3.78 (1H, m), 3.81 (1H, m), 3.75-3.69 (1H, m), 3.52-3.47 (1H, m), 3.40-3.38 (2H, m). $^{13}$C NMR (125 MHz, MeOD): δ ppm 168.6, 163.7, 145.3, 142.5, 141.0, 136.8, 134.4, 127.9, 126.9, 124.3, 121.6, 119.0, 117.6, 111.4, 106.4, 100.2, 86.7, 77.0, 76.0, 60.7, 53.5, 26.7. HRMS (ES, M-Cl$^-$) calculated 441.1774 for C$_{22}$H$_{25}$N$_4$O$_6$, found 441. 1790.

EXAMPLE 9

A. Synthetic Preparation of Reduced Nicotinamide N-Tert-Butyloxycarbonyl-Isoleucine Riboside (Compound 19): Compound of Formula (II): R$^1$=H, n=0, Z$^2$=NH, R$^2$=R$^3$=R$^4$=R$^5$=R$^7$=R$^8$=Hydrogen, R$^6$=N-Tert-Butyloxycarbonyl-Isoleucine

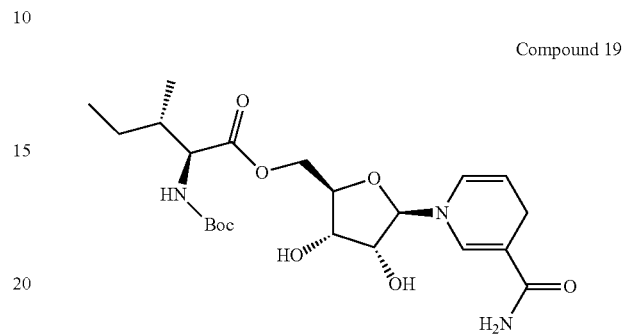

Compound 19

Compound 19 was prepared by the reaction of NRH with N-tert-butyloxycarbonylisoleucine according to General NRH-amino acid Coupling Method 2 to yield 723 mg of the desired product as a yellow crystalline solid (63% yield).

$^1$H NMR (400 MHz, MeOD): δ ppm 7.19 (1H, s), 6.15 (1H, d, J=3.2 Hz), 5.15-5.13 (1H, m), 5.00 (1H, q, J=5.8 Hz), 4.76 (1H, d, J=7.3 Hz), 4.26 (1H, t, J=6.4 Hz), 4.17-4.07 (1H, m), 3.92 (1H, q, J=2.7 Hz), 3.70-3.67 (2H, m), 3.08 (2H, br), 1.94-1.84 (1H, br), 1.46 (9H, s), 0.99-0.88 (8H, m). HRMS (ES, M+H$^+$) calculated 468.2346 for C$_{22}$H$_{34}$N$_3$O$_8$, found 468.2336.

B. Synthetic Preparation of Nicotinamide N-Tert-butyloxycarbonyl-Isoleucine Riboside Chloride (Compound 20): Compound of Formula (I): X$^-$=Chloride, R$^1$=H, Z$^2$=NH, R$^2$=R$^3$=R$^4$=R$^5$=R$^7$=R$^8$=Hydrogen, R$^6$=N-Tert-Butyloxycarbonyl-Isoleucine

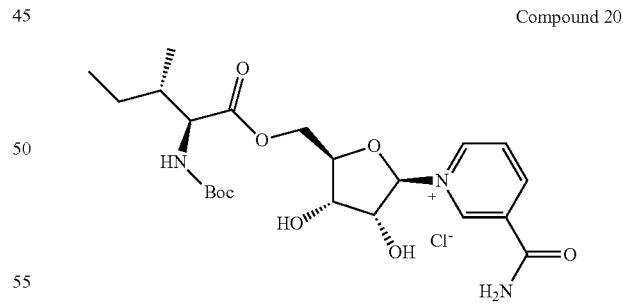

Compound 20

Compound 20 was prepared according to General Oxidation Method 2 to yield 0.46 g (72% yield) of the desired conjugate as a yellow crystalline solid.

$^1$H NMR (400 MHz, MeOD): δ ppm 9.61 (1H, s), 9.32 (1H, d, J=9.3 Hz), 8.96 (1H, d, J=8.1 Hz), 8.22-8.18 (1H, m), 6.12 (1H, d, J=5.7 Hz), 5.32-5.29 (1H, m), 4.59 (1H, t, J=5.4 Hz), 4.47-4.45 (1H, m), 4.11-4.07 (1H, m), 3.85 (2H, AB$_q$, Δδ$_{AB}$=0.06, J$_{AB}$=11.6 Hz), 1.89-1.79 (1H, m), 1.36 (9H, s), 0.93-0.82 (8H, m). $^{13}$C NMR (125 MHz, MeOD): δ ppm 164.7, 145.2, 143.2, 140.9, 134.5, 127.8, 100.7, 87.0, 77.2, 74.0, 60.4, 58.3, 36.9, 27.6, 14.5, 13.6, 10.2. HRMS (ES, M+H$^+$) calculated 468.2346 for $C_{22}H_{34}N_3O_8$, found 468.2364.

C. Synthetic Preparation of Nicotinamide Isoleucine Riboside Chloride (Compound 21): Compound of Formula (I): X$^-$=Chloride, R$^1$=H, n=0, Z$^2$=NH, R$^2$=R$^3$=R$^4$=R$^5$=R$^7$=R$^8$=Hydrogen, R$^6$=Isoleucine Compound 21

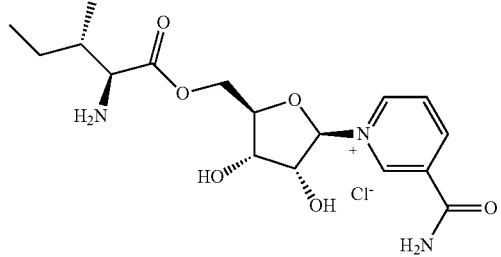

Compound 21 was prepared according to General Boc Deprotection Method 2 to yield 13 mg (14% yield) of the desired NR conjugate as an off-white crystalline solid.

$^1$H NMR (400 MHz, MeOD): δ ppm 9.62 (1H, s), 9.32 (1H, d, J=5.6 Hz), 8.98 (1H, d, J=7.7 Hz), 8.22-8.18 (1H, m), 6.16 (1H, d, J=6.1 Hz), 5.55-5.44 (1H, m), 4.66 (1H, t, J=5.7 Hz), 4.59-4.55 (1H, m), 4.13-4.10 (1H, m), 3.88 (2H, AB$_q$, Δδ$_{AB}$=0.06, J$_{AB}$=14.4 Hz, H-5), 2.08-1.98 (1H, m), 1.62-1.50 (1H, m), 0.93-0.86 (81H, m). HRMS (ES, M+H) calculated 368.1812 for $C_{17}H_{26}N_3O_6$, found 368.1790.

EXAMPLE 10

A. Synthetic Preparation of Reduced Nicotinamide N-Tert-Butyloxycarbonyl-Alanine Riboside (Compound 22): Compound of Formula (II): R$^1$=H, n=0, Z$^2$=NH, R$^2$=R$^3$=R$^4$=R$^5$=R$^7$=R$^8$=Hydrogen, R$^6$=N-Tert-Butyloxycarbonyl-Alanine Compound 22

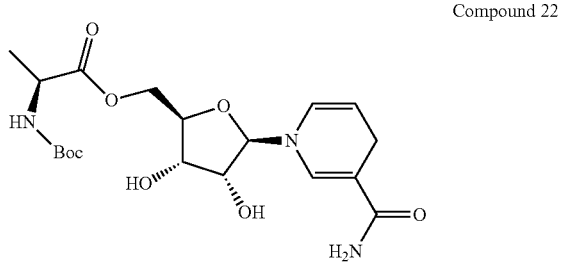 [SMILES: C[C@H](NC(=O)OC(C)(C)C)C(=O)OC[C@H]1O[C@@H](N2C=CCC(C(N)=O)=C2)[C@H](O)[C@@H]1O]

Compound 22 was prepared by the reaction of NRH with N-tert-butyloxycarbonyl-alanine according to General NRH-amino acid Coupling Method 2 to yield the desired product as a brown solid (33% yield).

$^1$H NMR (400 MHz, MeOD): δ ppm 7.09 (1H, s), 6.06 (1H, d, J=7.2 Hz), 5.05 (1H, dd, J=2.1, 3.6 Hz), 4.89-4.88 (1H, m), 4.67 (1H, d, J=12.4 Hz), 4.19-4.08 (2H, m), 4.03-3.97 (2H, m, H-5), 3.84-3.81 (1H, m), 3.61-3.57 (1H, m), 3.01-2.89 (2H, m), 1.35 (9H, s), 1.28 (3H, d, J=7.8 Hz). HRMS (ES, M+H$^+$) calculated 428.2033 for $C_{19}H_{30}N_3O_8$, found 428.2038.

B. Synthetic Preparation of Nicotinamide N-Tert-Butyloxycarbonyl-Alanine Riboside Chloride (Compound 23): Compound of Formula (I): X$^-$=Chloride, R$^1$=H, n=0, Z$^2$=NH, R$^2$=R$^3$=R$^4$=R$^5$=R$^7$=R$^8$=Hydrogen, R$^6$=N-Tert-Butyloxycarbonyl-Alanine Compound 23

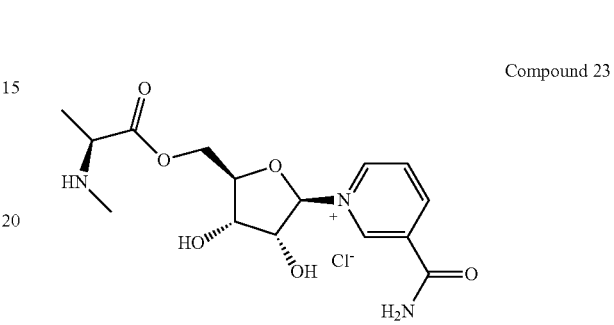

Compound 23 was prepared according to General Oxidation Method 2 to yield 78 mg (72% yield) of the desired conjugate as a brown solid.

$^1$H NMR (400 MHz, MeOD): δ ppm 9.61 (1H, s, Ar), 9.32 (1H, d, J=6.1 Hz), 8.95 (1H, d, J=8.3 Hz), 8.23-8.18 (1H, m), 6.12 (1H, d, J=5.6 Hz), 5.30 (1H, dd, J=2.8, 2.3 Hz), 4.58-4.47 (1H, tm), 4.48-4.45 (1H, m), 4.20-4.13 (1H, m), 3.88 (2H, AB$_q$, Δδ$_{AB}$=0.04, J$_{AB}$=12.2 Hz), 1.36 (9H, s), 1.34 (311, d, J=4.7 Hz). HRMS (ES, M+H$^+$) calculated 426.1876 for $C_{19}H_{28}N_3O_8$, found 426.1868.

C. Synthetic Preparation of Nicotinamide Alanine Riboside Chloride (Compound 24): Compound of Formula (I): X$^-$=Chloride, R$^1$=H, n=0, Z$^2$=NH, R$^2$=R$^3$=R$^4$=R$^8$=R$^7$=R$^8$=Hydrogen, R$^6$=Alanine Compound 24

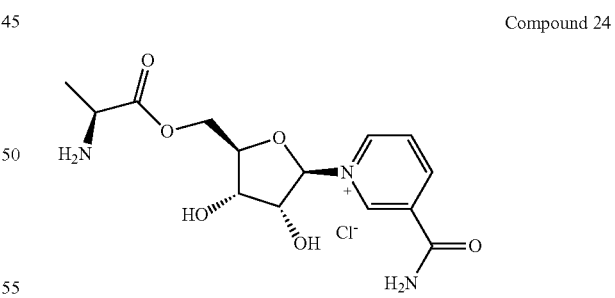

Compound 24 was prepared according to General Boc Deprotection Method 2 to yield 21 mg (40% yield) of the desired product as an off-white solid.

$^1$H NMR (400 MHz, MeOD): δ ppm 9.60 (1H, s), 9.33 (1H, d, J=6.2 Hz), 8.99 (1H, d, J=8.0 Hz), 8.23 (1H, t, J=7.1 Hz), 6.22 (1H, d, J=6.2 Hz), 5.45-5.41 (1H, m), 4.59-4.56 (1H, m), 4.25-4.19 (1H, m), 4.44 (2H, AB$_q$, Δδ$_{AB}$=0.06, J$_{AB}$=12.2 Hz), 1.57 (3H, d, J=7.2 Hz), 1.52-1.44 (1H, m). HRMS (ES, M+H$^{+)}$ calculated 326.1352 for $C_{14}H_{20}N_3O_6$, found 326.1349.

EXAMPLE 11

A. Synthetic Preparation of Reduced Nicotinamide N-Tert-Butyloxycarbonyl-Phenylalanine Riboside (Compound 25): Compound of Formula (I): $R^1$=H, n=0, $Z^2$=NH, $R^2$=$R^3$=$R^4$=$R^5$=$R^7$=$R^8$=Hydrogen, $R^6$=N-Tert-butyloxycarbonyl-Phenylalanine Compound 25

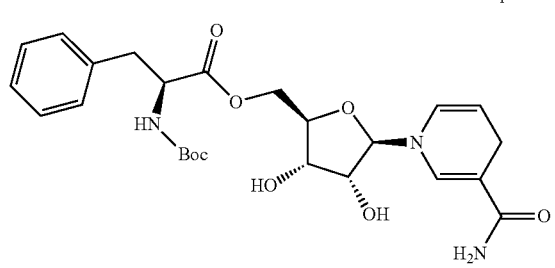

Compound 25 was prepared according to General NRH-amino acid Coupling Method 2 by the reaction of NRH with N-tert-butyloxycarbonyl-phenylalanine to yield 430 mg (46% yield) of the desired intermediate as a yellow gum.

$^1$H NMR (400 MHz, MeOD): δ ppm 7.88 (1H, s), 7.24-7.12 (5H, m), 6.04 (1H, d, J=8.1 Hz), 4.99 (1H, dd, J=5.5, 1.7 Hz), 4.78-4.73 (1H, m), 4.50 (1H, d, J=7.6 Hz), 4.35 (1H, t, J=7.7 Hz), 4.11 (1H, t, J=6.6 Hz), 3.01-2.96 (2H, m), 2.99 (1H, s), 1.31 (9H, s). $^{13}$C NMR (125 MHz, MeOD): δ ppm 171.9, 163.5, 137.1, 129.3, 128.4, 126.5, 125.9, 103.3, 101.1, 96.0, 95.1, 84.5, 82.0, 79.5, 70.8, 61.6, 60.2, 55.7, 37.8, 35.8, 27.4, 22.4, 19.6, 13.4. HRMS (ES, M+H$^+$) calculated 543.2455 for $C_{27}H_{35}N_3O_8$, found 543.2458.

B. Synthetic Preparation of Nicotinamide N-Tert-Butyloxycarbonyl-Phenlalanine Riboside Chloride (Compound 26): Compound of Formula (I): X$^-$=Chloride, $R^1$=H, n=0, $Z^2$=NH, $R^2$=$R^3$=$R^4$=$R^5$=$R^7$=$R^8$=Hydrogen, $R^6$=N-Tert-butyloxycarbonyl-Phenlalanine Compound 26

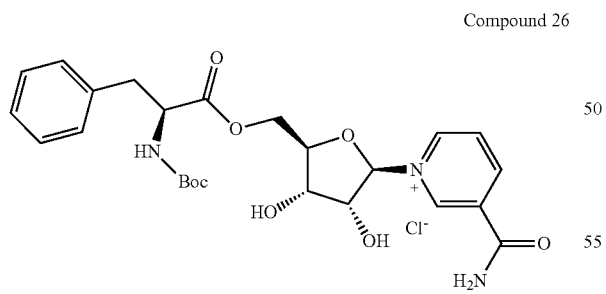

Compound 26 was prepared according to General Oxidation Method 2 to yield the desired N-tert-butyloxycarbonyl-phenylalanine conjugate in 64% yield as a fluffy white solid.

$^1$H NMR (400 MHz, MeOD): δ ppm 9.29 (1H, s), 9.28 (1H, d, J=6.1 Hz), 8.95 (1H, d, J=8.3 Hz), 8.19 (1H, t, J=7.2 Hz), 6.01 (1H, J=6.0 Hz), 5.23 (1H, d, J=3.6 Hz), 4.53 (1H, t, J=5.5 Hz), 4.40 (1H, t, J=7.8 Hz), 3.88-3.81 (1H, m), 3.69-3.64 (1H, m), 3.08-2.88 (3H, m), 1.32 (9H, s). $^{13}$C NMR (125 MHz, MeOD): δ ppm 171.5, 163.7, 145.2, 142.3, 140.9, 134.5, 129.0, 128.2, 127.8, 126.6, 100.5, 87.1, 79.5, 77.1, 74.1, 60.5, 55.4, 37.9, 27.3. HRMS (ES, M+H$^+$) calculated 502.2189 for $C_{25}H_{32}N_3O_8$, found 502.2188.

C. Synthetic Preparation of Nicotinamide Phenylalanine Riboside Chloride (Compound 27): Compound of Formula (I): X$^-$=Chloride, $R^1$=n=0 $Z^2$=NH, $R^2$=$R^3$=$R^4$=$R^5$=$R^7$=$R^8$=Hydrogen, $R^6$=Phenylalanine Compound 27

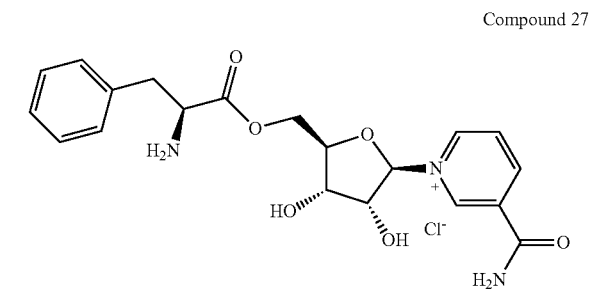

Compound 27 was prepared according to General Boc Deprotection Method 2 to yield 32 mg (40% yield) of the desired product as a white solid.

$^1$H NMR (400 MHz, MeOD): 3 ppm 9.56 (1H, s), 9.28 (1H, d, J=5.9 Hz), 9.00 (1H, d, J=7.8 Hz), 8.23-8.19 (1H, m), 7.29 (5H, m), 6.02 (1H, J=6.1 Hz), 5.37 (1H, d, J=4.8 Hz), 4.59 (1H, t, J=5.5 hz), 4.44 (1H, t, J=6.9 Hz), 4.24 (1H, s), 4.04-4.02 (1H, m), 3.88-3.81 (1H, m), 3.79-3.78 (1H, m), 3.72-3.68 (1H, m). $^{13}$C NMR (125 MHz, MeOD): δ ppm 168.3, 163.7, 145.3, 142.3, 141.0, 134.5, 129.2, 129.0, 128.9, 127.9, 127.6, 100.3, 86.8, 79.5, 77.1, 76.1, 60.7, 53.9, 36.5. HRMS (ES, M+H$^+$) calculated 403.1696 for $C_{20}H_{24}N_3O_6$, found 403.1732.

EXAMPLE 12

A. Synthetic Preparation of Reduced Nicotinamide N-Tert-Butyloxycarbonyl-Valine Riboside (Compound 28): Compound of Formula (II): $R^1$=H, n=0. $Z^2$=NH, $R^2$=$R^3$=$R^4$=$R^5$=$R^7$=$R^8$=Hydrogen, $R^6$=N-Tert-Butyloxycarbonyl-Valine Compound 28

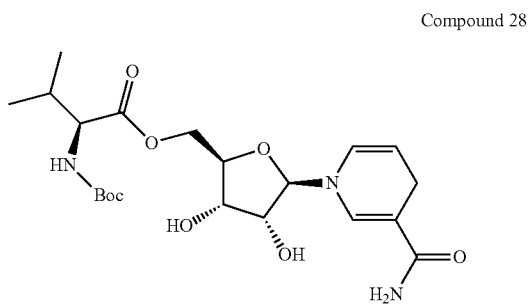 [SMILES: CC(C)[C@H](NC(=O)OC(C)(C)C)C(=O)OC[C@H]1O[C@@H](N2C=CCC(C(N)=O)=C2)[C@H](O)[C@@H]1O]

Compound 28 was prepared according to General NRH-amino acid Coupling Method 2 between NRH and N-tert-butyloxycarbonylvaline to yield 360 mg (34% yield) of the desired product as a yellow solid.

¹H NMR (400 MHz, MeOD): δ ppm 7.09 (1H, s), 6.07 (1H, d, J=8.2 Hz), 5.07-5.04 (1H, m), 4.94-4.89 (1H, m), 4.79-4.72 (1H, m), 4.66 (1H, d, J=7.4 Hz), 4.14-4.13 (1H, m), 4.03-3.97 (1H, m), 3.85-3.81 (1H, m), 3.69-3.54 (2H, m), 3.01-2.95 (2H, m), 2.11-2.02 (1H, m), 1.36 (9H, s), 0.91-0.83 (6H, m). ¹³C NMR (125 MHz, MeOD): δ ppm 171.6, 164.1, 137.2, 125.9, 103.8, 101.0, 95.7, 82.2, 79.9, 73.9, 70.6, 61.8, 59.8, 35.9, 30.4, 27.6, 22.6, 18.6, 17.3. HRMS (ES, M+H⁺) calculated 454.2189 for $C_{21}H_{32}N_3O_8$, found 454.2163.

B. Synthetic Preparation of Nicotinamide N-Tert-Butyloxycarbonyl-Valine Riboside Chloride (Compound 29): Compound of Formula (I): X⁻=Chloride, $R^1$=H, n=0, $Z^2$=NH, $R^2$=$R^3$=$R^4$=$R^5$=$R^7$=$R^8$=Hydrogen, $R^6$=N-Tert-Butyloxycarbonyl-Valine Compound 29

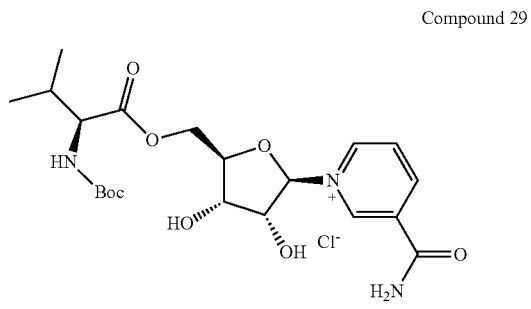

Compound 29 was prepared according to General Oxidation Method 2 to yield 143 mg (44% yield) of the desired conjugate as a yellow solid.

¹H NMR (400 MHz, MeOD): δ ppm 9.61 (1H, s), 9.32 (1H, d, J=6.1 Hz), 8.98 (1H, d, J=8.0 Hz), 8.22-8.18 (1H, m), 6.14 (1H, d, J=5.7 Hz), 5.31-5.29 (1H, m), 4.57-4.52 (1H, m), 4.48-4.45 (1H, m), 4.03 (1H, d, J=6.0 Hz), 3.88 (2H, $AB_q$, $\Delta\delta_{AB}$=0.06, $J_{AB}$=12.4 Hz), 2.16-2.07 (1H, m), 1.62-1.50 (1H, m), 1.37 (9H, s), 0.96-0.88 (6H, m). ¹³C NMR (125 MHz, MeOD): δ ppm 172.8, 161.3, 145.6, 141.8, 140.3, 134.9, 128.3, 99.2, 83.1, 79.4, 76.4, 73.1, 68.1, 59.8, 30.3, 27.3, 18.6, 17.3. HRMS (ES, M+H⁺) calculated 454.2189 for $C_{21}H_{32}N_3O_8$, found 454.2200.

C. Synthetic Preparation of Nicotinamide Valine Riboside Chloride (Compound 30): Compound of Formula (I): X⁻=Chloride, $R^1$=H, n=0, $Z^2$=NH, $R^2$=$R^3$=$R^4$=$R^5$=$R^7$=$R^8$=Hydrogen, $R^6$=Valine Compound 30

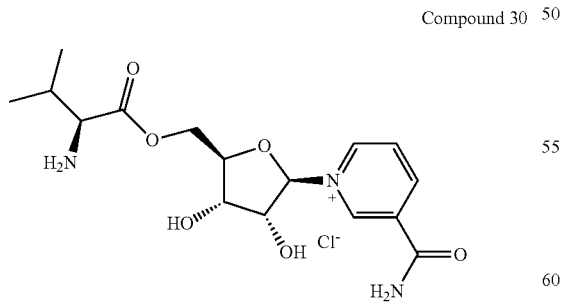

Compound 30 was prepared according to General Boc Deprotection Method 2 to yield 12 mg (13% yield) of the desired product as an off-white solid.

¹H NMR (400 MHz, MeOD): δ ppm 9.40 (1H, s, Ar), 9.20 (1H, m), 8.90 (1H, m), 8.22-8.06 (1H, m), 6.20-6.08 (1H, m), 5.43-5.33 (1H, m), 4.60-4.49 (2H, m), 4.39-4.29 (1H, m), 4.10-4.01 (1H, m, riboside), 3.93-3.70 (2H, m), 2.40-2.23 (1H, m), 0.97-0.87 (6H, m). ¹³C NMR (125 MHz, MeOD): δ ppm 168.4, 165.6, 146.0, 142.8, 140.4, 133.9, 128.6, 99.3, 85.9, 75.9, 74.8, 60.4, 58.3, 29.3, 17.3, 17.2. HRMS (ES, M+H⁺) calculated 354.1665 for $C_{16}H_{24}N_3O_6$, found 354.1666.

EXAMPLE 13

A. Synthetic Preparation of Reduced Nicotinamide N-Tert-Butyloxycarbonyl-Methionine Riboside (Compound 31): Compound of Formula (II): $R^1$=H, n=0, $Z^2$=NH, $R^2$=$R^3$=$R^4$=$R^5$=$R^7$=$R^8$=Hydrogen, $R^6$=N-Tert-Butyloxycarbonyl-Methionine Compound 31

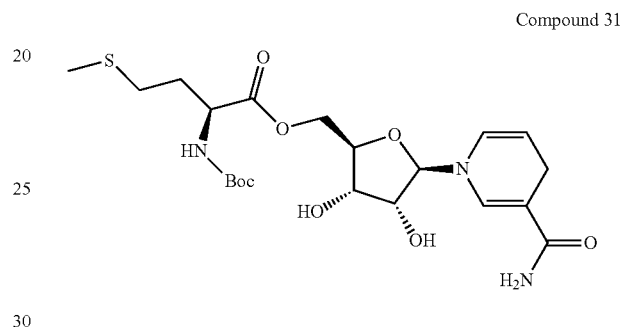

Compound 31 was prepared according to General NRH-amino acid Coupling Method 2 between NRH and N-tert-butyloxycarbonyl-methionine to yield 0.240 g (25% yield) of the desired product as a yellow solid.

¹H NMR (400 MHz, MeOD): δ ppm 7.09 (1H, s), 6.06 (1H, d, J=8.2 Hz), 5.07 (1H, d, J=5.6 Hz), 4.90-4.85 (1H, m), 4.78-4.73 (1H, m), 4.65 (1H, d, J=7.5 Hz), 4.28-4.22 (1H, m), 4.21-4.14 (1H, m), 3.84 (1H, s), 3.68-3.55 (3H, m), 3.24-3.19 (2H, m), 3.00-2.86 (2H, m), 2.57-2.42 (4H, m), 2.00 (3H, s, S—CH₃), 1.35 (9H, s). ¹³C NMR (125 MHz, MeOD): δ ppm 172.3, 163.6, 137.4, 126.1, 103.5, 100.5, 96.0, 84.2, 72.1, 70.8, 62.3, 36.2, 27.6, 22.4, 14.1. HRMS (ES, M+H⁺) calculated 488.2067 for $C_{21}H_{34}N_3O_8S$, found 488.2061.

B. Synthetic Preparation of Nicotinamide N-Tert-Butyloxycarbonyl-Methionine Riboside Chloride (Compound 32): Compound of Formula (I): X⁻=Chloride, $R^1$=H, n=0, $Z^2$=NH, $R^2$=$R^3$=$R^4$=$R^5$=$R^7$=$R^8$=Hydrogen, $R^6$=N-Tert-Butyloxycarbonyl-Methionine Compound 32

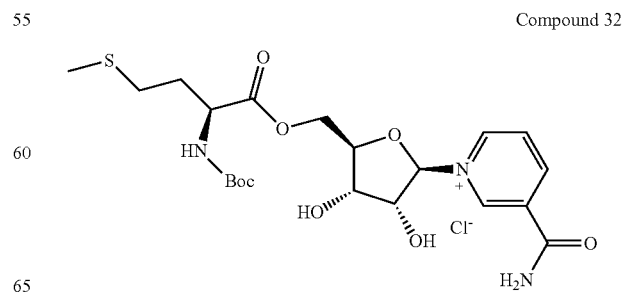

Compound 32 was prepared according to General Oxidation Method 2 to yield 113 mg (53% yield) of the desired conjugate as a yellow solid.

$^1$H NMR (400 MHz, MeOD): δ ppm 9.62 (1H, s), 9.33 (1H, d, J=6.2 Hz), 8.98 (1H, d, J=8.0 Hz), 8.22-8.18 (1H, m), 6.14 (1H, d, J=5.7, βH-1), 5.33 (1H, dd, J=3.0, 2.0 Hz), 4.58-4.53 (1H, m), 4.48-4.45 (1H, m), 4.36-4.26 (2H, m), 3.86 (2H, AB$_q$, Δδ$_{AB}$=0.06, J$_{AB}$=12.3 Hz), 2.63-2.45 (2H, m), 2.16-2.00 (2H, m), 1.94 (3H, s), 1.36 (91H, s).

C. Synthetic Preparation of Nicotinamide Methionine Riboside Chloride (Compound 33): Compound of Formula (I): X$^-$=Chloride, R$^1$=H, n=0, Z$^2$=NH, R$^2$=R$^3$=R$^4$=R$^5$=R$^7$=R$^8$=Hydrogen, R$^6$=Methionine

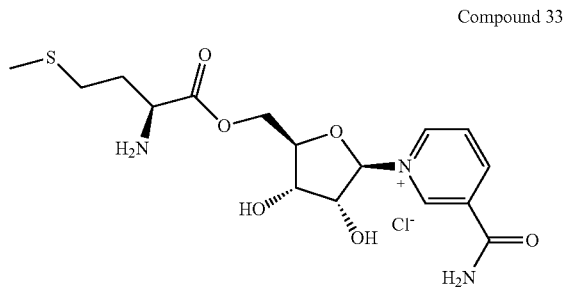

Compound 33

Compound 33 was prepared according to General Boc Deprotection Method 2 to yield 32 mg (24% yield) of the desired product as a yellow crystalline solid.

$^1$H NMR (400 MHz, D$_2$O): δ ppm 9.66 (1H, s), 9.20-9.15 (1H, m), 8.93-8.88 (1H, m), 8.22-8.17 (1H, m), 6.19 (1H, d, J=4.8 Hz), 5.47-5.41 (1H, m), 4.66-4.62 (1H, m), 4.41-4.35 (1H, m), 3.97-3.91 (1H, m), 3.86-3.73 (1H, m), 2.67-2.61 (1H, m), 2.34-2.17 (2H, m), 2.03 (3H, s). $^{13}$C NMR (125 MHz, D$_2$O): δ ppm 168.7, 165.7, 146.1, 142.8, 140.5, 134.1, 128.6, 99.4, 86.0, 76.1, 60.5, 51.8, 28.8, 28.5, 14.0. HRMS (ES, M+H+) calculated 386.1386 for C$_{16}$H$_{24}$N$_3$O$_6$S, found 386.1360.

EXAMPLE 14

A. Synthetic Preparation of Reduced Nicotinamide N-Tert-Butyloxycarbonyl-Leucine Riboside (Compound 34): Compound of Formula (II): R$^1$=H, n=0, Z$^2$=NH, R$^2$=R$^3$=R$^4$=R$^5$=R$^7$=R$^8$=Hydrogen, R$^6$=N-Tert-Butyloxycarbonyl-Leucine Compound 34

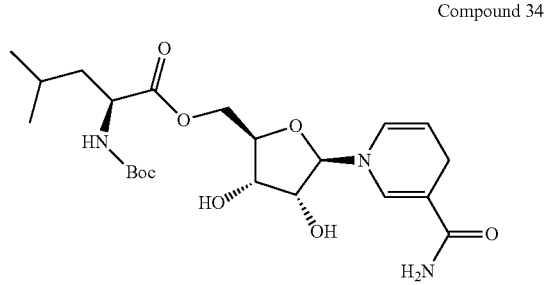 [SMILES: CC(C)C[C@H](NC(=O)OC(C)(C)C)C(=O)OC[C@H]1O[C@@H](N2C=CCC(C(N)=O)=C2)[C@H](O)[C@@H]1O]

Compound 34 was prepared according to General NRH-amino acid Coupling Method 2 between NRH and N-tert-butyloxycarbonyl-leucine to yield 350 mg (34% yield) of the desired intermediate as a yellow crystalline solid.

$^1$H NMR (400 MHz, MeOD): δ ppm 7.09 (1H, s), 6.06 (1H, d, J=8.2 Hz), 5.04 (1H, dd, J=3.6, 2.1 Hz), 4.90-4.88 (1H, m), 4.78-4.73 (1H, m), 4.67 (1H, d, J=7.6 Hz), 4.35 (1H, t, J=7.7 Hz), 4.11 (1H, t, J=6.6 Hz), 3.70-3.55 (2H, m), 3.01-2.97 (2H, m), 2.99 (1H, s), 1.37 (9H, s), 1.71-1.58 (1H, m), 0.86 (6H, m). HRMS (ES, M+H$^)$ calculated 470.2502 for C$_{22}$H$_{33}$N$_3$O$_8$, found 470.2480).

B. Synthetic Preparation of Nicotinamide Leucine Riboside Chloride (Compound 35): Compound of Formula (I): X$^-$=Chloride, R$^1$=H, n=0, Z$^2$=NH, R$^2$=R$^3$=R$^4$=R$^5$=R$^7$=R$^8$=Hydrogen, R$^6$=Leucine Compound 35

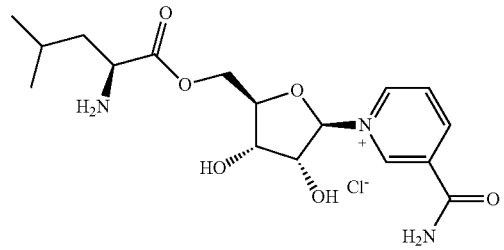

Compound 34 (300 mg, 0.64 mmol, 1.0 eq) was solubilized in EtOAc (5 mL) to which was added hexachloroacetone (1.17 mL, 0.01 mol, 10.0 eq), then the flask was sealed and left vigorously stirring overnight. EtOAc was removed under reduced pressure followed by the addition of a 1:1 mixture of petroleum ether:ether (15 mL). The orange precipitate was then isolated by decanting off the solvent. The solid was solubilized in water and then freeze-dried. HRMS (ES, M+H$^+$) calculated 502.1956 for C$_{22}$H$_{33}$N$_3$O$_8$Cl, found 502.2073. To this solid was added a freshly prepared solution of HCl/EtOAc (10 mL) and the flask was left sealed overnight. The precipitated product was isolated by filtration and washed with additional EtOAc. The product was then solubilized in water and purified using C$_{18}$ Biotage chromatography, and then freeze-dried to yield the desired product as a yellow crystalline solid in 17% yield.

$^1$H NMR (400 MHz, MeOD): δ ppm 9.60 (1H, s), 9.33 (1H, d, J=6.2 Hz), 8.98 (1H, d, J=8.0 Hz), 8.22-8.18 (1H, m), 6.12 (1H, d, J=5.7 Hz), 5.48-5.45 (1H, m), 4.66-4.64 (1H, m), 4.58-4.55 (1H, m), 4.11 (1H, d, J=4.1 Hz), 3.98-3.92 (1H, m), 3.83-3.77 (1H, m), 2.07-1.97 (1H, m), 1.60-1.47 (1H, m), 1.37-1.34 (2H, m), 1.05-0.94 (6H, m). HRMS (ES, M+H$^+$) calculated 368.1822 for C$_{17}$H$_{26}$N$_3$O$_6$, found 368.1809.

EXAMPLE 15

A. Synthetic Preparation of 2-Bromoethyl Pyridine-3-Carboxylate (Compound 36): Compound Having Formula (1): R$^1$=2-Bromoethyl, n=0, Z$^2$=Oxygen, R$^2$=R$^3$=R$^4$=R$^5$=Hydrogen Compound 36

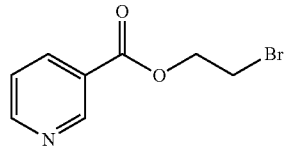

To a dry round-bottom flask containing nicotinoyl chloride hydrochloride (5.00 g, 0.030 mol, 1.0 eq) in anhydrous DCM (5 mL) was added 2-bromoethanol (2.15 mL, 0.03 mol, 1.0 eq), followed by DMAP (0.34 g, 0.003 mol, 0.1 eq) and TEA (4.31 mL, 0.03 mol, 1.0 eq) by syringe. This mixture was then left stirring overnight at room temperature under an atmosphere of $N_2$. The solution was poured into water and mixed, the organic phase was separated and washed an additional two times, then dried over magnesium sulfate. The organic phase was then concentrated and used in the next step without any additional purification (83% yield).

$^1$H NMR (400 MHz, CDCl$_3$): δ ppm 9.27 (1H, s), 8.80 (1H, d, J=4.8 Hz), 8.32 (1H, d, J=3.0 Hz), 7.44-7.40 (1H, m), 4.67 (2H, t, J=2.6 Hz), 3.67 (2H, t, J=4.0 Hz). $^{13}$C NMR (125 MHz, CDCl$_3$): δ ppm 164.7, 153.7, 151.0, 137.1, 125.5, 123.4, 64.5, 43.5.

B. Synthetic Preparation of 2-Bromoethyl Nicotinate Riboside Triacetate Triflate (Compound 37): Compound of Formula (I): X$^-$=Triflate (Trifluoromethanesulfonate), R$^1$=2-Bromoethyl, n=0, Z$^2$=Oxygen, R$^2$=R$^3$=R$^4$=R$^5$=Hydrogen, R$^6$=R$^7$=R$^8$=Acetyl Compound 37

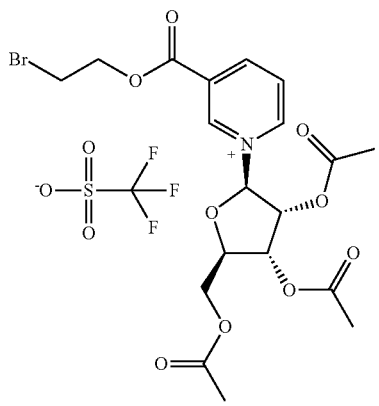

To a dry round-bottom flask was added Compound 36 (500 mg, 2.17 mmol, 1.0 eq) and solubilized in anhydrous DCE (15 mL) followed by the addition of tetra-O-acetyl-β-D-ribofuranose (760.9 mg, 2.39 mmol, 1.1 eq). TMSOTf (0.43 mL, 2.39 mmol, 1.1 eq) was added dropwise by syringe and the solution was heated to 40° C. under an atmosphere of $N_2$. After the reaction was deemed complete by TLC analysis, the mixture was poured into distilled water (10 mL) and the organic phase was separated and then concentrated. The crude was then purified Biotage silica column chromatography using an eluent of 7.5% MeOH in EtOAc, the product fractions were pooled and concentrated to yield the desired product in 43% yield as an orange solid.

$^1$H NMR (400 MHz, CDCl$_3$): δ ppm 9.69 (1H, s, Ar), 9.54-9.51 (1H, d, J=6.3 Hz), 9.24 (1H, d, J=8.0 Hz), 8.45-8.40 (1H, m), 6.65 (1H, d, J=3.8 Hz), 5.60 (1H, m), 5.46 (1H, m), 4.85-4.79 (2H, m), 4.69 (1H, t, J=5.8 Hz), 4.57 (2H, AB$_q$, Δδ$_{AB}$=0.08, J$_{AB}$=9.0 Hz), 4.58 (2H, t, J=5.7 Hz), 3.77 (1H, m), 2.21 (3H, s), 2.18 (3H, s), 2.17 (3H, s).

C. Synthetic Preparation of Choline Nicotinate Riboside Triflate (Compound 38): Compound of Formula (I): X$^-$=Triflate (Trifluoromethanesulfonate R$^1$=Choline, n=0, Z$^2$=Oxygen, R$^2$=R$^3$=R$^4$=R$^5$=R$^6$=R$^7$=R$^8$=Hydrogen Compound 38

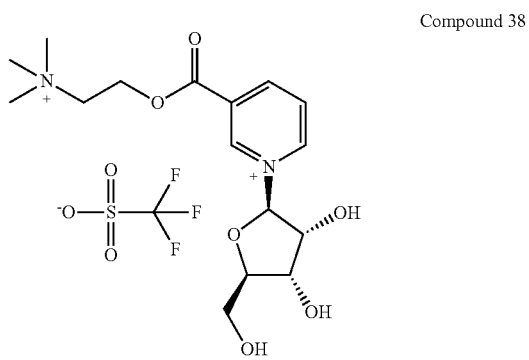

To a round-bottom flask was added Compound 37 (200 mg, 0.38 mmol, 1.0 eq) followed by the addition of an aqueous solution of trimethylamine (0.28 mL, 1.91 mmol, 5.0 eq). The flask was sealed using a glass stopper and was stirred overnight at room temperature, after which the sample was freeze-dried and purified using C18 Biotage chromatography using an eluent of 100% water to 10% MeOH over 1 L. The product fractions were pooled and concentrated to yield 53 mg (20% yield) of the desired product as a pale brown hygroscopic solid.

$^1$H NMR (400 MHz, CDCl$_3$): δ ppm 9.27 (1H, s), 8.98 (1H, d, J=6.2 Hz), 8.85 (1H, d, J=8.0 Hz), 8.13-8.07 (1H, m), 6.13 (1H, d, J=4.6 Hz), 4.61-4.57 (1H, m), 4.67-4.39 (4H, m), 4.27-4.22 (1H, m), 3.97-3.93 (1H, m), 3.65-3.60 (1H, m), 2.79 (9H, s).

The use of the terms "a," "an," "the," and similar referents in the context of describing the present invention (especially in the context of the claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Use of the term "about" is intended to describe values either above or below the stated value in a range of approximately ±10%; in other embodiments, the values may range in value above or below the stated value in a range of approximately ±5%; in other embodiments, the values may range in value above or below the stated value in a range of approximately ±2%; in other embodiments, the values may range in value above or below the stated value in a range of approximately ±1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise stated. No language in the specification should be construed as indicating any non-claimed element as essential to the practice of the invention.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entireties. The present invention may be embodied in other specific forms without departing from the spirit or essential attributes thereof, and, accordingly, reference should be made to the appended claims, rather than to the foregoing specification, as indicating the scope of the invention.

We claim:
1. A nicotinate/nicotinamide riboside compound or derivative of formula (I), or a salt, hydrate, or solvate thereof:

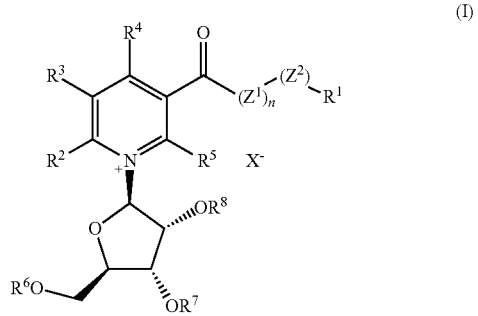

(I)

wherein X⁻ as counterion is absent, or when X⁻ is present, X⁻ is selected from the group consisting of fluoride, chloride, bromide, iodide, formate, acetate, ascorbate, benzoate, carbonate, citrate, carbamate, formate, gluconate, lactate, methyl bromide, methyl sulfate, nitrate, phosphate, diphosphate, succinate, sulfate, trifluoromethanesulfonate, trichloromethanesulfonate, tribromomethanesulfonate, and trifluoroacetate;

$Z^1$ and $Z^2$ are independently NH or oxygen;

n is 0 or 1;

$R^1$ is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$SO$_2$N$R^C$, —S$R^C$, —S(O)$R^C$, —SO$_2R^C$, —OSO$_2$($C_1$-$C_6$)alkyl, —SO$_2$N$R^C_2$, —($C_6$-$C_6$)perfluoroalkyl, and —($C_1$-$C_6$)alkylene-O$R^C$;

$R^A$ is selected from the group consisting of —H, —($C_1$-$C_6$)alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$, and —CH$_2$—CH$_3$;

$R^B$ is hydrogen or —($C_1$-$C_8$)alkyl;

each $R^C$ is independently selected from the group consisting of hydrogen, —($C_1$-$C_8$)alkyl, substituted or unsubstituted pyridyl, substituted or unsubstituted 1,4-dihydropyridyl, a radical of the compound of formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_1$-$C_6$)alkenyl, —($C_2$-$C_6$)alkynyl, halogen, —CN, —$NO_2$, —C(O)$R^B$, —C(O)O$R^B$, —C(O)N$R^B_2$, —C(=N$R^B$)N$R^B_2$, —O$R^B$, —OC(O)($C_1$-$C_6$)alkyl, —OC(O)O($C_1$-$C_6$)alkyl, —OC(O)N$R^B_2$, —($C_1$-$C_6$)alkylene-N$R^B_2$, —N$R^B_2$, —N$R^B$C(O)$R^B$, —N$R^B$C(O)O($C_1$-$C_6$)alkyl, —N$R^B$C(O)N$R^B_2$, —N$R^B$SO$_2$N$R^B$, —S$R^B$, —S(O)$R^B$, —SO$_2R^B$, —OSO$_2$($C_1$-$C_6$)alkyl, —SO$_2$N$R^B_2$, —($C_1$-$C_6$)perfluoroalkyl, and —($C_1$-$C_6$)alkylene-O$R^B$;

$R^2$, $R^3$, $R^4$, and $R^5$ are each independently selected from the group consisting of hydrogen, —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$SO$_2$N$R^C$, —S$R^C$, —S(O)$R^C$, —SO$_2R^C$, —OSO$_2$($C_1$-$C_6$)alkyl, —SO$_2$N$R^C_2$, —($C_1$-$C_6$)perfluoroalkyl, and —($C_2$-$C_6$)alkylene-O$R^C$;

$R^6$ is selected from the group consisting of hydrogen, —C(O)R', —C(O)OR', —C(O)NHR', —P(O)(OY$^1$)(OY$^2$), —P(O)(OY$^1$)(NHR"), substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$SO$_2$N$R^C$, —S$R^C$, —S(O)$R^C$, —SO$_2R^C$, —OSO$_2$($C_1$-$C_6$)alkyl, —SO$_2$N$R^C_2$, —($C_1$-$C_6$)perfluoroalkyl, and —($C_1$-$C_6$)alkylene-O$R^C$;

R' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$S$O_2$N$R^C$, —S$R^C$, —S(O)$R^C$, —S$O_2R^C$, —OS$O_2$($C_1$-$C_6$)alkyl, —S$O_2$N$R^C_2$, —($C_1$-$C_6$)perfluoroalkyl, and —($C_1$-$C_6$)alkylene-O$R^C$;

R″ is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—($R^)$C$O_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)allylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$S$O_2$N$R^C$, —S$R^C$, —S(O)$R^C$, —S$O_2R^C$, —OS$O_2$($C_1$-$C_6$)alkyl, —S$O_2$N$R^C_2$, —($C_1$-$C_6$)perfluoroalkyl, and —($C_1$-$C_6$)alkylene-O$R^C$;

$R^7$ and $R^8$ are independently selected from the group consisting of hydrogen, —C(O)R′, —C(O)OR′, —C(O)NHR′, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$)cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$S$O_2$N$R^C$, —S$R^C$, —S(O)$R^C$, —S$O_2R^C$, —OS$O_2$($C_1$-$C_6$)alkyl, —S$O_2$N$R^C_2$, —($C_1$-$C_6$)perfluoroalkyl, and —($C_1$-$C_6$)alkylene-O$R^C$;

$Y^1$ and $Y^2$ are independently selected from the group consisting of hydrogen, sodium, potassium, lithium, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$) alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$S$O_2$N$R^C$, —S$R^C$, —S(O)$R^C$, —S$O_2R^C$, —OS$O_2$($C_1$-$C_6$)alkyl, —S$O_2$N$R^C_2$, —($C_1$-$C_6$)perfluoroalkyl, and —($C_1$-$C_6$)alkylene-O$R^C$;

or, alternatively, $Y^1$ and $Y^2$ taken together are selected from the group consisting of sodium, potassium, lithium, magnesium, calcium, strontium, and barium;

provided that when $Z^2$ is NH, the absolute configuration of C** is R or S, or a mixture of R and S;

further provided that when n is 0, $Z^2$ is NH, and $R^1$ is hydrogen, then $R^6$, $R^7$, and $R^8$ are not all simultaneously hydrogen;

further provided that when n is 0, $Z^2$ is NH, and $R^1$, $R^2$, $R^3$, $R^4$, and $R^5$ are each hydrogen, then $R^6$ is not —C(O)R′ or —C(O)OR′ where R′ is alkyl, and each of $R^7$ and $R^8$ are not independently hydrogen, —C(O)R′, or —C(O)OR′, where R′ is alkyl;

further provided that when n is 0, $Z^2$ is NH, $R^1$ is ($C_1$-$C_8$)alkyl or ($C_1$-$C_8$)cycloalkyl, and $R^2$, $R^3$, $R^4$, and $R^5$ are each hydrogen, then each of $R^6$, $R^7$, and $R^8$ are not independently hydrogen or —C(O)R′;

further provided that when n is 0, $Z^2$ is oxygen, $R^1$ is ($C_1$-$C_8$)alkyl, ($C_1$-$C_8$)cycloalkyl, aryl, or substituted aryl, and $R^2$, $R^3$, $R^4$, and $R^5$ are each hydrogen, then $R^6$, $R^7$, and $R^8$ are not all simultaneously —C(O)R′;

further provided that when X— is absent, n is 0, Z2 is oxygen, R1 is hydrogen, R2, R3, and R5 are each hydrogen, and R4 is hydrogen or —(C1-C6)alkyl, then each of R6 and R7 is not independently hydrogen or —C(O)R′, where R′ is unsubstituted aryl, and R8 is not hydrogen.

2. A reduced nicotinate/nicotinamide riboside compound or derivative of formula (II), or a salt, hydrate, or solvate thereof:

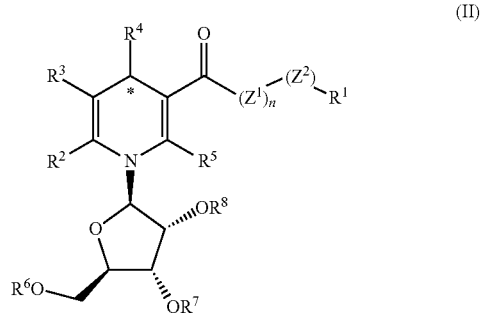

(II)

$Z^1$ and $Z^2$ are independently NH or oxygen;

n is 0 or 1;

$R^1$ is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^A$)—C$O_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$$SO_2$N$R^C$, —S$R^C$, —S(O)$R^C$, —$SO_2$$R^C$, —OS$O_2$($C_1$-$C_6$)alkyl, —$SO_2$N$R^C_2$, —($C_1$-$C_6$)perfluoroalkyl, and —($C_1$-$C_6$)alkylene-O$R^C$;

$R^4$ is selected from the group consisting of —H, —($C_1$-$C_6$)alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$, and —CH$_2$—CH$_3$;

$R^B$ is hydrogen or —($C_1$-$C_8$)alkyl;

each $R^C$ is independently selected from the group consisting of hydrogen, —($C_1$-$C_8$)alkyl, substituted or unsubstituted pyridyl, substituted or unsubstituted 1,4-dihydropyridyl, a radical of the compound of formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^B$, —C(O)O$R^B$, —C(O)N$R^B_2$, —C(=N$R^B$)N$R^B_2$, —O$R^B$, —OC(O)($C_1$-$C_6$)alkyl, —OC(O)O($C_1$-$C_6$)alkyl, —OC(O)N$R^B_2$, —($C_1$-$C_6$)alkylene-N$R^B_2$, —N$R^B_2$, —N$R^B$C(O)$R^B$, —N$R^B$C(O)O($C_1$-$C_6$)alkyl, —N$R^B$C(O)N$R^B_2$, —N$R^B$$SO_2$N$R^B$, —S$R^B$, —S(O)$R^B$, —$SO_2$$R^B$, —OS$O_2$($C_1$-$C_6$)alkyl, —$SO_2$N$R^B_2$, —($C_1$-$C_6$)perfluoroalkyl, and —($C_1$-$C_6$)alkylene-O$R^B$;

$R^2$ and $R^3$ are each independently selected from the group consisting of hydrogen, —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$$SO_2$N$R^C$, —S$R^C$, —S(O)$R^C$, —$SO_2$$R^C$, —OS$O_2$($C_1$-$C_6$)alkyl, —$SO_2$N$R^C_2$, —($C_1$-$C_6$)perfluoroalkyl, and —($C_1$-$C_6$)alkylene-O$R^C$;

$R^4$ is selected from the group consisting of hydrogen, —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —NR$_2$, —N$R^C$C(O)$R^C$, —N$R^C$C(O)O($C_1$-$C_6$)alkyl, —N$R^C$C(O)N$R^C_2$, —N$R^C$$SO_2$N$R^C$, —S$R^C$, —S(O)$R^C$, —$SO_2$$R^C$, —OS$O_2$($C_1$-$C_6$)alkyl, —$SO_2$N$R^C_2$, —($C_1$-$C_6$)perfluoroalkyl, and —($C_1$-$C_6$)alkylene-O$R^C$;

wherein C* has an absolute configuration of R or S, or a mixture of R and S;

$R^5$ is selected from the group consisting of hydrogen, —($C_1$-$C_6$)alkyl, —($C_1$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$$SO_2$N$R^C$, —S$R^C$, —S(O)$R^C$, —$SO_2$$R^C$, —OS$O_2$($C_1$-$C_6$)alkyl, —$SO_2$N$R^C_2$, —($C_1$-$C_6$)perfluoroalkyl, and —($C_1$-$C_6$)alkylene-O$R^C$;

$R^6$ is selected from the group consisting of hydrogen, —C(O)R', —C(O)OR', —C(O)NHR', —P(O)(O$Y^1$)(O$Y^2$), —P(O)(O$Y^1$)(NHR''), substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^4$)—CO$_2$$R^B$; wherein the substituted ($C_1$-$C_6$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$$SO_2$N$R^C$, —S$R^C$, —S(O)$R^C$, —$SO_2$$R^C$, —OS$O_2$($C_1$-$C_6$)alkyl, —$SO_2$N$R^C_2$, —($C_1$-$C_6$)perfluoroalkyl, and —($C_1$-$C_6$)alkylene-O$R^C$;

R' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—($R^4$)—CO$_2$$R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_6$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$$SO_2$N$R^C$, —S$R^C$, —S(O)$R^C$, —$SO_2$$R^C$, —OS$O_2$($C_1$-$C_6$)alkyl, —$SO_2$N$R^C_2$, —($C_1$-$C_6$)perfluoroalkyl, and —($C_1$-$C_6$)alkylene-O$R^C$;

R'' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and **H—($R^4$)—CO$_2$$R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, ($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$$SO_2$N$R^C$, —S$R^C$, —S(O)$R^C$, —$SO_2$$R^C$, —OS$O_2$($C_1$-$C_6$)alkyl, —$SO_2$N$R^C_2$, —($C_1$-$C_6$)perfluoroalkyl, and —($C_1$-$C_6$)alkylene-O$R^C$;

R⁷ and R⁸ are independently selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$)cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —NO₂, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$SO₂N$R^C$, —S$R^C$, —S(O)$R^C$, —SO₂$R^C$, —OSO₂($C_1$-$C_6$)alkyl, —SO₂N$R^C_2$, —($C_1$-$C_6$)perfluoroalkyl, and —($C_1$-$C_6$)alkylene-O$R^C$;

Y¹ and Y² are independently selected from the group consisting of hydrogen, sodium, potassium, lithium, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —NO₂, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$SO₂N$R^C$, —S$R^C$, —S(O)$R^C$, —SO₂$R^C$, —OSO₂($C_1$-$C_6$)alkyl, —SO₂N$R^C_2$, —($C_1$-$C_6$)perfluoroalkyl, and —($C_1$-$C_6$)alkylene-O$R^C$;

or, alternatively, Y¹ and Y² taken together are selected from the group consisting of sodium, potassium, lithium, magnesium, calcium, strontium, and barium;

provided that when Z² is NH, the absolute configuration of C** is R or S, or a mixture of R and S;

further provided that when n is 0, Z² is NH, and R¹, R², R³, R⁴, and R⁵ are each hydrogen, then R⁶ is not —C(O)R' or —C(O)OR' where R' is alkyl, and each of R⁷ and R⁸ are not independently hydrogen, —C(O)R', or —C(O)OR', where R' is alkyl;

further provided that when n is 0 and Z² is oxygen, then R¹, R², R³, R⁴, R⁵, R⁶, R⁷, and R⁸ are not all simultaneously hydrogen;

further provided that when n is 0, Z² is oxygen, R¹ is hydrogen or ($C_1$-$C_4$)alkyl, and R², R³, R⁴, and R⁵ are each hydrogen, then each of R⁶, R⁷, and R⁸ is not —C(O)R', —C(O)OR', or —C(O)NHR', where R' is hydrogen, unsubstituted ($C_1$-$C_8$)alkyl, unsubstituted ($C_1$-$C_8$)cycloalkyl, unsubstituted aryl, unsubstituted heteroaryl, unsubstituted aryl($C_1$-$C_4$)alkyl, or unsubstituted heterocycle($C_1$-$C_6$)alkyl.

3. A method of making a nicotinate/nicotinamide riboside compound or derivative of formula (I), or a salt, hydrate, or solvate thereof:

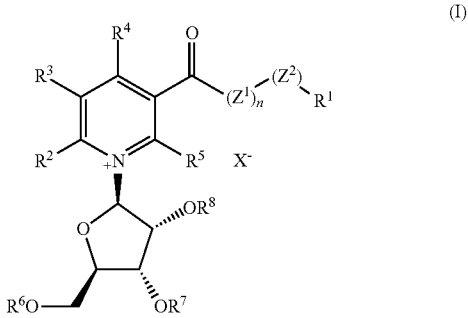

wherein X⁻ as counterion is absent, or when X⁻ is present, X⁻ is selected from the group consisting of fluoride, chloride, bromide, iodide, formate, acetate, ascorbate, benzoate, carbonate, citrate, carbamate, formate, gluconate, lactate, methyl bromide, methyl sulfate, nitrate, phosphate, diphosphate, succinate, sulfate, trifluoromethanesulfonate, trichloromethanesulfonate, tribromomethanesulfonate, and trifluoroacetate;

Z¹ and Z² are independently NH or oxygen;

n is 0 or 1;

R¹ is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^A$)—CO₂$R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —NO₂, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-NH₂, —N$R^C_2$, —N$R^C$C(O)$R^C$, —N$R^C$C(O)O($C_1$-$C_6$)alkyl, —N$R^C$C(O)N$R^C_2$, —N$R^C$SO₂N$R^C$, —S$R^C$, —S(O)$R^C$, —SO₂$R^C$, —OSO₂($C_1$-$C_6$)alkyl, —SO₂N$R^C_2$, —($C_1$-$C_6$)perfluoroalkyl, and —($C_1$-$C_6$)alkylene-O$R^C$;

$R^A$ is selected from the group consisting of —H, —($C_1$-$C_6$)alkyl, —(CH₂)₃—NH—C(NH₂)(=NH), —CH₂C(=O)NH₂, —CH₂COOH, —CH₂SH, —(CH₂)₂C(=O)—NH₂, —(CH₂)₂COOH, —CH₂-(2-imidazolyl), —CH(CH₃)—CH₂—CH₃, —CH₂CH(CH₃)₂, —(CH₂)₄—NH₂, —(CH₂)₂—S—CH₃, phenyl, —CH₂-phenyl, —CH₂—OH, —CH(OH)—CH₃, —CH₂-(3-indolyl), —CH₂-(4-hydroxyphenyl), —CH(CH₃)₂, and —CH₂—CH₃;

$R^B$ is hydrogen or —($C_1$-$C_8$)alkyl;

each $R^C$ is independently selected from the group consisting of hydrogen, —($C_1$-$C_8$)alkyl, substituted or unsubstituted pyridyl, substituted or unsubstituted 1,4-dihydropyridyl, a radical of the compound of formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —NO₂, —C(O)$R^B$, —C(O)O$R^B$, —C(O)N$R^B_2$, —C(=N$R^B$)N$R^B_2$, —O$R^B$, —OC(O)($C_1$-$C_6$)alkyl, —OC(O)O($C_1$-$C_6$)alkyl, —OC(O)N$R^B_2$, —($C_1$-$C_6$)

alkylene-$NR^B_2$, —$NR^B_2$, —$NR^BC(O)R^B$, —$NR^BC(O)O(C_1$-$C_6)$alkyl, —$NR^BC(O)NR^B_2$, —$NR^BSO_2NR^B$, —$SR^B$, —$S(O)R^B$, —$SO_2R^B$, —$OSO_2(C_1$-$C_6)$alkyl, —$SO_2NR^B_2$, —$(C_1$-$C_6)$perfluoroalkyl, and —$(C_1$-$C_6)$alkylene-$OR^B$;

$R^2$, $R^3$, $R^4$, and $R^5$ are each independently selected from the group consisting of hydrogen, —$(C_1$-$C_6)$alkyl, —$(C_2$-$C_6)$alkenyl, —$(C_2$-$C_6)$alkynyl, halogen, —CN, —$NO_2$, —$C(O)R^C$, —$C(O)OR^C$, —$C(O)NR^C_2$, —$C(=NR^C)NR^C_2$, —$OR^C$, —$OC(O)(C_1$-$C_6)$alkyl, —$OC(O)O(C_1$-$C_6)$alkyl, —$OC(O)NR^C_2$, —$(C_1$-$C_6)$alkylene-$NR^C_2$, —$NR^C_2$, —$NR^CC(O)R^C$, —$NR^CC(O)O(C_1$-$C_6)$alkyl, —$NR^CC(O)NR^C_2$, —$NR^CSO_2NR^C$, —$SR^C$, —$S(O)R^C$, —$SO_2R^C$, —$OSO_2(C_1$-$C_6)$alkyl, —$SO_2NR^C_2$, —$(C_1$-$C_6)$perfluoroalkyl, and —$(C_1$-$C_6)$alkylene-$OR^C$;

$R^6$ is selected from the group consisting of hydrogen, —C(O)R', —C(O)OR', —C(O)NHR', —$P(O)(OY^1)(OY^2)$, —$P(O)(OY^1)(NHR'')$, substituted or unsubstituted ($C_1$-$C_8$)alkyl, substituted or unsubstituted ($C_1$-$C_8$) cycloalkyl, substituted or unsubstituted aryl, substituted or unsubstituted heteroaryl, and substituted or unsubstituted heterocycle, vitamin B ester, vitamin B2 ester, vitamin B6 ester, and —$C^{**}H$—$(R^A)$—$CO_2R^B$; wherein the substituted ($C_1$-$C_8$), substituted ($C_1$-$C_8$)cycloalkyl, substituted aryl, substituted heteroaryl, and substituted heterocycle are substituted with one to five substituents independently selected from the group consisting of —$(C_1$-$C_8)$alkyl, —$(C_2$-$C_6)$alkenyl, —$(C_2$-$C_6)$alkynyl, halogen, —CN, —$NO_2$, —$C(O)R^C$, —$C(O)R^C$, —$C(O)NR^C_2$, —$C(=NR^C)NR^C_2$, —$OR^C$, —$OC(O)O(C_1$-$C_8)$alkyl, —$OC(O)NR^C_2$, —$(C_1$-$C_6)$alkylene-$NR^C_2$, —$NR^C_2$, —$NR^CC(O)R^C$, —$NR^CC(O)O(C_1$-$C_6)$alkyl, —$NR^CC(O)NR_2$, —$NR^CSO_2NR^C$, —$SR^C$, —$S(O)R^C$, —$SO_2R^C$, —$OSO_2(C_1$-$C_6)$alkyl, —$SO_2NR^C_2$, —$(C_1$-$C_6)$perfluoroalkyl, and —$(C_1$-$C_6)$alkylene-$OR^C$;

R' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —$C^{**}H$—$(R^A)$—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —$(C_1$-$C_8)$ alkyl, —$(C_2$-$C_6)$alkenyl, —$(C_2$-$C_6)$alkynyl, halogen, —CN, —$NO_2$, —$C(O)R^C$, —$C(O)OR^C$, —$C(O)NR^C_2$, —$C(=NR^C)NR^C_2$, —$OR^C$, —$OC(O)(C_1$-$C_8)$alkyl, —$OC(O)O(C_1$-$C_8)$alkyl, —$OC(O)NR^C_2$, —$(C_1$-$C_6)$alkylene-$NR^C_2$, —$NR^C_2$, —$NR^CC(O)R^C$, —$NR^CC(O)O(C_1$-$C_6)$alkyl, —$NR^CC(O)NR^C_2$, —$NR^CSO_2NR^C$, —$SR^C$, —$S(O)R^C$, —$SO_2R^C$, —$OSO_2(C_1$-$C_6)$alkyl, —$SO_2NR^C_2$, —$(C_1$-$C_6)$perfluoroalkyl, and —$(C_1$-$C_6)$alkylene-$OR^C$;

R'' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —$C^{**}H$—$(R^A)$—$CO_2R$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —$(C_1$-$C_8)$ alkyl, —$(C_2$-$C_6)$alkenyl, —$(C_2$-$C_6)$alkynyl, halogen, —CN, —$NO_2$, —$C(O)R^C$, —$C(O)OR^C$, —$C(O)NR^C_2$, —$C(=NR^C)NR^C_2$, —$OR^C$, —$OC(O)(C_1$-$C_6)$alkyl, —$OC(O)O(C_1$-$C_{56})$alkyl, —$OC(O)NR^C_2$, —$(C_1$-$C_6)$alkylene-$NR^C_2$, —$NR^C_2$, —$NR^CC(O)R^C$, —$NR^CC(O)O(C_1$-$C_6)$alkyl, —$NR^CC(O)NR^C_2$, —$NR^CSO_2NR^C$, —$SR^C$, —$S(O)R^C$, —$SO_2R^C$, —$OSO_2(C_1$-$C_6)$alkyl, —$SO_2NR^C_2$, —$(C_1$-$C_6)$perfluoroalkyl, and —$(C_1$-$C_6)$alkylene-$OR^C$;

$R^7$ and $R^8$ independently selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$)cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —$C(O)R^C$, —$C(O)OR^C$, —$C(O)NR^C_2$, —$C(=NR^C)NR^C_2$, —$OR^C$, —$OC(O)(C_1$-$C_6)$alkyl, —$OC(O)O(C_1$-$C_6)$alkyl, —$OC(O)NR^C_2$, —$(C_1$-$C_6)$alkylene-$NR^C_2$, —$NR^C_2$, —$NR^CC(O)R^C$, —$NR^CC(O)O(C_1$-$C_6)$alkyl, —$NR^CC(O)NR^C_2$, —$NR^CSO_2NR^C$, —$SR^C$, —$S(O)R^C$, —$SO_2R^C$, —$OSO_2(C_1$-$C_6)$alkyl, —$SO_2NR^C_2$, —$(C_1$-$C_6)$perfluoroalkyl, and —$(C_1$-$C_6)$alkylene-$OR^C$;

$Y^1$ and $Y^2$ are independently selected from the group consisting of hydrogen, sodium, potassium, lithium, substituted or unsubstituted ($C_1$-$C_8$)alkyl, substituted or unsubstituted ($C_1$-$C_5$)cycloalkyl, substituted or unsubstituted aryl, substituted or unsubstituted heteroaryl, and substituted or unsubstituted heterocycle; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —$(C_1$-$C_8)$alkyl, —$(C_2$-$C_6)$alkenyl, —$(C_2$-$C_6)$alkynyl, halogen, —CN, —$NO_2$, —$C(O)R^C$, —$C(O)OR^C$, —$C(O)NR^C_2$, —$C(=NR^C)NR^C_2$, —$OR^C$, —$OC(O)(C_1$-$C_6)$alkyl, —$OC(O)O(C_1$-$C_6)$alkyl, —$OC(O)NR^C_2$, —$(C_1$-$C_6)$alkylene-$NR^C_2$, —$NR^C_2$, —$NR^CC(O)R^C$, —$NR^CC(O)O(C_1$-$C_6)$alkyl, —$NR^CC(O)NR^C_2$, —$NR^CSO_2NR^C$, —$SR^C$, —$S(O)R^C$, —$SO_2R^C$, —$SO_2(C_1$-$C_6)$alkyl, —$SO_2NR^C_2$, —$(C_1$-$C_6)$perfluoroalkyl, and —$(C_1$-$C_6)$alkylene-$OR^C$; or, alternatively, $Y^1$ and $Y^2$ taken together are selected from the group consisting of sodium, potassium, lithium, magnesium, calcium, strontium, and barium;

provided that when $Z^2$ is NH, the absolute configuration of $C^{**}$ is R or S, or a mixture of R and S;

comprising the steps of:
(a) providing a riboside compound or derivative having formula (2), or a salt thereof;

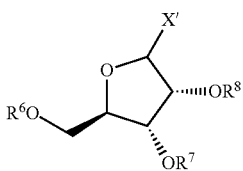

(2)

wherein X' is selected from fluoro, chloro, bromo, iodo, $HCO_2$, acetoxy, propionoxy, butyroxy, glutamyloxy, aspartyloxy, ascorbyloxy, benzoxy, $HOCO_2$, citryloxy, carbamyloxy, gluconyloxy, lactyloxy, succinyloxy, sulfoxy, trifluoromethanesulfoxy, trichloromethanesulfoxy, tribromomethanesulfoxy, and trifluoroacetoxy;

$R^6$ is selected from the group consisting of hydrogen, —C(O)R', —C(O)OR', —C(O)NHR', —P(O)($OY^1$)($OY^2$), —P(O)($OY^1$)(NHR"), substituted or unsubstituted ($C_1$-$C_8$)alkyl, substituted or unsubstituted ($C_1$-$C_8$) cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C SO_2 NR^C$, —$SR^C$, —S(O)$R^C$, —$SO_2 R^C$, —$OSO_2$($C_1$-$C_6$)alkyl, —$SO_2 NR^C_2$, —($C_1$-$C_6$)perfluoroalkyl, and —($C_1$-$C_6$)alkylene-$OR^C$;

$R^A$ is selected from the group consisting of —H, —($C_1$-$C_6$)alkyl, —($CH_2$)$_3$—NH—C($NH_2$)(=NH), —$CH_2$C(=O)$NH_2$, —$CH_2$COOH, —$CH_2$SH, —($CH_2$)$_2$C(=O)—$NH_2$, —($CH_2$)$_2$COOH, —$CH_2$-(2-imidazolyl), —CH($CH_3$)—$CH_2$—$CH_3$, —$CH_2$CH($CH_3$)$_2$, —($CH_2$)$_4$—$NH_2$, —($CH_2$)$_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —CH($CH_3$)$_2$, and —$CH_2$—$CH_3$;

$R^B$ is hydrogen or —($C_1$-$C_8$)alkyl;

each $R^C$ is independently selected from the group consisting of hydrogen, —($C_1$-$C_8$)alkyl, substituted or unsubstituted pyridyl, substituted or unsubstituted 1,4-dihydropyridyl, a radical of the compound of formula (I), and vitamin B7 ester (biotinyl); wherein the substituted pyridyl and substituted 1,4-dihydropyridyl are substituted with one to five substituents independently selected from the group consisting —($C_1$-$C_6$)alkyl, —($C_2$-$C_6$)alkenyl, —($C_2$-$C_6$)alkynyl, halogen, —CN, —$NO_2$, —C(O)$R^B$, —C(O)$OR^B$, —C(=$NR^B$)$NR^B_2$, —OR, —OC(O)($C_1$-$C_6$)alkyl, —OC(O)O($C_1$-$C_6$)alkyl, —OC(O)$NR^B_2$, —($C_1$-$C_6$)alkylene-$NR^B_2$, —$NR^B_2$, —$NR^B$C(O)$R^B$, —$NR^B$C(O)O($C_1$-$C_6$)alkyl, —$NR^B$C(O)$NR^B_2$, —$NR^B SO_2 NR^B$, —$SR^B$, —S(O)$R^B$, —$SO_2 R^B$, —$OSO_2$($C_1$-$C_6$)alkyl, —$SO_2 NR^B_2$, —($C_1$-$C_6$)perfluoroalkyl, and —($C_1$-$C_6$)alkylene-$OR^8$;

R' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$) alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C SO_2 NR^C$, —$SR^C$, —S(O)$R^C$, —$SO_2 R^C$, —$OSO_2$($C_1$-$C_6$)alkyl, —$SO_2 NR^C_2$, —($C_1$-$C_6$)perfluoroalkyl, and —($C_1$-$C_6$) alkylene-$OR^C$;

R" is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$) alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$) alkylene-$NR^C_2$, —$NR^C_2$, —$NR^C$C(O)$R^C$, —$NR^C$C(O) O($C_1$-$C_6$)alkyl, —$NR^C$C(O)$NR^C_2$, —$NR^C SO_2 NR^C$, —$SR^C$, —S(O)$R^C$, —$SO_2 R^C$, —$OSO_2$($C_1$-$C_6$)alkyl, —$SO_2 NR^C_2$, —($C_1$-$C_6$)perfluoroalkyl, and —($C_1$-$C_6$) alkylene $OR^C$;

$R^7$ and $R^8$ are independently selected from the group consisting of hydrogen, —C(O)R', —C(O)OR', —C(O)HR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$)cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$) $NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C SO_2 NR^C$, —$SR^C$, —S(O) $R^C$, —$SO_2 R^C$, —$OSO_2$($C_1$-$C_6$)alkyl, —$SO_2 NR^C_2$, —($C_1$-$C_6$)perfluoroalkyl, and —($C_1$-$C_6$)alkylene-$OR^C$;

$Y^1$ and $Y^2$ are independently selected from the group consisting of hydrogen, sodium, potassium, lithium, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle; wherein the substituted ($C_1$-$C_8$)alkyl, substituted ($C_1$-$C_5$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$$SO_2$N$R^C$, —S$R^C$, —S(O)$R^C$, —$SO_2$$R^C$, —$OSO_2$($C_1$-$C_6$)alkyl, —$SO_2$N$R^C_2$, —($C_1$-$C_6$)perfluoroalkyl, and —($C_1$-$C_6$)alkylene-O$R^C$; or, alternatively, $Y^1$ and $Y^2$ taken together are selected from the group consisting of sodium, potassium, lithium, magnesium, calcium, strontium, and barium;

provided that when $Z^2$ is NH, the absolute configuration of C** is R or S, or a mixture of R and S;

(b) treating the compound or derivative having formula (2), or salt thereof, with about one molar equivalent amount of a Lewis acid;

(c) treating the compound or derivative having formula (2), or salt thereof, and the Lewis acid with about one molar equivalent of a nicotinate/nicotinamide compound or derivative having formula (1), or a salt thereof;

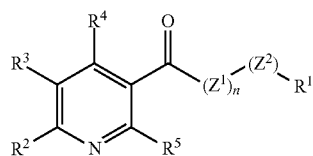

(1)

wherein $Z^1$ and $Z^2$ are independently NH or oxygen;
n is 0 or 1;
$R^1$ is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, —C**H—($R^A$)—$CO_2$$R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituent independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$$SO_2$N$R^C$, —S$R^C$, —S(O)$R^C$, —$OSO_2$($C_1$-$C_6$)alkyl, —$SO_2$N$R^C_2$, —($C_1$-$C_6$)perfluoroalkyl, and —($C_1$-$C_6$)alkylene-O$R^C$;
$R^A$ is selected from the group consisting of —H, —($C_1$-$C_6$)alkyl, —($CH_2$)$_3$—NH—C($NH_2$)(=NH), —$CH_2$C(=O)$NH_2$, —$CH_2$COOH, —$CH_2$SH, —($CH_2$)$_2$C(=O)—$NH_2$, —($CH_2$)$_2$COOH, —$CH_2$-(2-imidazolyl), —CH($CH_3$)—$CH_2$—$CH_3$, —$CH_2$CH($CH_3$)$_2$, —($CH_2$)$_4$—$NH_2$, —($CH_2$)$_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —CH($CH_3$)$_2$, and —$CH_2$—$CH_3$;

$R^B$ is hydrogen or —($C_1$-$C_8$)alkyl;
each $R^C$ is independently selected from the group consisting of hydrogen, —($C_1$-$C_8$)alkyl, substituted or unsubstituted pyridyl, substituted or unsubstituted 1,4-dihydropyridyl, a radical of the compound of formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^B$, —C(O)O$R^B$, —C(O)N$R^B_2$, —C(=N$R^B$)N$R^B_2$, —O$R^B$, —OC(O)($C_1$-$C_6$)alkyl, —OC(O)O($C_1$-$C_6$)alkyl, —OC(O)N$R^B_2$, —($C_1$-$C_6$)alkylene-N$R^B_2$, —N$R^B_2$, —N$R^B$C(O)$R^B$, —N$R^B$C(O)O($C_1$-$C_6$)alkyl, —N$R^B$C(O)N$R^B_2$, —N$R^B$$SO_2$N$R^B$, —S$R^B$, —S(O)$R^B$, —$SO_2$$R^B$, —$OSO_2$($C_1$-$C_6$)alkyl, —$SO_2$N$R^B_2$, —($C_1$-$C_6$)perfluoroalkyl, and —($C_1$-$C_6$)alkylene-O$R^B$;

$R^2$, $R^3$, $R^4$, and $R^5$ are each independently selected from the group consisting of hydrogen, —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$$SO_2$N$R^C$, —S$R^C$, —S(O)$R^C$, —$SO_2$$R^C$, —$OSO_2$($C_1$-$C_6$)alkyl, —$SO_2$N$R^C_2$, —($C_1$-$C_6$)perfluoroalkyl, and —($C_1$-$C_6$)alkylene-O$R^C$;

provided that when $Z^2$ is NH, the absolute configuration of C** is R or S, or a mixture of R and S;

(d) reacting the riboside compound or derivative having formula (2), or salt thereof, and the Lewis acid with the nicotinate/nicotinamide compound or derivative having formula (1), or salt thereof so as to produce the compound or derivative of formula (I), or salt, hydrate, or solvate thereof;

(e) adding water to the riboside compound or derivative having formula (2), or salt thereof, the Lewis acid, the nicotinate/nicotinamide compound or derivative having formula (1), or salt thereof, and the compound or derivative of formula (I), or salt, hydrate, or solvate thereof;

(f) extracting the riboside compound or derivative having formula (2), or salt thereof, the Lewis acid, the nicotinate/nicotinamide compound or derivative having formula (1), or salt thereof, the compound or derivative of formula (I), or salt, hydrate, or solvate thereof, and the water, with organic solvent; and (g) isolating the compound or derivative of formula (I), or salt, hydrate, or solvate thereof.

4. The method of claim 3, wherein the Lewis acid is selected from the group consisting of $BF_3$, TMSOTf, and $SnCl_4$.

5. A method of making a nicotinate/nicotinamide riboside compound or derivative of formula (I), or a salt, hydrate, or solvate thereof;

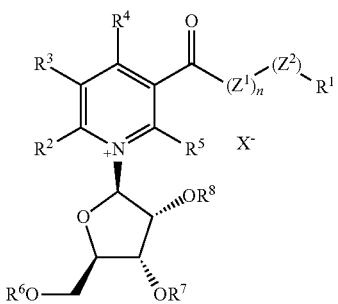

(I)

wherein X⁻ as counterion is absent, or when X⁻ is present, X⁻ is selected from the group consisting of fluoride, chloride, bromide, iodide, formate, acetate, ascorbate, benzoate, carbonate, citrate, carbamate, formate, gluconate, lactate, methyl bromide, methyl sulfate, nitrate, phosphate, diphosphate, succinate, trifluoromethanesulfonate, trichloromethanesulfonate, tribromomethanesulfonate, and trifluoroacetate;

$Z^1$ and $Z^2$ are independently NH or oxygen;

n is 0 or 1;

$R^1$ is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$$SO_2$N$R^C$, —S$R^C$, —S(O)$R^C$, —$SO_2R^C$, —O$SO_2$($C_1$-$C_6$)alkyl, —$SO_2$N$R^C_2$, —($C_1$-$C_6$)perfluoroalkyl, and —($C_1$-$C_6$)alkylene O$R^C$;

$R^A$ is selected from the group consisting of —H, —($C_1$-$C_6$)alkyl, —$(CH_2)_3$—NH—C($NH_2$)(=NH), —$CH_2$C(=O)$NH_2$, —$CH_2$COOH, —$CH_2$SH, —$(CH_2)_2$C(=O)—$NH_2$, —$(CH_2)_2$COOH, —$CH_2$-(2-imidazolyl), —CH($CH_3$)—$CH_2$—$CH_3$, —$CH_2$CH($CH_3$)$_2$, —$(CH_2)_4$—$NH_2$, —$(CH_2)_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —CH($CH_3$)$_2$, and —$CH_2$—$CH_3$;

$R^B$ is hydrogen or —($C_1$-$C_8$)alkyl;

each $R^C$ is independently selected from the group consisting of hydrogen, —($C_1$-$C_8$)alkyl, substituted or unsubstituted pyridyl, substituted or unsubstituted 1,4-dihydropyridyl, a radical of the compound of formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^B$, —C(O)O$R^B$, —C(O)N$R^B_2$, —C(=N$R^B$)N$R_2$, —OR, —OC(O)($C_1$-$C_6$)alkyl, —OC(O)O($C_3$-$C_6$)alkyl, —OC(O)N$R^B_2$, —($C_1$-$C_6$)alkylene-N$R^B_2$, —N$R^B_2$, —N$R^B$C(O)$R^B$, —N$R^B$C(O)O($C_1$-$C_6$)alkyl, —N$R^B$C(O)N$R^B_2$, —N$R^B$$SO_2$N$R^B$, —S$R^B$, —S(O)$R^B$, —$SO_2R^B$, —O$SO_2$($C_1$-$C_6$)alkyl, —$SO_2$N$R^B_2$, —($C_1$-$C_6$)perfluoroalkyl, and —($C_1$-$C_6$) alkylene-O$R^B$;

$R^2$, $R^3$, $R^4$, and $R^5$ are each independently selected from the group consisting of hydrogen, —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$) alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$$SO_2$N$R^C$, —S$R^C$, —S(O)$R^C$, —$SO_2R^C$, —O$SO_2$($C_1$-$C_6$)alkyl, —$SO_2$N$R^C_2$, —($C_1$-$C_6$)perfluoroalkyl, and —($C_1$-$C_6$) alkylene-O$R^C$;

$R^6$ is selected from the group consisting of hydrogen, —C(O)R', —C(O)OR', —C(O)NHR', —P(O)(O$Y^1$)(O$Y^2$), —P(O)(O$Y^1$)(NHR"), substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$$SO_2$N$R^C$, —S$R^C$, —S(O)$R^C$, —$SO_2R^C$, —O$SO_2$($C_1$-$C_6$)alkyl, —$SO_2$N$R^C_2$, —($C_1$-$C_6$)perfluoroalkyl, and —($C_1$-$C_6$)alkylene-O$R^C$;

R' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—($R^A$)—$CO_2R$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected form the group consisting of —($C_1$-$C_6$) alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —$C_1$—N$C_6$) alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$$SO_2$N$R^C$, —S$R^C$, —S(O)$R^C$, —$SO_2R^C$, —O$SO_2$($C_1$-$C_6$)alkyl, —$SO_2$N$R^C_2$, —($C_1$-$C_6$)perfluoroalkyl, and —($C_1$-$C_6$) alkylene-O$R^C$;

R" is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—(R$^A$)—CO$_2$R; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R$^7$ and R$^8$ are independently selected from the group consisting of hydrogen, —C(O)R', —C(O)OR', —C(O)NHR', substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$)alkyl, substituted (C$_1$-C$_8$)cycloalkyl, substituted aryl, substituted heteroaryl, substituted heterocycle, substituted aryl(C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

Y$^1$ and Y$^2$ are independently selected from the group consisting of hydrogen, sodium, potassium, lithium, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$) alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$; or, alternatively, Y$^1$ and Y$^2$ taken together are selected from the group consisting of sodium, potassium, lithium, magnesium, calcium, strontium, and barium;

provided that when Z$^2$ is NH, the absolute configuration of C** is R or S, or a mixture of R and S;

comprising the steps of:

(a) providing a nicotinate/nicotinamide riboside compound or derivative having formula (3), or a salt thereof;

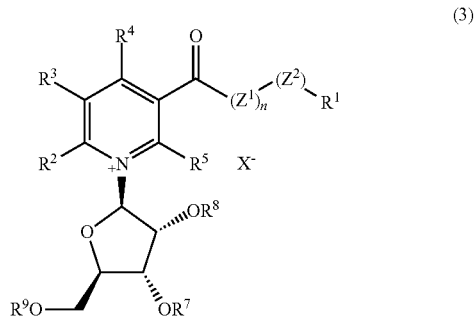

(3)

wherein X$^-$ as counterion is absent, or when X$^-$ is present, X$^-$ is selected from the group consisting of fluoride, chloride, bromide, iodide, formate, acetate, ascorbate, benzoate, carbonate, citrate, carbamate, gluconate, lactate, methyl bromide, methyl sulfate, nitrate, phosphate, diphosphate, succinate, sulfate, trifluoromethanesulfonate, trichloromethanesulfonate, tribromomethanesulfonate, and trifluoroacetate;

Z$^1$ and Z$^2$ are independently NH or oxygen;

n is 0 or 1;

R$^1$ is selected from the group consisting of hydrogen, substituted or unsubstituted (C$_1$-C$_8$)alkyl, substituted or unsubstituted (C$_1$-C$_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—(R$^A$)—CO$_2$R$^B$; wherein the substituted (C$_1$-C$_8$)alkyl, substituted (C$_1$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^C$, —C(O)OR$^C$, —C(O)NR$^C_2$, —C(=NR$^C$)NR$^C_2$, —OR$^C$, —OC(O)(C$_1$-C$_6$)alkyl, —OC(O)O(C$_1$-C$_6$)alkyl, —OC(O)NR$^C_2$, —(C$_1$-C$_6$)alkylene-NR$^C_2$, —NR$^C_2$, —NR$^C$C(O)R$^C$, —NR$^C$C(O)O(C$_1$-C$_6$)alkyl, —NR$^C$C(O)NR$^C_2$, —NR$^C$SO$_2$NR$^C$, —SR$^C$, —S(O)R$^C$, —SO$_2$R$^C$, —OSO$_2$(C$_1$-C$_6$)alkyl, —SO$_2$NR$^C_2$, —(C$_1$-C$_6$)perfluoroalkyl, and —(C$_1$-C$_6$)alkylene-OR$^C$;

R$^A$ is selected from the group consisting of —H, —(C$_1$-C$_6$)alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$, and —CH$_2$—CH$_3$;

R$^B$ is hydrogen or —(C$_1$-C$_8$)alkyl;

each R$^C$ is independently selected from the group consisting of hydrogen, —(C$_1$-C$_8$)alkyl, substituted or unsubstituted pyridyl, substituted or unsubstituted 1,4-dihydropyridyl, a radical of the compound of formula (I), and vitamin B7 ester (biotinyl); wherein the substituted pyridyl and substituted 1,4-dihydropyridyl are substituted with one to five substituents independently selected from the group consisting of —(C$_1$-C$_8$)alkyl, —(C$_2$-C$_6$)alkenyl, —(C$_2$-C$_6$)alkynyl, halogen, —CN, —NO$_2$, —C(O)R$^B$, —C(O)OR$^B$, —C(O)NR$^B_2$, —C(=NR$^B$)NR$^B_2$, —OR$^B$, —OC(O)(C$_1$-C$_6$)alkyl, —OC(O)O(C$_1$-C$_6$)alkyl, —OC(O)NR$^B_2$, —(C$_1$-C$_6$)

alkylene-$NR^B_2$, —$NR^B_2$, —$NR^BC(O)R^B$, —$NR^BC(O)O(C_1$-$C_6)$alkyl, —$NR^BC(O)NR^B_2$, —$NR^BSO_2NR^B$, —$SR^B$, —$S(O)R^B$, —$SO_2R^B$, —$OSO_2(C_1$-$C_6)$alkyl, —$SO_2NR^B_2$, —$(C_1$-$C_6)$perfluoroalkyl, and —$(C_1$-$C_6)$alkylene-$OR^B$;

$R^2$, $R^3$, $R^4$, and $R^5$ are each independently selected from the group consisting of hydrogen, —$(C_1$-$C_6)$alkyl, —$(C_2$-$C_6)$alkenyl, —$(C_2$-$C_6)$alkynyl, halogen, —CN, —$NO_2$, —$C(O)R^C$, —$C(O)OR^C$, —$C(O)NR^C_2$, —$C(=NR^C)NR^C_2$, —$OR^C$, —$OC(O)(C_1$-$C_6)$alkyl, —$OC(O)O(C_1$-$C_6)$alkyl, —$OC(O)NR^C_2$, —$(C_1$-$C_6)$alkylene-$NR^C_2$, —$NR^C_2$, —$NR^CC(O)R^C$, —$NR^CC(O)O(C_1$-$C_6)$alkyl, —$NR^CC(O)NR^C_2$, —$NR^CSO_2NR^C$, —$SR^C$, —$S(O)R^C$, —$SO_2R^C$, —$OSO_2(C_1$-$C_6)$alkyl, —$SO_2NR^C_2$, —$(C_1$-$C_6)$perfluoroalkyl, and —$(C_1$-$C_8)$alkylene-$OR^C$;

$R^7$ and $R^8$ are independently selected from the group consisting of hydrogen, —C(O)R', —C(O)OR', —C(O)NHR', substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, substituted or unsubstituted heterocycle, substituted or unsubstituted aryl$(C_1$-$C_4)$alkyl, and substituted or unsubstituted heterocycle$(C_1$-$C_4)$alkyl; wherein the substituted $(C_1$-$C_8)$alkyl, substituted $(C_1$-$C_8)$cycloalkyl, substituted aryl, substituted heteroaryl, substituted heterocycle, substituted aryl$(C_1$-$C_4)$alkyl, and substituted heterocycle$(C_1$-$C_4)$alkyl are substituted with one to five substituents independently selected from the group consisting of —$(C_1$-$C_8)$alkyl, —$(C_2$-$C_6)$alkenyl, —$(C_2$-$C_6)$alkynyl, halogen, —CN, —$NO_2$, —$C(O)R^C$, —$C(O)OR^C$, —$C(O)NR^C_2$, —$C(=NR^C)NR^C_2$, —$OR^C$, —$OC(O)(C_1$-$C_6)$alkyl, —$OC(O)O(C_1$-$C_6)$alkyl, —$OC(O)NR^C_2$, —$(C_1$-$C_6)$alkylene-$NR^C_2$, —$NR_2$, —$NR^CC(O)R^C$, —$NR^CC(O)O(C_1$-$C_6)$alkyl, —$NR^CC(O)NR^C_2$, —$NR^CSO_2NR^C$, —$SR^C$, —$S(O)R^C$, —$SO_2R^C$, —$OSO_2(C_1$-$C_6)$alkyl, —$SO_2NR^C_2$, —$(C_1$-$C_6)$perfluoroalkyl, and —$(C_1$-$C_6)$alkylene-$OR^C$;

R' is selected from the group consisting of hydrogen, substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl$(C_1$-$C_4)$alkyl, heterocycle$(C_1$-$C_4)$alkyl, and —C**H—$(R^A)$—$CO_2R^B$; wherein the substituted $(C_1$-$C_8)$alkyl, substituted $(C_1$-$C_8)$cycloalkyl, substituted aryl, substituted heteroaryl, and substituted heterocycle are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —$C(O)R^C$, —$C(O)OR^C$, —$C(O)NR^C_2$, —$C(=NR^C)NR^C_2$, —$OR^C$, —$OC(O)(C_1$-$C_6)$alkyl, —$OC(O)O(C_1$-$C_6)$alkyl, —$OC(O)NR^C_2$, $(C_1$-$C_6)$alkylene-$NR^C_2$, —$NR^C_2$, —$NR^CC(O)R^C$, —$NR^CC(O)O(C_1$-$C_6)$alkyl, —$NR^CC(O)NR^C_2$, —$NR^CSO_2NR^C$, —$SR^C$, —$S(O)R^C$, —$SO_2R^C$, —$OSO_2(C_1$-$C_6)$alkyl, —$SO_2NR^C_2$, —$(C_1$-$C_6)$perfluoroalkyl, and —$(C_1$-$C_6)$alkylene-$OR^C$;

$R^9$ is selected from the group consisting of hydrogen, —C(O)R', —C(O)OR', —C(O)NHR', —$P(O)(OY^1)(OY^2)$, —$P(O)(OY^1)(NHR'')$, substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—$(R^A)$—$CO_2R^B$; wherein the substituted $(C_1$-$C_8)$alkyl, substituted $(C_1$-$C_8)$cycloalkyl, substituted aryl, substituted heteroaryl, and substituted heterocycle are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —$C(O)R^C$, —$C(O)OR^C$, —$C(O)NR^C_2$, —$C(=NR^C)NR^C_2$, —$OR^C$, —$OC(O)(C_1$-$C_6)$alkyl, —$OC(O)O(C_1$-$C_6)$alkyl, —$OC(O)NR^C_2$, —$(C_1$-$C_8)$allylene-$NR^C_2$, —$NR^C_2$, —$NR^CC(O)R^C$, —$NR^CC(O)O(C_1$-$C_6)$alkyl, —$NR^CC(O)NR^C_2$, —$NR^CSO_2NR^C$, —$SR^C$, —$S(O)R^C$, —$SO_2R^C$, —$OSO_2(C_1$-$C_6)$alkyl, —$SO_2NR^C_2$, —$(C_1$-$C_6)$perfluoroalkyl, and —$(C_1$-$C_6)$alkylene-$OR^C$;

R" is selected from the group consisting of hydrogen, substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, aryl$(C_1$-$C_4)$alkyl, heterocycle$(C_1$-$C_4)$alkyl, and —C**H—$(R^A)$—$CO_2R^B$; wherein the substituted $(C_1$-$C_8)$alkyl, substituted $(C_1$-$C_8)$cycloalkyl, substituted aryl, substituted heteroaryl, and substituted heterocycle are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —$C(O)R^C$, —$C(O)OR^C$, —$C(O)NR^C_2$, —$C(=NR^C)NR^C_2$, —$OR^C$, —$OC(O)(C_1$-$C_6)$alkyl, —$OC(O)O(C_1$-$C_6)$alkyl, —$OC(O)NR^C_2$, —$(C_1$-$C_6)$alkylene-$NR^C_2$, —$NR^C_2$, —$NR^CC(O)R^C$, —$NR^CC(O)O(C_1$-$C_6)$alkyl, —$NR^CC(O)NR^C_2$, —$NR^CSO_2NR^C$, —$SR^C$, —$S(O)R^C$, —$SO_2R^C$, —$OSO_2(C_1$-$C_6)$alkyl, —$SO_2NR_2$, —$(C_1$-$C_6)$perfluoroalkyl, and —$(C_1$-$C_6)$alkylene-$OR^C$;

$Y^1$ and $Y^2$ are independently selected from the group consisting of hydrogen, sodium, potassium, lithium, substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, and substituted or unsubstituted heterocycle; wherein the substituted $(C_1$-$C_8)$alkyl, substituted $(C_1$-$C_8)$cycloalkyl, substituted aryl, substituted heteroaryl, and substituted heterocycle are substituted with one to five substituents independently selected from the group consisting of —$(C_1$-$C_6)$alkyl, —$(C_2$-$C_6)$alkenyl, —$(C_2$-$C_6)$alkynyl, halogen, —CN, —$NO_2$, —$C(O)R^C$, —$C(O)OR^C$, —$C(O)NR^C_2$, —$C(=NR^C)NR^C_2$, —$OR^C$, —$OC(O)(C_1$-$C_6)$alkyl, —$OC(O)O(C_1$-$C_6)$alkyl, —$OC(O)NR^C_2$, —$(C_1$-$C_6)$alkylene-$NR_2$, —$NR^C_2$, —$NR^CC(O)R^C$, —$NR^CC(O)O(C_1$-$C_6)$alkyl, —$NR^CC(O)NR^C_2$, —$NR^CSO_2NR^C$, —$SR^C$, —$S(O)R^C$, —$SO_2R^C$, —$OSO_2(C_1$-$C_6)$alkyl, —$SO_2NR^C_2$, —$(C_1$-$C_6)$perfluoroalkyl, and —$(C_1$-$C_6)$alkylene-$OR^C$, or, alternatively, $Y^1$ and $Y^2$ taken together are selected from the group consisting of sodium, potassium, lithium, magnesium, calcium, strontium, and barium;

provided that when $Z^2$ is NH, the absolute configuration of C** is R or S, or a mixture of R and S;

(b) treating the compound or derivative having formula (3), or salt thereof, with at least about one molar equivalent amount of one or more reagent(s);

(c) reacting the nicotinate/nicotinamide riboside compound or derivative having formula (3), or salt thereof, with the one or more reagent(s) so as to produce the compound or derivative of formula (I), or salt, hydrate, or solvate thereof;
(d) adding water to the nicotinate/nicotinamide riboside compound or derivative having formula (3), or salt thereof, the one or more reagent(s), and the compound or derivative of formula (I), or salt, hydrate, or solvate thereof;
(e) extracting the nicotinate/nicotinamide riboside compound or derivative having formula (3), or salt thereof, the one or more reagent(s), the compound or derivative of formula (I), or salt, hydrate, or solvate thereof, and the water, with organic solvent; and
(f) isolating the compound or derivative of formula (I), or salt, hydrate, or solvate thereof.

6. A method of making a nicotinate/nicotinamide riboside compound or derivative of formula (I), or a salt, hydrate, or solvate thereof:

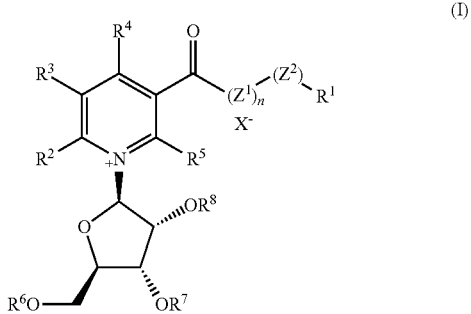

(I)

wherein $X^-$ as counterion is absent, or when $X^-$ is present, $X^-$ is selected from the group consisting of fluoride, chloride, bromide, iodide, formate, acetate, ascorbate, benzoate, carbonate, citrate, carbamate, gluconate, lactate, methyl bromide, methyl sulfate, nitrate, phosphate, diphosphate, succinate, sulfate, trifluoromethanesulfonate, trichloromethanesulfonate, tribromomethanesulfonate, and trifluoroacetate;

$Z^1$ and $Z^2$ are independently NH or oxygen;
n is 0 or 1;
$R^1$ is selected from the group consisting of hydrogen, substituted or unsubstituted $(C_1$-$C_8)$alkyl, substituted or unsubstituted $(C_1$-$C_8)$cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^A$)—$CO_2R^B$; wherein the substituted $(C_1$-$C_8)$alkyl, substituted $(C_1$-$C_8)$cycloalkyl, substituted aryl, substituted heteroaryl, and substituted heterocycle are substituted with one to five substituents independently selected from the group consisting —$(C_1$-$C_6)$alkyl, —$(C_2$-$C_6)$alkenyl, —$(C_2$-$C_6)$alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$SO$_2$N$R^C$, —S$R^C$, —S(O)$R^C$, —SO$_2R^C$, —OSO$_2$($C_1$-$C_6$)alkyl, —SO$_2$N$R^C_2$, —($C_1$-$C_6$)perfluoroalkyl, and —($C_1$-$C_6$)alkylene-O$R^C$;

$R^A$ is selected from the group consisting of —H, —($C_1$-$C_6$)alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, -phenyl, —CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$, and —CH$_2$—CH$_3$;

$R^B$ is hydrogen or —($C_1$-$C_8$)alkyl;

each $R^C$ is independently selected from the group consisting of hydrogen, —($C_1$-$C_8$)alkyl, substituted or unsubstituted pyridyl, substituted or unsubstituted 1,4-dihydropyridyl, a radical of the compound of formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^B$, —C(O)O$R^B$, —C(O)N$R^B_2$, —C(=N$R^B$)N$R^B_2$, —O$R^B$, —OC(O)($C_1$-$C_6$)alkyl, —OC(O)O($C_1$-$C_6$)alkyl, —OC(O)N$R^B_2$, ($C_1$-$C_6$)alkylene-N$R^B_2$, —N$R^B_2$, —N$R^B$C(O)$R^B$, —N$R^B$C(O)O($C_1$-$C_6$)alkyl, —N$R^B$C(O)N$R^B_2$, —N$R^B$SO$_2$N$R^B$, —S$R^B$, —S(O)$R^B$, —SO$_2R^B$, —OSO$_2$($C_1$-$C_6$)alkyl, —SO$_2$N$R^B_2$, —($C_1$-$C_6$)perfluoroalkyl, and —($C_1$-$C_6$)alkylene-O$R^B$;

$R^2$, $R^3$, $R^4$, and $R^5$ are each independently selected from the group consisting of hydrogen, —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_6$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$SO$_2$N$R^C$, —S$R^C$, —S(O)$R^C$, —SO$_2R^C$, —OSO$_2$($C_1$-$C_6$)alkyl, —SO$_2$N$R^C_2$, —($C_1$-$C_6$)perfluoroalkyl, and —($C_1$-$C_6$)alkylene-O$R^C$;

$R^6$ is selected from the group consisting of hydrogen, —C(O)R', —C(O)OR', —C(O)NHR', —P(O)(OY$^1$)(OY$^2$), —P(O)(OY$^1$)(NHR"), substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)N$R^C_2$, —C(=N$R^C$)N$R^C_2$, —O$R^C$, —OC(O)($C_1$-$C_8$)alkyl, —OC(O)O($C_1$-$C_6$)alkyl, —OC(O)N$R^C_2$, —($C_1$-$C_6$)alkylene-N$R^C_2$, —N$R^C_2$, —N$R^C$C(O)$R^C$, —N$R^C$C(O)O($C_1$-$C_6$)alkyl, —N$R^C$C(O)N$R^C_2$, —N$R^C$SO$_2$N$R^C$, —S$R^C$, —S(O)$R^C$, —SO$_2R^C$, —OSO$_2$($C_1$-$C_6$)alkyl, —SO$_2$N$R^C_2$, —($C_1$-$C_6$)perfluoroalkyl, and —($C_1$-$C_6$)alkylene-O$R^C$;

R' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C$, —$SR^C$, —S(O)$R^C$, —$SO_2$$R^C$, —$OSO_2$($C_1$-$C_6$)alkyl, —$SO_2$$NR^C_2$, —($C_1$-$C_6$)perfluoroalkyl, and —($C_1$-$C_6$)alkylene-$OR^C$;

R" is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—($R^A$)—$CO_2$$R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C$, —$SR^C$, —S(O)$R^C$, —$SO_2$$R^C$, —$OSO_2$($C_1$-$C_6$)alkyl, —$SO_2$$NR^C_2$, —($C_1$-$C_6$)perfluoroalkyl, and —($C_1$-$C_6$)alkylene-$OR^C$;

$R^7$ and $R^8$ are independently selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-s)alkyl, and substituted or unsubstituted heterocycle($C_1$-$C_4$)alkyl; wherein the substituted ($C_1$-$C_8$)alkyl, substituted ($C_1$-$C_8$)cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C$, —$SR^C$, —S(O)$R^C$, —$SO_2$$R^C$, —$OSO_2$($C_1$-$C_6$)alkyl, —$SO_2$$NR^C_2$, —($C_1$-$C_6$)perfluoroalkyl, and —($C_1$-$C_6$)alkylene-$OR^C$;

$Y^1$ and $Y^2$ are independently selected from the group consisting of hydrogen, sodium, potassium, lithium, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —$OR^C$, —OC(O)($C_1$-$C_6$)alkyl, —OC(O)O($C_1$-$C_6$)

alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C$, —$SR^C$, —S(O)$R^C$, —$SO_2$$R^C$, —$OSO_2$($C_1$-$C_6$)alkyl, —$SO_2$$NR^C_2$, —($C_1$-$C_6$)perfluoroalkyl, and —($C_1$-$C_6$)alkylene-$OR^C$; or, alternatively, $Y^1$ and $Y^2$ taken together are selected from the group consisting of sodium, potassium, lithium, magnesium, calcium, strontium, and barium;

provided that when $Z^2$ is NH, the absolute configuration of C** is R or S, or a mixture of R and S;

(a) providing a reduced nicotinate/nicotinamide riboside compound or derivative of formula (II), or a salt, hydrate, or solvate thereof;

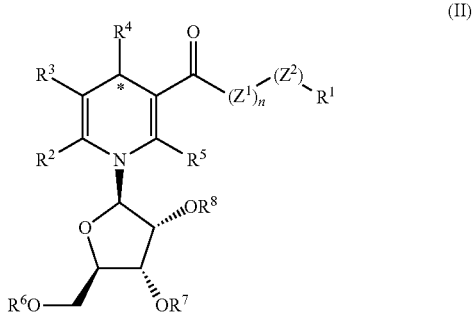

(II)

$Z^1$ and $Z^2$ are independently NH or oxygen;

n is 0 or 1;

$R^1$ is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^A$)—$CO_2$$R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C$, —$SR^C$, —S(O)$R^C$, —$SO_2$$R^C$, —$OSO_2$($C_1$-$C_6$)alkyl, —$SO_2$$NR^C_2$, —($C_1$-$C_6$)perfluoroalkyl, and —($C_1$-$C_6$)alkylene-$OR^C$;

$R^A$ is selected from the group consisting of —H, —($C_1$-$C_6$)alkyl, —($CH_2$)$_3$—NH—C($NH_2$)(=NH), —$CH_2$C(=O)$NH_2$, —$CH_2$COOH, —$CH_2$SH, —($CH_2$)$_2$C(=O)—$NH_2$, —($CH_2$)$_2$COOH, —$CH_2$-(2-imidazolyl), —CH($CH_3$)—$CH_2$—$CH_3$, —$CH_2$CH($CH_3$)$_2$, —($CH_2$)$_4$—$NH_2$, —($CH_2$)$_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —CH($CH_3$)$_2$, and —$CH_2$—$CH_3$;

$R^B$ is hydrogen or —($C_1$-$C_8$)alkyl;

each $R^C$ is independently selected from the group consisting of hydrogen, —($C_1$-$C_8$)alkyl, substituted or unsubstituted pyridyl, substituted or unsubstituted 1,4-dihydropyridyl, a radical of the compound of formula (I), and vitamin B7 ester (biotinyl); wherein the substituted pyridyl and substituted 1,4-dihydropyridyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^B$, —C(O)O$R^B$, —C(O)$NR^B{}_2$, —C(=$NR^B$)$NR^B{}_2$, —O$R^B$, —OC(O)($C_1$-$C_6$)alkyl, —OC(O)O($C_1$-$C_6$)alkyl, —OC(O)$NR^B{}_2$, —($C_1$-$C_6$)alkylene-$NR^B{}_2$, —$NR^B{}_2$, —$NR^B$C(O)$R^B$, —$NR^B$C(O)O($C_1$-$C_6$)alkyl, —$NR^B$C(O)$NR^B{}_2$, —$NR^B$$SO_2$$NR^B$, —$SR^B$, —S(O)$R^B$, —$SO_2R^B$, —$OSO_2$($C_1$-$C_6$)alkyl, —$SO_2NR^B{}_2$, —($C_1$-$C_6$)perfluoroalkyl, and —($C_1$-$C_6$)alkylene-$OR^B$;

$R^2$ and $R^3$ are each independently selected from the group consisting of hydrogen, —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C{}_2$, —C(=$NR^C$)$NR^C{}_2$, —O$R^C$, —OC(O)($C_1$-$C_6$)alkyl, —OC(O)O($C_1$-$C_6$)alkyl, —OC(O)$NR^C{}_2$, —($C_1$-$C_6$)alkylene-$NR^C{}_2$, —$NR^C{}_2$, —$NR^C$C(O)$R^C$, —$NR^C$C(O)O($C_1$-$C_6$)alkyl, —$NR^C$C(O)$NR^C{}_2$, —$NR^C$$SO_2$$NR^C$, —$SR^C$, —S(O)$R^C$, —$SO_2R^C$, —$OSO_2$($C_1$-$C_6$)alkyl, —$SO_2NR^C{}_2$, —($C_1$-$C_6$)perfluoroalkyl, and —($C_1$-$C_6$)alkylene-$OR^C$;

$R^4$ is selected from the group consisting of hydrogen, —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C{}_2$, —C(=$NR^C$)$NR^C{}_2$, —O$R^C$, —OC(O)($C_1$-$C_6$)alkyl, —OC(O)O($C_1$-$C_6$)alkyl, —OC(O)$NR^C{}_2$, —($C_1$-$C_6$)alkylene-$NR^C{}_2$, —$NR^C{}_2$, —$NR^C$C(O)$R^C$, —$NR^C$C(O)O($C_1$-$C_6$)alkyl, —$NR^C$C(O)$NR^C{}_2$, —$NR^C$$SO_2$$NR^C$, —$SR^C$, —S(O)$R^C$, —$SO_2R^C$, —$OSO_2$($C_1$-$C_6$)alkyl, —$SO_2NR^C{}_2$, —($C_1$-$C_6$)perfluoroalkyl, and —($C_1$-$C_6$)alkylene-$OR^C$;

wherein C* has an absolute configuration of R or S, or a mixture of R and S;

$R^5$ is selected from the group consisting of hydrogen, —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C{}_2$, —C(=$NR^C$)$NR^C{}_2$, —O$R^C$, —OC(O)($C_1$-$C_6$)alkyl, —OC(O)O($C_1$-$C_6$)alkyl, —OC(O)$NR^C{}_2$, —($C_1$-$C_6$)alkylene-$NR^C{}_2$, —$NR^C{}_2$, —$NR^C$C(O)$R^C$, —$NR^C$C(O)O($C_1$-$C_6$)alkyl, —$NR^C$C(O)$NR^C{}_2$, —$NR^C$$SO_2$$NR^C$, —$SR^C$, —S(O)$R^C$, —$SO_2R^C$, —$OSO_2$($C_1$-$C_6$)alkyl, —$SO_2NR^C{}_2$, —($C_1$-$C_6$)perfluoroalkyl, and —($C_1$-$C_6$)alkylene-$OR^C$;

$R^6$ is selected from the group consisting of hydrogen, —C(O)R', —C(O)OR', —C(O)NHR', —P(O)($OY^1$)($OY^2$), —P(O)($OY^1$)(NHR"), substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C{}_2$, —C(=$NR^C$)$NR^C{}_2$, —O$R^C$, —OC(O)($C_1$-$C_6$)alkyl, —OC(O)O($C_1$-$C_6$)alkyl, —OC(O)$NR^C{}_2$, —($C_1$-$C_6$)alkylene-$NR^C{}_2$, —$NR^C{}_2$, —$NR^C$C(O)$R^C$, —$NR^C$C(O)O($C_1$-$C_6$)alkyl, —$NR^C$C(O)$NR^C{}_2$, —$NR^C$$SO_2$$NR^C$, —$SR^C$, —S(O)$R^C$, —$SO_2R^C$, —$OSO_2$($C_1$-$C_6$)alkyl, —$SO_2NR^C{}_2$, —($C_1$-$C_6$)perfluoroalkyl, and —($C_1$-$C_6$)alkylene-$OR^C$;

R' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C{}_2$, —C(=$NR^C$)$NR^C{}_2$, —O$R^C$, —OC(O)($C_1$-$C_6$)alkyl, —OC(O)O($C_1$-$C_6$)alkyl, —OC(O)$NR^C{}_2$, —($C_1$-$C_6$)alkylene-$NR^C{}_2$, —$NR^C{}_2$, —$NR^C$C(O)$R^C$, —$NR^C$C(O)O($C_1$-$C_6$)alkyl, —$NR^C$C(O)$NR^C{}_2$, —$NR^C$$SO_2$$NR^C$, —$SR^C$, —S(O)$R^C$, —$SO_2R^C$, —$OSO_2$($C_1$-$C_6$)alkyl, —$SO_2NR_2$, —($C_1$-$C_6$)perfluoroalkyl, and —($C_1$-$C_6$)alkylene-$OR^C$;

R" is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C{}_2$, —C(=$NR^C$)$NR^C{}_2$, —O$R^C$, —OC(O)($C_1$-$C_6$)alkyl, —OC(O)O($C_1$-$C_6$)alkyl, —OC(O)$NR^C{}_2$, —($C_1$-$C_6$)alkylene-$NR^C{}_2$, —$NR^C{}_2$, —$NR^C$C(O)$R^C$, —$NR^C$C(O)O($C_1$-$C_6$)alkyl, —$NR^C$C(O)$NR^C{}_2$, —$NR^C$$SO_2$$NR^C$, —$SR^C$, —S(O)$R^C$, —$SO_2R^C$, —$OSO_2$($C_1$-$C_6$)alkyl, —$SO_2NR_2$, —($C_1$-$C_6$)perfluoroalkyl, and —($C_1$-$C_6$)alkylene-$OR^C$;

$R^7$ and $R^8$ are independently selected from the group consisting of hydrogen, —C(O)R', —C(O)OR', —C(O)NHR', substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$)cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C{}_2$, —C(=$NR^C$)$NR^C{}_2$, —O$R^C$, —OC(O)($C_1$-$C_8$)alkyl, —OC(O)O($C_1$-$C_6$)alkyl, —OC(O)$NR^C{}_2$, —($C_1$-$C_6$)alkylene-$NR^C{}_2$, —$NR^C{}_2$, —$NR^C$C(O)$R^C$, —$NR^C$C(O)O($C_1$-$C_6$)alkyl, —$NR^C$C(O)$NR^C{}_2$, —$NR^C$$SO_2$$NR^C$, —$SR^C$, —S(O)$R^C$, —$SO_2R^C$, —$OSO_2$($C_1$-$C_6$)alkyl, —$SO_2NR^C{}_2$, —($C_1$-$C_8$)perfluoroalkyl, and —($C_1$-$C_6$)alkylene-$OR^C$;

$Y^1$ and $Y^2$ are independently selected from the group consisting of hydrogen, sodium, potassium, lithium, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle; wherein the substituted $(C_1-C_8)$alkyl, substituted $(C_1-C_8)$cycloalkyl, substituted aryl, substituted heteroaryl, and substituted heterocycle are substituted with one to five substituents independently selected from the group consisting of —$(C_1-C_6)$alkyl, —$(C_2-C_6)$alkenyl, —$(C_2-C_6)$alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1-C_6$)alkyl, —OC(O)O($C_1-C_6$)alkyl, —OC(O)$NR^C_2$, —($C_1-C_6$)alkylene-$NR^C_2$, —$NR^C_2$, —$NR^C$C(O)$R^C$, —$NR^C$C(O)O($C_1-C_6$)alkyl, —$NR^C$C(O)$NR^C_2$, —$NR^C$SO$_2$$NR^C$, —$SR^C$, —S(O)$R^C$, —SO$_2$$R^C$, —OSO$_2$($C_1-C_6$)alkyl, —SO$_2$$NR^C_2$, —($C_1-C_6$)perfluoroalkyl, and —($C_1-C_6$)alkylene-O$R^C$; or, alternatively, $Y^1$ and $Y^2$ taken together are selected from the group consisting of sodium, potassium, lithium, magnesium, calcium, strontium, and barium; provided that when $Z^2$ is NH, the absolute configuration of C** is R or S, or a mixture of R and S;

(b) oxidizing a compound or derivative of formula (II), or a salt, hydrate, or solvate thereof, with at least about one molar equivalent amount of an oxidizing agent so as to produce the compound or derivative of formula (I), or salt, hydrate, or solvate thereof; and (c) isolating the compound or derivative of formula (I), or salt, hydrate, or solvate thereof.

7. The method of claim 6, further comprising the steps of:

(a1) providing a reduced nicotinate/nicotinamide riboside compound or derivative having formula 4), or a salt thereof:

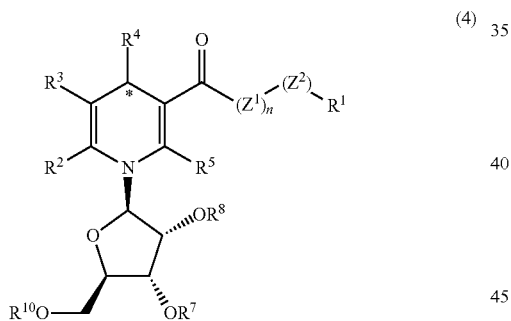

(4)

wherein $Z^1$ and $Z^2$ are independently NH or oxygen;
n is 0 or 1;
$R^1$ is selected from the group consisting of hydrogen, substituted or unsubstituted $(C_1-C_8)$alkyl, substituted or unsubstituted $(C_1-C_8)$cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^A$)—CO$_2$$R^B$; wherein the substituted $(C_1-C_8)$alkyl, substituted $(C_1-C_8)$cycloalkyl, substituted aryl, substituted heteroaryl, and substituted heterocycle are substituted with one to five substituents independently selected from the group consisting of —$(C_1-C_6)$alkyl, —$(C_2-C_6)$alkenyl, —$(C_2-C_6)$alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1-C_6$)alkyl, —OC(O)O($C_1-C_6$)alkyl, —OC(O)$NR^C_2$, —($C_1-C_6$)alkylene-$NR^C_2$, —$NR^C_2$, —$NR^C$C(O)$R^C$, —$NR^C$C(O)O($C_1-C_6$)alkyl, —$NR^C$C(O)$NR^C_2$, —$NR^C$SO$_2$$NR^C$, —$SR^C$, —S(O)$R^C$, —SO$_2$$R^C$, —OSO$_2$($C_1-C_6$)alkyl, —SO$_2$$NR^C_2$, —($C_1-C_6$)perfluoroalkyl, and —($C_1-C_6$)alkylene-O$R^C$;

$R^A$ is selected from the group consisting of —H, —($C_1-C_6$)alkyl, —(CH$_2$)$_3$NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, —CH$_2$-phenyl, —CH$_2$OH, —CH(OH)—CH$_3$, —CH$_2$-(3-indolyl), —CH$_2$-(4-hydroxyphenyl), —CH(CH$_3$)$_2$, —CH$_2$—CH$_3$;

$R^B$ is hydrogen or —($C_1-C_8$)alkyl;

each $R^C$ is independently selected from the group consisting of hydrogen, —($C_1-C_8$)alkyl, substituted or unsubstituted pyridyl, substituted or unsubstituted 1,4-dihydropyridyl, a radical of the compound of formula (I), and vitamin B7 ester (biotinyl); wherein the substituted pyridyl and substituted 1,4-dihydropyridyl are substituted with one to five substituents independently selected from the group consisting of —$(C_1-C_6)$alkyl, —$(C_2-C_6)$alkenyl, —$(C_2-C_6)$alkynyl, halogen, —CN, —$NO_2$, —C(O)$R^B$, —C(O)O$R^B$, —C(O)$NR^C_2$, —C(=$NR^B$)$NR^B_2$, —O$R^B$, —OC(O)($C_1-C_6$)alkyl, —OC(O)O($C_1-C_6$)alkyl, —OC(O)$NR^B_2$, —($C_1-C_6$)alkylene-$NR^B_2$, —$NR^B_2$, —$NR^B$C(O)$R^B$, —$NR^B$C(O)O($C_1-C_6$)alkyl, —$NR^B$C(O)$NR^B_2$, —$NR^B$SO$_2$$NR^B$, —$SR^B$, —S(O)$R^B$, —SO$_2$$R^B$, —OSO$_2$($C_1-C_6$)alkyl, —SO$_2$$NR^B_2$, —($C_1-C_6$)perfluoroalkyl, and —($C_1-C_6$)alkylene-O$R^B$;

$R^2$ and $R^3$ are each independently selected from the group consisting of hydrogen, —$(C_1-C_6)$alkyl, —$(C_2-C_6)$alkenyl, —$(C_2-C_6)$alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1-C_6$)alkyl, —OC(O)O($C_1-C_6$)alkyl, —OC(O)$NR^C_2$, —($C_1-C_6$)alkylene-$NR^C_2$, —$NR^C_2$, —$NR^C$C(O)$R^C$, —$NR^C$C(O)O($C_1-C_6$)alkyl, —$NR^C$C(O)$NR^C_2$, —$NR^C$SO$_2$$NR^C$, —$SR^C$, —S(O)$R^C$, —SO$_2$$R^C$, —OSO$_2$($C_1-C_6$)alkyl, —SO$_2$$NR^C_2$, —($C_1-C_6$)perfluoroalkyl, and —($C_1-C_6$)alkylene-O$R^C$;

$R^4$ is selected from the group consisting of hydrogen, —$(C_1-C_6)$alkyl, —$(C_2-C_6)$alkenyl, —$(C_2-C_6)$alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1-C_6$)alkyl, —OC(O)O($C_1-C_6$)alkyl, —OC(O)$NR^C_2$, —($C_1-C_6$)alkylene-$NR^C_2$, —$NR^C_2$, —$NR^C$C(O)$R^C$, —$NR^C$C(O)O($C_1-C_6$)alkyl, —$NR^C$C(O)$NR^C_2$, —$NR^C$SO$_2$$NR^C$, —$SR^C$, —S(O)$R^C$, —SO$_2$$R^C$, —OSO$_2$($C_1-C_6$)alkyl, —SO$_2$$NR^C_2$, —($C_1-C_6$)perfluoroalkyl, and —($C_1-C_6$)alkylene-O$R^C$;

wherein C* has an absolute configuration of R or S, or a mixture of R and S;

$R^5$ is selected from the group consisting of hydrogen, —$(C_1-C_6)$alkyl, —$(C_2-C_6)$alkenyl, —$(C_2-C_6)$alkynyl, halogen, —CN, —$NO_2$, —C(O)$R^C$, —C(O)O$R^C$, —C(O)$NR^C_2$, —C(=$NR^C$)$NR^C_2$, —O$R^C$, —OC(O)($C_1-C_6$)alkyl, —OC(O)O($C_1-C_6$)alkyl, —OC(O)$NR^C_2$, —($C_1-C_6$)alkylene-$NR^C_2$, —$NR^C_2$, —$NR^C$C(O)$R^C$, —$NR^C$C(O)O($C_1-C_6$)alkyl, —$NR^C$C(O)$NR^C_2$, —$NR^C$SO$_2$$NR^C$, —$SR^C$, —S(O)$R^C$, —SO$_2$$R^C$, —OSO$_2$($C_1-C_6$)alkyl, —SO$_2$$NR^C_2$, —($C_1-C_6$)perfluoroalkyl, and —($C_1-C_6$)alkylene-O$R^C$;

$R^7$ and $R^8$ are independently selected from the group consisting of hydrogen, —C(O)R', —C(O)OR', —C(O)NHR', substituted or unsubstituted $(C_1-C_8)$alkyl, substituted or unsubstituted $(C_1-C_8)$cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_1$-$C_8$)cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-$OR^C$;

R' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-$OR^C$;

$R^{10}$ is selected from the group consisting of hydrogen, —C(O)R', —C(O)OR', —C(O)NHR', —P(O)($OY^1$)($OY^2$), —P(O)($OY^1$)(NHR''), substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-$OR^C$;

R'' is selected from the group consisting of hydrogen, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—($R^A$)—$CO_2R^B$; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —$OR^C$, —OC(O)($C_1$-$C_6$)alkyl, —OC(O)O($C_1$-$C_6$)alkyl, —OC(O)$NR^C_2$, —($C_1$-$C_6$) alkylene-$NR^C_2$, —$NR^C_2$, —$NR^C$C(O)$R^C$, —$NR^C$C(O) O($C_1$-$C_6$)alkyl, —$NR^C$C(O)$NR^C_2$, —$NR^C$$SO_2$$NR^C$, —$SR^C$, —S(O)$R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$) alkylene $OR^C$;

$Y^1$ and $Y^2$ are independently selected from the group consisting of hydrogen, sodium, potassium, lithium, substituted or unsubstituted ($C_1$-$C_8$)alkyl, substituted or unsubstituted ($C_1$-$C_8$)cycloalkyl, substituted or unsubstituted aryl, substituted or unsubstituted heteroaryl, and substituted or unsubstituted heterocycle; wherein the substituted ($C_1$-$C_8$)alkyl, substituted ($C_1$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^C$, —C(O)O$R^C$, —C(O)$NR^C_2$, —C(=$NR^C$)$NR^C_2$, —$OR^C$, —OC(O)($C_1$-$C_6$)alkyl, —OC(O)O($C_1$-$C_6$) alkyl, —OC(O)$NR^C_2$, —($C_1$-$C_6$)alkylene-$NR^C_2$, —$NR^C_2$, —$NR^C$C(O)$R^C$, —$NR^C$C(O)O($C_1$-$C_6$)alkyl, —$NR^C$C(O)$NR^C_2$, —$NR^C$$SO_2$$NR^C$, —$SR^C$, —S(O) $R^C$, —$SO_2R^C$, —$OSO_2$($C_1$-$C_6$)alkyl, —$SO_2NR^C_2$, —($C_1$-$C_6$)perfluoroalkyl, and —($C_1$-$C_6$)alkylene-$OR^C$; or, alternatively, $Y^1$ and $Y^2$ taken together are selected from the group consisting of sodium, potassium, lithium, magnesium, calcium, strontium, and barium;

provided that when $Z^2$ is NH, the absolute configuration of C** is R or S, or a mixture of R and S;

(a2) treating the compound or derivative having formula (4), or salt thereof, with at least about 0.5 molar equivalent amount of one or more activated reagent(s);

(a3) reacting the reduced nicotinate/nicotinamide riboside compound or derivative having formula (4), or salt thereof, with the one or more activated reagent(s) so as to produce a reduced nicotinate/nicotinamide riboside compound or derivative of formula (II), or salt, hydrate, or solvate thereof;

(a4) adding water to the reduced nicotinate/nicotinamide riboside compound or derivative having formula (4), or salt thereof, the one or more activated reagent(s), and a compound or derivative of formula (II), or salt, hydrate, or solvate thereof;

(a5) extracting the reduced nicotinate/nicotinamide riboside compound or derivative having formula (4), or salt thereof, the one or more activated reagent(s), a compound or derivative of formula (II), or salt, hydrate, or solvate thereof, and the water with organic solvent; and (a6) isolating a compound or derivative of formula (II), or salt, hydrate, or solvate thereof;

wherein steps (a1) through (a6) are performed sequentially before providing step (a).

8. A nicotinate/nicotinamide riboside compound or derivative of formula (I), or a salt thereof of claim 1, selected from the group consisting of:

pterostilbene nicotinate riboside triflate, wherein $R^1$ is pterostilbenyl (4-[(E)-2-(3,5-dimethoxyphenyl)ethenyl]phenyl), n=0, $Z^2$=oxygen, $R^2$=$R^3$=$R^4$=$R^5$ hydrogen, X⁻=triflate (trifluoromethanesulfonate), $R^6=R^7=R^8$=acetyl, or a salt thereof;

pterostilbene nicotinate riboside bromide, wherein $R^1$ is pterostilbenyl (4-[(E)-2-(3,5-dimethoxyphenyl)ethenyl]phenyl), n=0, $Z^2$=oxygen, $R^2=R^3=R^4=R^5$=hydrogen, X⁻=bromide, $R^6=R^7=R^8$=acetyl, or a salt thereof;

resveratrol trinicotinate riboside triflate, wherein $R^1$ is resveratryl (trans-3,5,4-trihydroxystilbenyl), n=0, $Z^2$=oxygen, $R^2=R^3=R^4=R^5$=hydrogen, X⁻=triflate (trifluoromethanesulfonate), $R^6=R^7=R^8$=acetyl, or a salt thereof;

nicotinamide N-tert-butyloxycarbonyl-tryptophan riboside chloride, wherein X⁻=chloride, $R^1$=hydrogen, n=0, $Z^2$=NH, $R^2=R^3=R^4=R^5=R^7=R^8$=hydrogen, $R^6$=N-tert-butyloxycarbonyl-tryptophan, or a salt thereof;

nicotinamide tryptophan riboside chloride, wherein X⁻=chloride, $R^1$=hydrogen, n=0, $Z^2$=NH, $R^2=R^3=R^4=R^5=R^7=R^8$=hydrogen, $R^6$=tryptophan, or a salt thereof;

nicotinamide N-tert-butyloxycarbonyl-isoleucine riboside chloride, wherein X⁻=chloride, $R^1$=hydrogen, n=0, $Z^2$=NH, $R^2=R^3=R^4=R^5=R^7=R^8$=hydrogen, $R^6$=N-tert-butyloxycarbonyl-isoleucine, or a salt thereof;

nicotinamide isoleucine riboside chloride, wherein X⁻=chloride, $R^1$=hydrogen, n=0, $Z^2$=NH, $R^2=R^3=R^4=R^5=R^7=R^8$=hydrogen, $R^6$=isoleucine, or a salt thereof;

nicotinamide N-tert-butyloxycarbonyl-alanine riboside chloride, wherein X⁻=chloride, $R^1$=hydrogen, n=0, $Z^2$=NH, $R^2=R^3=R^4=R^5=R^7=R^8$=hydrogen, $R^6$=N-tert-butyloxycarbonyl-alanine, or a salt thereof;

nicotinamide alanine riboside chloride, wherein X⁻=chloride, $R^1$=hydrogen, n=0, $Z^2$=NH, $R^2=R^3=R^4=R^5=R^7=R^8$=hydrogen, $R^6$=alanine, or a salt thereof;

nicotinamide N-tert-butyloxycarbonyl-phenylalanine riboside chloride, wherein X⁻=chloride, $R^1$=hydrogen, n=0, $Z^2$=NH, $R^2=R^3=R^4=R^5=R^7=R^8$=hydrogen, $R^6$=N-tert-butyloxycarbonyl-phenylalanine, or a salt thereof;

nicotinamide phenylalanine riboside chloride, wherein X⁻=chloride, $R^1$=hydrogen, n=0, $Z^2$=NH, $R^2=R^3=R^4=R^5=R^7=R^8$=hydrogen, $R^6$=phenylalanine, or a salt thereof;

nicotinamide N-tert-butyloxycarbonyl-valine riboside chloride, wherein X⁻=chloride, $R^1$=hydrogen, n=0, $Z^2$=NH, $R^2=R^3=R^4=R^5=R^7=R^8$=hydrogen, $R^6$=N-tert-butyloxycarbonyl-valine, or a salt thereof;

nicotinamide valine riboside chloride, wherein X⁻=chloride, $R^1$=hydrogen, n=0, $Z^2$=NH, $R^2=R^3=R^4=R^5=R^7=R^8$=hydrogen, $R^6$=valine, or a salt thereof;

nicotinamide N-tert-butyloxycarbonyl-methionine riboside chloride, wherein X⁻=chloride, $R^1$=hydrogen, n=0, $Z^2$=NH, $R^2=R^3=R^4=R^5=R^7=R^1$=hydrogen, $R^6$=N-tert-butyloxycarbonyl-methionine, or a salt thereof;

nicotinamide methionine riboside chloride, wherein X⁻=chloride, $R^1$=hydrogen, n=0, $Z^2$=NH, $R^2=R^3=R^4=R^5=R^7=R^8$=hydrogen, $R^6$=methionine, or a salt thereof;

2-bromoethyl nicotinate riboside triacetate triflate, wherein X⁻=triflate (trifluoromethanesulfonate), $R^1$=2-bromoethyl, n=0, $Z^2$=oxygen, $R^2=R^3=R^4=R^5$=hydrogen, $R^6=R^7=R^8$=acetyl, or a salt thereof; and choline nicotinate riboside triflate, wherein X⁻=triflate (trifluoromethanesulfonate), $R^1$=choline, n=0, $Z^2$=oxygen, $R^2=R^3=R^4=R^5=R^6=R^7=R^8$=hydrogen.

9. A reduced nicotinate/nicotinamide riboside compound or derivative of formula (II), or a salt thereof of claim 2, selected from the group consisting of:

reduced nicotinamide N-fluorenylmethyloxycarbonyl-tryptophan riboside, wherein $R^1$=hydrogen, n=0, $Z^2$=NH, $R^2=R^3=R^4=R^5=R^7=R^8$=hydrogen, $R^6$=N-fluorenylmethyloxycarbonyl-tryptophan, or a salt thereof;

reduced nicotinamide N-tert-butyloxycarbonyl-tryptophan riboside, wherein $R^1$=hydrogen, n=0, $Z^2$=NH, $R^2=R^3=R^4=R^5=R^7=R^8$=hydrogen, $R^6$=N-tert-butyloxycarbonyl-tryptophan, or a salt thereof;

reduced nicotinamide N-tert-butyloxycarbonyl-isoleucine riboside, wherein $R^1$=hydrogen, n=0, $Z^2$=NH, $R^2=R^3=R^4=R^5=R^7=R^8$=hydrogen, $R^6$=N-tert-butyloxycarbonyl-isoleucine, or a salt thereof;

reduced nicotinamide N-tert-butyloxycarbonyl-alanine riboside, wherein $R^1$=hydrogen, n=0, $Z^2$=NH, $R^2=R^3=R^4=R^5=R^7=R^8$=hydrogen, $R^6$=N-tert-butyloxycarbonyl-alanine, or a salt thereof;

reduced nicotinamide N-tert-butyloxycarbonyl-phenylalanine riboside, wherein $R^1$=hydrogen, n=0, $Z^2$=NH, $R^2=R^3=R^4=R^5=R^7=R^8$=hydrogen, $R^6$=N-tert-butyloxycarbonyl-phenylalanine, or a salt thereof;

reduced nicotinamide N-tert-butyloxycarbonyl-valine riboside, wherein $R^1$=hydrogen, n=0, $Z^2$=NH, $R^2=R^3=R^4=R^5=R^7=R^8$=hydrogen, $R^6$=N-tert-butyloxycarbonyl-valine, or a salt thereof;

reduced nicotinamide N-tert-butyloxycarbonyl-methionine riboside, wherein $R^1$=hydrogen, n=0, $Z^2$=NH, $R^2=R^3=R^4=R^5=R^7=R^8$=hydrogen, $R^6$=N-tert-butyloxycarbonyl-methionine, or a salt thereof; and reduced nicotinamide N-tert-butyloxycarbonyl-leucine riboside, wherein $R^1$=hydrogen, n=0, $Z^2$=NH, $R^2=R^3=R^4=R^5=R^7=R^8$=hydrogen, $R^6$=N-tert-butyloxycarbonyl-leucine, or a salt thereof.

* * * * *

UNITED STATES PATENT AND TRADEMARK OFFICE
CERTIFICATE OF CORRECTION

PATENT NO. : 10,000,520 B2
APPLICATION NO. : 15/461126
DATED : June 19, 2018
INVENTOR(S) : Marie Eugenie Migaud et al.

It is certified that error appears in the above-identified patent and that said Letters Patent is hereby corrected as shown below:

On the Title Page

In the Title, change "OFNICOTINOYL" to --OF NICOTINOYL--.

In the Specification

In Column 15, Line 27, change "$(C_1-C_8)$cycloalkyl" to --$(C_3-C_8)$cycloalkyl--.
In Column 15, Line 32, change "$(C_1-C_8)$cycloalkyl" to --$(C_3-C_8)$cycloalkyl--.
In Column 16, Line 14, change "$(C_1-C_8)$cycloalkyl" to --$(C_3-C_8)$cycloalkyl--.
In Column 16, Line 19, change "$(C_1-C_8)$cycloalkyl" to --$(C_3-C_8)$cycloalkyl--.
In Column 16, Line 26, change "$(C_1-C_6)$alkylene–$NR^C{}_2$" to -- –$(C_1-C_6)$alkylene–$NR^C{}_2$--.
In Column 16, Line 26, change "–$N_2$" to -- –$NR^C{}_2$--.
In Column 16, Line 33, change "$(C_1-C_8)$cycloalkyl" to --$(C_3-C_8)$cycloalkyl--.
In Column 16, Line 39, change "$(C_1-C_8)$cycloalkyl" to --$(C_3-C_8)$cycloalkyl--.
In Column 16, Line 53, change "$(C_1-C_8)$cycloalkyl" to --$(C_3-C_8)$cycloalkyl--.
In Column 16, Line 59, change "$(C_1-C_8)$cycloalkyl" to --$(C_3-C_8)$cycloalkyl--.
In Column 16, Line 66, change "$(C_1-C_6)$alkylene–$NR^C{}_2$" to -- –$(C_1-C_6)$alkylene-$NR^C{}_2$--.
In Column 17, Line 7, change "$(C_1-C_8)$cycloalkyl" to --$(C_3-C_8)$cycloalkyl--.
In Column 17, Line 14, change "$(C_1-C_8)$cycloalkyl" to --$(C_3-C_8)$cycloalkyl--.
In Column 17, Line 33, change "$(C_1-C_8)$cycloalkyl" to --$(C_3-C_8)$cycloalkyl--.
In Column 17, Line 37, change "$(C_1-C_8)$cycloalkyl" to --$(C_3-C_8)$cycloalkyl--.
In Column 17, Line 44, change "$(C_1-C_6)$alkylene–$NR^C{}_2$" to -- –$(C_1-C_6)$alkylene–$NR^C{}_2$--.
In Column 18, Line 27, change "$(C_1-C_8)$cycloalkyl" to --$(C_3-C_8)$cycloalkyl--.
In Column 18, Line 32, change "$(C_1-C_8)$cycloalkyl" to --$(C_3-C_8)$cycloalkyl--.
In Column 18, Line 35, change "$(C_2-C_6)$alkynyl" to -- –$(C_2-C_6)$alkynyl--.
In Column 18, Line 45, change "–$(CH_2)_3$–NH $C(NH_2)(=NH)$" to -- –$(CH_2)_3$–NH–$C(NH_2)(=NH)$--.
In Column 18, Line 46, change "–$(CH_2)_2C(=O)$ $NH_2$" to -- –$(CH_2)_2C(=O)$–$NH_2$--.
In Column 19, Line 14, change "$(C_1-C_8)$cycloalkyl" to --$(C_3-C_8)$cycloalkyl--.
In Column 19, Line 19, change "$(C_1-C_8)$cycloalkyl" to --$(C_3-C_8)$cycloalkyl--.
In Column 19, Line 33, change "$(C_1-C_8)$cycloalkyl" to --$(C_3-C_8)$cycloalkyl--.

Signed and Sealed this
Eleventh Day of December, 2018

Andrei Iancu
*Director of the United States Patent and Trademark Office*

CERTIFICATE OF CORRECTION (continued)  Page 2 of 10
U.S. Pat. No. 10,000,520 B2

In Column 19, Line 39, change "$(C_1\text{-}C_8)$cycloalkyl" to --$(C_3\text{-}C_8)$cycloalkyl--.
In Column 19, Line 53, change "$(C_1\text{-}C_8)$cycloalkyl" to --$(C_3\text{-}C_8)$cycloalkyl--.
In Column 19, Line 59, change "$(C_1\text{-}C_8)$cycloalkyl" to --$(C_3\text{-}C_8)$cycloalkyl--.
In Column 20, Line 7, change "$(C_1\text{-}C_8)$cycloalkyl" to --$(C_3\text{-}C_8)$cycloalkyl--.
In Column 20, Line 12, change "$(C_1\text{-}C_8)$cycloalkyl" to --$(C_3\text{-}C_8)$cycloalkyl--.
In Column 20, Lines 24-25, change "–$(C^1\text{-}C_6)$perfluoroalkyl" to -- –$(C_1\text{-}C_6)$perfluoroalkyl--.
In Column 20, Line 29, change "$(C_1\text{-}C_8)$cycloalkyl" to --$(C_3\text{-}C_8)$cycloalkyl--.
In Column 20, Line 32, change "$(C_1\text{-}C_8)$cycloalkyl" to --$(C_3\text{-}C_8)$cycloalkyl--.
In Column 20, Line 58, change "$(C_1\text{-}C_8)$cycloalkyl" to --$(C_3\text{-}C_8)$cycloalkyl--.
In Column 20, Line 62, change "$(C_1\text{-}C_8)$cycloalkyl" to --$(C_3\text{-}C_8)$cycloalkyl--.
In Column 21, Line 22, change "$(C_1\text{-}C_8)$cycloalkyl" to --$(C_3\text{-}C_8)$cycloalkyl--.
In Column 21, Line 28, change "$(C_1\text{-}C_8)$cycloalkyl" to --$(C_3\text{-}C_8)$cycloalkyl--.
In Column 21, Line 43, change "–$(CH_2)_4$–$N_2$" to -- –$(CH_2)_4$–$NH_2$--.
In Column 22, Line 29, change "$(C_1\text{-}C_8)$cycloalkyl" to --$(C_3\text{-}C_8)$cycloalkyl--.
In Column 22, Line 34, change "$(C_1\text{-}C_8)$cycloalkyl" to --$(C_3\text{-}C_8)$cycloalkyl--.
In Column 22, Line 48, change "$(C_1\text{-}C_8)$cycloalkyl" to --$(C_3\text{-}C_8)$cycloalkyl--.
In Column 22, Line 54, change "$(C_1\text{-}C_8)$cycloalkyl" to --$(C_3\text{-}C_8)$cycloalkyl--.
In Column 23, Line 1, change "$(C_1\text{-}C_8)$cycloalkyl" to --$(C_3\text{-}C_8)$cycloalkyl--.
In Column 23, Line 7, change "$(C_1\text{-}C_8)$cycloalkyl" to --$(C_3\text{-}C_8)$cycloalkyl--.
In Column 23, Line 22, change "$(C_1\text{-}C_8)$cycloalkyl" to --$(C_3\text{-}C_8)$cycloalkyl--.
In Column 23, Line 27, change "$(C_1\text{-}C_8)$cycloalkyl" to --$(C_3\text{-}C_8)$cycloalkyl--.
In Column 23, Line 43, change "$(C_1\text{-}C_8)$cycloalkyl" to --$(C_3\text{-}C_8)$cycloalkyl--.
In Column 23, Line 46, change "$(C_1\text{-}C_8)$cycloalkyl" to --$(C_3\text{-}C_8)$cycloalkyl--.
In Column 24, Line 20, change "$(C_1\text{-}C_8)$cycloalkyl" to --$(C_3\text{-}C_8)$cycloalkyl--.
In Column 24, Line 25, change "$(C_1\text{-}C_8)$cycloalkyl" to --$(C_3\text{-}C_8)$cycloalkyl--.
In Column 24, Line 55, change "–$C(O)NR^B2$" to -- –$C(O)NR^B_2$--.
In Column 24, Line 55, change "–$C(=NR)NR^B_2$" to -- –$C(=NR^B)NR^B_2$--.
In Column 24, Line 58, change "–SR" to -- –$SR^B$--.
In Column 25, Lines 22-23, change "$(C_1\text{-}C_6)$perfluoroalkyl" to -- –$(C_1\text{-}C_6)$perfluoroalkyl--.
In Column 25, Line 27, change "$(C_1\text{-}C_8)$cycloalkyl" to --$(C_3\text{-}C_8)$cycloalkyl--.
In Column 25, Line 32, change "$(C_1\text{-}C_8)$cycloalkyl" to --$(C_3\text{-}C_8)$cycloalkyl--.
In Column 25, Line 46, change "$(C_1\text{-}C_8)$cycloalkyl" to --$(C_3\text{-}C_8)$cycloalkyl--.
In Column 25, Lines 50-51, change "heterocyle$(C_1\text{-}C_4)$alkyl" to --heterocycle$(C_1\text{-}C_4)$alkyl--.
In Column 25, Line 51, change "–$CH\ (R^A)$–$CO_2R$" to -- –$CH$–$(R^A)$–$CO_2R^B$--.
In Column 25, Line 52, change "$(C_1\text{-}C_8)$cycloalkyl" to --$(C_3\text{-}C_8)$cycloalkyl--.
In Column 25, Line 66, change "$(C_1\text{-}C_8)$cycloalkyl" to --$(C_3\text{-}C_8)$cycloalkyl--.
In Column 26, Line 5, change "$(C_1\text{-}C_8)$cycloalkyl" to --$(C_3\text{-}C_8)$cycloalkyl--.
In Column 26, Line 21, change "$(C_1\text{-}C_8)$cycloalkyl" to --$(C_3\text{-}C_8)$cycloalkyl--.
In Column 26, Line 26, change "$(C_1\text{-}C_8)$cycloalkyl" to --$(C_3\text{-}C_8)$cycloalkyl--.
In Column 26, Line 43, change "$(C_1\text{-}C_8)$cycloalkyl" to --$(C_3\text{-}C_8)$cycloalkyl--.
In Column 26, Line 46, change "$(C_1\text{-}C_8)$cycloalkyl" to --$(C_3\text{-}C_8)$cycloalkyl--.
In Column 26, Line 53, change "$(C_1\text{-}C_6)$alkylene–$NR^C_2$" to -- –$(C_1\text{-}C_6)$alkylene–$NR^C_2$--.
In Column 27, Line 8, change "$(C_1\text{-}C_8)$cycloalkyl" to --$(C_3\text{-}C_8)$cycloalkyl--.
In Column 31, Line 18, change "$(C_1\text{-}C_8)$cycloalkyl" to --$(C_3\text{-}C_8)$cycloalkyl--.
In Column 31, Line 21, change "–$CH$–$(R^A)$–$CO_2R$" to -- –$CH$–$(R^A)$–$CO_2R^B$--.
In Column 31, Lines 22-23, change "$(C_1\text{-}C_8)$cycloalkyl" to --$(C_3\text{-}C_8)$cycloalkyl--.

CERTIFICATE OF CORRECTION (continued)
U.S. Pat. No. 10,000,520 B2

In Column 31, Line 61, change "–C(O)R$^B$" to -- –C(O)R$^C$--.
In Column 32, Line 28, change "(C$_1$-C$_8$)cycloalkyl" to --(C$_3$-C$_8$)cycloalkyl--.
In Column 32, Line 33, change "(C$_1$-C$_8$)cycloalkyl" to --(C$_3$-C$_8$)cycloalkyl--.
In Column 32, Line 64, change "–C(NR$^B$)NR$^B{}_2$" to -- –C(=NR$^B$)NR$^B{}_2$--.
In Column 33, Line 5, change "(C$_1$-C$_8$)cycloalkyl" to --(C$_3$-C$_8$)cycloalkyl--.
In Column 33, Line 11, change "(C$_1$-C$_8$)cycloalkyl" to --(C$_3$-C$_8$)cycloalkyl--.
In Column 33, Line 25, change "(C$_1$-C$_8$)cycloalkyl" to --(C$_3$-C$_8$)cycloalkyl--.
In Column 33, Line 31, change "(C$_1$-C$_8$)cycloalkyl" to --(C$_3$-C$_8$)cycloalkyl--.
In Column 33, Line 46, change "(C$_1$-C$_8$)cycloalkyl" to --(C$_3$-C$_8$)cycloalkyl--.
In Column 33, Line 51, change "(C$_1$-C$_8$)cycloalkyl" to --(C$_3$-C$_8$)cycloalkyl--.
In Column 33, Line 67, change "(C$_1$-C$_8$)cycloalkyl" to --(C$_3$-C$_8$)cycloalkyl--.
In Column 34, Line 3, change "(C$_1$-C$_8$)cycloalkyl" to --(C$_3$-C$_8$)cycloalkyl--.
In Column 35, Line 60, change "(C$_1$-C$_8$)cycloalkyl" to --(C$_3$-C$_8$)cycloalkyl--.
In Column 35, Line 65, change "(C$_1$-C$_8$)cycloalkyl" to --(C$_3$-C$_8$)cycloalkyl--.
In Column 36, Line 6, change "NR$^C$C(O)NR$^C{}_2$" to -- –NR$^C$C(O)NR$^C{}_2$--.
In Column 36, Line 46, change "(C$_1$-C$_8$)cycloalkyl" to --(C$_3$-C$_8$)cycloalkyl--.
In Column 36, Line 51, change "(C$_1$-C$_8$)cycloalkyl" to --(C$_3$-C$_8$)cycloalkyl--.
In Column 36, Line 66, change "(C$_1$-C$_8$)cycloalkyl" to --(C$_3$-C$_8$)cycloalkyl--.
In Column 37, Line 5, change "(C$_1$-C$_8$)cycloalkyl" to --(C$_3$-C$_8$)cycloalkyl--.
In Column 37, Line 20, change "(C$_1$-C$_8$)cycloalkyl" to --(C$_3$-C$_8$)cycloalkyl--.
In Column 37, Line 25, change "(C$_1$-C$_8$)cycloalkyl" to --(C$_3$-C$_8$)cycloalkyl--.
In Column 37, Line 39, change "(C$_1$-C$_8$)cycloalkyl" to --(C$_3$-C$_8$)cycloalkyl--.
In Column 37, Line 45, change "(C$_1$-C$_8$)cycloalkyl" to --(C$_3$-C$_8$)cycloalkyl--.
In Column 37, Line 60, change "(C$_1$-C$_8$)cycloalkyl" to --(C$_3$-C$_8$)cycloalkyl--.
In Column 37, Line 63, change "(C$_1$-C$_8$)cycloalkyl" to --(C$_3$-C$_8$)cycloalkyl--.
In Column 40, Line 20, change "(C$_1$-C$_8$)cycloalkyl" to --(C$_3$-C$_8$)cycloalkyl--.
In Column 40, Line 25, change "(C$_1$-C$_8$)cycloalkyl" to --(C$_3$-C$_8$)cycloalkyl--.
In Column 41, Line 27, change "(C$_1$-C$_8$)cycloalkyl" to --(C$_3$-C$_8$)cycloalkyl--.
In Column 41, Line 32, change "(C$_1$-C$_8$)cycloalkyl" to --(C$_3$-C$_8$)cycloalkyl--.
In Column 41, Line 47, change "(C$_1$-C$_8$)cycloalkyl" to --(C$_3$-C$_8$)cycloalkyl--.
In Column 41, Line 53, change "(C$_1$-C$_8$)cycloalkyl" to --(C$_3$-C$_8$)cycloalkyl--.
In Column 42, Line 1, change "(C$_1$-C$_8$)cycloalkyl" to --(C$_3$-C$_8$)cycloalkyl--.
In Column 42, Line 6, change "(C$_1$-C$_8$)cycloalkyl" to --(C$_3$-C$_8$)cycloalkyl--.
In Column 42, Line 20, change "(C$_1$-C$_8$)cycloalkyl" to --(C$_3$-C$_8$)cycloalkyl--.
In Column 42, Line 26, change "(C$_1$-C$_8$)cycloalkyl" to --(C$_3$-C$_8$)cycloalkyl--.
In Column 42, Line 41, change "(C$_1$-C$_8$)cycloalkyl" to --(C$_3$-C$_8$)cycloalkyl--.
In Column 42, Line 44, change "(C$_1$-C$_8$)cycloalkyl" to --(C$_3$-C$_8$)cycloalkyl--.
In Column 47, Line 22, change "(C$_1$-C$_8$)cycloalkyl" to --(C$_3$-C$_8$)cycloalkyl--.
In Column 47, Line 27, change "(C$_1$-C$_8$)cycloalkyl" to --(C$_3$-C$_8$)cycloalkyl--.
In Column 48, Line 8, change "(C$_1$-C$_8$)cycloalkyl" to --(C$_3$-C$_8$)cycloalkyl--.
In Column 48, Line 13, change "(C$_1$-C$_8$)cycloalkyl" to --(C$_3$-C$_8$)cycloalkyl--.
In Column 48, Line 27, change "(C$_1$-C$_8$)cycloalkyl" to --(C$_3$-C$_8$)cycloalkyl--.
In Column 48, Line 33, change "(C$_1$-C$_8$)cycloalkyl" to --(C$_3$-C$_8$)cycloalkyl--.
In Column 48, Line 47, change "(C$_1$-C$_8$)cycloalkyl" to --(C$_3$-C$_8$)cycloalkyl--.
In Column 48, Line 53, change "(C$_1$-C$_7$)alkyl" to --(C$_1$-C$_8$)alkyl--.
In Column 48, Line 53, change "(C$_1$-C$_7$)cycloalkyl" to --(C$_3$-C$_8$)cycloalkyl--.

In Column 49, Line 1, change "($C_1$-$C_8$)cycloalkyl" to --($C_3$-$C_8$)cycloalkyl--.
In Column 49, Line 7, change "($C_1$-$C_8$)cycloalkyl" to --($C_3$-$C_8$)cycloalkyl--.
In Column 49, Line 27, change "($C_1$-$C_8$)cycloalkyl" to --($C_3$-$C_8$)cycloalkyl--.
In Column 49, Line 31, change "($C_1$-$C_8$)cycloalkyl" to --($C_3$-$C_8$)cycloalkyl--.
In Column 51, Line 5, change "($C_1$-$C_8$)cycloalkyl" to --($C_3$-$C_8$)cycloalkyl--.
In Column 51, Line 10, change "($C_1$-$C_8$)cycloalkyl" to --($C_3$-$C_8$)cycloalkyl--.
In Column 51, Line 58, change "($C_1$-$C_8$)cycloalkyl" to --($C_3$-$C_8$)cycloalkyl--.
In Column 51, Line 63, change "($C_1$-$C_8$)cycloalkyl" to --($C_3$-$C_8$)cycloalkyl--.
In Column 52, Line 10, change "($C_1$-$C_8$)cycloalkyl" to --($C_3$-$C_8$)cycloalkyl--.
In Column 52, Line 17, change "($C_1$-$C_8$)cycloalkyl" to --($C_3$-$C_8$)cycloalkyl--.
In Column 52, Line 31, change "($C_1$-$C_8$)cycloalkyl" to --($C_3$-$C_8$)cycloalkyl--.
In Column 52, Line 37, change "($C_1$-$C_8$)cycloalkyl" to --($C_3$-$C_8$)cycloalkyl--.
In Column 52, Line 52, change "($C_1$-$C_8$)cycloalkyl" to --($C_3$-$C_8$)cycloalkyl--.
In Column 52, Line 57, change "($C_1$-$C_8$)cycloalkyl" to --($C_3$-$C_8$)cycloalkyl--.
In Column 53, Line 6, change "($C_1$-$C_8$)cycloalkyl" to --($C_3$-$C_8$)cycloalkyl--.
In Column 53, Line 9, change "($C_1$-$C_8$)cycloalkyl" to --($C_3$-$C_8$)cycloalkyl--.
In Column 53, Line 35, change "($C_1$-$C_8$)cycloalkyl" to --($C_3$-$C_8$)cycloalkyl--.
In Column 53, Line 39, change "($C_1$-$C_8$)cycloalkyl" to --($C_3$-$C_8$)cycloalkyl--.
In Column 53, Line 67, change "($C_1$-$C_8$)cycloalkyl" to --($C_3$-$C_8$)cycloalkyl--.
In Column 54, Line 5, change "($C_1$-$C_8$)cycloalkyl" to --($C_3$-$C_8$)cycloalkyl--.
In Column 54, Line 57, change "–$SO_2NR_2$" to -- –$SO_2NR^C_2$--.
In Column 55, Line 6, change "($C_1$-$C_8$)cycloalkyl" to --($C_3$-$C_8$)cycloalkyl--.
In Column 55, Line 11, change "($C_1$-$C_8$)cycloalkyl" to --($C_3$-$C_8$)cycloalkyl--.
In Column 55, Line 25, change "($C_1$-$C_8$)cycloalkyl" to --($C_3$-$C_8$)cycloalkyl--.
In Column 55, Line 31, change "($C_1$-$C_8$)cycloalkyl" to --($C_3$-$C_8$)cycloalkyl--.
In Column 55, Line 45, change "($C_1$-$C_8$)cycloalkyl" to --($C_3$-$C_8$)cycloalkyl--.
In Column 55, Line 51, change "($C_1$-$C_8$)cycloalkyl" to --($C_3$-$C_8$)cycloalkyl--.
In Column 55, Line 66, change "($C_1$-$C_8$)cycloalkyl" to --($C_3$-$C_8$)cycloalkyl--.
In Column 56, Line 4, change "($C_1$-$C_8$)cycloalkyl" to --($C_3$-$C_8$)cycloalkyl--.
In Column 56, Line 21, change "($C_1$-$C_8$)cycloalkyl" to --($C_3$-$C_8$)cycloalkyl--.
In Column 56, Line 24, change "($C_1$-$C_8$)cycloalkyl" to --($C_3$-$C_8$)cycloalkyl--.
In Column 56, Line 65, change "($C_1$-$C_8$)cycloalkyl" to --($C_3$-$C_8$)cycloalkyl--.
In Column 57, Line 3, change "($C_1$-$C_8$)cycloalkyl" to --($C_3$-$C_8$)cycloalkyl--.
In Column 57, Line 43, change "–$NR_2$" to -- –$NR^C_2$--.
In Column 57, Line 64, change "–$NR^B_2$" to -- –$NR^C_2$--.
In Column 58, Line 4, change "($C_1$-$C_8$)cycloalkyl" to --($C_3$-$C_8$)cycloalkyl--.
In Column 58, Line 9, change "($C_1$-$C_8$)cycloalkyl" to --($C_3$-$C_8$)cycloalkyl--.
In Column 58, Line 23, change "($C_1$-$C_8$)cycloalkyl" to --($C_3$-$C_8$)cycloalkyl--.
In Column 58, Line 29, change "($C_1$-$C_8$)cycloalkyl" to --($C_3$-$C_8$)cycloalkyl--.
In Column 58, Line 43, change "($C_1$-$C_8$)cycloalkyl" to --($C_3$-$C_8$)cycloalkyl--.
In Column 58, Line 49, change "($C_1$-$C_8$)cycloalkyl" to --($C_3$-$C_8$)cycloalkyl--.
In Column 58, Line 64, change "($C_1$-$C_8$)cycloalkyl" to --($C_3$-$C_8$)cycloalkyl--.
In Column 59, Line 2, change "($C_1$-$C_8$)cycloalkyl" to --($C_3$-$C_8$)cycloalkyl--.
In Column 59, Line 8, change "–OR" to -- –$OR^C$--.
In Column 59, Line 9, change "($C_1$-$C_6$)alkylene–$NR_2$" to -- –($C_1$-$C_6$)alkylene–$NR^C_2$--.
In Column 59, Line 16, change "($C_1$-$C_8$)cycloalkyl" to --($C_3$-$C_8$)cycloalkyl--.

CERTIFICATE OF CORRECTION (continued)
U.S. Pat. No. 10,000,520 B2

In Column 59, Line 19, change "$(C_1-C_8)$cycloalkyl" to --$(C_3-C_8)$cycloalkyl--.
In Column 59, Line 46, change "$(C_1-C_8)$cycloalkyl" to --$(C_3-C_8)$cycloalkyl--.
In Column 60, Line 1, change "$(C_1-C_8)$cycloalkyl" to --$(C_3-C_8)$cycloalkyl--.
In Column 60, Line 6, change "$(C_1-C_8)$cycloalkyl" to --$(C_3-C_8)$cycloalkyl--.
In Column 60, Line 35, change "–OR" to -- –OR$^B$--.
In Column 60, Line 39, change "–S(O)" to -- –S(O)R$^B$--.
In Column 61, Line 65, change "$(C_1-C_8)$cycloalkyl" to --$(C_3-C_8)$cycloalkyl--.
In Column 62, Line 3, change "$(C_1-C_8)$cycloalkyl" to --$(C_3-C_8)$cycloalkyl--.
In Column 62, Line 33, change "–C(=NR$^B$)NR$_2$" to -- –C(=NR$^B$)NR$^B_2$--.
In Column 62, Line 41, change "$(C_1-C_8)$cycloalkyl" to --$(C_3-C_8)$cycloalkyl--.
In Column 62, Line 47, change "$(C_1-C_8)$cycloalkyl" to --$(C_3-C_8)$cycloalkyl--.
In Column 62, Line 61, change "$(C_1-C_8)$cycloalkyl" to --$(C_3-C_8)$cycloalkyl--.
In Column 62, Line 67, change "$(C_1-C_8)$cycloalkyl" to --$(C_3-C_8)$cycloalkyl--.
In Column 63, Line 18, change "$(C_1-C_8)$cycloalkyl" to --$(C_3-C_8)$cycloalkyl--.
In Column 63, Line 24, change "$(C_1-C_8)$cycloalkyl" to --$(C_3-C_8)$cycloalkyl--.
In Column 63, Line 32, change "–OR" to -- –OR$^C$--.
In Column 63, Line 42, change "$(C_1-C_8)$cycloalkyl" to --$(C_3-C_8)$cycloalkyl--.
In Column 63, Line 45, change "$(C_1-C_8)$cycloalkyl" to --$(C_3-C_8)$cycloalkyl--.
In Column 65, Line 5, change "$(C_1-C_8)$cycloalkyl" to --$(C_3-C_8)$cycloalkyl--.
In Column 65, Line 10, change "$(C_1-C_8)$cycloalkyl" to --$(C_3-C_8)$cycloalkyl--.
In Column 65, Line 42, change "–NR$^B$C(O)NR$_2$" to -- –NR$^B$C(O)NR$^B_2$--.
In Column 65, Lines 51-52, change "–NR$^C$C(O)NR$_2$" to -- –NR$^C$C(O)NR$^C_2$--.
In Column 65, Line 58, change "$(C_1-C_8)$cycloalkyl" to --$(C_3-C_8)$cycloalkyl--.
In Column 65, Line 63, change "$(C_1-C_8)$cycloalkyl" to --$(C_3-C_8)$cycloalkyl--.
In Column 66, Line 12, change "$(C_1-C_8)$cycloalkyl" to --$(C_3-C_8)$cycloalkyl--.
In Column 66, Line 18, change "$(C_1-C_8)$cycloalkyl" to --$(C_3-C_8)$cycloalkyl--.
In Column 66, Line 33, change "$(C_1-C_8)$cycloalkyl" to --$(C_3-C_8)$cycloalkyl--.
In Column 66, Line 38, change "$(C_1-C_8)$cycloalkyl" to --$(C_3-C_8)$cycloalkyl--.
In Column 66, Line 52, change "$(C_1-C_8)$cycloalkyl" to --$(C_3-C_8)$cycloalkyl--.
In Column 66, Line 58, change "$(C_1-C_8)$cycloalkyl" to --$(C_3-C_8)$cycloalkyl--.
In Column 67, Line 6, change "$(C_1-C_8)$cycloalkyl" to --$(C_3-C_8)$cycloalkyl--.
In Column 67, Line 9, change "$(C_1-C_8)$cycloalkyl" to --$(C_3-C_8)$cycloalkyl--.
In Column 67, Line 52, change "$(C_1-C_8)$cycloalkyl" to --$(C_3-C_8)$cycloalkyl--.
In Column 67, Line 57, change "$(C_1-C_8)$cycloalkyl" to --$(C_3-C_8)$cycloalkyl--.
In Column 68, Line 58, change "$(C_1-C_8)$cycloalkyl" to --$(C_3-C_8)$cycloalkyl--.
In Coluum 68, Line 63, change "$(C_1-C_8)$cycloalkyl" to --$(C_3-C_8)$cycloalkyl--.
In Column 69, Line 11, change "$(C_1-C_8)$cycloalkyl" to --$(C_3-C_8)$cycloalkyl--.
In Column 69, Line 18, change "$(C_1-C_8)$cycloalkyl" to --$(C_3-C_8)$cycloalkyl--.
In Column 69, Line 33, change "$(C_1-C_8)$cycloalkyl" to --$(C_3-C_8)$cycloalkyl--.
In Column 69, Line 38, change "$(C_1-C_8)$cycloalkyl" to --$(C_3-C_8)$cycloalkyl--.
In Column 69, Line 52, change "$(C_1-C_8)$cycloalkyl" to --$(C_3-C_8)$cycloalkyl--.
In Column 69, Line 58, change "$(C_1-C_8)$cycloalkyl" to --$(C_3-C_8)$cycloalkyl--.
In Column 69, Line 66, change "NR$^C$C(O)O$(C_1-C_6)$alkyl" to -- –NR$^C$C(O)O$(C_1-C_6)$alkyl--.
In Column 70, Line 6, change "$(C_1-C_8)$cycloalkyl" to --$(C_3-C_8)$cycloalkyl--.
In Column 70, Line 10, change "$(C_1-C_8)$cycloalkyl" to --$(C_3-C_8)$cycloalkyl--.
In Column 90, Line 18, change "$(C_1-C_8)$cycloalkyl" to --$(C_3-C_8)$cycloalkyl--.

CERTIFICATE OF CORRECTION (continued)
U.S. Pat. No. 10,000,520 B2

In Column 90, Line 23, change "($C_1$-$C_8$)cycloalkyl" to --($C_3$-$C_8$)cycloalkyl--.
In Column 90, Lines 32-33, change "($C_1$-$C_6$)perfluoroalkyl" to -- –($C_1$-$C_6$)perfluoroalkyl--.
In Column 90, Line 35, change "–($CH_2$)$_3$–NH C($NH_2$)(=NH)" to -- –($CH_2$)$_3$–NH–C($NH_2$)(=NH)--.
In Column 90, Line 59, change "($C_1$-$C_6$)alkyl" to -- –($C_1$-$C_6$)alkyl--.
In Column 91, Line 4, change "–OC(O)($C_1$(C)alkyl" to -- –OC(O)($C_1$-$C_6$)alkyl--.
In Column 91, Line 20, change "–($C_1$-$C_8$)alkylene–OR$^C$" to -- –($C_1$-$C_6$)alkylene–OR$^C$--.
In Column 91, Line 24, change "($C_1$-$C_8$)cycloalkyl" to --($C_3$-$C_8$)cycloalkyl--.
In Column 91, Line 29, change "($C_1$-$C_8$)cycloalkyl" to --($C_3$-$C_8$)cycloalkyl--.
In Column 91, Line 43, change "($C_1$-$C_8$)cycloalkyl" to --($C_3$-$C_8$)cycloalkyl--.
In Column 91, Line 49, change "($C_1$-$C_8$)cycloalkyl" to --($C_3$-$C_8$)cycloalkyl--.
In Column 91, Lines 55-56, change "–OC(O)O($C_1$-$C_8$)alkyl" to -- –OC(O)O($C_1$-$C_6$)alkyl--.
In Column 91, Line 63, change "($C_1$-$C_8$)cycloalkyl" to --($C_3$-$C_8$)cycloalkyl--.
In Column 92, Line 2, change "($C_1$-$C_8$)cycloalkyl" to --($C_3$-$C_8$)cycloalkyl--.
In Column 92, Line 17, change "($C_1$-$C_8$)cycloalkyl" to --($C_3$-$C_8$)cycloalkyl--.
In Column 92, Line 22, change "($C_1$-$C_8$)cycloalkyl" to --($C_3$-$C_8$)cycloalkyl--.
In Column 92, Line 38, change "($C_1$-$C_8$)cycloalkyl" to --($C_3$-$C_8$)cycloalkyl--.
In Column 92, Line 43, change "($C_1$-$C_8$)cycloalkyl" to --($C_3$-$C_8$)cycloalkyl--.
In Column 92, Lines 52-53, change "–OSO$_2$($C_1$-$C_8$)alkyl" to -- –OSO$_2$($C_1$-$C_6$)alkyl--.
In Column 92, Line 58, change "($C_1$-$C_8$)cycloalkyl" to --($C_3$-$C_8$)cycloalkyl--.
In Column 92, Line 63, change "($C_1$-$C_8$)cycloalkyl" to --($C_3$-$C_8$)cycloalkyl--.
In Column 93, Line 11, change "($C_1$-$C_8$)cycloalkyl" to --($C_3$-$C_8$)cycloalkyl--.
In Column 93, Line 14, change "($C_1$-$C_8$)cycloalkyl" to --($C_3$-$C_8$)cycloalkyl--.

In the Claims

In Claim 1, Column 125, Line 48, change "($C_1$-$C_8$)cycloalkyl" to --($C_3$-$C_8$)cycloalkyl--.
In Claim 1, Column 125, Line 53, change "($C_1$-$C_8$)cycloalkyl" to --($C_3$-$C_8$)cycloalkyl--.
In Claim 1, Column 125, Lines 64-65, change "–($C_6$-$C_6$)perfluoroalkyl" to -- –($C_1$-$C_6$)perfluoroalkyl--.
In Claim 1, Column 126, Lines 35-36, change "–($C_2$-$C_6$)alkylene–OR$^C$" to
-- –($C_1$-$C_6$)alkylene–OR$^C$--.
In Claim 1, Column 126, Lines 40-41, change "($C_1$-$C_8$)cycloalkyl" to --($C_3$-$C_8$)cycloalkyl--.
In Claim 1, Column 126, Line 46, change "($C_1$-$C_8$)cycloalkyl" to --($C_3$-$C_8$)cycloalkyl--.
In Claim 1, Column 126, Line 60, change "($C_1$-$C_8$)cycloalkyl" to --($C_3$-$C_8$)cycloalkyl--.
In Claim 1, Column 126, Line 67, change "($C_1$-$C_8$)cycloalkyl" to --($C_3$-$C_8$)cycloalkyl--.
In Claim 1, Column 127, Lines 7-8, change "–($C_1$-$C_6$)alkylene NR$^C$$_2$" to -- –($C_1$-$C_6$)alkylene–NR$^C$$_2$--.
In Claim 1, Column 127, Line 15, change "($C_1$-$C_8$)cycloalkyl" to --($C_3$-$C_8$)cycloalkyl--.
In Claim 1, Column 127, Line 21, change "–CH–(R$^)$CO$_2$R$^B$" to -- –CH–(R$^A$)–CO$_2$R$^B$--.
In Claim 1, Column 127, Line 22, change "($C_1$-$C_8$)cycloalkyl" to --($C_3$-$C_8$)cycloalkyl--.
In Claim 1, Column 127, Line 38, change "($C_1$-$C_8$)cycloalkyl" to --($C_3$-$C_8$)cycloalkyl--.
In Claim 1, Column 127, Lines 43-44, change "($C_1$-$C_8$)cycloalkyl" to --($C_3$-$C_8$)cycloalkyl--.
In Claim 1, Column 127, Line 60, change "($C_1$-$C_8$)cycloalkyl" to --($C_3$-$C_8$)cycloalkyl--.
In Claim 1, Column 127, Lines 63-64, change "($C_1$-$C_8$)cycloalkyl" to --($C_3$-$C_8$)cycloalkyl--.
In Claim 1, Column 128, Line 24, change "($C_1$-$C_8$)cycloalkyl" to --($C_3$-$C_8$)cycloalkyl--.
In Claim 1, Column 128, Line 28, change "($C_1$-$C_8$)cycloalkyl" to --($C_3$-$C_8$)cycloalkyl--.
In Claim 1, Column 128, Line 30, change "X–" to --X$^-$--.
In Claim 1, Column 128, Line 30, change "0,Z2" to --0, $Z^2$--.

CERTIFICATE OF CORRECTION (continued)
U.S. Pat. No. 10,000,520 B2

Page 7 of 10

In Claim 1, Column 128, Line 31, change "R1" to --$R^1$--.
In Claim 1, Column 128, Line 31, change "R2" to --$R^2$--.
In Claim 1, Column 128, Line 31, change "R3" to --$R^3$--.
In Claim 1, Column 128, Line 31, change "R5" to --$R^5$--.
In Claim 1, Column 128, Line 32, change "R4" to --$R^4$--.
In Claim 1, Column 128, Line 32, change "–(C1-C6)alkyl" to -- –$(C_1-C_6)$alkyl--.
In Claim 1, Column 128, Line 33, change "R6" to --$R^6$--.
In Claim 1, Column 128, Line 33, change "R7" to --$R^7$--.
In Claim 1, Column 128, Line 34, change "R8" to --$R^8$--.
In Claim 2, Column 128, Line 59, change "$(C_1-C_8)$cycloalkyl" to --$(C_3-C_8)$cycloalkyl--.
In Claim 2, Column 128, Line 64, change "$(C_1-C_8)$cycloalkyl" to --$(C_3-C_8)$cycloalkyl--.
In Claim 2, Column 129, Line 53, change "–$NR_2$" to -- –$NR^C_2$--.
In Claim 2, Column 130, Lines 6-7, change "$(C_1-C_8)$cycloalkyl" to --$(C_3-C_8)$cycloalkyl--.
In Claim 2, Column 130, Line 11, change "$(C_1-C_6)$alkyl" to --$(C_1-C_8)$alkyl--.
In Claim 2, Column 130, Line 26, change "$(C_1-C_8)$cycloalkyl" to --$(C_3-C_8)$cycloalkyl--.
In Claim 2, Column 130, Line 33, change "$(C_1-C_8)$cycloalkyl" to --$(C_3-C_8)$cycloalkyl--.
In Claim 2, Column 130, Lines 40-41, change "–$(C_6-C_6)$alkylene–$NR^C_2$" to
-- –$(C_1-C_6)$alkylene–$NR^C_2$--.
In Claim 2, Column 130, Line 48, change "$(C_1-C_8)$cycloalkyl" to --$(C_3-C_8)$cycloalkyl--.
In Claim 2, Column 130, Line 55, change "$(C_1-C_8)$cycloalkyl" to --$(C_3-C_8)$cycloalkyl--.
In Claim 2, Column 130, Lines 62-63, change "$(C_1-C_6)$alkylene–$NR^C_2$" to
-- –$(C_1-C_6)$alkylene–$NR^C_2$--.
In Claim 2, Column 131, Line 4, change "$(C_1-C_8)$cycloalkyl" to --$(C_3-C_8)$cycloalkyl--.
In Claim 2, Column 131, Lines 9-10, change "$(C_1-C_8)$cycloalkyl" to --$(C_3-C_8)$cycloalkyl--.
In Claim 2, Column 131, Line 27, change "$(C_1-C_8)$cycloalkyl" to --$(C_3-C_8)$cycloalkyl--.
In Claim 2, Column 131, Lines 30-31, change "$(C_1-C_8)$cycloalkyl" to --$(C_3-C_8)$cycloalkyl--.
In Claim 2, Column 131, Line 62, change "$(C_1-C_8)$cycloalkyl" to --$(C_3-C_8)$cycloalkyl--.
In Claim 3, Column 132, Line 28, change "$(C_1-C_8)$cycloalkyl" to --$(C_3-C_8)$cycloalkyl--.
In Claim 3, Column 132, Line 33, change "$(C_1-C_8)$cycloalkyl" to --$(C_3-C_8)$cycloalkyl--.
In Claim 3, Column 132, Line 41, change "–$(C_1-C_6)$alkylene–$NR_2$" to -- –$(C_1-C_6)$alkylene–$NR^C_2$--.
In Claim 3, Column 133, Lines 20-21, change "$(C_1-C_8)$cycloalkyl" to --$(C_3-C_8)$cycloalkyl--.
In Claim 3, Column 133, Line 26, change "$(C_1-C_8)$cycloalkyl" to --$(C_3-C_8)$cycloalkyl--.
In Claim 3, Column 133, Line 29, change "–$(C_1-C_8)$alkyl" to -- –$(C_1-C_6)$alkyl--.
In Claim 3, Column 133, Line 32, change "–$OC(O)O(C_1-C_8)$alkyl" to -- –$OC(O)O(C_1-C_6)$alkyl--.
In Claim 3, Column 133, Line 34, change "–$NR^CC(O)NR_2$" to -- –$NR^CC(O)NR^C_2$--.
In Claim 3, Column 133, Line 40, change "$(C_1-C_8)$cycloalkyl" to --$(C_3-C_8)$cycloalkyl--.
In Claim 3, Column 133, Line 47, change "$(C_1-C_8)$cycloalkyl" to --$(C_3-C_8)$cycloalkyl--.
In Claim 3, Column 133, Lines 50-51, change "–$(C_1-C_8)$alkyl" to -- –$(C_1-C_6)$alkyl--.
In Claim 3, Column 133, Line 53, change "–$OC(O)(C_1-C_8)$alkyl" to -- –$OC(O)(C_1-C_6)$alkyl--.
In Claim 3, Column 133, Line 54, change "–$OC(O)O(C_1-C_8)$alkyl" to -- –$OC(O)O(C_1-C_6)$alkyl--.
In Claim 3, Column 133, Line 62, change "$(C_1-C_8)$cycloalkyl" to --$(C_3-C_8)$cycloalkyl--.
In Claim 3, Column 134, Line 1, change "–$C^{}H$–$(R^A)$–$CO_2R$" to -- –$C^{}H$–$(R^A)$–$CO_2R^B$--.
In Claim 3, Column 134, Line 2, change "$(C_1-C_8)$cycloalkyl" to --$(C_3-C_8)$cycloalkyl--.
In Claim 3, Column 134, Lines 5-6, change "–$(C_1-C_8)$alkyl" to -- –$(C_1-C_6)$alkyl--.
In Claim 3, Column 134, Line 9, change "–$OC(O)O(C_1-C_{56})$alkyl" to -- –$OC(O)O(C_1-C_6)$alkyl--.
In Claim 3, Column 134, Line 19, change "$(C_1-C_8)$cycloalkyl" to --$(C_3-C_8)$cycloalkyl--.

CERTIFICATE OF CORRECTION (continued)

In Claim 3, Column 134, Lines 24-25, change "$(C_1-C_8)$cycloalkyl" to --$(C_3-C_8)$cycloalkyl--.
In Claim 3, Column 134, Line 43, change "$(C_1-C_5)$cycloalkyl" to --$(C_3-C_8)$cycloalkyl--.
In Claim 3, Column 134, Lines 46-47, change "$(C_1-C_8)$cycloalkyl" to --$(C_3-C_8)$cycloalkyl--.
In Claim 3, Column 134, Line 50, change "–$(C_1-C_8)$alkyl" to -- –$(C_1-C_6)$alkyl--.
In Claim 3, Column 135, Lines 20-21, change "$(C_1-C_8)$cycloalkyl" to --$(C_3-C_8)$cycloalkyl--.
In Claim 3, Column 135, Line 26, change "$(C_1-C_8)$cycloalkyl" to --$(C_3-C_8)$cycloalkyl--.
In Claim 3, Column 135, Line 66, change "$(C_1-C_8)$cycloalkyl" to --$(C_3-C_8)$cycloalkyl--.
In Claim 3, Column 136, Line 6, change "$(C_1-C_8)$cycloalkyl" to --$(C_3-C_8)$cycloalkyl--.
In Claim 3, Column 136, Line 21, change "$(C_1-C_8)$cycloalkyl" to --$(C_3-C_8)$cycloalkyl--.
In Claim 3, Column 136, Line 28, change "$(C_1-C_8)$cycloalkyl" to --$(C_3-C_8)$cycloalkyl--.
In Claim 3, Column 136, Lines 42-43, change "–C(O)HR'" to -- –C(O)NHR'--.
In Claim 3, Column 136, Line 44, change "$(C_1-C_8)$cycloalkyl" to --$(C_3-C_8)$cycloalkyl--.
In Claim 3, Column 136, Lines 49-50, change "$(C_1-C_8)$cycloalkyl" to --$(C_3-C_8)$cycloalkyl--.
In Claim 3, Column 136, Line 66, change "$(C_1-C_8)$cycloalkyl" to --$(C_3-C_8)$cycloalkyl--.
In Claim 3, Column 137, Lines 2-3, change "$(C_1-C_5)$cycloalkyl" to --$(C_3-C_8)$cycloalkyl--.
In Claim 3, Column 137, Line 42, change "$(C_1-C_8)$cycloalkyl" to --$(C_3-C_8)$cycloalkyl--.
In Claim 3, Column 137, Line 47, change "$(C_1-C_8)$cycloalkyl" to --$(C_3-C_8)$cycloalkyl--.
In Claim 5, Column 139, Line 28, change "$(C_1-C_8)$cycloalkyl" to --$(C_3-C_8)$cycloalkyl--.
In Claim 5, Column 139, Line 33, change "$(C_1-C_8)$cycloalkyl" to --$(C_3-C_8)$cycloalkyl--.
In Claim 5, Column 139, Line 66, change "–C(=NR$^B$)NR$_2$" to -- –C(=NR$^B$)NR$^B_2$--.
In Claim 5, Column 139, Line 66, change "–OR" to -- –OR$^B$--.
In Claim 5, Column 139, Lines 66-67, change "–OC(O)O($C_3-C_6$)alkyl" to -- –OC(O)O($C_1-C_6$)alkyl--.
In Claim 5, Column 140, Lines 20-21, change "$(C_1-C_8)$cycloalkyl" to --$(C_3-C_8)$cycloalkyl--.
In Claim 5, Column 140, Line 26, change "$(C_1-C_8)$cycloalkyl" to --$(C_3-C_8)$cycloalkyl--.
In Claim 5, Column 140, Line 31, change "–C(O)NR$_2$" to -- –C(O)NR$^C_2$--.
In Claim 5, Column 140, Line 40, change "$(C_1-C_8)$cycloalkyl" to --$(C_3-C_8)$cycloalkyl--.
In Claim 5, Column 140, Line 46, change "–CH–(R$^A$)–CO$_2$R" to -- –CH–(R$^A$)–CO$_2$R$^B$--.
In Claim 5, Column 140, Line 47, change "$(C_1-C_8)$cycloalkyl" to --$(C_3-C_8)$cycloalkyl--.
In Claim 5, Column 140, Line 50, change "form" to --from--.
In Claim 5, Column 140, Lines 54-55, change "–$C_1$–NC$_6$)alkylene–NR$^C_2$" to -- –($C_1$-$C_6$)alkylene–NR$^C_2$--.
In Claim 5, Column 140, Line 62, change "$(C_1-C_8)$cycloalkyl" to --$(C_3-C_8)$cycloalkyl--.
In Claim 5, Column 141, Line 2, change "$(C_1-C_8)$cycloalkyl" to --$(C_3-C_8)$cycloalkyl--.
In Claim 5, Column 141, Line 7, change "–C(O)NR$_2$" to -- –C(O)NR$^C_2$--.
In Claim 5, Column 141, Line 19, change "$(C_1-C_8)$cycloalkyl" to --$(C_3-C_8)$cycloalkyl--.
In Claim 5, Column 141, Lines 24-25, change "$(C_1-C_8)$cycloalkyl" to --$(C_3-C_8)$cycloalkyl--.
In Claim 5, Column 141, Line 42, change "$(C_1-C_8)$cycloalkyl" to --$(C_3-C_8)$cycloalkyl--.
In Claim 5, Column 141, Lines 45-46, change "$(C_1-C_8)$cycloalkyl" to --$(C_3-C_8)$cycloalkyl--.
In Claim 5, Column 142, Line 28, change "$(C_1-C_8)$cycloalkyl" to --$(C_3-C_8)$cycloalkyl--.
In Claim 5, Column 142, Line 33, change "$(C_1-C_8)$cycloalkyl" to --$(C_3-C_8)$cycloalkyl--.
In Claim 5, Column 142, Line 63, change "–$(C_1-C_8)$alkyl" to -- –$(C_1-C_6)$alkyl--.
In Claim 5, Column 143, Lines 15-16, change "–$(C_1-C_8)$alkylene–OR$^C$" to -- –$(C_1-C_6)$alkylene–OR$^C$--.
In Claim 5, Column 143, Line 20, change "$(C_1-C_8)$cycloalkyl" to --$(C_3-C_8)$cycloalkyl--.
In Claim 5, Column 143, Lines 25-26, change "$(C_1-C_8)$cycloalkyl" to --$(C_3-C_8)$cycloalkyl--.
In Claim 5, Column 143, Line 30, change "–$(C_1-C_8)$alkyl" to -- –$(C_1-C_6)$alkyl--.
In Claim 5, Column 143, Line 35, change "–NR$_2$" to -- –NR$^C_2$--.

CERTIFICATE OF CORRECTION (continued)
U.S. Pat. No. 10,000,520 B2

In Claim 5, Column 143, Line 41, change "$(C_1-C_8)$cycloalkyl" to --$(C_3-C_8)$cycloalkyl--.
In Claim 5, Column 143, Line 48, change "$(C_1-C_8)$cycloalkyl" to --$(C_3-C_8)$cycloalkyl--.
In Claim 5, Column 143, Lines 55-56, change "$(C_1-C_6)$alkylene–NR$^C_2$" to
-- –$(C_1-C_6)$alkylene–NR$^C_2$--.
In Claim 5, Column 143, Lines 64-65, change "$(C_1-C_8)$cycloalkyl" to --$(C_3-C_8)$cycloalkyl--.
In Claim 5, Column 144, Line 3, change "$(C_1-C_8)$cycloalkyl" to --$(C_3-C_8)$cycloalkyl--.
In Claim 5, Column 144, Line 10, change "–$(C_1-C_8)$allylene–NR$^C_2$" to -- –$(C_1-C_6)$alkylene–NR$^C_2$--.
In Claim 5, Column 144, Line 18, change "$(C_1-C_8)$cycloalkyl" to --$(C_3-C_8)$cycloalkyl--.
In Claim 5, Column 144, Line 25, change "$(C_1-C_8)$cycloalkyl" to --$(C_3-C_8)$cycloalkyl--.
In Claim 5, Column 144, Line 36, change "–SO$_2$NR$_2$" to -- –SO$_2$NR$^C_2$--.
In Claim 5, Column 144, Line 41, change "$(C_1-C_8)$cycloalkyl" to --$(C_3-C_8)$cycloalkyl--.
In Claim 5, Column 144, Line 52, change "–$(C_1-C_6)$alkylene–NR$_2$" to -- –$(C_1-C_6)$alkylene–NR$^C_2$--.
In Claim 6, Column 145, Line 47, change "$(C_1-C_8)$cycloalkyl" to --$(C_3-C_8)$cycloalkyl--.
In Claim 6, Column 145, Line 52, change "$(C_1-C_8)$cycloalkyl" to --$(C_3-C_8)$cycloalkyl--.
In Claim 6, Column 146, Lines 39-40, change "$(C_1-C_8)$cycloalkyl" to --$(C_3-C_8)$cycloalkyl--.
In Claim 6, Column 146, Line 45, change "$(C_1-C_8)$cycloalkyl" to --$(C_3-C_8)$cycloalkyl--.
In Claim 6, Column 146, Line 51, change "–OC(O)$(C_1-C_8)$alkyl" to -- –OC(O)$(C_1-C_6)$alkyl--.
In Claim 6, Column 146, Line 59, change "$(C_1-C_8)$cycloalkyl" to --$(C_3-C_8)$cycloalkyl--.
In Claim 6, Column 146, Line 66, change "$(C_1-C_8)$cycloalkyl" to --$(C_3-C_8)$cycloalkyl--.
In Claim 6, Column 147, Line 12, change "$(C_1-C_8)$cycloalkyl" to --$(C_3-C_8)$cycloalkyl--.
In Claim 6, Column 147, Line 19, change "$(C_1-C_8)$cycloalkyl" to --$(C_3-C_8)$cycloalkyl--.
In Claim 6, Column 147, Line 35, change "$(C_1-C_8)$cycloalkyl" to --$(C_3-C_8)$cycloalkyl--.
In Claim 6, Column 147, Lines 40-41, change "$(C_1-C_8)$cycloalkyl" to --$(C_3-C_8)$cycloalkyl--.
In Claim 6, Column 147, Line 57, change "$(C_1-C_8)$cycloalkyl" to --$(C_3-C_8)$cycloalkyl--.
In Claim 6, Column 147, Lines 60-61, change "$(C_1-C_8)$cycloalkyl" to --$(C_3-C_8)$cycloalkyl--.
In Claim 6, Column 148, Line 34, change "$(C_1-C_8)$cycloalkyl" to --$(C_3-C_8)$cycloalkyl--.
In Claim 6, Column 148, Line 39, change "$(C_1-C_8)$cycloalkyl" to --$(C_3-C_8)$cycloalkyl--.
In Claim 6, Column 149, Lines 47-48, change "$(C_1-C_8)$cycloalkyl" to --$(C_3-C_8)$cycloalkyl--.
In Claim 6, Column 149, Line 53, change "$(C_1-C_8)$cycloalkyl" to --$(C_3-C_8)$cycloalkyl--.
In Claim 6, Column 149, Line 67, change "$(C_1-C_8)$cycloalkyl" to --$(C_3-C_8)$cycloalkyl--.
In Claim 6, Column 150, Line 7, change "$(C_1-C_8)$cycloalkyl" to --$(C_3-C_8)$cycloalkyl--.
In Claim 6, Column 150, Line 22, change "$(C_1-C_8)$cycloalkyl" to --$(C_3-C_8)$cycloalkyl--.
In Claim 6, Column 150, Line 29, change "$(C_1-C_8)$cycloalkyl" to --$(C_3-C_8)$cycloalkyl--.
In Claim 6, Column 150, Line 45, change "$(C_1-C_8)$cycloalkyl" to --$(C_3-C_8)$cycloalkyl--.
In Claim 6, Column 150, Lines 50-51, change "$(C_1-C_8)$cycloalkyl" to --$(C_3-C_8)$cycloalkyl--.
In Claim 6, Column 150, Line 58, change "–OC(O)$(C_1-C_8)$alkyl" to -- –OC(O)$(C_1-C_6)$alkyl--.
In Claim 6, Column 150, Line 63, change "–$(C_1-C_8)$perfluoroalkyl" to -- –$(C_1-C_6)$perfluoroalkyl--.
In Claim 6, Column 150, Line 67, change "$(C_1-C_8)$cycloalkyl" to --$(C_3-C_8)$cycloalkyl--.
In Claim 6, Column 151, Lines 3-4, change "$(C_1-C_8)$cycloalkyl" to --$(C_3-C_8)$cycloalkyl--.
In Claim 7, Column 151, Line 52, change "$(C_1-C_8)$cycloalkyl" to --$(C_3-C_8)$cycloalkyl--.
In Claim 7, Column 151, Line 57, change "$(C_1-C_8)$cycloalkyl" to --$(C_3-C_8)$cycloalkyl--.
In Claim 7, Column 151, Line 65, change "$(C_1-C_6)$alkylene–NR$^C_2$" to -- –$(C_1-C_6)$alkylene–NR$^C_2$--.
In Claim 7, Column 152, Line 22, change "–C(O)NR$^C_2$" to -- –C(O)NR$^B_2$--.
In Claim 7, Column 152, Line 65, change "$(C_1-C_8)$cycloalkyl" to --$(C_3-C_8)$cycloalkyl--.
In Claim 7, Column 153, Lines 3-4, change "$(C_1-C_8)$cycloalkyl" to --$(C_3-C_8)$cycloalkyl--.
In Claim 7, Column 153, Line 19, change "$(C_1-C_8)$cycloalkyl" to --$(C_3-C_8)$cycloalkyl--.

CERTIFICATE OF CORRECTION (continued)
U.S. Pat. No. 10,000,520 B2

In Claim 7, Column 153, Line 26, change "$(C_1-C_8)$cycloalkyl" to --$(C_3-C_8)$cycloalkyl--.
In Claim 7, Column 153, Lines 42-43, change "$(C_1-C_8)$cycloalkyl" to --$(C_3-C_8)$cycloalkyl--.
In Claim 7, Column 153, Line 48, change "$(C_1-C_8)$cycloalkyl" to --$(C_3-C_8)$cycloalkyl--.
In Claim 7, Column 153, Line 62, change "$(C_1-C_8)$cycloalkyl" to --$(C_3-C_8)$cycloalkyl--.
In Claim 7, Column 154, Line 2, change "$(C_1-C_8)$cycloalkyl" to --$(C_3-C_8)$cycloalkyl--.
In Claim 7, Column 154, Line 18, change "$(C_1-C_8)$cycloalkyl" to --$(C_3-C_8)$cycloalkyl--.
In Claim 7, Column 154, Lines 21-22, change "$(C_1-C_8)$cycloalkyl" to --$(C_3-C_8)$cycloalkyl--.

EX PARTE REEXAMINATION CERTIFICATE (12622nd)

United States Patent
Migaud et al.

(10) Number: US 10,000,520 C1
(45) Certificate Issued: Jun. 12, 2024

(54) B-VITAMIN AND AMINO ACID CONJUGATES OF NICOTINOYL RIBOSIDES AND REDUCED NICOTINOYL RIBOSIDES, DERIVATIVES THEREOF, AND METHODS OF PREPARATION THEREOF

(71) Applicants: ChromaDex Inc., Irvine, CA (US); The Queen's University of Belfast, Belfast (GB)

(72) Inventors: Marie Eugenie Migaud, Lurgan (GB); Philip Redpath, Portadown (GB); Kerri Crossey, Magherafelt (GB); Richard Cunningham, Portadown (GB); Ryan Dellinger, Azusa, CA (US); Troy Rhonemus, Mission Viejo, CA (US); Sylesh Venkataraman, Irvine, CA (US); Brian Nettles, Irvine, CA (US)

(73) Assignee: CHROMADEX, INC., Irvine, CA (US)

Reexamination Request:
No. 90/019,344, Dec. 20, 2023

Reexamination Certificate for:
Patent No.: 10,000,520
Issued: Jun. 19, 2018
Appl. No.: 15/461,126
Filed: Mar. 16, 2017

Certificate of Correction issued Dec. 11, 2018

Related U.S. Application Data

(60) Provisional application No. 62/309,273, filed on Mar. 16, 2016.

(51) Int. Cl.
C07H 19/048 (2006.01)
C07H 1/00 (2006.01)
C07H 19/04 (2006.01)

(52) U.S. Cl.
CPC ............ *C07H 19/048* (2013.01); *C07H 1/00* (2013.01); *C07H 19/04* (2013.01)

(58) Field of Classification Search
None
See application file for complete search history.

(56) References Cited

To view the complete listing of prior art documents cited during the proceeding for Reexamination Control Number 90/019,344, please refer to the USPTO's Patent Electronic System.

*Primary Examiner* — Jerry D Johnson

(57) ABSTRACT

The present disclosure provides nicotinate/nicotinamide riboside compounds or derivatives of formula (I):

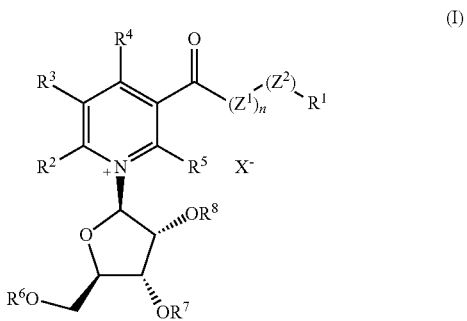

wherein $X^-$, $Z^1$, $Z^2$, n, $R^1$, $R^2$, $R^3$, $R^4$, $R^5$, $R^6$, $R^7$, and $R^8$ are described herein, reduced analogs thereof, and synthetic processes for the preparation thereof.

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 3-7 is confirmed.

Claims 1 and 2 are determined to be patentable as amended.

Claims 8 and 9, dependent on an amended claim, are determined to be patentable.

New claims 10-18 are added and determined to be patentable.

1. A nicotinate/nicotinamide riboside compound or derivative of formula (I), or a salt, hydrate, or solvate thereof:

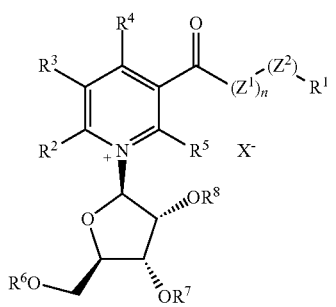

(I)

wherein $X^-$ as counterion is absent, or when $X^-$ is present, $X^-$ is selected from the group consisting of fluoride, chloride, bromide, iodide, formate, acetate, ascorbate, benzoate, carbonate, citrate, carbamate, formate, gluconate, lactate, methyl bromide, methyl sulfate, nitrate, phosphate, diphosphate, succinate, sulfate, trifluoromethanesulfonate, trichloromethanesulfonate, tribromomethanesulfonate, and trifluoroacetate;

$Z^1$ and $Z^2$ re independently NH or oxygen;

n is 0 or 1;

$R^1$ is selected from the group consisting of hydrogen, substituted or unsubstituted $(C_1-C_8)$alkyl, substituted or unsubstituted $(C_3-C_8)$cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—$(R^A)$—$CO_2R^B$; wherein the substituted $(C_1-C_8)$alkyl, substituted $(C_3-C_8)$cycloalkyl, substituted aryl, substituted heteroaryl, and substituted heterocycle are substituted with one to five substituents independently selected from the group consisting of —$(C_1-C_6)$alkyl, —$(C_2-C_6)$alkenyl, —$(C_2-C_6)$alkynyl, halogen, —CN, —$NO_2$, —$C(O)R^c$, —$C(O)OR^c$, —$C(O)NR^c_2$, —$C(=NR^c)NR^c_2$, —$OR^c$, —$OC(O)(C_1-C_6)$alkyl, —$OC(O)O(C_1-C_6)$alkyl, —$OC(O)NR^c_2$, —$(C_1-C_6)$alkylene—$NR^c_2$, —$NR^c_2$, —$NR^cC(O)R^c$, —$NR^cC(O)O(C_1-C_6)$alkyl, —$NR^cC(O)NR^c_2$, —$NR^cSO_2NR^c_2$, —$SR^c$, —$S(O)R^c$, —$SO_2R^c$, —$OSO_2(C_1-C_6)$alkyl, —$SO_2NR^c_2$, —$(C_1-C_6)$perfluoroalkyl, and —$(C_1-C_6)$alkylene—$OR^c$;

$R^A$ is selected from the group consisting of —H, —$(C_1-C_6)$alkyl, —$(CH_2)_3$—NH—$C(NH_2)(=NH)$, —$CH_2C(=O)NH_2$, —$CH_2COOH$, —$CH_2SH$, —$(CH_2)_2C(=O)$—$NH_2$, —$(CH_2)_2COOH$, —$CH_2$—(2-imidazolyl), —$CH(CH_3)$—$CH_2$—$CH_3$, —$CH_2CH(CH_3)_2$, —$(CH_2)_4$—$NH_2$, —$(CH_2)_2S$—$CH_3$, phenyl, —$CH_2$—phenyl, —$CH_2$—OH, —$CH(OH)$—$CH_3$, —$CH_2$—(3-indoly), —$CH_2$-(4-hydroxyphenyl), —$CH(CH_3)_2$, and —$CH_2$—$CH_3$;

$R^B$ is hydrogen or —$(C_1-C_8)$alkyl;

each $R^c$ is independently selected from the group consisting of hydrogen, —$(C_1-C_8)$alkyl, substituted or unsubstituted pyridyl, substituted or unsubstituted 1,4-dihydropyridyl, a radical of the compound of formula (I), and vitamin B7 ester (biotinyl); wherein the substituted pyridyl and substituted 1,4-dihydropyridyl are substituted with one to five substituents independently selected from the group consisting of —$(C_1-C_6)$alkyl, —$(C_1-C_6)$alkenyl, —$(C_2-C_6)$alkynyl, halogen, —CN, —$NO_2$, —$C(O)R^B$, —$C(O)OR^B$, —$C(O)NR^B_2$, —$C(=NR^B)NR^B_2$, —$OR^B$, —$OC(O)(C_1-C_6)$alkyl, —$OC(O)O(C_1-C_6)$alkyl, —$OC(O)NR^B_2$, —$(C_1-C_6)$alkylene-$NR^B_2$, —$NR^B_2$, —$NR^BC(O)R^B$, —$NR^BC(O)O(C_1-C_6)$alkyl, —$NR^BC(O)NR^B_2$, —$NR^BSO_2NR^B_2$, —$SR^B$, —$S(O)R^B$, —$SO_2R^B$, —$OSO_2(C_1-C_6)$alkyl, —$SO_2NR^B_2$, —$(C_1-C_6)$perfluoroalkyl, and —$(C_1-C_6)$alkylene—$OR^B$;

$R^2$, $R^3$, $R^4$, and $R^5$ are each independently selected from the group consisting of hydrogen, —$(C_1-C_6)$alkyl, —$(C_2-C_6)$alkenyl, —$(C_2-C_6)$alkynyl, halogen, —CN, —$NO_2$, —$C(O)R^c$, —$C(O)OR^c$, —$C(O)NR^c_2$, —$C(=NR^c)NR^c_2$, —$OR^c$, —$OC(O)(C_1-C_6)$alkyl, —$OC(O)O(C_1-C_6)$alkyl, —$OC(O)NR^c_2$, —$(C_1-C_6)$alkylene—$NR^c_2$, —$NR^c_2$, —$NR^cC(O)R^c$, —$NR^cC(O)O(C_1-C_6)$alkyl, —$NR^cC(O)NR^c_2$, —$NR^cSO_2NR^c_2$, —$SR^c$, —$S(O)R^c$, —$SO_2R^c$, —$OSO_2(C_1-C_6)$alkyl, —$SO_2NR^c_2$, —$(C_1-C_6)$perfluoroalkyl, and —$(C_1-C_6)$alkylene—$OR^c$;

$R^6$ is selected from the group consisting of hydrogen, —C(O)R', —C(O)OR', —C(O)NHR', —$P(O)(OY^1)(OY^2)$, —$P(O)(OY^1)(NHR'')$, substituted or unsubstituted $(C_1-C_8)$alkyl, substituted or unsubstituted $(C_3-C_8)$cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—$(R^A)$—$CO_2R^B$; wherein the substituted $(C_1-C_8)$alkyl, substituted $(C_3-C_8)$cycloalkyl, substituted aryl, substituted heteroaryl, and substituted heterocycle are substituted with one to five substituents independently selected from the group consisting of —$(C_1-C_6)$alkyl, —$(C_2-C_6)$alkenyl, —$(C_2-C_6)$alkynyl, halogen, —CN, —$NO_2$, —$C(O)R^c$, —$C(O)OR^c$, —$C(O)NR^c_2$, —$C(=NR^c)NR^c_2$, —$OR^c$, —$OC(O)(C_1-C_6)$alkyl, —$OC(O)O(C_1-C_6)$alkyl, —$OC(O)NR^c_2$, —$(C_1-C_6)$alkylene-$NR^c_2$, —$NR^c_2$, —$NR^cC(O)R^c$, —$NR^cC(O)O(C_1-C_6)$alkyl, —$NR^cC(O)NR^c_2$, —$NR^cSO_2NR^c_2$, —$SR^c$, —$S(O)R^c$, —$SO_2R^c$, —$OSO_2(C_1-C_6)$alkyl, —$SO_2NR^c_2$, —$(C_1-C_6)$perfluoroalkyl, and —$(C_1-C_6)$alkylene—$OR^c$;

R' is selected from the group consisting of hydrogen, substituted or unsubstituted $(C_1-C_8)$alkyl, substituted or unsubstituted $(C_3-C_8)$cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—($R^A$)—$CO_2R^B$; wherein the substituted ($C_1C_8$)alkyl, substituted ($C_3$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN —$NO_2$, —C(O)$R^c$, —C(O)O$R^c$, —C(O)$NR^c_2$, —C(=$NR^c$)$NR^c_2$, —O$R^c$, —OC(O)($C_1$-$C_6$)alkyl, —OC(O)O($C_1$-$C_6$)alkyl, —OC(O)$NR^c_2$, —($C_1$-$C_6$)alkylene-$NR^c_2$, —$NR^c_2$, —$NR^c$C(O)$R^c$, —$NR^c$C(O)O ($C_1$-$C_6$)alkyl, —$NR^c$C(O)$NR^c_2$, —$NR^c$$SO_2NR^c_2$, —$SR^c$, —S(O)$R^c$, —$SO_2R^c$, —$OSO_2$($C_1$-$C_6$)alkyl, —$SO_2NR^c_2$, —($C_1$-$C_6$)perfluoroalkyl, and —($C_1$-$C_6$)alkylene-O$R^c$;

R" is selected from the group consisting of hydrogen, substituted or unsubstituted ($C_1$-$C_8$)alkyl, substituted or unsubstituted ($C_3$-$C_8$)cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—($R^A$)—$CO_2R^B$; wherein the substituted ($C_1$-$C_8$)alkyl, substituted ($C_3$-$C_8$)cycloalkyl, substituted aryl, substituted heteroaryl, and substituted heterocycle are substituted with one to five substituents independently selected from the group consisting of —($C_1C_6$)alkyl, —($C_2$-$C_6$)alkenyl, —($C_2$-$C_6$)alkynyl, halogen, —CN, —$NO_2$, —C(O)$R^c$, —C(O)O$R^c$, —C(O)$NR^c_2$, —C(=$NR^c$)$NR^c_2$, —O$R^c$, —OC(O)($C_1$-$C_6$)alkyl, —OC(O)O($C_1$-$C_6$)alkyl, —OC(O)$NR^c_2$, —($C_1$-$C_6$)alkylene—$NR^c_2$, —$NR^c_2$, —$NR^c$C(O)$R^c$, —$NR^c$C(O)O ($C_1C_6$)alkyl, —$NR^c$C(O)$NR^c_2$, —$NR^c$$SO_2NR^c_2$, —$SR^c$, —S(O)$R^c$, —$SO_2R^c$, —$OSO_2$($C_1C_6$)alkyl, —$SO_2NR^c_2$, —($C_1$-$C_6$)perfluoroalkyl, and —($C_1$-$C_6$)alkylene—O$R^c$;

$R^7$ and $R^8$ are independently selected from the group consisting of hydrogen, —C(O)R', —C(O)OR', —C(O)NHR', substituted or unsubstituted ($C_1$-$C_8$)alkyl, substituted or unsubstituted ($C_3$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl; wherein the substituted ($C_1$-$C_8$)alkyl, substituted ($C_3$-$C_8$)cycloalkyl, substituted aryl, substituted heteroaryl, substituted heterocycle, substituted aryl($C_1$-$C_4$)alkyl, and substituted heterocycle($C_1$-$C_4$)alkyl are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^c$, —C(O)O$R^c$, —C(O)$NR^c_2$, —C(=N=$NR^c$)$NR^c_2$, —O$R^c$, —OC(O)($C_1$-$C_6$)alkyl, —OC(O)O($C_1$-$C_6$)alkyl, —OC(O)$NR^c_2$, —($C_1$-$C_6$)alkylene—$NR^c_2$, $NR^c_2$, —$NR^c$C(O)$R^c$, $NR^c$C(O)O($C_1$-$C_6$)alkyl, —$NR^c$C(O)$NR^c_2$, —$NR^c$$SO_2NR^c_2$, —$SR^c$, —S(O)$R^c$, —$SO_2R^c$, —$OSO_2$($C_1$-$C_6$)alkyl, —$SO_2NR^c_2$, —($C_1$-$C_6$)perfluoroalkyl, and —($C_1$-$C_6$)alkylene-O$R^c$;

$Y^1$ and $Y^2$ are independently selected from the group consisting of hydrogen, sodium, potassium, lithium, substituted or unsubstituted ($C_1$-$C_8$)alkyl, substituted or unsubstituted ($C_3$-$C_8$)cycloalkyl, substituted or unsubstituted aryl, substituted or unsubstituted heteroaryl, and substituted or unsubstituted heterocycle; wherein the substituted ($C_1$-$C_8$)alkyl, substituted ($C_3$-$C_8$)cycloalkyl, substituted aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^c$, —C(O)O$R^c$, —C(O)$NR^c_2$, —C(=$NR^c$)$NR^c_2$, —O$R^c$, —OC(O)($C_1$-$C_6$)alkyl, —OC(O)O($C_1$-$C_6$)alkyl, —OC(O)$NR^c_2$, —($C_1$-$C_6$)alkylene—$NR^c_2$, —$NR^c_2$, —$NR^c$C(O)$R^c$, —$NR^c$C(O)O($C_1$-$C_6$)alkyl, —$NR^c$C(O)$NR^c_2$, —$NR^c$$SO_2NR^c_2$, —$SR^c$, —S(O)$R^c$, —$SO_2R^c$, —$OSO_2$($C_1$-$C_6$)alkyl, —$SO_2NR^c_2$, —($C_1$-$C_6$)perfluoroalkyl, and —($C_1$-$C_6$)alkylene—O$R^c$; or, alternatively, $Y^1$ and $Y^2$ taken together are selected from the group consisting of sodium, potassium, lithium, magnesium, calcium, strontium, and barium;

provided that when $Z^2$ is NH, the absolute configuration of C** is R or S, or a mixture of R and S;

further provided that when n is 0, $Z^2$ is NH, and $R^1$ is hydrogen, then $R^6$, $R^7$, and $R^8$ are not all simultaneously hydrogen;

further provided that when n is 0, $Z^2$ is NH, and $R^1$, $R^2$, $R^3$, $R^4$, and $R^5$ are each hydrogen, then $R^6$ is not —C(O)R' or —C(O)OR' where R' is alkyl, and each of $R^7$ and $R^8$ are not independently hydrogen, —C(O)R', or —C(O)OR', where R' is alkyl;

further provided that when n is 0, $Z^2$ is NH, $R^1$ is *hydrogen,* ($C_1$-$C_8$)alkyl or ($C_3$-$C_8$)cycloalkyl, and $R^2$, $R^3$, $R^4$, and $R^5$ are each hydrogen, then each of $R^6$, $R^7$, and $R^8$ are not independently hydrogen or —C(O)R';

further provided that when n is 0, $Z^2$ is oxygen, $R^1$ is ($C_1$-$C_8$)alkyl, ($C_3$-$C_8$)cycloalkyl, aryl, or substituted aryl, and $R^2$, $R^3$, $R^4$, and $R^5$ are each hydrogen, then $R^6$, $R^7$, $R^8$ are not all simultaneously —C(O)R' further provided that when $X^-$ is absent, n is 0, $Z^2$ is oxygen, $R^1$ is hydrogen, $R^2$, $R^3$, and $R^5$ are each hydrogen, and $R^4$ is hydrogen or —($C_1$-$C_6$)alkyl, then each of $R^6$ and $R^7$is not independently hydrogen or —C(O)R', where R' is unsubstituted aryl, and $R^8$ is not hydrogen;

*further provided that when $X^-$is absent, n is 0, $Z^2$ is NH or oxygen, and $R^1$, $R^2$, $R^3$, $R^4$, and $R^5$ are each hydrogen, and $R^6$ is —P(O)(O$Y^1$)(O$Y^2$), then $Y^1$, $Y^2$, $R^7$, and $R^8$ are not all simultaneously hydrogen.*

2. A reduced nicotinate/nicotinamide riboside compound or derivative of formula (II), or a salt, hydrate, or solvate thereof:

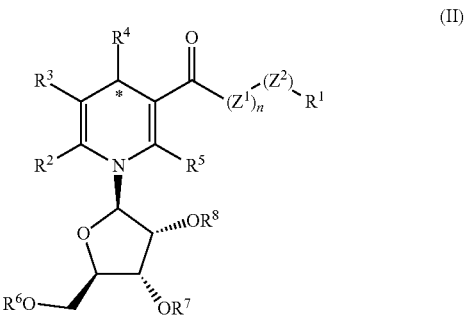

(II)

$Z^1$ and $Z^2$ are independently NH or oxygen;
n is 0 or 1;

$R^1$ is selected from the group consisting of hydrogen, substituted or unsubstituted $(C_1-C_8)$alkyl, substituted or unsubstituted $(C_3-C_8)$cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^A$)—$CO_2R^B$; wherein the substituted $(C_1-C_8)$alkyl, substituted $(C_3-C_8)$cycloalkyl, substituted aryl, substituted heteroaryl, and substituted heterocycle are substituted with one to five substituents independently selected from the group consisting of —$(C_1-C_6)$alkyl, —$(C_2-C_6)$alkenyl, —$(C_2-C_6)$alkynyl, halogen, —CN, —$NO_2$, —C(O)$R^c$, —C(O)O$R^c$, —C(O)N$R^c_2$, —C(=N$R^c$)N$R^c_2$, —O$R^c$, —OC(O)($C_1$-$C_6$)alkyl, —OC(O)O($C_1$-$C_6$)alkyl, —OC(O)N$R^c_2$, —$(C_1-C_6)$alkylene—N$R^c_2$, —N$R^c_2$, —N$R^c$C(O)$R^c$, —N$R^c$C(O)O($C_1$-$C_6$)alkyl, —N$R^c$C(O)N$R^c_2$, —N$R^c$SO$_2$N$R^c_2$, —S$R^c$, —S(O)$R^c$, —SO$_2R^c$, —OSO$_2$($C_1$-$C_6$)alkyl, —SO$_2$N$R^c_2$, —$(C_1-C_6)$perfluoroalkyl, and —$(C_1-C_6)$alkylene—O$R^c$;

$R^A$ is selected from the group consisting of —H, —$(C_1$-$C_6)$alkyl, —$(CH_2)_3$—NH—C(NH$_2$)(=NH), —CH$_2$C(=O)NH$_2$, —CH$_2$COOH, —CH$_2$SH, —(CH$_2)_2$C(=O)—NH$_2$, —(CH$_2)_2$COOH, —CH$_2$—(2-imidazolyl), —CH(CH$_3$)—CH$_2$—CH$_3$, —CH$_2$CH(CH$_3)_2$, —(CH$_2)_4$—NH$_2$, —(CH$_2)_2$—S—CH$_3$, phenyl, —CH$_2$—phenyl, —CH$_2$—OH, —CH(OH)—CH$_3$, —CH$_2$—(3-indolyl), —CH$_2$-(4-hydroxyphenyl), —CH(CH$_3)_2$, and —CH$_2$—CH$_3$;

$R^B$ is hydrogen or —$(C_1-C_8)$alkyl;

each $R^c$ is independently selected from the group consisting of hydrogen, —$(C_1-C_8)$alkyl, substituted or unsubstituted pyridyl, substituted or unsubstituted 1,4-dihydropyridyl, a radical of the compound of formula (I), and vitamin B7 ester (biotinyl); wherein the substituted pyridyl and substituted 1,4-dihydropyridyl are substituted with one to five substituents independently selected from the group consisting of —$(C_1-C_6)$alkyl, —$(C_2-C_6)$alkenyl, —$(C_2-C_6)$alkynyl, halogen, —CN, —$NO_2$, —C(O)$R^B$, —C(O)O$R^B$, —C(O)N$R^B_2$, —C(=N$R^B$)N$R^B_2$, —O$R^B$, —OC(O)($C_1$-$C_6$)alkyl, —OC(O)O($C_1$-$C_6$)alkyl, —OC(O)N$R^B_2$, —$(C_1-C_6)$alkylene-N$R^B_2$, —N$R^B_2$, —N$R^B$C(O)$R^B$, —N$R^B$C(O)O($C_1$-$C_6$)alkyl, —N$R^B$C(O)N$R^B_2$, —N$R^B$SO$_2$N$R^B_2$, —S$R^B$, —S(O)$R^B$, —SO$_2R^B$, —OSO$_2$($C_1$-$C_6$)alkyl, —SO$_2$N$R^B_2$, —$(C_1-C_6)$perfluoroalkyl, and —$(C_1-C_6)$alkylene—O$R^B$;

$R^2$ and $R^3$ are each independently selected from the group consisting of hydrogen, —$(C_1-C_6)$alkyl, —$(C_2-C_6)$alkenyl, —$(C_2-C_6)$alkynyl, halogen, —CN, —$NO_2$, —C(O)$R^c$, —C(O)O$R^c$, —C(O)N$R^c_2$, —C(=N$R^c$)N$R^c_2$, —O$R^c$, —OC(O)($C_1$-$C_6$)alkyl, —OC(O)O($C_1$-$C_6$)alkyl, —OC(O)N$R^c_2$, —$(C_1-C_6)$alkylene—N$R^c_2$, —N$R^c_2$, —N$R^c$C(O)$R^c$, —N$R^c$C(O)O($C_1$-$C_6$)alkyl, —N$R^c$C(O)N$R^c_2$, —N$R^c$SO$_2$N$R^c_2$, —S$R^c$, —S(O)$R^c$, —SO$_2R^c$, —OSO$_2$($C_1$-$C_6$)alkyl, —SO$_2$N$R^c_2$, —$(C_1$-$C_6)$perfluoroalkyl, and —$(C_1-C_6)$alkylene-O$R^c$;

$R^4$ is selected from the group consisting of hydrogen, —$(C_1-C_6)$alkyl, —$(C_2-C_6)$alkenyl, —$(C_2-C_6)$alkynyl, halogen, —CN, —$NO_2$, —C(O)$R^c$, —C(O)O$R^c$, —C(O)N$R^c_2$, —C(=N$R^c$)N$R^c_2$, —O$R^c$, —OC(O)($C_1$-$C_6$)alkyl, —OC(O)O($C_1$-$C_6$)alkyl, —OC(O)N$R^c_2$, —$(C_1-C_6)$alkylene—N$R^c_2$, —N$R^c_2$, —N$R^c$C(O)$R^c$, —N$R^c$C(O)O($C_1$-$C_6$)alkyl, —N$R^c$C(O)N$R^c_2$, —N$R^c$SO$_2$N$R^c_2$, —S$R^c$, —S(O)$R^c$, —SO$_2R^c$, —OSO$_2$($C_1$-$C_6$)alkyl, —SO$_2$N$R^c_2$, —$(C_1-C_6)$perfluoroalkyl, and —$(C_1-C_6)$alkylene—O$R^c$;

wherein C* has an absolute configuration of R or S, or a mixture of R and S;

$R^5$ is selected from the group consisting of hydrogen, —$(C_1-C_6)$alkyl, —$(C_1-C_6)$alkenyl, —$(C_2-C_6)$alkynyl, halogen, —CN, —$NO_2$, —C(O)$R^c$, —C(O)O$R^c$, —C(O)N$R^c_2$, —C(=N$R^c$)N$R^c_2$, —O$R^c$, —OC(O)($C_1$-$C_6$)alkyl, —OC(O)O($C_1$-$C_6$)alkyl, —OC(O)N$R^c_2$, —$(C_1-C_6)$alkylene—N$R^c_2$, —N$R^c_2$, —N$R^c$C(O)$R^c$, —N$R^c$C(O)O($C_1$-$C_6$)alkyl, —N$R^c$C(O)N$R^c_2$, —N$R^c$SO$_2$N$R^c_2$, —S$R^c$, —S(O)$R^c$, —SO$_2R^c$, —OSO$_2$($C_1$-$C_6$)alkyl, —SO$_2$N$R^c_2$, —$(C_1-C_6)$perfluoroalkyl, and —$(C_1-C_6)$alkylene—O$R^c$;

$R^6$ is selected from the group consisting of hydrogen, —C(O)R', —C(O)OR', —C(O)NHR', —P(O)(O$Y^1$)(O$Y^2$), —P(O)(O$Y^1$)(NHR''), substituted or unsubstituted $(C_1-C_8)$alkyl, substituted or unsubstituted $(C_3-C_8)$cycloalkyl, substituted or unsubstituted aryl, substituted or unsubstituted heteroaryl, and substituted or unsubstituted heterocycle, vitamin B1 ester, vitamin B2 ester, vitamin B6 ester, and —C**H—($R^A$)—$CO_2R^B$; wherein the substituted $(C_1-C_8)$alkyl, substituted [$(C_1$-$C_8)$cycloalkyl] *$(C_3$-$C_8)$cycloalkyl,* substituted aryl, substituted heteroaryl, and substituted heterocycle are substituted with one to five substituents independently selected from the group consisting of —$(C_1-C_6)$alkyl, —$(C_2-C_6)$alkenyl, —$(C_2-C_6)$alkynyl, halogen, —CN, —$NO_2$, —C(O)$R^c$, —C(O)O$R^c$, —C(O)N$R^c_2$, —C(=N$R^c$)N$R^c_2$, —O$R^c$, —OC(O)($C_1$-$C_6$)alkyl, —OC(O)O($C_1$-$C_6$)alkyl, —OC(O)N$R^c_2$, —$(C_1-C_6)$alkylene-N$R^c_2$, —N$R^c_2$, —N$R^c$C(O)$R^c$, —N$R^c$C(O)O($C_1$-$C_6$)alkyl, —N$R^c$C(O)N$R^c_2$, —N$R^c$SO$_2$N$R^c_2$, —S$R^c$, —S(O)$R^c$, —SO$_2R^c$, —OSO$_2$($C_1$-$C_6$)alkyl, —SO$_2$N$R^c_2$, —$(C_1-C_6)$perfluoroalkyl, and —$(C_1-C_6)$alkylene—O$R^c$;

R' is selected from the group consisting of hydrogen, substituted or unsubstituted $(C_1-C_8)$alkyl, substituted or unsubstituted $(C_3-C_8)$cycloalkyl, substituted or unsubstituted aryl, substituted or unsubstituted heteroaryl, substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—($R^A$)—$CO_2R^B$; wherein the substituted $(C_1C_8)$alkyl, substituted $(C_1-C_8)$cycloalkyl, substituted aryl, substituted heteroaryl, and substituted heterocycle are substituted with one to five substituents independently selected from the group consisting of —$(C_1-C_6)$alkyl, —$(C_2-C_6)$alkenyl, —$(C_2-C_6)$alkynyl, halogen, —CN —$NO_2$, —C(O)$R^c$, —C(O)O$R^c$, —C(O)N$R^c_2$, —C(=N$R^c$)N$R^c_2$, —O$R^c$, —OC(O)($C_1$-$C_6$)alkyl, —OC(O)O($C_1$-$C_6$)alkyl, —OC(O)N$R^c_2$, —$(C_1-C_6)$alkylene-N$R^c_2$, —N$R^c_2$, —N$R^c$C(O)$R^c$, —N$R^c$C(O)O($C_1$-$C_6$)alkyl, —N$R^c$C(O)N$R^c_2$, —N$R^c$SO$_2$N$R^c_2$, —S$R^c$, —S(O)$R^c$, —SO$_2R^c$, —OSO$_2$($C_1$-$C_6$)alkyl, —SO$_2$N$R^c_2$, —$(C_1-C_6)$perfluoroalkyl, and —$(C_1-C_6)$alkylene—O$R^c$;

R" is selected from the group consisting of hydrogen, substituted or unsubstituted $(C_1-C_8)$alkyl, substituted or unsubstituted $(C_3-C_8)$cycloalkyl, substituted or unsubstituted aryl, substituted or unsubstituted heteroaryl, and substituted or unsubstituted heterocycle, vitamin B1 ester, vitamin B2 ester, vitamin B6 ester, choline ester, biotin ester, vitamin A ester, resveratrol ester, aryl($C_1$-$C_4$)alkyl, heterocycle($C_1$-$C_4$)alkyl, and —C**H—($R^A$)—$CO_2R^B$; wherein the substituted $(C_1$-$C_8)$alkyl, substituted $(C_3$-$C_8)$cycloalkyl, substituted aryl, substituted heteroaryl, and substituted heterocycle are substituted with one to five substituents independently selected from the group consisting of $—(C_1C_6)$ alkyl, $—(C_2-C_6)$alkenyl, $—(C_2-C_6)$alkynyl, halogen, —CN, —NO$_2$, —C(O)R$^c$, —C(O)OR$^c$, —C(O)NR$^c{}_2$, —C(=NR$^c$)NR$^c{}_2$, —OR$^c$, —OC(O)(C$_1$-C$_6$)alkyl, —OC(O)O(C$_1$-C$_6$)alkyl, —OC(O)NR$^c{}_2$, —(C$_1$-C$_6$)alkylene—NR$^c{}_2$, —NR$^c{}_2$, —NR$^c$C(O)R$^c$, —NR$^c$C(O)O (C$_1$C$_6$)alkyl, —NR$^c$C(O)NR$^c{}_2$, —NR$^c$SO$_2$NR$^c{}_2$, —SR$^c$, —S(O)R$^c$, —SO$_2$R$^c$, —OSO$_2$(C$_1$C$_6$)alkyl, —SO$_2$NR$^c{}_2$, —(C$_1$-C$_6$)perfluoroalkyl, and —(C$_1$-C$_6$) alkylene—OR$^c$;

R$^7$ and R$^8$ are independently selected from the group consisting of hydrogen, —C(O)R', —C(O)OR', —C(O) NHR', substituted or unsubstituted (C$_1$-C$_8$)alkyl, substituted or unsubstituted (C$_3$-C$_8$)cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl; wherein the substituted (C$_1$-C$_8$)alkyl, substituted (C$_3$-C$_8$)cycloalkyl, substituted aryl, substituted heteroaryl, substituted heterocycle, substituted aryl(C$_1$-C$_4$)alkyl, and substituted heterocycle(C$_1$-C$_4$)alkyl are substituted with one to five substituents independently selected from the group consisting of —(C$_1$-C$_6$)alkyl, —(C$_2$-C$_6$)alkenyl, -(C$_2$-C$_6$)alkynyl, halogen, —CN, —NO$_2$, —C(O)R$^c$, —C(O)OR$^c$, —C(O)NR$^c{}_2$, —C(=NR$^c$) NR$^c{}_2$, —OR$^c$, —OC(O)(C$_1$-C$_6$)alkyl, —OC(O)O(C$_1$-C$_6$)alkyl, —OC(O)NR$^c{}_2$, —(C$_1$-C$_6$)alkylene-NR$^c{}_2$, NR$^c{}_2$, —NR$^c$C(O)R$^c$, NR$^c$C(O)O(C$_1$-C$_6$)alkyl, —NR$^c$C(O)NR$^c{}_2$, —NR$^c$SO$_2$NR$^c{}_2$, —SR$^c$, —S(O)R$^c$, —SO$_2$R$^c$, —OSO$_2$(C$_1$-C$_6$)alkyl, —SO$_2$NR$^c{}_2$, —(C$_1$-C$_6$)perfluoroalkyl, and —(C$_1$-C$_6$)alkylene-OR$^c$;

Y$^1$ and Y$^2$ are independently selected from the group consisting of hydrogen, sodium, potassium, lithium, substituted or unsubstituted (C$_1$-C$_8$)alkyl, substituted or unsubstituted (C$_3$-C$_8$)cycloalkyl, substituted or unsubstituted aryl, substituted or unsubstituted heteroaryl, and substituted or unsubstituted heterocycle; wherein the substituted (C$_1$-C$_8$)alkyl, substituted (C$_3$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^c$, —C(O)OR$^c$, —C(O)NR$^c{}_2$, —C(=NR$^c$)NR$^c{}_2$, —OR$^c$, —OC(O)(C$_1$-C$_6$)alkyl, —OC(O)O(C$_1$-C$_6$)alkyl, —OC (O)NR$^c{}_2$, —(C$_1$-C$_6$)alkylene—NR$^c{}_2$, —NR$^c{}_2$, —NR$^c$C(O)R$^c$, —NR$^c$C(O)O(C$_1$-C$_6$)alkyl, —NR$^c$C (O)NR$^c{}_2$, —NR$^c$SO$_2$NR$^c{}_2$, —SR$^c$, —S(O)R$^c$, —SO$_2$R$^c$, —OSO$_2$(C$_1$-C$_6$)alkyl, —SO$_2$NR$^c{}_2$, —(C$_1$-C$_6$)perfluoroalkyl, and —(C$_1$-C$_6$)alkylene—OR$^c$; or, alternatively, Y$^1$ and Y$^2$ taken together are selected from the group consisting of sodium, potassium, lithium, magnesium, calcium, strontium, and barium;

provided that when Z$^2$ is NH, the absolute configuration of C** is R or S, or a mixture of R and S;

further provided that when n is 0, Z$^2$ is NH, and R$^1$, R$^2$, R$^3$, R$^4$, and R$^5$ are each hydrogen, then R$^6$ is not —C(O)R' or —C(O)OR' where R' is alkyl, and each of R$^7$ and R$^8$ are not independently hydrogen, —C(O)R', or —C(O)OR', where R' is alkyl;

further provided that when n is 0 and Z$^2$ is NH or oxygen, then R$^1$, R$^2$, R$^3$, R$^4$, R$^5$, R$^6$, R$^7$, and R$^8$ are not all simultaneously hydrogen;

further provided that when n is 0, Z$^2$ is oxygen, R$^1$ is hydrogen or (C$_1$-C$_4$)alkyl, and R$^2$, R$^3$, R$^4$, and R$^5$ are each hydrogen, then each of R$^6$, R$^7$, and R$^8$ is not —C(O)R', —C(O)OR', or —C(O)NHR', where R' is hydrogen, unsubstituted (C$_1$-C$_8$)alkyl, unsubstituted (C$_3$-C$_8$)cycloalkyl, unsubstituted aryl, unsubstituted heteroaryl, unsubstituted aryl(C$_1$-C$_4$)alkyl, or unsubstituted heterocycle(C$_1$-C$_6$)alkyl;

*further provided that when n is 0, Z$^2$ is NH or oxygen, and R$^1$, R$^2$, R$^3$, R$^4$, and R$^5$ are each hydrogen, and R$^6$ is —P(O)(OY$^1$)(OY$^2$), then Y$^1$, Y$^2$, R$^7$, and R$^8$ are not all simultaneously hydrogen.*

10. *A reduced nicotinate/nicotinamide riboside compound or derivative of formula (II), or a salt thereof of claim 2, wherein Z$^2$ is NH or oxygen, n is 0, R$^1$, R$^2$, R$^3$, R$^4$, and R$^5$ are each hydrogen, R$^6$ is —P(O)(OY$^1$)(OY$^2$), R$^7$ and R$^8$ are as described in claim 2, and*

*Y$^1$ and Y$^2$ are independently selected from the group consisting of sodium, potassium, lithium, or, alternatively, Y$^1$ and Y$^2$ taken together are selected from the group consisting of sodium, potassium, lithium, magnesium, calcium, strontium, and barium.*

11. *A reduced nicotinate/nicotinamide riboside compound or derivative of formula (II), or a salt thereof of claim 2, wherein Z$^2$ is NH or oxygen, n is 0, R$^1$, R$^2$, R$^3$, R$^4$, and R$^5$ are each hydrogen, R$^6$ is —P(O)(OY$^1$)(OY$^2$), R$^7$ and R$^8$ are as described in claim 2, and*

*Y$^1$ and Y$^2$ are independently selected from the group consisting of hydrogen, substituted or unsubstituted (C$_1$-C$_8$)alkyl, substituted or unsubstituted (C$_3$-C$_8$)cycloalkyl, substituted or unsubstituted aryl, substituted or unsubstituted heteroaryl, and substituted or unsubstituted heterocycle; wherein the substituted (C$_1$-C$_8$) alkyl, substituted (C$_3$-C$_8$)cycloalkyl, substituted aryl, substituted heteroaryl, and substituted heterocycle are substituted with one to five substituents independently selected from the group consisting of —(C$_1$-C$_6$)alkyl, —(C$_2$-C$_6$)alkenyl, —(C$_2$-C$_6$)alkynyl, halogen, —CN, —NO$_2$, —C(O)R$^c$, —C(O)OR$^c$, —C(O)NR$^c{}_2$, —C(=NR$^c$)NR$^c{}_2$, —OR$^c$, —OC(O)(C$_1$-C$_6$)alkyl, —OC (O)O(C$_1$-C$_6$)alkyl, —OC(O)NR$^c{}_2$, —(C$_1$-C$_6$)alkylene-NR$^c{}_2$, —NR$^c{}_2$, —NR$^c$C(O)R$^c$, —NR$^c$C(O)O(C$_1$-C$_6$)alkyl, —NR$^c$C(O)NR$^c{}_2$, —NR$^c$SO$_2$NR$^c{}_2$, —SR$^c$, —S(O) R$^c$, —SO$_2$R$^c$, —OSO$_2$(C$_1$-C$_6$)alkyl, —SO$_2$NR$^c{}_2$, —(C$_1$-C$_6$)perfluoroalkyl, and —(C$_1$-C$_6$)alkylene—OR$^c$;*

*Y$^1$ and Y$^2$ cannot both be hydrogen, and*

*R$^B$ and R$^c$ are as described in claim 2.*

12. *A reduced nicotinate/nicotinamide riboside compound or derivative of formula (II), or a salt thereof of claim 2, wherein Z$^2$ is NH or oxygen, n is 0, R$^1$, R$^2$, R$^3$, R$^4$, and R$^5$ are each hydrogen, R$^6$ is —P(O)(OY$^1$)(NHR''), R'' is as described in claim 2, R$^7$ and R$^8$ are as described in claim 2, and*

*Y$^1$ is selected from the group consisting of hydrogen, sodium, potassium, lithium, substituted or unsubstituted (C$_1$-C$_8$)alkyl, substituted or unsubstituted (C$_3$-C$_8$) cycloalkyl, substituted or unsubstituted aryl, substituted or unsubstituted heteroaryl, and substituted or unsubstituted heterocycle; wherein the substituted (C$_1$-C$_8$)alkyl, substituted (C$_3$-C$_8$)cycloalkyl, substituted* aryl, substituted heteroaryl, and substituted heterocycle are substituted with one to five substituents independently selected from the group consisting of —($C_1$-$C_6$)alkyl, —($C_2$-$C_6$)alkenyl, —($C_2$-$C_6$)alkynyl, halogen, —CN, —$NO_2$, —C(O)$R^c$, —C(O)O$R^c$, —C(O)N$R^c_2$, —C(=N$R^c$)N$R^c_2$, —O$R^c$, —OC(O)($C_1$-$C_6$)alkyl, —OC(O)O($C_1$-$C_6$)alkyl, —OC(O)N$R^c_2$, —($C_1$-$C_6$)alkylene-N$R^c_2$, N$R^c_2$, —N$R^c$C(O)$R^c$, N$R^c$C(O)O($C_1$-$C_6$)alkyl, —N$R^c$C(O)N$R^c_2$, —N$R^c$$SO_2$N$R^c_2$, —S$R^c$, —S(O)$R^c$, —$SO_2$$R^c$, —$OSO_2$($C_1$-$C_6$)alkyl, —$SO_2$N$R^c_2$, —($C_1$-$C_6$)perfluoroalkyl, and —($C_1$-$C_6$)alkylene-O$R^c$;

$R^B$ and $R^c$ are as described in claim 2.

13. A reduced nicotinate/nicotinamide riboside compound or derivative of formula (II), or a salt thereof of claim 2, wherein $Z^1$ and $Z^2$ are independently NH or oxygen, n is 0 or 1, $R^1$, $R^2$, $R^3$, $R^4$, and $R^5$ are each hydrogen, $R^6$ is selected from the group consisting of vitamin B1 ester, vitamin B2 ester, vitamin B6 ester, and —C**H—($R^4$)—$CO_2$$R^B$, $R^4$, $R^B$ and $R^c$ are as described in claim 2, and $R^7$ and $R^8$ are as described in claim 2.

14. A reduced nicotinate/nicotinamide riboside compound or derivative of formula (II), or a salt thereof of claim 2, wherein $Z^1$ and $Z^2$ are independently NH or oxygen, n is 0 or 1, $R^1$ is selected from the group consisting of vitamin B1 ester, vitamin B2 ester, vitamin B6 ester, and —C**H—($R^4$)—$CO_2$$R^B$;

$R^4$, $R^B$ and $R^c$ are as described in claim 2, $R^2$, $R^3$, $R^4$, $R^5$ and $R^6$ are each hydrogen, and $R^7$ and $R^8$ are as described in claim 2.

15. A reduced nicotinate/nicotinamide riboside compound or derivative of formula (II), or a salt, hydrate, or solvate thereof:

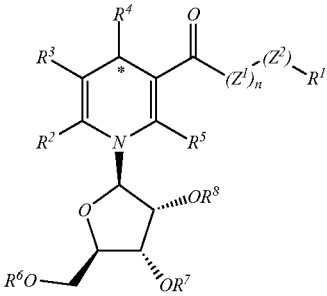

(II)

$Z^2$ is NH or oxygen;

n is 0;

$R^1$, $R^2$, $R^3$, $R^4$, $R^5$ are each hydrogen, $R^6$ is —P(O)(O$Y^1$)(O$Y^2$)

$R^7$ and $R^8$ are each hydrogen, and $Y^1$ and $Y^2$ are independently selected from the group consisting of hydrogen, sodium, potassium, lithium, or, alternatively, $Y^1$ and $Y^2$ taken together are selected from the group consisting of sodium, potassium, lithium, magnesium, calcium, strontium, and barium, wherein $Y^1$ and $Y^2$ are not simultaneously hydrogen.

16. The compound according to claim 15 wherein $Z^2$ is NH and $Y^1$ and $Y^2$ are each sodium.

17. The compound according to claim 15 wherein $Z^2$ is NH and $Y^1$ and $Y^2$ are each potassium.

18. A nicotinate/nicotinamide riboside compound or derivative of formula (I), or a salt thereof of claim 1, wherein $X^-$, $Y^1$, $Y^2$, $Z^1$, $Z^2$, $R''$, $R^1$, $R^2$, $R^3$, $R^4$, $R^5$, $R^7$ and $R^8$ are as described in claim 1, and wherein $R^6$ is not —P(O)(O$Y^1$)(O$Y^2$) or —P(O)(O$Y^1$)(NHR'').

* * * * *